(12) United States Patent
Yamazaki et al.

(10) Patent No.: US 10,018,630 B2
(45) Date of Patent: Jul. 10, 2018

(54) CANCER STEM CELL ISOLATION

(75) Inventors: Tatsumi Yamazaki, Tokyo (JP);
Hisafumi Okabe, Shizuoka (JP);
Shinta Kobayashi, Helios (SG);
Takeshi Watanabe, Shizuoka (JP);
Koichi Matsubara, Helios (SG);
Atsuhiko Kato, Shizuoka (JP); Masami Suzuki, Shizuoka (JP)

(73) Assignees: CHUGAI SEIYAKU KABUSHIKI KAISHA, Tokyo (JP);
PHARMALOGICALS RESEARCH PTE. LTD., Helios (SG)

( * ) Notice: Subject to any disclaimer, the term of this patent is extended or adjusted under 35 U.S.C. 154(b) by 55 days.

(21) Appl. No.: 14/343,364

(22) PCT Filed: Sep. 7, 2012

(86) PCT No.: PCT/JP2012/072852
§ 371 (c)(1),
(2), (4) Date: Jul. 10, 2014

(87) PCT Pub. No.: WO2013/035824
PCT Pub. Date: Mar. 14, 2013

(65) Prior Publication Data
US 2014/0314675 A1    Oct. 23, 2014

(30) Foreign Application Priority Data

Sep. 7, 2011  (JP) ................................ 2011-194643
Apr. 12, 2012 (JP) ................................ 2012-091135

(51) Int. Cl.
| | | |
|---|---|---|
| *G01N 33/574* | (2006.01) |
| *G01N 33/50* | (2006.01) |
| *G01N 33/569* | (2006.01) |
| *C12N 5/095* | (2010.01) |
| *A61K 31/4745* | (2006.01) |
| *A61K 31/513* | (2006.01) |
| *A61K 31/555* | (2006.01) |
| *A61K 31/7088* | (2006.01) |
| *A61K 39/00* | (2006.01) |
| *A61K 39/395* | (2006.01) |
| *A61K 45/06* | (2006.01) |
| *C07K 16/18* | (2006.01) |
| *A61K 31/7105* | (2006.01) |
| *A61K 31/713* | (2006.01) |
| *C07K 16/30* | (2006.01) |

(52) U.S. Cl.
CPC ....... *G01N 33/574* (2013.01); *A61K 31/4745* (2013.01); *A61K 31/513* (2013.01); *A61K 31/555* (2013.01); *A61K 31/7088* (2013.01); *A61K 31/713* (2013.01); *A61K 31/7105* (2013.01); *A61K 39/0011* (2013.01); *A61K 39/3955* (2013.01); *A61K 45/06* (2013.01); *C07K 16/18* (2013.01); *C07K 16/30* (2013.01); *C12N 5/0695* (2013.01); *G01N 33/5073* (2013.01); *G01N 33/56966* (2013.01); *G01N 2500/04* (2013.01)

(58) Field of Classification Search
CPC ..................................................... C12N 5/0695
USPC .................................................. 435/366, 325
See application file for complete search history.

(56) References Cited

U.S. PATENT DOCUMENTS

| | | |
|---|---|---|
| 5,573,924 A | 11/1996 | Beckmann et al. |
| 7,145,055 B2 | 12/2006 | Ito et al. |
| 2002/0119565 A1 | 8/2002 | Clarke et al. |
| 2007/0220621 A1 | 9/2007 | Clarke et al. |
| 2008/0064049 A1 | 3/2008 | Clarke et al. |
| 2008/0178305 A1 | 7/2008 | Clark et al. |
| 2009/0081221 A1 | 3/2009 | Tokoro |
| 2009/0148942 A1 | 6/2009 | McDonagh et al. |

(Continued)

FOREIGN PATENT DOCUMENTS

| | | |
|---|---|---|
| CA | 2 447 400 | 3/2005 |
| CN | 101014608 A | 8/2007 |

(Continued)

OTHER PUBLICATIONS

Kim et al. (Biochemical and Biophysical Research Communications 2010, 402: 631-636).*

(Continued)

*Primary Examiner* — Yan Xiao
(74) *Attorney, Agent, or Firm* — Klarquist Sparkman, LLP

(57) ABSTRACT

An objective of the present invention is to provide: a cancer stem cell isolated using a cell marker; a substantively homogeneous cancer stem cell population including said cancer stem cell; and a method of preparing said cancer stem cell population. Another objective of the present invention is to provide: a method for separating cancer stem cells with a high proliferative potential and those with a low proliferative potential; a method for inducing cancer stem cells to have a different proliferative potential; and cancer stem cells separated or induced by these separation or induction methods. A further objective of the present invention is to provide: a method of screening for pharmaceuticals using said cancer stem cell or cancer stem cell population; a method for detecting the presence of said cancer stem cell or cancer stem cell population and for identifying or quantifying the same. The present inventors discovered that highly pure colon cancer stem cells (CSC) can be obtained in a large quantity, and identified two types of states of colon CSCs distinguishable through Lgr5 expression.

8 Claims, 68 Drawing Sheets

(56) References Cited

U.S. PATENT DOCUMENTS

| | | |
|---|---|---|
| 2009/0226396 A1 | 9/2009 | Haley et al. |
| 2009/0324491 A1 | 12/2009 | Aburatani et al. |
| 2010/0275280 A1 | 10/2010 | Clevers et al. |
| 2010/0287638 A1 | 11/2010 | Dirks et al. |
| 2011/0182904 A1 | 7/2011 | Zimmerman et al. |
| 2011/0244502 A1 | 10/2011 | Ince |
| 2013/0019327 A1 | 1/2013 | Suzuki et al. |
| 2013/0288248 A1 | 10/2013 | Yamazaki et al. |
| 2014/0302511 A1 | 10/2014 | Yamazaki et al. |
| 2016/0017028 A1 | 1/2016 | Yoshida et al. |

FOREIGN PATENT DOCUMENTS

| | | |
|---|---|---|
| CN | 101506352 | 8/2009 |
| EP | 1 338 198 A1 | 8/2003 |
| EP | 1 637 589 A1 | 3/2006 |
| EP | 1 686 173 A1 | 8/2006 |
| EP | 1 792 979 | 6/2007 |
| EP | 1815864 | 8/2007 |
| EP | 2070548 | 6/2009 |
| EP | 2517555 | 10/2012 |
| EP | 2626414 A1 | 8/2013 |
| JP | 3753321 | 12/2005 |
| JP | 2007-530588 | 11/2007 |
| JP | 2008-500838 | 1/2008 |
| JP | 2008-102012 | 5/2008 |
| JP | 2008-514205 | 5/2008 |
| JP | 2008-182912 | 8/2008 |
| JP | 2009-502156 | 1/2009 |
| JP | 2009-509510 | 3/2009 |
| JP | 2009-519242 | 5/2009 |
| JP | 2009-539374 | 11/2009 |
| JP | 2010-516259 | 5/2010 |
| JP | 2011-519567 | 7/2011 |
| WO | WO 02/12447 | 2/2002 |
| WO | WO 03/104401 | 12/2003 |
| WO | WO 2004/101775 A1 | 11/2004 |
| WO | WO 2005/035740 A1 | 4/2005 |
| WO | WO 2005/092927 | 10/2005 |
| WO | WO 2005/118824 A2 | 12/2005 |
| WO | WO 2006/039671 | 4/2006 |
| WO | WO 2006/039678 A2 | 4/2006 |
| WO | WO 2006/051405 | 5/2006 |
| WO | WO 2006/051984 A1 | 5/2006 |
| WO | WO 2006/138275 | 12/2006 |
| WO | WO 2007/012811 | 2/2007 |
| WO | WO 2007/038637 | 4/2007 |
| WO | WO 2007/064945 A2 | 6/2007 |
| WO | WO 2007/132883 | 11/2007 |
| WO | WO 2007/132883 A1 | 11/2007 |
| WO | WO 2007/145901 | 12/2007 |
| WO | WO 2008/017171 | 2/2008 |
| WO | WO 2008/047723 | 4/2008 |
| WO | WO 2008/091908 | 7/2008 |
| WO | WO 2008/143954 | 11/2008 |
| WO | WO 2008/149803 | 12/2008 |
| WO | WO 2009/005809 | 1/2009 |
| WO | WO 2009/064301 | 5/2009 |
| WO | WO 2009/135181 | 11/2009 |
| WO | WO 2010/009121 | 1/2010 |
| WO | WO 2010/016766 | 2/2010 |
| WO | WO 2010/102244 | 9/2010 |
| WO | WO 2010/113117 | 10/2010 |
| WO | WO 2010/123891 | 10/2010 |
| WO | WO 2010/126074 | 11/2010 |
| WO | WO 2011/027308 | 3/2011 |
| WO | WO 2011/078301 | 6/2011 |
| WO | WO 2011/083088 | 7/2011 |
| WO | WO 2012/046797 A1 | 4/2012 |
| WO | WO 2013/062083 | 5/2013 |

OTHER PUBLICATIONS

Ku et al. (Carcinogenesis, 2010, vol. 31 No. 6 pp. 1003-1009).*
Hu and Smyth, ELDA; Extreme Limiting Dilution analysis for comparing depleted and enriched populations in stem cell and other assays. Journal of Immunological Methods, 2009. 347, 70-78.
U.S. Appl. No. 14/354,517, filed Apr. 25, 2014, Yamazaki, et al.
Al-Hajj, et al. "Prospective identification of tumorigenic breast cancer cells." *Proceedings of the National Academy of Sciences* 100:3983-3988, 2003 (epub Mar. 10, 2003).
Barker, et al. "Crypt stem cells as the cells-of-origin of intestinal cancer." *Nature* 457: 608-611, 2009 (epub Dec. 17, 2008).
Barker, et al. "Identification of stem cells in small intestine and colon by marker gene Lgr5." *Nature* 449: 1003-1007, 2007 (epub Oct. 14, 2007).
Boiko, et al. "Human melanoma-initiating cells express neural crest nerve growth factor receptor CD271." *Nature* 466(7302): 133-137, 2010.
Bonnet et al. "Human acute myeloid leukemia is organized as a hierarchy that originates from a primitive hematopoietic cell." *Nature Medicine* 3: 730-737, 1997.
Chu, et al. "Characterization of a subpopulation of colon cancer cells with stem cell-like properties." *International Journal of Cancer* 124: 1312-1321, 2009.
Clevers. "The cancer stem cell: premises, promises and challenges." *Nature Medicine* 17:313-319, 2011.
Collins, et al. "Prospective identification of tumorigenic prostate cancer stem cells." *Cancer Research* 65: 10946-10951, 2005.
Dalerba, et al. "Phenotypic characterization of human colorectal cancer stem cells." *Proceedings of the National Academy of Sciences* 104: 10158-10163, 2007 (epub Jun. 4, 2007).
Eramo, et al. "Identification and expansion of the tumorigenic lung cancer stem cell population." *Cell Death & Differentiation* 15: 504-514, 2007 (epub Nov. 30, 2007).
Haraguchi, et al. "CD133+ CD44+ population efficiently enriches colon cancer initiating cells." *Annals of Surgical Oncology* 15:2927-2933, 2008 (epub Jul. 29, 2008).
Hsu, et al. "Characterization of Two LGR Genes Homologous to Gonadotropin and Thyrotropin Receptors with Extracellular Leucine-Rich Repeats and a G Protein-Coupled, Seven-Transmembrane Region." *Molecular Endocrinology* 12: 1830-1845, 1998.
Huang, et al. "ALDH1 is a marker for normal and malignant human colonic stem cells and tracks stem cell overpopulation during colon tumorigenesis."*Cancer Res* 69: 3382-3389, 2009 (epub Mar. 31, 2009).
International Search Report for PCT/JP2012/077714, mailed by the ISA (Japanese Patent Office) dated Jan. 29, 2013 (5 pages).
Ishizawa, et al. "Tumor-initiating cells are rare in many human tumors." *Cell Stem Cell* 7: 279-282, 2010.
Kowalczyk, et al. "Molecular and therapeutic characterization of anti-ectodysplasin A receptor (EDAR) agonist monoclonal antibodies." *Journal of Biological Chemistry* 286: 30769-30779, 2011.
Lapidot, et al. "A cell initiating human acute myeloid leukaemia after transplantation into SCID mice." *Nature* 367: 645-648, 1994.
Li, et al. "Identification of pancreatic cancer stem cells." *Cancer Research* 67: 1030-1037, 2007.
McDonald, et al. "Identification and cloning of an orphan G protein-coupled receptor of the glycoprotein hormone receptor subfamily." *Biochemical and Biophysical Research Communications* 247: 266-270, 1998.
O'Brien, et al. "A human colon cancer cell capable of initiating tumour growth in immunodeficient mice." *Nature* 445: 106-110, 2007 (epub Nov. 19, 2006).
Pang, et al. "A Subpopulation of CD26+ Cancer Stem Cells with Metastatic Capacity in Human Colorectal Cancer." *Cell Stem Cell* 6: 603-615, 2010.
Park, et al. "Cancer stem cell—directed therapies: recent data from the laboratory and clinic." *Molecular Therapy* 17: 219-230, 2009 (epub Dec. 9, 2008).
Patrawala, et al. "Highly purified CD44+ prostate cancer cells from xenograft human tumors are enriched in tumorigenic and metastatic progenitor cells." *Oncogene* 25: 1696-1708, 2006.
Prince, et al. "Identification of a subpopulation of cells with cancer stem cell properties in head and neck squamous cell carcinoma." *Proceedings of the National Academy of Sciences* 104:973-978, 2007 (epub Jan. 8, 2007).

(56) References Cited

OTHER PUBLICATIONS

Reya, et al. "Stem cells, cancer, and cancer stem cells." *Nature* 414: 105-111, 2001.
Ricci-Vitiani, et al. "Identification and expansion of human colon-cancer-initiating cells." *Nature* 445: 111-115, 2007 (epub Nov. 19, 2006).
Sato, et al. "Single Lgr5 stem cells build crypt villus structures in vitro without a mesenchymal niche." *Nature* 459: 262-265, 2009 (epub Mar. 29, 2009).
Schatton, et al. "Identification of cells initiating human melanomas." *Nature* 451: 345-349, 2008.
Singh, et al. "Identification of human brain tumour initiating cells." *Nature* 432: 396-401, 2004.
Vermeulen, et al. "Wnt activity defines colon cancer stem cells and is regulated by the microenvironment." *Nature Cell Biology* 12: 468-476, 2010 (epub Apr. 25, 2010).
Wu, et al. "Side population cells isolated from mesenchymal neoplasms have tumor initiating potential." *Cancer Research* 67: 8216-8222, 2007.
Mani et al., "The epithelial-mesenchymal transition generates cells with properties of stem cells," *Cell* 133(4):704-715, 2008.
Martin et al., "Expression of the Transcription Factors Snail, Slug, and Twist and Their Clinical Significance in Human Breast Cancer," *Ann Surg Oncol* 12:1-9, 2005.
Suemizu et al., "Identification of a key molecular regulator of liver metastasis in human pancreatic carcinoma using a novel quantitative model of metastasis in NOD/SCID/$\gamma_c^{null}$ (NOG) mice," *Int J Oncol* 31:741-751, 2007.
Fang et al., "A Tumorigenic Subpopulation with Stem Cell Properties in Melanomas," *Cancer Res.*, vol. 65:9328-9337, 2005.
Perego et al., "Heterogeneous Phenotype of Human Melanoma Cells with In Vitro and In Vivo Features of Tumor-Initiating Cells," *J. Invest. Dermatol.*, vol. 130:1877-1886, 2010.
Thenappan et al., "New Therapeutics Targeting Colon Cancer Stem Cells," *Curr. Colorectal Cancer Rep.*, vol. 5:209-216, 2009.
Oka et al., "Immunohistochemical evaluation of E-cadherin adhesion molecule expression in human gastric cancer," *Virchows Archiv A Pathol Anat* 421:149-159, 1992.
Kobayashi et al., "LGR5-Positive Colon Cancer Stem Cells Interconvert with Drug-Resistant LGR5-Negative Cells and are Capable of Tumor Reconstitution," *Stem Cells*, vol. 30:2631-2644, 2012.
Munoz et al., "The Lgr5 Intestinal Stem Cell Signature: Robust Expression of Proposed Quiescent '+ 4' Cell Markers," *EMBO J.*, vol. 31:3079-3091, 2012.
Walker et al., "LGR5 is a Negative Regulator of Tumourigenicity, Antagonizes Wnt Signalling and Regulates Cell Adhesion in Colorectal Cancer Cell Lines," *PLoS ONE*, vol. 6:e22733, 2011.
European Search Report for EPC Patent Application No. 10839531.0 (5 pages) (dated Aug. 27, 2014).
Fujii et al., "The potential of the NOD/SCID$\gamma_c^{null}$ (NOG) mouse as an in vivo human tissue model," *Toxicol Pathol* 191-P5 (Jan. 2007).
Fujii et al., Poster Presentations: *The 25th Annual Meeting of the Society of Toxicologic Pathology* Lawrence, KS, US, Canada (Jun. 18-22, 2006).
Kobayashi et al., "LGR5-positive colon cancer stem cells interconvert with drug-resistant LGR5-negative cells and are capable of tumor reconstitution," *Stem Cells* 30:2631-2644 (2012).
Hermann et al., "Distinct populations of cancer stem cells determine tumor growth and metastatic activity in human pancreatic cancer," *Cell Stem Cell*, 1:313-323, (Sep. 13, 2007).
International Preliminary Report on Patentability from parent PCT Application PCT/JP2012/072852 (in English), 12 pages (dated Mar. 12, 2014).
Ku et al., "Establishment and characterization of 13 human colorectal carcinoma cell lines: mutations of genes and expressions of drug-sensitivity genes and cancer stem cell markers" *Carcinogenesis* 31(6):1003-1009 (Jun. 2010).

Vermeulen et al., "Single-cell cloning of colon cancer stem cells reveals a multi-lineage differentiation capacity," *PNAS* 105(36):13427-13432 (Sep. 9, 2008).
Machine translation of JP 2008-102012, Hirao et al., published May 1, 2008.
Machida et al., "Higher susceptibility of NOG mice to xenotransplanted tumors," *J. Toxicol. Sci.* vol. 34, No. 1, pp. 123-127, 2009.
Carlone and Breault, "Slowly cycling versus rapidly cycling intestinal stem cells," *Cell Cycle* 10(5):723-724, 2011.
English translation of the International Search Report for PCT/JP2012/072852, dated Nov. 27, 2012.
Brabletz et al., "Migrating cancer stem cells—an integrated concept of malignant tumour progression," *Nature Reviews Cancer*, 5:744-749 (2005).
Dalerba et al., "Cancer Stem Cells: Models and Concepts," *The Annual Review of Medicine*, 58:267-284 (2007) (published online Sep. 26, 2006).
Fang et al., "Expansion of CD133+ colon cancer cultures retaining stem cell properties to enable cancer stem cell target discovery," *British Journal of Cancer*, 102:1265-1275 (2010).
Fujii et al., "Establishment and characterization of in vivo human tumor models in the NOD/SCID/$\gamma_c^{null}$ mouse," *Pathology International*, 58:559-567 (2008).
Gou et al., "Establishment of Clonal Colony-Forming Assay for Propagation of Pancreatic Cancer Cells With Stem Cell Properties," *Pancreas* 34(4): 429-435 (2007).
Imada et al., "Serial Transplantation of Adult T Cell Leukemia Cells into Severe Combined Immunodeficient Mice," *Jpn. J. Cancer Res.* 87:887-892 (Sep. 1996).
Inagaki et al., "Long-term maintenance of brain tumor stem cell properties under at non-adherent and adherent culture conditions," *Biochem. Biophys. Res. Commun.*, 361(3):586-592 (2007).
International Preliminary Report on Patentability (English language translation) for PCT Application No. PCT/JP2012/077714, 13 pages (dated Apr. 29, 2014).
International Search Report on Patentability from PCT/JP2010/073266 (2 pages) (dated Mar. 28, 2011).
Kirchner and Brabletz "Patterning a Nuclear β-Catenin Expression in the Colonic Adenoma-Carcinoma Sequence," *American Journal of Pathology*, 157(4):1113-1121 (2000).
Machine English translation of PCT Publication No. WO 2010/126074, Matsumoto et al., published Nov. 4, 2010.
Morisot et al., "Leukemia Stem Cells (LSCs) Are Frequent in Childhood Precursor B Acute Lymphoblastic Leukemia (ALL)," *50th ASH Annual Meeting and Exposition* (2 pages) (Dec. 6, 2008).
Quintana et al., "Efficient tumour formation by single human melanoma cells," *Nature* 456:593-598 (2008).
Translation of the International Preliminary Report on Patentability, International Application No. PCT/JP2011/073067, dated May 16, 2013.
Yeung et al., "Cancer stem cells from colorectal cancer-derived cell lines," *Proc. Natl. Acad. Sci. USA*, 107(8):3722-3727 (2010).
Zahidunnabi et al., "Potential role of NK cells in tumor growth and metastasis of breast cancer cells in NOD/SCID/γcnull (NOG) mice: Implication of immune therapy," *Proc. Amer. Assoc. Cancer Res.*, 46, Abstract #4683 (2005) (2 pages).
Amendment and Response After Final Office Action submitted in U.S. Appl. No. 13/878,181, 9 pages. (dated Aug. 21, 2015).
Amendment and Response to Office Action submitted in U.S. Appl. No. 13/878,181, 15 pages. (dated Jan. 22, 2015).
Final Office Action from U.S. Appl. No. 13/878,181, 14 pages. (dated Apr. 24, 2015).
Hirsch et al., "LGR5 positivity defines stem-like cells in colorectal cancer," *Carcinogenesis* 35(4):849-858 (2014).
Office Action from U.S. Appl. No. 13/878,181, 17 pages. (dated Mar. 25, 2016).
Office Action from U.S. Appl. No. 13/878,181, 18 pages. (dated Jul. 22, 2014).
Pollard et al., "Glioma stem cell lines expanded in adherent culture have tumor-specific phenotypes and are suitable for chemical and genetic screens," *Cell Stem Cell* 4(6):568-580 (Jun. 5, 2009).

(56) References Cited

OTHER PUBLICATIONS

Chen et al., "Intestinal Adenomagenesis Involves Core Molecular Signatures of the Epithelial-Mesenchymal Transition," *J Mol Histol* 39(3):283-294, 2008.
Advisory Action dated Sep. 3, 2015, issued in U.S. Appl. No. 13/878,181 (4 pages).
Final Office Action dated Dec. 1, 2016, issued in U.S. Appl. No. 13/878,181 (18 pages).
Restriction Requirement dated Feb. 25, 2014, issued in U.S. Appl. No. 13/878,181 (10 pages).
Ito et al., "NOD/SCID/$\gamma c^{null}$ mouse: an excellent recipient mouse model for engraftment of human cells," *Blood* 100(9):3175-3182, 2002.
Hamada et al., "Liver metastasis models of colon cancer for evaluation of drug efficacy using NOD/Shi-scid IL2R $\gamma^{null}$ (NOG) mice," *Int J Oncol* 32(1):153-159, 2008.
Office Action issued for U.S. Appl. No. 13/878,181 dated Jan. 17, 2018 (24 pages).

\* cited by examiner

| Cell line | Cell count per inoculation site | | |
|---|---|---|---|
| | 1,000 | 100 | 10 |
| PLR59 | 6/6 | 6/6 | 6/6 |
| PLR123 | 6/6 | 6/6 | 6/6 |

FIG. 31

| Organ | Frequency of tumor formation |
|---|---|
| Lung | 5/5 |
| Liver | 4/5 |
| Kidney | 1/5 |
| Brain, pia mater | 1/5 |
| Lymph node, Armpit | 2/5 |
| Subcutaneous tissue | 5/5 |

PLR59 Lgr5+ CSC in spheroid culture

B

PLR123 Lgr5+ CSC in spheroid culture

CANCER STEM CELL ISOLATION

CROSS REFERENCE TO RELATED APPLICATION

This is the U.S. national stage of PCT Application No. PCT/JP2012/072852, filed Sep. 7, 2012, which claims the benefit of Japanese Patent Application No. 2011-194643, filed Sep. 7, 2011, and Japanese Patent Application No. 2012-091135, filed Apr. 12, 2012.

The Sequence Listing is submitted as an ASCII text file [6235-92657-01_Sequence_Listing.txt, Mar. 6, 2014, 53.6 KB], which is incorporated by reference herein.

TECHNICAL FIELD

The present invention relates to substantially homogeneous cancer stem cell populations containing cancer stem cells, which cancer stem cells are separated using cell markers, and methods for producing the cancer stem cell populations. The present invention also relates to methods for separating cancer stem cells with a high proliferative potential and cancer stem cells with a low proliferative potential, methods for inducing cancer stem cells into those with a different proliferative potential, and cancer stem cells separated/induced by these separation methods or induction methods. The present invention also relates to methods of screening for pharmaceutical agents, which use these cancer stem cells or cancer stem cell populations, and methods for detecting, identifying, or quantifying the cancer stem cells or cancer stem cell populations.

BACKGROUND ART

Cancer stem cells (CSCs) are considered to be the origins of cancer. The reason is that these cells have the ability to self-renew and differentiate to form a tumor hierarchy (Non-patent Document 1). Furthermore, CSCs can migrate and be tolerant to anti-cancer drug therapy (Non-patent Document 1). Since CSCs are believed to be a rare subset in tumors, they have been characterized based on cell surface markers and tumor-initiating activity in xenograft transplantations. CSCs have been identified and characterized in several types of cancer, including acute myelocytic leukemia (AML) (Non-patent Documents 2 and 3), breast cancer (Non-patent Document 4), glioma (Non-patent Document 5), head and neck cancer (Non-patent Document 6), pancreatic cancer (Non-patent Documents 7 and 8), lung cancer (Non-patent Document 9), prostatic cancer (Non-patent Documents 10 and 11), mesenchymal neoplasm (Non-patent Document 12), and melanoma (Non-patent Documents 13 and 14). Earlier studies of O'Brien et al. (Non-patent Document 15) and Ricci-Vitiani et al. (Non-patent Document 16) showed that CD133 served as a CSC marker for colon cancer. Thereafter, different research groups have reported other markers: CD44, EpCAM, CD 166 (Non-patent Document 17), and ALDH (Non-patent Documents 18 and 19). Recently, Pang et al. demonstrated that CD26 serves as a marker for a CSC subpopulation with metastatic capacity (Non-patent Document 20).

To isolate CSCs, most studies have employed a cell selection approach using in combination CSC markers such as $EpCAM^{high}/CD44^+/CD166^+$ (Non-patent Document 17), $CD133^+/CD44^+$ (Non-patent Document 21), $CD44^{high}/ALDH^+$ (Non-patent Document 18), and $ALDH1^+/CD133^+$ (Non-patent Document 19). In vitro spheroid (cell mass) cultures and direct cancer cell xenograft transplantation to immunodeficient mice have also been used to enrich CSCs (Non-patent Document 22). However, the number and purity of stem cells are still insufficient for further understanding the properties of CSCs.

One challenge in isolating CSCs arises from the phenotypic heterogeneity and/or instability of these cells (Non-patent Document 29). Three-dimensional spheroid cultures are often used as a CSC source. Spheroid cultures are applicable directly to primary tumor cells of clinically resected specimens; thus, maintenance of heterogeneous CSC populations can have certain potential advantages compared to xenograft transplantations. Due to the heterogeneity, however, results of biochemical analyses often show complicated CSC characteristics. CSC selection using antibodies against cell surface marker proteins is commonly used to isolate CSCs, but the number and purity of cells obtained by this method is limited. Phenotypes from xenografts remain stable even after frequent passages, and using xenografts as a source of CSCs is also a common approach. However, there is an argument that xenograft passages in mice only select cells viable in mice and result in elimination of cells that are hardly affected by such an environment. It goes without saying that CSCs in xenograft tumors reflect the characteristics of original CSCs, as long as they maintain the self-renewability and lineage differentiation capacity of the original tumor.

Leucine-rich repeat-containing G-protein-coupled receptor 5 (Lgr5) was originally identified as an orphan G-protein-coupled receptor of the glycoprotein hormone receptor family (Non-patent Documents 23 and 24) and was demonstrated to be a Wnt target gene whose expression is restricted to the crypt (Non-patent Document 25). The discovery that Lgr5-positive columnar cells can regenerate all epithelial lineages (Non-patent Document 25) and that a single Lgr5-positive cell can form crypt-villus organoids in vitro without a mesenchymal niche (Non-patent Document 26), conclusively proves that Lgr5-positive cells are stem cells in the normal intestine and colon. It has also been reported that Lgr5-positive cells form adenomas in the absence of Apc (Non-patent Document 27) and Lgr5 is expressed in colon cancer cell lines (Non-patent Document 25). When considered together, the findings described above suggest that Lgr5-positive cells are an origin of intestine and colon cancers (Non-patent Document 25). It has been proven that, as in stem cells of the normal colon and intestine, Wnt activity is essential for in vitro and in vivo proliferation of CSCs and that exogenous HGF enhances Wnt activity (Non-patent Document 28).

Lgr5 was identified as a marker for normal colon and intestine stem cells, and has been demonstrated to serve as a marker for origins of colon cancer (Patent Document 1 and Non-patent Document 30). Furthermore, Lgr5 was reported to be a protein that is over-expressed in colon cancer stem cells (Patent Document 2). The biological role of Lgr5 in the development of colon cancer remains poorly understood.

To date, various anti-cancer drugs and cancer therapeutic methods have been developed, but there are still issues to be solved, such as poor effectiveness, adverse effects, or being effective in only a limited number of patients. In recent years, therapeutic methods for targeting cancer stem cells have drawn attention, but their effectiveness and adverse effects remain poorly understood (Non-patent Document 31).

PRIOR ART DOCUMENTS

Patent Documents

Patent Document 1: US20100275280
Patent Document 2: WO09/005,809

Non-patent Documents

Non-patent Document 1: Reya T, Morrison S J, Clarke M F, Weissman I L (2001) Stem cells, cancer, and cancer stem cells. Nature 414:105-111.
Non-patent Document 2: Bonnet D, Dick J E (1997) Human acute myeloid leukemia is organized as a hierarchy that originates from a primitive hematopoietic cell. Nat Med 3:730-737.
Non-patent Document 3: Lapidot T, et al. (1994) A cell initiating human acute myeloid leukaemia after transplantation into SCID mice. Nature 367:645-648.
Non-patent Document 4: Al-Hajj M, Wicha M S, Benito-Hernandez A, Morrison S J, Clarke M F (2003) Prospective identification of tumorigenic breast cancer cells. Proc Natl Acad Sci USA 100:3983-3988.
Non-patent Document 5: Singh S K, et al. (2004) Identification of human brain tumour initiating cells. Nature 432:396-401.
Non-patent Document 6: Prince M E, et al. (2007) Identification of a subpopulation of cells with cancer stem cell properties in head and neck squamous cell carcinoma. Proc Natl Acad Sci USA 104:973-978.
Non-patent Document 7: Hermann P C, et al. (2007) Distinct populations of cancer stem cells determine tumor growth and metastatic activity in human pancreatic cancer. Cell Stem Cell 1: 313-323.
Non-patent Document 8: Li C, et al. (2007) Identification of pancreatic cancer stem cells. Cancer Res 67:1030-1037.
Non-patent Document 9: Eramo A, et al. (2008) Identification and expansion of the tumorigenic lung cancer stem cell population. Cell Death Differ 15:504-514.
Non-patent Document 10: Collins A T, Berry P A, Hyde C, Stower M J, Maitland N J (2005) Prospective identification of tumorigenic prostate cancer stem cells. Cancer Res 65:10946-10951.
Non-patent Document 11: Patrawala L, et al. (2006) Highly purified CD44+ prostate cancer cells from xenograft human tumors are enriched in tumorigenic and metastatic progenitor cells. Oncogene 25:1696-1708.
Non-patent Document 12: Wu C, et al. (2007) Side population cells isolated from mesenchymal neoplasms have tumor initiating potential. Cancer Res 1:8216-8222.
Non-patent Document 13: Schatton T, et al. (2008) Identification of cells initiating human melanomas. Nature 451:345-349.
Non-patent Document 14: Boiko A D, et al. (2010) Human melanoma-initiating cells express neural crest nerve growth factor receptor CD271. Nature 446:133-137.
Non-patent Document 15: O'Brien C A, Pollett A, Gallinger S, Dick J E (2007) A human colon cancer cell capable of initiating tumour growth in immunodeficient mice. Nature 445:106-110.
Non-patent Document 16: Ricci-Vitiani L, et al. (2007) Identification and expansion of human colon-cancer-initiating cells. Nature 445:111-115
Non-patent Document 17: Dalerba P, et al. (2007) Phenotypic characterization of human colorectal cancer stem cells. Proc Natl Acad Sci USA 104:10158-10163.
Non-patent Document 18: Chu P, et al. (2009) Characterization of a subpopulation of colon cancer cells with stem cell-like properties. Int J Cancer 124:1312-1321.
Non-patent Document 19: Huang E H, et al. (2009) Aldehyde dehydrogenase 1 is a marker for normal and malignant human colonic stem cells (SC) and tracks SC overpopulation during colon tumorigenesis. Cancer Res 69:3382-3389.
Non-patent Document 20: Pang R, et al. (2010) A subpopulation of CD26+ cancer stem cells with metastatic capacity in human colorectal cancer. Cell Stem Cell 6:603-615.
Non-patent Document 21: Haraguchi N, et al. (2008) CD133+CD44+ population efficiently enriches colon cancer initiating cells. Ann Surg Oncol 15:2927-2933.
Non-patent Document 22: Ishizawa K, et al. (2010) Tumor-initiating cells are rare in many human tumors. Cell Stem Cell 7:279-282.
Non-patent Document 23: McDonald T, et al. (1998) Identification and cloning of an orphan G protein-coupled receptor of the glycoprotein hormone receptor subfamily. Biochem Biophys Res Commun 247:266-270.
Non-patent Document 24: Hsu S Y, Liang S G, Hsueh A J (1998) Characterization of two LGR genes homologous to gonadotropin and thyrotropin receptors with extracellular leucine-rich repeats and a G protein-coupled, seven-transmembrane region. Mol Endcrinol 12:1830-1845.
Non-patent Document 25: Barker N, et al. (2007) Identification of stem cells in small intestine and colon by marker gene Lgr5. Nature 449:1003-1007.
Non-patent Document 26: Sato T, et al. (2009) Single Lgr5 stem cells build crypt-villus structures in vitro without a mesenchymal niche. Nature 459:262-265.
Non-patent Document 27: Barker N, et al. (2009) Crypt stem cells as the cells-of-origin of intestinal cancer. Nature 457:608-611.
Non-patent Document 28: Vermeulen L, et al. (2010) Wnt activity defines colon cancer stem cells and is regulated by the microenvironment. Nat Cell Biol 12:468-476.
Non-patent Document 29: Clevers H (2011) The cancer stem cell: premises, promises and challenges. Nat Med 17:313-319.
Non-patent Document 30: Barker N, et al. (2007) Identification of stem cells in small intestine and colon by marker gene Lgr5. Nature 449:1003-1007.
Non-patent Document 31: Park C Y, et al. (2009) Cancer stem cell-directed therapies:recent data from the laboratory and clinic. Mol Ther 17(2):219-230.

SUMMARY OF THE INVENTION

Problems to be Solved by the Invention

The present invention was achieved in view of the circumstances described above. An objective of the present invention is to provide substantially homogeneous cancer stem cell populations containing cancer stem cells, which cancer stem cells are separated using cell markers, and methods for producing the cancer stem cell populations. Another objective of the present invention is to provide methods for separating cancer stem cells with a high proliferative potential and cancer stem cells with a low proliferative potential, methods for inducing cancer stem cells into those with a different proliferative potential, and cancer stem cells separated/induced by these separation methods or induction methods. Still another objective of the present invention is to provide methods of screening for pharmaceutical agents, which use these cancer stem cells or cancer stem cell populations, and methods for detecting, identifying, or quantifying the cancer stem cells or cancer stem cell populations.

Means for Solving the Problems

To prove the stem cell theory which can explain the mechanism of oncogenesis, utmost efforts have been exerted to identify, isolate, and characterize cancer stem cells (CSCs). However, it was still difficult to prepare highly pure CSCs in an amount sufficient to characterize them. The present inventors conducted dedicated studies to achieve this objective.

To isolate colon CSCs from xenografts maintained in NOG mice, the present inventors established, for the first time, a method for preparing a large quantity of highly pure colon CSCs by an in vitro monolayer culture that does not use serum, but uses EGF and FGE Specifically, the present inventors discovered that a large quantity of highly pure colon CSCs can be prepared by culturing in vitro cells derived from moderately-differentiated human colon cancer xenografts maintained in NOD/Shi-scid, IL-2Rγnull (NOG) mice. Under this condition, colon CSCs alone can proliferate, survive, and expand, and highly pure and homogeneous colon CSCs were obtained thereby. Colon CSCs acquired by the present method were stably maintained and did not show phenotypic alterations for one month. The cells expressed all reported colon cancer stem cell markers and exhibited tumor-initiating activity, and formed tumors having the same histopathological features as the original primary tumors.

Vermeulen et al. demonstrated that colon CSCs acquired by spheroid culture expressed CD133, CD24, CD29, CD44, and CD166, and recognized the presence of cells that are stained by an Lgr5 antibody in a heterogeneous population (Vermeulen L, et al. (2008) Single-cell cloning of colon cancer stem cells reveals a multi-lineage differentiation capacity. Proc Natl Acad Sci USA 105:13427-13432).

In the present invention, it was found that Lgr5 is expressed in isolated, pure colon CSCs which proliferate rapidly under a monolayer culture. By using ultra low adherence plates, the present inventors were able to isolate slowly proliferating CSCs which did not express Lgr5. The most important discovery was the function of self interconversion. After changing the culture conditions of the CSCs or exposing them to an anti-cancer drug, actively proliferating Lgr5-positive colon CSCs converted into a quiescent Lgr5-negative state because of this ability. Alternatively, Lgr5-negative CSCs became actively proliferating Lgr5-positive CSCs. This interconversion of CSCs between the two types of states due to changes in the environment may help in explaining drug resistance and recurrence of cancer. The oncogenic process of melanoma seems to be different from the oncogenic process of colon cancer; however, similar reversible phenotypic conversions in terms of markers, cell proliferation, and drug resistance have also been reported (Quintana E, et al. (2008) Efficient tumor formation by single human melanoma cells. Nature 456:593-598.; Roesch A, et al. (2010) A temporarily distinct subpopulation of slow-cycling melanoma cells is required for continuous tumor growth. Cell 141:583-594; Sharma S V, et al. (2010) A chromatin-mediated reversible drug-tolerant state in cancer cell subpopulations. Cell 141:69-80). In these studies, a small subpopulation of slow-cycling cells which express the histone demethylase JARID1B is resistant to anti-cancer drugs, and after release of anti-cancer drugs, CSCs resume cell proliferation and re-acquire the drug-sensitive phenotype. Interestingly, slow-proliferating ARID1B-positive cells give rise to rapidly-proliferating progenies, and these in turn reconstitute a mixture containing populations that are positive and negative for JARID1B. Likewise, in the development of adenoma from Apc-deficient Lgr5-positive stem cells, the expression of Lgr5 was reduced in the majority of TA cells; however, expression was later detected in cells disseminated within the adenoma (Barker N, et al. (2009) Crypt stem cells as the cells-of-origin of intestinal cancer. Nature 457:608-611). Thus, reversible conversion between a rapidly-proliferating state and a slow-cycling state may be a typical property of CSCs.

Another important factor to understand Lgr5 expression is the point that Wnt signaling is mediated by TCF4, and dominant negative TCF4 reduced the expression of Lgr5 in a cell system (Barker N, et al. (2007) Identification of stem cells in small intestine and colon by marker gene Lgr5. Nature 449:1003-1007). Consistent with this report, results by the present inventors demonstrated that proliferation of Lgr5-positive colon CSCs is mediated by TCF since TCF inhibitors blocked proliferation of colon CSCs. Elsewhere, it has been demonstrated that exogenous HGF is essential for the maintenance and proliferation of colon CSCs in in vitro spheroid culture of primary colon tumor, and that niche cells secrete HGF in vivo (Vermeulen L, et al. (2010) Wnt activity defines colon cancer stem cells and is regulated by the microenvironment. Nat Cell Biol 12:468-476). Considering these previous findings, the present inventors examined the levels of EGF, FGF, and HGF required for proliferation of colon CSCs. Unexpectedly, proliferation and survival of colon CSCs did not require any exogenous factors or niche cells. As a result, the existence of an intrinsic mechanism or autocrine mechanism to modulate the Wnt signaling was shown; thus, this may give a new insight into the mechanism for Wnt signaling activation in colon CSCs.

In the field of CSCs, it is postulated that specific subpopulations of CSCs that can overcome environmental stress and have acquired an aggressive phenotype (for example, EMT) survive and cause metastatic tumors (Mani S A, et al. (2008) The epithelial-mesenchymal transition generates cells with properties of stem cells. Cell 133:704-715). The present inventors discovered that formation of highly-differentiated tumors by injection of Lgr5-positive colon CSCs is influenced by the metastatic sites. As described above, the $CD26^+$ CSC subpopulation has metastatic activity (Pang R, et al. (2010) A subpopulation of CD26+ cancer stem cells with metastatic capacity in human colorectal cancer. Cell Stem Cell 6:603-615). In the present invention, the present inventors analyzed the expression of CD26 in Lgr5-positive and Lgr5-negative colon CSCs and found that both colon CSCs were positive for CD26. Further studies are needed to understand the importance of CD26 as a marker for metastasis. Hermann et al. reported that $CD133^+/CXCR4^+$ pancreatic CSCs were detected in circulating blood, and CXCR4 was shown to be a marker for metastasis (Hermann P C, et al. (2007) Distinct populations of cancer stem cells determine tumor growth and metastatic activity in human pancreatic cancer. Cell Stem Cell 1: 313-323).

The presence of Lgr5-negative CSCs in oncogenesis may correlate with the basic properties of stem cells. A possible hypothesis is that CSCs can use an intrinsic means to convert themselves to a different cell population subset under environmental changes such as aggressive treatment with anti-cancer drugs. This may mean that CSCs have a self-defense ability based on an intrinsic mechanism to adapt to new environments (FIG. 36).

Specifically, the present invention provides the following:

[1] an isolated cancer stem cell, which is positive for cell marker Lgr5 and is adherent in serum-free culture;

[2] the cancer stem cell of [1] which is a mesenchymal cell;

[3] an isolated cancer stem cell, which is negative for cell marker Lgr5 and is non-adherent in serum-free culture;

[4] the cancer stem cell of [3] which is an epithelial cell;

[5] the cancer stem cell of any one of [1] to [4], which is derived from a gastrointestinal cancer;

[6] the cancer stem cell of [5], wherein the gastrointestinal cancer is a large intestine cancer;

[7] the cancer stem cell of any one of [1] to [6], which is positive for one or more of cell markers CD133, CD44, EpCAM, CD166, CD24, CD26, CD29, and EREG;

[8] the cancer stem cell of [7], which is positive for cell markers CD133, CD44, EpCAM, CD166, CD24, CD26, CD29, and EREG;

[9] the cancer stem cell of any one of [1], [2], and [5] to [8], which is positive for ALDH activity cell marker or positive for cell markers LCK, FGFBP1, ROR1, and/or PIGU;

[10] the cancer stem cell of any one of [3] to [8], which is negative for ALDH activity cell marker or positive for cell markers HLA-DMA, TMEM173, ZMAT3, TNFSF15, AMIGO2, PROM2, GPR87, BLNK, HLA-DMB, GPR172B, GNAI1, FAS, GM2A, FLRT3, STOM, GJB5, ABCA1, SLC6A14, BMPR2, CLDN1, and/or GPR110;

[11] the cancer stem cell of any one of [1], [2], and [5] to [9], which regenerates the hierarchical organization of cancer tissues;

[12] the cancer stem cell of any one of [3] to [8], and [10], which regenerates the hierarchical organization of cancer tissues;

[13] the cancer stem cell of any one of [1], [2], [5] to [9], and [11], which has the ability of epithelial-mesenchymal transition;

[14] the cancer stem cell of any one of [3] to [8], [10], and [12], which has the ability of epithelial-mesenchymal transition;

[15] a substantially homogeneous cancer stem cell population comprising the cancer stem cell of any one of [1], [2], [5] to [9], [11], and [13];

[16] a substantially homogeneous cancer stem cell population comprising the cancer stem cell of any one of [3] to [8], [10], [12], and [14];

[17] a method for producing the cancer stem cell of any one of [1], [2], [5] to [9], [11], and [13] or the substantially homogeneous cancer stem cell population of [15], which comprises the step of culturing a cancer stem cell or a cell population comprising a cancer stem cell in adherent culture;

[18] a method for producing the cancer stem cell of any one of [3] to [8], [10], [12], and [14], or the substantially homogeneous cancer stem cell population of [16], which comprises the step of culturing a cancer stem cell or a cell population comprising a cancer stem cell in suspension culture, or in the presence of a growth inhibitor;

[19] a method of screening for a pharmaceutical agent, which comprises the steps of:
(a) preparing a substantially homogeneous cancer stem cell population comprising the cancer stem cell of any one of [1], [2], [5] to [9], [11], and [13];
(b) treating the cancer stem cell population or a cancer stem cell in the cancer stem cell population with a test substance; and
(c) detecting a change in a biological property of a cancer stem cell population or cancer stem cell treated with the test substance;

[20] the screening method of [19], wherein the pharmaceutical agent is an anti-cancer agent or a metastasis or recurrence inhibitor;

[21] a method of screening for a pharmaceutical agent, which comprises the steps of:
(a) preparing a substantially homogeneous cancer stem cell population comprising the cancer stem cell of any one of [3] to [8], [10], [12], and [14];
(b) treating the cancer stem cell population or a cancer stem cell in the cancer stem cell population with a test substance; and
(c) detecting a change in a biological property of a cancer stem cell population or cancer stem cell treated with the test substance;

[22] the screening method of [21], wherein the pharmaceutical agent is an anti-cancer agent;

[23] a method of screening for a pharmaceutical agent, which comprises the steps of:
(a) preparing a substantially homogeneous cancer stem cell population comprising the cancer stem cell of any one of [1], [2], [5] to [9], [11], and [13];
(b) administering a non-human animal with a test substance and the cell population or a cancer stem cell comprised in the cancer stem cell population; and
(c) detecting tumor formation in the non-human animal;

[24] a method of screening for a pharmaceutical agent, which comprises the steps of:
(a) preparing a substantially homogeneous cancer stem cell population comprising the cancer stem cell of any one of [3] to [8], [10], [12], and [14];
(b) administering a non-human animal with a test substance and the cell population or a cancer stem cell comprised in the cancer stem cell population; and
(c) detecting tumor formation in the non-human animal;

[25] a method of screening for a pharmaceutical agent, which comprises the steps of:
(a) preparing a substantially homogeneous cancer stem cell population comprising the cancer stem cell of any one of [1], [2], [5] to [9], [11], and [13];
(b) administering a non-human animal with a growth inhibitor and the cell population or a cancer stem cell comprised in the cancer stem cell population;
(c) administering a test substance; and
(d) detecting tumor formation in the non-human animal;

[26] the screening method of any one of [23] to [35], wherein the step of administering the cell population is subcutaneous or intravenous administration;

[27] the screening method of any one of [23] to [26], wherein the pharmaceutical agent is an anti-cancer agent or a metastasis or recurrence inhibitor;

[28] a method for isolating or detecting the cancer stem cell of any one of [1], [2], [5] to [9], [11], and [13], or the substantially homogeneous cancer stem cell population of [15], which comprises the steps of:
(a) preparing a cell population comprising cancer stem cells;
(b) contacting an Lgr5 antibody with the cell population or a cell comprised in the cell population; and
(c) isolating or detecting an Lgr5-positive cell population or cell from the cell population or cell;

[29] a method for isolating or detecting the cancer stem cell of any one of [1], [2], [5] to [9], [11], and [13], or the substantially homogeneous cancer stem cell population of [15], which comprises the steps of:

(a) preparing a cell population comprising cancer stem cells;
(b) contacting the cell population or a cell comprised in the cell population with an E-cadherin antibody, a Snail antibody, an LCK antibody, an FGFBP1 antibody, an ROR1 antibody, a PIGU antibody, and/or a β-catenin antibody; and
(c) isolating or detecting, from the cell population or cell, a cell population or cell that is negative for cell-surface E-cadherin, positive for Snail, positive for LCK, positive for FGFBP1, positive for ROR1, positive for PIGU, and/or in which β-catenin is localized in the nucleus;

[30] a method for isolating or detecting the cancer stem cell of any one of [3] to [8], [10], [12], and [14], or the substantially homogeneous cancer stem cell population of [16], which comprises the steps of:
(a) preparing a cell population comprising cancer stem cells;
(b) contacting an Lgr5 antibody with the cell population or a cell comprised in the cell population; and
(c) isolating or detecting an Lgr5-negative cell population or cell from the cell population or cell;

[31] a method for isolating or detecting the cancer stem cell of any one of [3] to [8], [10], [12], and [14], or the substantially homogeneous cancer stem cell population of [16], which comprises the steps of:
(a) preparing a cell population comprising cancer stem cells;
(b) contacting the cell population or a cell comprised in the cell population with an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, an FAS antibody, a GM2A antibody, an FLRT3 antibody, an STOM antibody, a GJB5 antibody, an ABCA1 antibody, an SLC6A14 antibody, a BMPR2 antibody, a CLDN1 antibody, and/or a GPR110 antibody; and
(c) isolating or detecting, from the cell population or cell, a cell population or cell that is positive for cell-surface E-cadherin, negative for Snail, does not have β-catenin localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110;

[32] a kit or set for use in the method of any one of [28] to [31], which comprises an Lgr5 antibody;

[33] a method for detecting, identifying, or quantifying the cancer stem cell of any one of [1], [2], [5] to [9], [11], and [13], or the substantially homogeneous cancer stem cell population of [15], which comprises the steps of:
(a) preparing a cell population comprising cancer stem cells; and
(b) contacting an Lgr5 antibody with the cell population or a cell comprised in the cell population;

[34] a kit or set for use in the method of [33], which comprises an Lgr5 antibody;

[35] a method for separating or detecting a cancer stem cell with a high proliferative potential and a cancer stem cell with a low proliferative potential;

[36] the method of [35], wherein the separation is achieved by an adherent culture;

[37] the method of [35], wherein the separation or detection is achieved by culturing in the presence of a growth inhibitor;

[38] the method of [35], wherein the separation is achieved by a suspension culture;

[39] the method of any one of [35] to [38], wherein the separation is achieved by using the cell marker Lgr5;

[40] the method of [39], wherein the separation is achieved by additionally using the cell markers: HLA-DMA, TMEM173, ZMAT3, TNFSF15, AMIGO2, PROM2, GPR87, BLNK, HLA-DMB, GPR172B, GNAI1, FAS, GM2A, FLRT3, STOM, GJB5, ABCA1, SLC6A14, BMPR2, CLDN1, and/or GPR110;

[41] a method for inducing into a cancer stem cell with a different proliferative potential;

[42] the method of [41], wherein a cancer stem cell with a high proliferative potential is cultured in suspension culture to induce it into a cancer stem cell with a low proliferative potential;

[43] the method of [41] or [42], wherein the cancer stem cell with a high proliferative potential is cultured in a low adherence plate to induce it into a cancer stem cell with a low proliferative potential;

[44] the method of [41], wherein a cancer stem cell with a high proliferative potential is induced into a cancer stem cell with a low proliferative potential using a growth inhibitor;

[45] the method of [44], wherein a culture is carried out in the presence of the growth inhibitor;

[46] the method of [44], wherein the growth inhibitor is administered to a non-human animal bearing a cancer stem cell with a high proliferative potential;

[47] the method of [41], wherein a cancer stem cell with a low proliferative potential is cultured in adherent culture to induce it into a cancer stem cell with a high proliferative potential;

[48] the method of [41] or [47], wherein a cancer stem cell with a low proliferative potential is cultured in an adherent plate to induce it into a cancer stem cell with a high proliferative potential;

[49] the method of [41], wherein a cancer stem cell with a low proliferative potential is grafted onto a non-human animal to induce it into a cancer stem cell with a high proliferative potential;

[50] a cancer stem cell with a high proliferative potential isolated and/or induced by the method of any one of [35], [36], [39] to [41], and [47] to [49];

[51] a cancer stem cell with a low proliferative potential isolated and/or induced by the method of any one of [35] and [38] to [46];

[52] a method of screening for an anti-cancer agent, which uses a cancer stem cell isolated and/or induced by the method of any one of [35] and [38] to [46];

[53] a method for assessing a compound, which uses a cancer stem cell isolated and/or induced by the method of any one of [35], [36], [39] to [41], and [47] to [49];

[54] an agent for inhibiting the growth of a cancer stem cell of any one of [1], [2], [5] to [9], [11], and [13], which is a combination of a β-catenin inhibitor and a TCF inhibitor;

[55] the agent for inhibiting the growth of cancer stem cell of [54], which is an anti-cancer agent;

[56] an agent for suppressing metastasis or recurrence of the cancer stem cell of any one of [1], [2], [5] to [9], [11], and [13], which comprises 5-FU, oxaliplatin, or irinotecan as an active ingredient;

[57] a method for detecting, identifying, or quantifying the cancer stem cell of any one of [1] to [14], or the substantially homogeneous cancer stem cell population of [15] or [16], which comprises the steps of:

(a) preparing a sample obtained from a cancer patient; and
(b) contacting the sample with an Lgr5 antibody, a HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, an FAS antibody, a GM2A antibody, an FLRT3 antibody, an STOM antibody, a GJB5 antibody, an ABCA1 antibody, an SLC6A14 antibody, a BMPR2 antibody, a CLDN1 antibody, and/or a GPR110 antibody;

[58] the method of [57], wherein the detection, identification, or quantitation method is cancer diagnosis, selection of a cancer patient, prediction of drug effectiveness, treatment monitoring, or cancer imaging;

[59] a kit or set for use in the method of [57] or [58], which comprises an Lgr5 antibody;

[60] an agent for inhibiting cancer stem cell which comprises a modulator for the protein encoded by a gene comprising the nucleotide sequence of any one of:
(a) a polynucleotide comprising the nucleotide sequence of any one of SEQ ID NOs: 7 to 13;
(b) a polynucleotide which:
hybridizes under stringent conditions to a polynucleotide that comprises a nucleotide sequence complementary to a polynucleotide comprising the nucleotide sequence of any one of SEQ ID NOs: 7 to 13,
and which comprises a nucleotide sequence encoding a protein functionally equivalent to the protein encoded by a gene comprising the nucleotide sequence of any one of SEQ ID NOs: 7 to 13;
(c) a polynucleotide that comprises a nucleotide sequence encoding a protein which:
has an addition, deletion, or substitution of at least one amino acid residue in the protein encoded by a gene comprising the nucleotide sequence of any one of SEQ ID NOs: 7 to 13,
and which is functionally equivalent to the protein encoded by the gene that comprises the nucleotide sequence of any one of SEQ ID NOs: 7 to 13;

[61] the agent for inhibiting cancer stem cell of [60], wherein the modulator is an antibody that binds to the protein;

[62] the agent for inhibiting cancer stem cell of [61], wherein the antibody is a chimeric antibody, humanized antibody, human antibody, antibody fragment, or bispecific antibody;

[63] the agent for inhibiting cancer stem cell of [60], wherein the modulator comprises one or more substances selected from the group consisting of: an antisense oligonucleotide, a ribozyme, an aptamer, and an siRNA;

[64] the agent for inhibiting the cancer stem cell of any one of [60] to [63], which is used in combination with an anti-cancer agent; and

[65] a cancer stem cell vaccine that comprises:
a polynucleotide comprising the nucleotide sequence of any one of (a) to (c) below;
a protein encoded by a gene comprising the nucleotide sequence;
or a portion or modification product thereof
(a) a polynucleotide comprising the nucleotide sequence of any one of SEQ ID NOs: 7 to 13;
(b) a polynucleotide which
hybridizes under stringent conditions to a polynucleotide that comprises a nucleotide sequence complementary to a polynucleotide comprising the nucleotide sequence of any one of SEQ ID NOs: 7 to 13,
and which comprises a nucleotide sequence encoding a protein functionally equivalent to the protein encoded by a gene comprising the nucleotide sequence of any one of SEQ ID NOs: 7 to 13; and
(c) a polynucleotide that comprises a nucleotide sequence encoding a protein which:
has an addition, deletion, or substitution of at least one amino acid residue in the protein encoded by a gene comprising the nucleotide sequence of any one of SEQ ID NOs: 7 to 13,
and which is functionally equivalent to the protein encoded by the gene that comprises the nucleotide sequence of any one of SEQ ID NOs: 7 to 13.

BRIEF DESCRIPTION OF THE DRAWINGS

FIG. 31 After culturing for one month, adherent CSCs derived from xenografts PLR59 and PLR123 were analyzed by flow cytometry (FIG. 30), and injected to NOG mice. The indicated numbers of adherent CSCs were injected subcutaneously in the lateral abdomen of NOG mice to assess the tumor-forming activity in NOG mice. This figure is a diagram showing the result of assessment of tumorigenesis 47 hours after inoculation. Even subcutaneous injection of 10 adherent CSCs allowed tumor formation at all of the injection sites. The tumors were highly similar in histopathological morphology to the original tumors.

FIG. 34 is a diagram showing the tumor-forming activity of adherent CSCs in various organs. $5 \times 10^5$ adherent CSCs from PLR123 were injected to the caudal vein (n=5). The tumor formation frequency on day 40 after administration is shown for various organs.

FIGS. 39A, B, and C show stained images of the cells for 0, 48, and 72 hours, respectively. Scale bar represents 20 µm.

FIGS. 40A and 40C show images after a single division, while FIGS. 40B and 40D show images after second or third division.

FIG. 41-1 shows photographs depicting immunostained images of colon CSCs that varied to negative for Lgr5 after three days of exposure to irinotecan. The cells were stained with antibodies specific to HLA-DMA (A) and TMEM173 (B).

FIG. 41-2 shows photographs depicting immunostained images of colon CSCs that varied to negative for Lgr5 after three days of exposure to irinotecan. The cells were stained with antibodies specific to ZMAT3 (C) and GPR110 (D).

MODE FOR CARRYING OUT THE INVENTION

Figure 1:
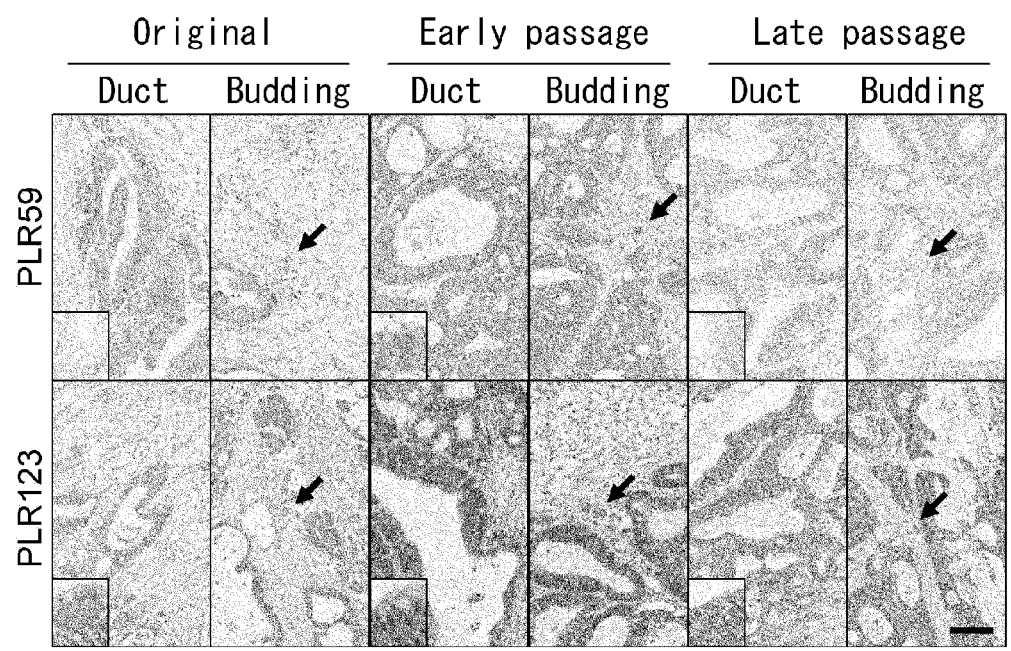
FIG. 1 shows photographs depicting histological images (HE stain) of colon tumor xenografts PLR59 and PLR123 derived from moderately-differentiated colon tumor. Even after 15 passages, cells derived from xenografts PLR59 and PLR123 formed tumors with a morphology very similar to the original tumor, and had budding clusters (arrow) and ductal structures with goblet cells (inset). "Original" indicates tumors obtained by surgical resection; "Early passage" indicates xenografts PLR59 and PLR123 after 4 passages; and "Late passage" indicates xenograft PLR59 after 15 passages and PLR123 after 19 passages. Scale bar represents 100 μm.

Herein, the term "and/or" includes all combinations resulting from appropriate combinations of "and" and "or". Specifically, for example, "E-cadherin antibody, Snail antibody, and/or GPR110 antibody" includes the following seven combinations of antibodies: (a) E-cadherin antibody, (b) Snail antibody, (c) GPR110 antibody, (d) E-cadherin antibody and Snail antibody, (e) E-cadherin antibody and GPR110 antibody, (f) Snail antibody and GPR110 antibody, (g) E-cadherin antibody, Snail antibody, and GPR110 antibody.

The present invention relates to cancer stem cells that are separated by using cell markers.

Herein, "cancer" refers to the physiological condition in mammals, which is typically characterized by unregulated cell growth, or such a physiological condition. Herein, cancer types are not particularly limited, and include those listed below. Carcinomas (epithelial cancers) include pancreatic cancer, prostatic cancer, breast cancer, skin cancer, cancers of the digestive tract, lung cancer, hepatocellular carcinoma, cervical cancer, uterine cancer, ovary cancer, fallopian tube cancer, vaginal cancer, liver cancer, bile duct cancer, bladder cancer, ureter cancer, thyroid cancer, adrenal cancer, kidney cancer, and cancers of other glandular tissues. Sarcomas (non-epithelial tumors) include liposarcoma, leiomyosarcoma, rhabdomyosarcoma, synovial sarcoma, angiosarcoma, fibrosarcoma, malignant peripheral nerve sheath tumor, gastrointestinal stromal tumor, desmoid tumor, Ewing's sarcoma, osteosarcoma, chondrosarcoma, leukemia, lymphoma, myeloma, tumors of other parenchymal organs, for example, melanoma and brain tumor (Kumar V, Abbas A K, Fausio N. Robbins and Cotran Pathologic Basis of Disease. 7th Ed. Unit I: General Pathology, 7: Neoplasia, Biology of tumor growth: Benign and malignant neoplasms. 269-342, 2005).

Herein, cancer stem cell refers to cells having the abilities described in (i) and/or (ii) below.
(i) The ability to self-renew. The self-renewal ability refers to the ability of either or both of the divided daughter cells to produce cells which maintain the same capacity and the degree of differentiation as the parental cell in terms of cell lineage.
(ii) The ability to differentiate into various types of cancer cells that constitute a cancer cell mass. Like normal stem cells, various types of cancer cells differentiated from cancer stem cells generate a hierarchical organization with cancer stem cells at the top in terms of cell lineage. Various types of cancer cells are generated in a sequential manner from cancer stem cells. This results in the formation of a cancer cell mass that exhibits a variety of features.

Cancer stem cell refers to a cancer cell that has the ability to form cancers as well as, like normal stem cell, pluripotency and self-renewal ability. Cancer stem cells generate a hierarchical organization with cancer stem cells at the top. Various types of cancer cells are generated in a sequential manner from cancer stem cells. This results in the formation of a cancer cell mass that exhibits a variety of features. Cancer cell mass refers to, not a group of individual cells, but a mass formed by the adhesion of cells etc., as in human tumor tissue, which is built with cancer cells, and other cells such as stromal cells and blood cells, extracellular matrix such as collagen and laminin, and so on.

The origin of cancer stem cells of the present invention is not particularly limited; it is possible to use those derived from mammals such as humans, monkeys, chimpanzees, dogs, bovines, pigs, rabbits, rats, and mice. However, cancer stem cells derived from human are preferred, and those derived from human tumor tissues are more preferred.

The cancer stem cells to be used include cells introduced with genes of oncogenic viruses such as SV40 or oncogenes such as Ras, and cell lines established from cancer tissues.

The preferred cancer stem cells to be used are those obtained from a group of cells which regenerate the hierarchical structure of cancer tissues. It is possible to use, for example, collected cancer tissues; however, preferably, established cancer cell lines generated by grafting cancer into non-human animals and passaging, more preferably established cancer cell lines generated by grafting cancer into immunodeficient animals and passaging, and still more preferably established NOG cancer cell lines generated by grafting cancer tissues into NOG mice which lack functional T cells, B cells, and natural killer cells and passaging are used.

Alternatively, spheroids (cell masses) formed by spheroid culture may be used as cancer stem cells. "Spheroid culture" means that cancer stem cells are inoculated in a culture vessel such as non-adherent or low-adherent cell culture flasks, plates, or dishes using a medium capable of culturing cancer stem cells, and then the cells are cultured under a three-dimensionally floating condition. A cell mass formed by this method is called "spheroid".

NOG-established cancer cell lines can be generated by a method known to those skilled in the art, for example, the method described in Fujii E. et al., Pathol int. 2008; 58: 559-567. Human large intestine cancer, stomach cancer, lung cancer, breast cancer, pancreatic cancer, or the like is resected surgically. After mechanically mincing it with scissors, the cancer is grafted subcutaneously in NOG mice and passaged to establish cell lines. Even after passages, NOG-established cancer cell lines maintain the properties of the original human cancer tissues.

The cancer stem cells of the present invention can be selected by using cell markers. Cell markers used in the present invention include, for example, leucine-rich repeat-containing G-protein-coupled receptor 5 (Lgr5), CD133, CD44, EpCAM, CD166, CD24, CD26, CD29, and EREG.

The present invention provides isolated cancer stem cells that are positive for the expression of the cell marker Lgr5 and are adherent under serum-free culture. Hereinafter, these cancer stem cells are sometimes referred to as "Lgr5-positive adherent cancer stem cells". In the present invention, "isolated" indicates cells and cell populations separated from at least some components of the natural environment and indicates, for example, substantially homogeneous cell populations such as those described below.

Furthermore, the present invention provides isolated cancer stem cells that are negative for expression of the cell marker Lgr5 and are non-adherent under serum-free culture. Hereinafter, these cancer stem cells are sometimes referred to as "Lgr5-negative non-adherent cancer stem cells".

Any culture media or liquids can be used to culture cancer stem cells of the present invention as long as they are serum-free media and capable of culturing cancer stem cells. There is no particular limitation on the culture media or liquids. For example, it is possible to use conventional basal media or mixtures thereof that are supplemented with EGF, bFGF, hLIF, HGF, NGF, NSF-1, TGF β, TNFα, heparin, BSA, insulin, transferrin, putrescine, selenite, progesterone, hydrocortisone, D-(+)-glucose, sodium bicarbonate, HEPES, L-glutamine, or N-acetylcysteine. The concentration of EGF is not particularly limited; however, it ranges from 0.1 to 100 ng/ml, preferably from 0.5 to 50 ng/ml, and more preferably from 1 to 20 ng/ml. The concentration of bFGF is not particularly limited; however, it ranges from 0.1 to 100 ng/ml, preferably from 0.5 to 50 ng/ml, and more preferably from 1 to 20 ng/ml. The concentration of hLIF is not particularly limited; however, it ranges from 0.1 to 100 ng/ml, preferably from 0.5 to 50 ng/ml, and more preferably from 1 to 20 ng/ml. The concentration of HGF is not particularly limited; however, it ranges from 0.1 to 100 ng/ml, preferably from 1 to 50 ng/ml. The concentration of NGF is not particularly limited; however, it ranges from 0.1 to 100 ng/ml, preferably from 1 to 50 ng/ml. The concentration of NSF-1 is not particularly limited; however, it ranges from 0.1 to 100 ng/ml, preferably from 1 to 50 ng/ml. The concentration of TGFβ is not particularly limited; however, it ranges from 0.1 to 100 ng/ml, preferably from 1 to 50 ng/ml. The concentration of TNFα is not particularly limited; however, it ranges from 0.1 to 100 ng/ml, preferably from 1 to 50 ng/ml. The concentration of heparin is not particularly limited; however, it ranges from 10 ng/ml to 10 μg/ml, preferably from 2 to 5 μg/ml. The concentration of BSA is not particularly limited; however, it ranges from 0.1 to 10 mg/ml, preferably from 1 to 8 mg/ml. The concentration of insulin is not particularly limited; however, it ranges from 1 to 100 μg/ml, preferably from 10 to 50 μg/ml. The concentration of transferrin is not particularly limited; however, it ranges from 10 to 500 μg/ml, preferably from 50 to 200 μg/ml. The concentration of putrescine is not particularly limited; however, it ranges from 1 to 50 μg/ml, preferably from 10 to 20 μg/ml. The concentration of selenite is not particularly limited; however, it ranges from 1 to 50 nM, preferably from 20 to 40 nM. The concentration of progesterone is not particularly limited; however, it ranges from 1 to 50 nM, preferably from 10 to 30 nM. The concentration of hydrocortisone is not particularly limited; however, it ranges from 10 ng/ml to 10 μg/ml, preferably from 100 ng/ml to 1 μg/ml. The concentration of D-(+)-glucose is not particularly limited; however, it ranges from 1 to 20 mg/ml, preferably from 5 to 10 mg/ml. The concentration of sodium bicarbonate is not particularly limited; however, it ranges from 0.1 to 5 mg/ml, preferably from 0.5 to 2 mg/ml. The concentration of HEPES is not particularly limited; however, it ranges from 0.1 to 50 mM, preferably from 1 to 20 mM. The concentration of L-glutamine is not particularly limited; however, it ranges from 0.1 to 10 mM, preferably from 1 to 5 mM. The concentration of N-acetylcysteine is not particularly limited; however, it ranges from 1 to 200 μg/ml, preferably from 10 to 100 μg/ml. Known basal culture liquids, which are not particularly limited as long as they are suitable for culturing cancer cells from which cancer stem cells are derived, include, for example, DMEM/F12, DMEM, F10, F12, IMDM, EMEM, RPMI-1640, MEM, BME, Mocoy's 5A, and MCDB131. Of them, DMEM/F12 is preferred.

The most preferred stem cell media include DMEM/F12 medium supplemented with 20 ng/ml human EGF, 10 ng/ml human bFGF, 4 µg/ml heparin, 4 mg/ml BSA, 25 µg/ml human insulin, and 2.9 mg/ml glucose where each concentration a final concentration.

Lgr5-positive adherent cancer stem cells obtained by the present invention exhibit characteristics of mesenchymal cells. On the other hand, Lgr5-negative non-adherent cancer stem cells obtained by the present invention have characteristics of epithelial cells. In the present invention, an epithelial cell refers to a cell that constitutes an epithelial tissue in vivo.

In the present invention, the origin of cancer stem cells is not particularly limited; however, the cells are preferably derived from gastrointestinal cancers. Gastrointestinal cancers include, for example, esophageal cancer, stomach cancer, duodenal cancer, pancreatic cancer, bile duct cancer, gallbladder cancer, biliary tract cancer, large intestine cancer, colon cancer, rectal cancer, preferably large intestine cancer, and more preferably colon cancer.

Furthermore, the cancer stem cells of the present invention are preferably positive for one or more of the cell markers CD133, CD44, EpCAM, CD166, CD24, CD26, CD29, and EREG, more preferably positive for CD133, CD44, EpCAM, CD166, CD24, CD26, CD29, and EREG.

In addition, in the present invention, acetaldehyde dehydrogenase (ALDH) activity can be used as a cell marker. In the present invention, Lgr5-positive adherent cancer stem cells are positive for the ALDH activity cell marker, whereas Lgr5-negative cancer stem cells are negative for ALDH activity.

In the present invention, one or more of LCK, ROR1, PIGU, and STX8 can be used as a cell marker. An Lgr5-positive adherent cancer stem cell is positive for any of the cell markers of LCK, ROR1, PIGU, and STX8, while an Lgr5-negative cancer stem cell is negative for any of the cell markers of LCK, ROR1, PIGU, and STX8.

Alternatively, in the present invention, one or more of HLA-DMA, TMEM173, ZMAT3, TNFSF15, AMIGO2, PROM2, GPR87, BLNK, HLA-DMB, GPR172B, GNAI1, FAS, GM2A, FLRT3, STOM, GJB5, ABCA1, SLC6A14, BMPR2, CLDN1, and GPR110 can be used as a cell marker. An Lgr5-positive adherent cancer stem cell is negative for any of the cell markers of HLA-DMA, TMEM173, ZMAT3, TNFSF15, AMIGO2, PROM2, GPR87, BLNK, HLA-DMB, GPR172B, GNAI1, FAS, GM2A, FLRT3, STOM, GJB5, ABCA1, SLC6A14, BMPR2, CLDN1, and GPR110. Meanwhile, an Lgr5-negative cancer stem cell is positive for any of the cell markers of HLA-DMA, TMEM173, ZMAT3, TNFSF15, AMIGO2, PROM2, GPR87, BLNK, HLA-DMB, GPR172B, GNAI1, FAS, GM2A, FLRT3, STOM, GJB5, ABCA1, SLC6A14, BMPR2, CLDN1, and GPR110.

In the present invention, preferred cancer stem cells are those which regenerate the hierarchical structure of cancer tissues.

Herein, "hierarchical structure" means that some of unique and characteristic structures observed in a normal tissue are detected histopathologically in the structure of a tumor originated from the tissue. In general, highly-differentiated cancers highly reconstitute the hierarchical structure. For example, lumen formation and mucous cells are observed in the case of tumors of glandular lumen-forming organs (stomach cancer, large intestine cancer, pancreatic cancer, liver cancer, bile duct cancer, breast cancer, lung adenocarcinoma, prostatic cancer, etc.). In the case of tumors that form squamous epithelial structures (squamous cell carcinoma of lung, skin, vaginal mucosa, etc.), layer structure formation, the tendency to keratosis, and such are observed in the epithelium. On the other hand, poorly-differentiated cancers insufficiently reconstitute the hierarchical structure, and they are said to be highly atypical (Kumar V, Abbas AK, Fausio N. Robbins and Cotran Pathologic Basis of Disease. 7th Ed. Unit I: General Pathology, 7: Neoplasia, Biology of tumor growth: Benign and malignant neoplasms. 272-281, 2005). Since the hierarchical structure is considered to be reconstituted as a result of various biological reactions, cancer stem cells that reconstitute it are thought to be highly useful.

"Reconstitution of the hierarchical structure" means that the unique and characteristic structure possessed by the original cancer stem cells is also observed even after isolation or induction of cancer stem cells.

Furthermore, cancer stem cells of the present invention preferably have the ability of epithelial-mesenchymal transition (EMT). Herein, the ability of epithelial-mesenchymal transition means both that epithelial cells transition into mesenchymal cells by obtaining their characteristics, and that mesenchymal cells transition into epithelial cells by obtaining their characteristics. EMT does not occur in normal cells except during the process of embryogenesis. Epithelial cells, which are bound together tightly and exhibit polarity, change into mesenchymal cells that are bound together more loosely, exhibit a loss of polarity, and have the ability to move. These mesenchymal cells can spread into tissues around the primary tumor, and also separate from the tumor, invade blood and lymph vessels, and move to new locations where they divide and form additional tumors. Drug resistance, metastasis, or recurrence of cancer can be explained by such additional tumor formation.

Furthermore, the present invention provides substantially homogeneous cancer stem cell populations comprising the above cancer stem cells of the present invention. "Substantially homogeneous" means that, when immunodeficient animals are grafted with 1000 cells, 100 cells, or 10 cells and analyzed for the frequency of formation of cancer cell populations using Extreme Limiting Dilution Analysis (Hu Y & Smyth G K., J Immunol Methods. 2009 Aug. 15; 347(1-2): 70-8) utilizing, for example, the method described in Hu Y & Smyth G K., J Immunol Methods. 2009 Aug. 15; 347 (1-2):70-8 or Ishizawa K & Rasheed Z A. et al., Cell Stem Cell. 2010 Sep. 3; 7(3):279-82, the frequency of cancer stem cells is 1/20 or more, preferably 1/10 or more, more preferably 1/5 or more, even more preferably 1/3 or more, still more preferably 1/2 or more, and yet more preferably 1/1.

A cancer stem cell population of the present invention can be prepared, for example, by culturing a cell(s) containing a cancer stem cell of the present invention or a group of cells containing a cancer stem cell of the present invention.

The present invention also provides methods for producing the above-described cancer stem cells of the present invention or the above-described substantially homogeneous cancer stem cell populations of the present invention. Herein, production of a cell population means, for example, expanding cells that constitute a cell population by culturing or purifying/separating a cell population from a large number of cells; however, the production is not limited thereto. The above-described cancer stem cells or substantially homogeneous cancer stem cell populations of the present invention can be obtained by culturing a cancer stem cell(s) or a group of cells containing a cancer stem cell(s) in adherent or floating culture.

Herein, "adherent culture" means that, after seeding cells into culture vessels for adherent culture, the adhered cells are cultured and passaged while non-adherent cells are removed. The cells grown to confluency are detached with Accutase and passaged into fresh adherent culture flasks, adherent culture plates, or adherent culture dishes for further culture. Culture vessels for adherent culture are not particularly limited as long as they are used for adherent culture. It is possible to appropriately select and use flasks for adherent culture or highly adherent flasks, plates for adherent culture or highly adherent plates, flat-bottomed plates for adherent culture or highly adherent flat-bottomed plates, dishes for adherent culture or highly adherent dishes, etc.

Media used for adherent culture are not particularly limited; however, it is preferable to use serum-free stem cell culture media.

Herein, "adherent" refers to the property of adhering to culture vessels for adherent culture when cultured in the vessels.

Herein, "suspension culture" means that, after seeding cells into culture vessels for floating culture, the suspension cells are cultured and passaged while adherent cells are removed. The cells grown to confluency are passaged into fresh low adherent cell culture flasks, ultra low adherent cell culture flasks, low adherent plates, ultra low adherent plates, low adherent dishes, or ultra low adherent dishes for further culture. Culture vessels for suspension culture are not particularly limited as long as they are used for suspension culture. It is possible to appropriately select and use low adherent cell culture flasks, ultra low adherent cell culture flasks, low adherent plates, ultra low adherent plates, low adherent dishes, ultra low adherent dishes, etc.

Media used for suspension culture are not particularly limited; however, it is preferable to use serum-free stem cell culture media. A cell group containing cancer stem cells are preferably expanded before performing adherent or suspension culture.

Herein, "non-adherent" refers to the property of being culturable in a floating state without adherence to culture vessels for suspension culture when cultured in the vessels.

"Expansion of a cell group" means, for example, proliferation by spheroid culture or grafting and passaging in non-human animals, but is not particularly limited thereto.

As non-human animals, immunodeficient animals can be used for the grafting of the present invention since they are unlikely to have rejection reactions. Immunodeficient animals preferably used include non-human animals that lack functional T cells, for example, nude mice and nude rats, and non-human animals that lack both functional T and B cells, for example, SCID mice and NOD-SCID mice. It is more preferably to use mice that lack T, B, and NK cells and have excellent transplantability, including, for example, NOG mice.

Regarding the weekly age of non-human animals, for example, 4 to 100-week-old athymic nude mice, SCID mice, NOD-SCID mice, or NOG mice are preferably used.

NOG mice can be prepared, for example, by the method described in WO 2002/043477, and are available from the Central Institute for Experimental Animals or the Jackson Laboratory (NSG mice).

Cells to be grafted may be any cells, including cell masses, tissue fragments, individually dispersed cells, cells cultured after isolation, and cells isolated from a different animal into which the cells have been grafted; however, dispersed cells are preferred. The number of grafted cells may be $10^6$ or less; however, it is acceptable to graft more cells.

With respect to the grafting site, subcutaneous grafting is preferred because the graft technique is simple. The grafting site is not particularly limited, and it is preferable to select an appropriate grafting site depending on the animal used. There is no particular limitation on the grafting operation of NOG-established cancer cell lines, and the cells can be grafted by conventional grafting operations.

Cancer stem cells or a cancer stem cell population of the present invention can be prepared, for example, by collecting cancer tissues from patients and culturing the tissues in a serum-free stem cell culture medium under an adherent or floating culture condition. Alternatively, cancer tissues collected from patients can be spheroid-cultured, and then cultured in a serum-free stem cell culture medium under an adherent or floating culture condition to prepare cancer stem cells or a cancer stem cell population Alternatively, cancer tissues collected from patients can be grafted and passaged in non-human animals, and then cultured in a serum-free stem cell culture medium under an adherent or floating culture condition to prepare cancer stem cells or a cancer stem cell population. Alternatively, it is possible to use a method in which cancer tissues collected from patients are grafted and passaged in NOG mice to prepare NOG-established cancer cell lines, and they are cultured in a serum-free stem cell culture medium under an adherent or suspension culture condition.

Cancer stem cells and cancer stem cell populations of the present invention can be used in methods of screening for pharmaceutical agents, anti-cancer agents, or the like.

In an embodiment of methods of screening for pharmaceutical agents, the present invention provides methods comprising the steps of:
(a) preparing a substantially homogeneous cancer stem cell population comprising an Lgr5-positive adherent cancer stem cell;
(b) treating the cancer stem cell population or a cancer stem cell comprised in the cancer stem cell population with a test substance; and
(c) detecting a change in a biological property of the cancer stem cell population or cancer stem cell treated with the test substance.

In these methods, first, a substantially homogeneous cancer stem cell population containing Lgr5-positive adherent cancer stem cells is prepared. Then, the prepared cancer stem cell population or cancer stem cells contained in the cancer stem cell population is treated with a test substance. In these methods, there is no particular limitation on the method for treating a cancer stem cell population or cancer stem cells contained in the cancer stem cell population with a test substance. For example, cultured cells of a cancer stem cell population or cancer stem cells contained in the cancer stem cell population can be treated with the test substance. This treatment can be carried out by adding a test substance to a cell culture medium or cell extract. When a test substance is a protein, this treatment can be performed, for example, as follows: a vector comprising a DNA encoding the protein is introduced into a cancer stem cell population or cancer stem cells contained in the cancer stem cell population; or the vector is added to a cell extract of a cancer stem cell population or cancer stem cells contained in the cancer stem cell population. Alternatively, it is possible, for example, to use the two-hybrid method utilizing yeast, animal cells, or the like.

In these methods, then, a change in a biological property of the cancer stem cell population or cancer stem cells treated with the test substance is detected. Such a change in a biological property includes, for example, a change in a tissue structure characteristic of the process of cancer progression of the cancer stem cell population or cancer stem cells, and a change in the expression of a DNA, RNA, protein, or metabolite in the cancer stem cell population or cancer stem cells. A change in a biological property can be detected, for example, by the methods described below.

Observations to detect characteristic structures of tissues or cell lines during cancer progression can be achieved by performing HE staining and immunohistochemistry (IHC) following preparation of thin tissue specimens by the AMeX method or the like.

There is no particular limitation on the assessment of the expression of DNAs, RNAs, proteins, peptides, and metabolites; the expression can be assessed by conventional expression assessment methods. RNAs include microRNAs, siRNAs, tRNAs, snRNAs, mRNAs, and non-coding RNAs. For example, mRNAs of a gene are extracted according to a conventional method. Using the mRNAs as a template, the transcriptional level of the gene can be determined using the Northern hybridization or RT-PCR method. DNA array techniques can also be used to determine the expression level of the gene. Alternatively, fractions containing a protein encoded by a gene are collected according to a conventional method. The translational level of the gene can be determined by detecting the protein expression by an electrophoresis method such as SDS-PAGE. The translational level of a gene can also be determined by performing the Western blotting method using an antibody against a protein and detecting the protein expression. These methods can be used to screen for pharmaceutical agents.

For example, when there is no change in a biological property of a cancer stem cell population or cancer stem cells, or the degree of the change is reduced after treatment with a test substance compared to before the treatment, the test substance is expected to be useful as a pharmaceutical agent that has the activity of suppressing cancer progression, metastasis, or recurrence (for example, an anti-cancer agent or an agent for suppressing metastasis or recurrence). Such test substances can be selected as effective substances that have the therapeutic or preventive effect against cancerous diseases. Such pharmaceutical agents having the activity of suppressing cancer progression are used as an anti-cancer agent or an agent for suppressing metastasis or recurrence.

In the present invention, the above pharmaceutical agents are not particularly limited to anti-cancer agents or agents for suppressing metastasis or recurrence, and they can also be used as an agent for inhibiting angiogenesis or cell growth. The pharmaceutical agents are not particularly limited, and they include proteinaceous agents, nucleic acid agents, low-molecular-weight agents, and cellular agents.

In another embodiment of the screening methods, the present invention provides methods of screening for pharmaceutical agents, which comprise the steps of:
(a) preparing a substantially homogeneous cancer stem cell population comprising an Lgr5-negative non-adherent cancer stem cell;
(b) treating the cancer stem cell population or a cancer stem cell comprised in the cancer stem cell population with a test substance; and
(c) detecting a change in a biological property of the cancer stem cell population or cancer stem cell treated with the test substance.

In these methods, first, a substantially homogeneous cancer stem cell population containing Lgr5-negative non-adherent cancer stem cells is prepared. Then, the prepared cancer stem cell population or cancer stem cells contained in the cancer stem cell population are treated with a test substance. Next, a change in a biological property of the cancer stem cell population or cancer stem cells treated with the test substance is detected.

Pharmaceutical agents that are obtained by the screening methods are not particularly limited, and they can be used as anti-cancer agents.

Still another embodiment of the screening methods of the present invention includes methods that use non-human animals administered with a test substance, and a cancer stem cell population of the present invention or cancer stem cells contained in the cancer stem cell population. Specifically, the present invention provides methods of screening for pharmaceutical agents, which comprise the steps of:
(a) preparing a substantially homogeneous cancer stem cell population comprising an Lgr5-positive adherent cancer stem cell;
(b) administering a non-human animal with a test substance and the cell population or a cancer stem cell comprised in the cancer stem cell population; and
(c) detecting tumor formation in the non-human animal.

In these methods, first, a substantially homogeneous cancer stem cell population containing Lgr5-positive adherent cancer stem cells is prepared. Then, non-human animals are administered with a test substance, and the cancer stem cell population prepared or cancer stem cells contained in the cancer stem cell population.

Another non-limiting embodiment of the methods of the present invention includes a method of screening for pharmaceutical agents, which comprises the steps of:
(a) preparing a substantially homogeneous cancer stem cell population containing an Lgr5-negative non-adherent cancer stem cell;
(b) administering the cell population or the cancer stem cell contained in the cancer stem cell population and a test substance to a non-human animal; and
(c) detecting formation of tumor in the non-human animal.

In the present method, a substantially homogeneous cancer stem cell population containing an Lgr5-negative non-adherent cancer stem cell(s) is first prepared. Then, a non-human animal is administered with the prepared cancer stem cell population or the cancer stem cell(s) contained in the cancer stem cell population and a test substance.

Another non-limiting embodiment of the present methods include a method of screening for pharmaceutical agents, which comprises the steps of:
(a) preparing a substantially homogeneous cancer stem cell population containing an Lgr5-positive adherent cancer stem cell(s);
(b) administering the cell population or the cancer stem cell(s) contained in the cancer stem cell population and a growth inhibitor to a non-human animal;
(c) administering a test substance; and
(d) detecting formation of tumor in the non-human animal.

In the present method, a substantially homogeneous cancer stem cell population containing an Lgr5-positive adherent cancer stem cell(s) is first prepared. Then, a non-human animal is administered with the prepared cancer stem cell population or the cancer stem cell(s) contained in the cancer stem cell population and a growth inhibitor. Next, a test substance is administered.

In these methods, the method for administering a test substance to non-human animals is not particularly limited.

Oral administration, or parenteral administration such as subcutaneous, intravenous, local, transdermal, or transintestinal (transrectal) administration can be appropriately selected depending on the type of a test substance to be administered.

Furthermore, in these methods, there is no particular limitation on the method for administering a cancer stem cell population or cancer stem cells to non-human animals, and an appropriate method can be selected depending on the cell population to be administered. The preferred method is subcutaneous or intravenous administration.

In these methods, then, tumor formation is detected in the non-human animals.

The assessment of a test substance can be performed as follows: tissues administered with a test substance and a cancer stem cell population or cancer stem cells are excised from non-human animals, and then histological features of the tissues are observed to determine the presence or absence of tumor formation. When tumor formation is not detected, the test substance is expected to be useful as a pharmaceutical agent having the activity of suppressing cancer progression, metastasis, or recurrence (for example, an anti-cancer agent or an agent for suppressing metastasis or recurrence), and the test substance can be selected as an effective substance that has the therapeutic or preventive effect against cancerous diseases. That is, pharmaceutical agents obtained by the screening methods are not particularly limited, and can be used as an anti-cancer agent, or an agent for suppressing metastasis or recurrence.

"Test substances" used in the methods of the present invention are not particularly limited, and include, for example, single compounds such as natural compounds, organic compounds, inorganic compounds, proteins, antibodies, peptides, and amino acids, as well as compound libraries, expression products of gene libraries, cell extracts, cell culture supernatants, products of fermenting microorganisms, extracts of marine organisms, plant extracts, prokaryotic cell extracts, unicellular eukaryote extracts, and animal cell extracts. These may be purified products or crude purified products such as extracts of plants, animals, and microorganisms. Also, methods for producing test substances are not particularly limited; test substances may be isolated from natural materials, synthesized chemically or biochemically, or prepared by genetic engineering.

If needed, the above test substances can be appropriately labeled and used. Labels include, for example, radiolabels and fluorescent labels. Mixtures of an above-mentioned test substance and multiple kinds of such labels are included in the test substances of the present invention.

Furthermore, pharmaceutical agents selected by the screening methods of the present invention may be further screened as necessary for more effective and practical preventive or therapeutic active substances by conducting additional drug effectiveness tests and safety tests, and further conducting clinical tests in human cancer patients. Based on results of structural analysis of pharmaceutical agents thus selected, they can be industrially manufactured by chemical synthesis, biochemical synthesis (fermentation), or genetic engineering.

Furthermore, the present invention provides methods for separating or detecting cancer stem cells or substantially homogeneous cancer stem cell populations. An embodiment of the methods includes a method for separating or detecting Lgr5-positive adherent cancer stem cells or substantially homogeneous cancer stem cell populations, which comprises the steps of:

(a) preparing a cell population containing cancer stem cells;
(b) contacting an Lgr5 antibody with the cell population or cells contained in the cell population; and
(c) separating or detecting an Lgr5-positive cell population or cells from the cell population or cells.

In the present method, a cell population containing a cancer stem cell(s) is first prepared. Then, an Lgr5 antibody is contacted with the cell population or cell(s) contained in the cell population. Cancer stem cells or a substantially homogeneous cancer stem cell population that are positive for the cell marker Lgr5 can be separated or detected by selecting a cell population or cells that are positive for the cell marker Lgr5. This separation or detection can be carried out, for example, using a fluorescently labeled Lgr5 antibody and collecting cells to which the Lgr5 antibody binds using a cell sorter.

Another embodiment of the isolation or detection methods of the present invention includes a method for separating or detecting Lgr5-positive adherent cancer stem cells or substantially homogeneous cancer stem cell populations, which comprises the steps of:

(a) preparing a substantially homogeneous cancer stem cell population by culturing a cell population containing cancer stem cells in an adherent culture;
(b) contacting an anti-Lgr5 antibody with the cancer stem cell population or a cancer stem cell(s) contained in the cancer stem cell population; and
(c) separating or detecting an Lgr5-positive substantially homogeneous cancer stem cell population or a cancer stem cell(s) from the cancer stem cell population or the cancer stem cell(s).

In the present method, first, a cell population containing cancer stem cells is cultured in an adherent culture to prepare a substantially homogeneous cancer stem cell population. Then, an Lgr5 antibody is contacted with the cancer stem cell population or a cancer stem cell(s) contained in the cancer stem cell population. A substantially homogeneous Lgr5-positive cancer stem cell population or cancer stem cells can be separated or detected by selecting a substantially homogeneous cancer stem cell population or cancer stem cells that are positive for Lgr5.

Still another embodiment of the separation or detection methods of the present invention includes a method for separating or detecting Lgr5-positive cancer stem cells or substantially homogeneous cancer stem cell populations, which comprises the steps of:

(a) preparing a cell population containing cancer stem cells;
(b) contacting the cell population or a cell(s) from the cell population with an E-cadherin antibody, a SNAIL antibody, an LCK antibody, an ROR1 antibody, a PIGU antibody, and/or a β-catenin antibody; and
(c) separating or detecting, from the cell population or cell(s), a cell population or cell(s) that is negative for cell-surface E-cadherin and positive for Snail, and in which β-catenin is localized in the nucleus.

Herein, "and/or" indicates each of the subjects shown before and after "and/or", and any combinations thereof. For example, "A, B, and/or C" includes not only each of the subjects "A", "B", and "C", but also any combination selected from: "A and B", "A and C", "B and C", and "A and B and C".

In the present method, a cell population containing cancer stem cells is first prepared. Then, the cell population or a cell(s) contained in the cell population is contacted with an E-cadherin antibody, a Snail antibody, an LCK antibody, an ROR1 antibody, a PIGU antibody, and a β-catenin antibody. For example, a cell population or cell(s) that is negative for cell-surface E-cadherin, positive for Snail, positive for LCK, positive for ROR1, positive for PIGU, and/or in which β-catenin localizes in the nucleus can be selected by immunofluorescent staining or Western blot analysis using an E-cadherin antibody, a Snail antibody, and a β-catenin antibody to separate or detect Lgr5-positive cancer stem cells or substantially homogeneous cancer stem cell populations. Cancer stem cells or a substantially homogeneous cancer stem cell population separated or detected this way also has the ability of epithelial-mesenchymal transition (EMT).

Another embodiment of the separation or detection methods of the present invention includes a method for separating or detecting Lgr5-positive adherent cancer stem cells or substantially homogeneous cancer stem cell populations, which comprises the steps of:
(a) preparing a substantially homogeneous cancer stem cell population by culturing a cell population containing a cancer stem cell(s) in adherent culture;
(b) contacting the cancer stem cell population or a cancer stem cell(s) contained in the cancer stem cell population with an E-cadherin antibody, a Snail antibody, an LCK antibody, an ROR1 antibody, a PIGU antibody, and/or a β-catenin antibody; and
(c) separating or detecting, from the cancer stem cell population or cancer stem cell(s), a cancer stem cell population or cancer stem cell that is negative for cell-surface E-cadherin, positive for Snail, positive for LCK, positive for ROR1, positive for PIGU, and/or in which β-catenin localized to the nucleus.

In the present method, first, a cell population containing a cancer stem cell(s) is cultured in adherent culture to prepare a substantially homogeneous cancer stem cell population. Then, the cancer stem cell population or a cancer stem cell(s) contained in the cancer stem cell population is contacted with an E-cadherin antibody, a Snail antibody, an LCK antibody, an ROR1 antibody, a PIGU antibody, and a β-catenin antibody. Lgr5-positive adherent cancer stem cells or substantially homogeneous cancer stem cell populations can be separated or detected by selecting a cancer stem cell population or a cancer stem cell(s) that is negative for cell-surface E-cadherin, positive for Snail, positive for LCK, positive for ROR1, positive for PIGU, and/or in which β-catenin localized to the nucleus.

Another embodiment of the separation or detection methods of the present invention includes a method for separating or detecting Lgr5-negative non-adherent cancer stem cells or substantially homogeneous cancer stem cell populations, which comprises the steps of:
(a) preparing a cell population containing a cancer stem cell(s);
(b) contacting an Lgr5 antibody with the cell population or a cell(s) contained in the cell population; and
(c) separating or detecting an Lgr5-negative cell population or cell(s) from the cell population or cell(s).

In the present method, a cell population containing a cancer stem cell(s) is first prepared. Then, an Lgr5 antibody is contacted with the cell population or cell(s) contained in the cell population. Lgr5-negative cancer stem cells or substantially homogeneous cancer stem cell populations can be separated or detected by selecting a cell population or cell(s) that is negative for the cell marker Lgr5. This separation or detection can be carried out, for example, using a fluorescently labeled Lgr5 antibody by collecting cells to which the Lgr5 antibody did not bind or by removing cells to which the Lgr5 antibody bound using a cell sorter.

Known cell sorters include, for example the following:
BD InFlux™
BD FACSAria™ III
BD FACSAria™ II
FACSAria™
FACSVantage™ SE (all are names of BD Biosciences products)
EPICS ALTRA HyPerSort
MoFlo AstriosCytomics FC 500
MoFlo XDP (all are names of Beckman Coulter products)

Appropriate antibodies to detect the cell markers used in the present invention include, in addition to commercially available antibodies, antisera prepared by immunizing vertebrate animals with a portion of or a whole cell marker of the present invention, polyclonal antibodies prepared by purifying above-described antisera using Protein A or such, and monoclonal antibodies generated by known hybridoma methods. A non-limiting embodiment of such commercially available antibodies that can be used with a cell sorter includes, for example:
LCK antibody: clone Y123 (EMD Millipore), clone Lck-01 (Lifespan Biosciences);
ROR1 antibody: clone RB14753 (Aviva Systems Biology); and
PIGU antibody: rabbit pAb (Lifescience Biosciences, LS-C146514).

Another embodiment of the separation or detection methods of the present invention includes a method for separating or detecting Lgr5-negative non-adherent cancer stem cells or substantially homogeneous cancer stem cell populations, which comprises the steps of:
(a) preparing a substantially homogeneous cancer stem cell population by culturing a cell population containing a cancer stem cell(s) in a suspension culture;
(b) contacting an anti-Lgr5 antibody with the cancer stem cell population or a cancer stem cell(s) contained in the cancer stem cell population; and
(c) separating or detecting an Lgr5-negative substantially homogeneous cancer stem cell population or a cancer stem cell(s) from the cancer stem cell population or cancer stem cell(s).

In the present method, first, a cell population containing cancer stem cell(s) is cultured in suspension to prepare a substantially homogeneous cancer stem cell population. Then, an Lgr5 antibody is contacted with the cancer stem cell population or a cancer stem cell(s) contained in the cancer stem cell population. Lgr5-negative cancer stem cells or substantially homogeneous cancer stem cell populations can be separated or detected by selecting a cell population or cell(s) that is negative for Lgr5. This separation or detection can be carried out, for example, using a fluorescently labeled Lgr5 antibody by collecting cells to which the Lgr5 antibody did not bind or by removing cells to which the Lgr5 antibody bound using a cell sorter.

Another embodiment of the separation or detection methods of the present invention includes a method for separating or detecting Lgr5-negative non-adherent cancer stem cells or substantially homogeneous cancer stem cell populations, which comprises the steps of:
(a) preparing a cell population containing cancer stem cells;
(b) contacting the cell population or a cell(s) contained in the cell population with an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody; and (c) isolating or detecting, from the cell population or cell(s), a cell population or cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

In the present method, a cell population containing a cancer stem cell(s) is first prepared. Then, Lgr5-negative non-adherent cancer stem cells or substantially homogeneous cancer stem cell population can be separated or detected using the cell population or a cell(s) from the cell population and an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody by selecting a cell population or cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

Another embodiment of the separation or detection methods of the present invention includes a method for separating or detecting Lgr5-negative non-adherent cancer stem cells or substantially homogeneous cancer stem cell populations, which comprises the steps of:

(a) preparing a substantially homogeneous cancer stem cell population by culturing a cell population containing a cancer stem cell(s) in a suspension culture;

(b) contacting the cancer stem cell population or a cancer stem cell(s) contained in the cancer stem cell population with an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody; and (c) selecting or detecting, from the cancer stem cell population or cancer stem cells, a cancer stem cell population or cancer stem cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

In the present method, first, a substantially homogeneous cancer stem cell population is prepared by culturing a cell population containing a cancer stem cell(s) in suspension. Then, the cancer stem cell population or a cancer stem cell(s) contained in the cancer stem cell population is contacted with an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody. Lgr5-negative cancer stem cells or substantially homogeneous cancer stem cell population can be separated or detected by selecting a cancer stem cell(s) or a cancer stem cell population which is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

Another embodiment of the isolation or detection methods of the present invention includes methods for isolating or detecting proliferation inhibitor-resistant Lgr5-negative cancer stem cells or substantially homogeneous cancer stem cell populations, which comprise the steps of:

(a) preparing a cell population containing a cancer stem cell(s);

(b) contacting an Lgr5 antibody with the cell population or a cell(s) contained in the cell population; and (c) isolating or detecting an Lgr5-negative cell population or cell(s) from the cell population or cell(s).

In these methods, a cell population containing a cancer stem cell(s) is prepared as the first step. Then, an Lgr5 antibody is contacted with the cell population or a cell(s) contained in the cell population. Lgr5-negative cancer stem cells or a substantially homogeneous Lgr5-negative cancer stem cell population can be isolated or detected by selecting a cell population or cell(s) that is negative for cell marker Lgr5, for example, by sorting cells with a cell sorter using a fluorescently labeled Lgr5 antibody and collecting cells to which the Lgr5 antibody does not bind or removing cells to which the Lgr5 antibody binds.

Known cell sorters include, for example:
BD InFlux™
BD FACSAria™ III
BD FACSAria™ II
FACSAria™
FACSVantage™ SE (all are names of BD Biosciences products)
EPICS ALTRA HyPerSort
MoFlo AstriosCytomics FC 500
MoFlo XDP (all are names of Beckman Coulter products)

Appropriate antibodies to detect cell markers for use in the present invention include, in addition to commercially available antibodies, antisera obtained by immunizing vertebrates with a portion or the whole of a cell marker of the present invention, polyclonal antibodies obtained by purifying the above-described antisera using Protein A or such, and monoclonal antibodies prepared by known hybridoma methods. A non-limiting embodiment of such commercially available antibodies that can be used with a cell sorter includes, for example:

E-cadherin antibodies: clone 24E10 (Cell Signaling Technology), clone 67A4 (Merck), clone DECMA-1 (Affymetrics), clone MB2 (Santa cruz), clone 180224 (R&D Systems);
HLA-DMA antibodies: clone MaP.DM1 (BD Biosciences), clone TAL18.1 (Abcam), clone IBL-3/5 (Abcam), clone ER-TR 2 (Abcam), clone NIMR-4 (Abcam), clone 2G11 (Abcam), clone ER-TR 3 (Abcam), clone 3D6 (Abcam), clone MRC OX-6 (Abcam);
TMEM173 antibodies: clone 723505 (R&D Systems), clone 2C9 (Abcam);
TNFSF15 antibodies: clone L4G9 (Abnova);
PROM2 antibodies: clone 244029 (R&D Systems);
GPR87 antibodies: rabbit pAb (WO2008/031842);
BLNK antibodies: clone 5G9 (Abnova);
HLA-DMB antibodies: clone EPR7981 (Abcam);
GPR172B antibodies: rabbit pAb (antibodies-online.com, ABIN763170);
FAS antibodies: 5E2 (Santa cruz), 6D50 (Santa cruz), 2R2 (Santa cruz), LT95 (Santa cruz), UT-1 (Abnova), DX2 (R&D Systems), 4F8D6 (Abcam), B-R17 (Abcam), H11 (Abcam), 10F2 (Abcam), MFL7 (Abcam), Alf1.2 (Abcam), DX2 (Abcam), BD29 (Abcam);
STOM antibodies: mouse pAb (Abcam, ab67880);
ABCA1 antibodies: clone AB.H10 (Abcam), HJ1 (Abcam);
SLC6A14 antibodies: rabbit pAb (MBL International, BMP052);
BMPR2 antibodies: clone MM0060-9A10 (Abcam); and
CLDN1 antibodies: clone 421203 (R&D Systems).

Another embodiment of the isolation or detection methods of the present invention includes methods for isolating or detecting proliferation inhibitor-resistant Lgr5-negative cancer stem cells or substantially homogeneous cancer stem cell populations, which comprise the steps of:
(a) preparing a substantially homogeneous cancer stem cell population by culturing a cell population containing a cancer stem cell(s) in a medium containing a proliferation inhibitor;
(b) contacting an Lgr5 antibody with the cancer stem cell population or a cancer stem cell(s) contained in the cancer stem cell population; and
(c) isolating or detecting an Lgr5-negative substantially homogeneous cancer stem cell population or Lgr5-negative cancer stem cell(s) from the cancer stem cell population or cancer stem cell(s).

In these methods, first, a cell population containing a cancer stem cell(s) is cultured in a medium containing a proliferation inhibitor to prepare a substantially homogeneous cancer stem cell population. Then, an Lgr5 antibody is contacted with the cancer stem cell population or a cancer stem cell(s) contained in the cancer stem cell population. Lgr5-negative cancer stem cells or a substantially homogeneous Lgr5-negative cancer stem cell population can be isolated or detected by selecting a cancer stem cell population or cancer stem cell(s) that is negative for Lgr5.

Another embodiment of the isolation or detection methods of the present invention includes methods for isolating or detecting proliferation inhibitor-resistant Lgr5-negative cancer stem cells or substantially homogeneous cancer stem cell populations, which comprise the steps of:
(a) preparing a cell population containing a cancer stem cell(s);
(b) contacting the cell population or a cell(s) contained in the cell population with an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody;
(c) isolating or detecting, from the cell population or cell(s), a cell population or cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

In these methods, a cell population containing a cancer stem cell(s) is prepared as the first step. Then, the cell population or a cell(s) contained in the cell population is contacted with an E-cadherin antibody, a Snail antibody, a β-catenin antibody, an HLA-DMA antibody, a TMEM173 antibody, a ZMAT3 antibody, and/or a GPR110 antibody. Proliferation inhibitor-resistant Lgr5-negative cancer stem cells or a substantially homogeneous proliferation inhibitor-resistant Lgr5-negative cancer stem cell population can be isolated or detected, for example, by selecting a cell population or cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110, using an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody.

Another embodiment of the isolation or detection methods of the present invention includes methods for isolating or detecting proliferation inhibitor-resistant Lgr5-negative cancer stem cells or substantially homogeneous cancer stem cell populations, which comprise the steps of:
(a) preparing a substantially homogeneous cancer stem cell population by culturing a cell population containing a cancer stem cell(s) in a medium containing a proliferation inhibitor;
(b) contacting the cancer stem cell population or a cancer stem cell(s) contained in the cancer stem cell population with an E-cadherin antibody, an Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody;
(c) isolating or detecting, from the cancer stem cell population or cancer stem cell(s), a cancer stem cell population or cancer stem cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

In these methods, first, a cell population containing a cancer stem cell(s) is cultured in a medium containing a proliferation inhibitor to prepare a substantially homogeneous cancer stem cell population. Then, the cancer stem cell population or a cancer stem cell(s) contained in the cancer stem cell population is contacted with an E-cadherin antibody, a Snail antibody, a β-catenin antibody, an HLA-DMA antibody, a TMEM173 antibody, a ZMAT3 antibody, a TNFSF15 antibody, an AMIGO2 antibody, a PROM2 antibody, a GPR87 antibody, a BLNK antibody, an HLA-DMB antibody, a GPR172B antibody, a GNAI1 antibody, a FAS antibody, a GM2A antibody, an FLRT3 antibody, a STOM antibody, a GJB5 antibody, an ABCA1 antibody, an SLC6A14 antibody, a BMPR2 antibody, a CLDN1 antibody, and/or a GPR110 antibody. Lgr5-negative cancer stem cells or substantially homogeneous Lgr5-negative cancer stem cell population can be isolated or detected by selecting a cancer stem cell population or cancer stem cell(s) that is positive for cell-surface E-cadherin, negative for Snail, in which β-catenin is not localized in the nucleus, positive for HLA-DMA, positive for TMEM173, positive for ZMAT3, positive for TNFSF15, positive for AMIGO2, positive for PROM2, positive for GPR87, positive for BLNK, positive for HLA-DMB, positive for GPR172B, positive for GNAI1, positive for FAS, positive for GM2A, positive for FLRT3, positive for STOM, positive for GJB5, positive for ABCA1, positive for SLC6A14, positive for BMPR2, positive for CLDN1, and/or positive for GPR110.

The type of a proliferation inhibitor for use in the above-described methods is not particularly limited. In a non-limiting embodiment, such proliferation inhibitors may appropriately be selected from anti-cancer agents such as chemotherapeutic agents for use in cancer therapy. Anti-cancer agents include alkylating agents, anti-metabolites, natural products, platinum complexes, and other proliferation inhibitors. Alkylating agents include nitrogen mustards, ethylenimines, methylmelamines, alkyl sulfonates, nitrosoureas, and triazens. Nitrogen mustards include, for example, mechlorethamine, cyclophosphamide, ifosfamide, melphalan, and chlorambucil. Ethylenimines and methylmelamines include, for example, hexamethylmelamine and thiotepa. Alkyl sulfonates include busulfan. Nitrosoureas include, for example, carmustine (BCNU), lomustine (CCNU), semustine (methyl-CCNU), and streptozocin. Triazens include dacarbazine (DTIC). Anti-metabolites include folic acid analogs, pyrimidine analogs, and purine analogs. Folic acid analogs include methotrexate. Pyrimidine analogs include, for example, fluorouracil (5-FU), doxifluridine (5'-DFUR; trade name: FURTULON), capecitabine (trade name: Xeloda), floxuridine (FudR), and cytarabine. Purine analogs include, for example, mercaptopurine (6-MP), thioguanine (TG), and pentostatin. Natural products include vinca alkaloids, epipodophyllotoxins, and antibiotics. Vinca alkaloids include, for example, vinblastine (VLB) and vincristine (VCR). Epipodophyllotoxins include, for example, etoposide and teniposide. Antibiotics include, for example, dactinomycin (actinomycin D), daunorubicin, doxorubicin, bleomycin, plicamycin, and mitomycin. A platinum complex refers to a platinum coordination complex, and includes, for example, cisplatin (CDDP), carboplatin, and oxaliplatin. Other proliferation inhibitors include topoisomerase inhibitors such as irinotecan and camptothecin, taxols, for example, paclitaxel, docetaxel, anthracenediones, for example, mitoxantrone, urea-substituted derivatives, for example, hydroxyurea, methyl hydrazines, for example, procarbazine hydrochloride, trade name: Natulan), vitamin A metabolites, for example, tretinoin (trade name: VESANOID), as well as rituximab, alemtuzumab, trastuzumab, bevacizumab, cetuximab, panitumumab, trastuzumab, and gemtuzumab. In a non-limiting embodiment, it is preferable to use 5-FU or irinotecan.

Further, the present invention provides methods for separating cancer stem cells with a high proliferative potential and cancer stem cells with a low proliferative potential. In the present invention, cancer stem cells can be separated by using an adherent culture and a suspension culture. Cancer stem cells with a high proliferative potential can be separated by an adherent culture, and cancer stem cells with a low proliferative potential can be separated by s suspension culture.

Furthermore, in the present invention, cancer stem cells can be separated in the presence or absence of an above-described proliferation inhibitor. Cancer stem cells with a high proliferative potential can be separated by an adherent culture using a proliferation inhibitor-free medium, and cancer stem cells with a low proliferative potential can be separated by performing a culture in a medium containing a proliferation inhibitor. The concentration of a proliferation inhibitor added to a medium can be appropriately selected by those skilled in the art.

"High proliferative ability" means that the doubling time is 6 days or less, preferably 4 days or less, and more preferably 3 days or less when cells are cultured in a serum-free medium supplemented with EGF and FGF using the method described herein.

"Low proliferative ability" means that the doubling time is 7 days or more, preferably 14 days or more, and more preferably there is no significant proliferation when cells are cultured in a serum-free medium supplemented with EGF and FGF using the method described herein.

In the separation methods, the cells can be separated using the cell marker Lgr5. The separation methods include the following:
methods in which a cell population containing cancer stem cells is isolated by using an anti-Lgr5 antibody;
methods in which a substantially homogeneous cancer stem cell population is first prepared by culturing a population containing cancer stem cells under an adherent or suspension culture condition, and then the population is isolated by using an anti-Lgr5 antibody; and
methods in which a substantially homogeneous cancer stem cell population is first prepared by culturing a population containing cancer stem cells in a medium with or without a growth inhibitor under an adherent culture condition, and then the population is isolated by using an anti-Lgr5 antibody. Any of the above methods may be used in the present invention.

Furthermore, the present invention provides methods of inducing cancer stem cells into those having a different proliferation ability. Specifically, they are methods of inducing low proliferative cancer stem cells into high proliferative cancer stem cells, or methods of inducing high proliferative cancer stem cells into low proliferative cancer stem cells.

Specifically, the present invention provides cancer stem cells with a low proliferative potential which are isolated by maintaining cancer stem cells with a high proliferative potential under various types of stress, such as by a suspension culture or contact with a growth inhibitor. The present invention also provides methods for inducing cancer stem cells with a high proliferative potential into cancer stem cells with a low proliferative potential by maintaining cancer stem cells with a high proliferative potential under various types of stress, such as by dispersing them into individual liver cancer cells, suspension culture, or contact with a growth inhibitor. For example, high proliferative cancer stem cells can be converted to low proliferative cancer stem cells by culturing high proliferative cancer stem cells under a floating culture condition. Alternatively, high proliferative cancer stem cells can be converted to low proliferative cancer stem cells by culturing high proliferative cancer stem cells in low adherent or ultra low adherent cell culture vessels such as low adherent plates, ultra low adherent plates, low adherent dishes, ultra low adherent dishes, low adherent flasks, or ultra low adherent cell culture flasks. In other words, low proliferative cancer stem cells can be prepared by culturing high proliferative cancer stem cells in low adherent or ultra low adherent cell culture vessels such as low adherent plates, ultra low adherent plates, low adherent dishes, ultra low adherent dishes, low adherent flasks, or ultra low adherent cell culture flasks.

In a non-limiting embodiment, high proliferative cancer stem cells can be converted to low proliferative cancer stem cells by using a growth inhibitor such as 5-FU, oxaliplatin, or irinotecan. Specifically, low proliferative cancer stem cells can be produced by exposing high proliferative cancer stem cells to a growth inhibitor such as 5-FU or irinotecan. Exposure to a growth inhibitor can be achieved under any condition such as in vitro culture or inside the body of grafted non-human animals. In this case, those skilled in the art can select an appropriate exposure dose of a cell growth inhibitor for cancer stem cells. Alternatively, high proliferative cancer stem cells can be prepared by re-seeding low proliferative cancer stem cells into a medium without a growth inhibitor such as 5-FU or irinotecan. In another non-limiting embodiment, high proliferative cancer stem cells can be produced by discontinuing administration of a growth inhibitor to non-human animals having low proliferative cancer stem cells.

For example, low proliferative cancer stem cells can be cultured under an adherent culture condition to convert them to high proliferative cancer stem cells. Alternatively, low proliferative cancer stem cells can be converted to high proliferative cancer stem cells by culturing low proliferative cancer stem cells in a non-low-adherent but highly adherent cell culture vessel such as a flat-bottomed plate, plate, adherent culture plate, adherent culture flask, dish, or adherent culture dish. That is, high proliferative cancer stem cells can be produced by culturing low proliferative cancer stem cells in a non-low-adherent but highly adherent cell culture vessel such as a flat-bottomed plate, plate, adherent culture plate, adherent culture flask, dish, or adherent culture dish.

Furthermore, the present invention provides cancer stem cells with a high proliferative potential and cancer stem cells with a low proliferative potential which are separated or induced by the above-described separation/induction methods.

Furthermore, the present invention relates to methods of screening for anti-cancer agents, which use cancer stem cells separated or induced by the above-described methods of the present invention.

The present invention also relates to methods for assessing compounds, which use cancer stem cells separated or induced by the above-described methods of the present invention.

The present invention also provides proliferation inhibitors against cancer stem cells of the present invention. Proliferation inhibitors against cancer stem cells of the present invention are preferably those comprising β-catenin inhibitors and TCF inhibitors in combination. The preferred cancer stem cells are Lgr5-positive adherent cancer stem cells. Such cancer cell proliferation inhibitors are used as anti-cancer agents.

β-Catenin inhibitors include substances that suppress the expression of β-catenin, substances that inhibit the function of β-catenin, and substances that induce the degradation of β-catenin Specifically, the inhibitors include β-catenin antibodies, siRNAs against β-catenin, and cardamonin.

TCF inhibitors include substances that suppress the expression of TCF, substances that inhibit the function of TCF, and substances that induce the degradation of TCF. Specifically, the inhibitors include TCF antibodies, siRNAs against TCF, and FH535.

Furthermore, the present invention provides metastasis/recurrence inhibitors against cancer stem cells of the present invention. The preferred cancer stem cells are Lgr5-positive adherent cancer stem cells. The metastasis/recurrence inhibitors of the present invention preferably comprise 5-FU or irinotecan as an active ingredient.

In addition, the present invention provides proliferation inhibitors and metastasis/recurrence inhibitors against cancer stem cells of the present invention, which comprise modulators for proteins such as CD133 (SEQ ID NOs: 7 and 14), CD44 (SEQ ID NOs: 8 and 15), EpCAM (SEQ ID NOs: 9 and 16), CD166 (SEQ ID NOs: 10 and 17), CD24 (SEQ ID NOs: 11 and 18), CD26 (SEQ ID NOs: 12 and 19), and CD29 (SEQ ID NOs: 13 and 20), which are expressed at high levels in both Lgr5-positive adherent cancer stem cells and Lgr5-negative adherent cancer stem cells.

Furthermore, the present invention provides methods for detecting, identifying, or quantifying the presence of cancer stem cells of the present invention. Specifically, the present invention provides methods for detecting, identifying, or quantifying the presence of cancer stem cells or substantially homogeneous cancer stem cell populations of the present invention, which comprise the steps of:

(a) preparing a sample obtained from a cancer patient; and
(b) contacting a sample with an anti-Lgr5 antibody.

In these methods, first, samples obtained from cancer patients are prepared. In the present invention, a "sample" is not particularly limited as long as it is preferably an organ or tissue derived from a cancer patient. It is possible to use a frozen or unfrozen organ or tissue. Such samples include, for example, cancer (tumor) tissues isolated from cancer patients. In these methods, a sample is then contacted with an anti-Lgr5 antibody.

Methods for detecting, identifying, or quantifying the presence of above-described cancer stem cells or substantially homogeneous cancer stem cell populations of the present invention can be used in, for example, cancer diagnosis, selection of cancer patients, prediction of the effectiveness of an agent, treatment monitoring, and cancer imaging.

Specifically, for example, organs or tissues are isolated from cancer patients, and specimens are prepared. The specimens can be used to detect, identify, or quantify the presence of cancer stem cells. Specimens can be appropriately prepared by using known methods, for example, the PFA-AMeX-Paraffin method (WO 09/078,386). The samples include, for example, frozen or unfrozen organs or tissues. First, samples from cancer patients are fixed in a PFA solution. "PFA solution" refers to a cell fixation solution which is an aqueous solution of 1 to 6% paraformaldehyde combined with a buffer such as phosphate buffer. It is preferable to use 4% PFA fixation solution (4% paraformaldehyde/0.01 M PBS (pH7.4)). For fixation with a PFA fixation solution, organs or tissues of interest are immersed in a PFA solution containing 1 to 6%, preferably 4% paraformaldehyde, at 0 to 8° C., preferably at about 4° C., for 2 to 40 hours, preferably for 6 to 30 hours. Then, fixed organs or tissues are washed with phosphate buffered saline or such. Washing may be carried out after excising portions from the observed organs or tissues.

Organs or tissues thus prepared are then embedded in paraffin by the AMeX method. The AMeX method is a paraffin embedding method with a series of the following steps: cold acetone fixation, dehydration with acetone, clearing in methylbenzoate and xylene, and paraffin embedding. Specifically, tissues are immersed in acetone at −25 to 8° C., preferably at −20 to 6° C., for 2 to 24 hours, preferably for 4 to 16 hours. Then, the tissues in acetone are warmed to room temperature. Alternatively, organs or tissues are transferred into acetone at room temperature. Then, dehydration is performed for 0.5 to 5 hours, preferably 1 to 4 hours at room temperature. Subsequently, the organs or tissues are cleared by immersion in methylbenzoate at room temperature for 0.5 to 3 hours, preferably for 0.5 to 2 hours, followed by immersion in xylene at room temperature for 0.5 to 3 hours, preferably 0.5 to 2 hours. Next, the organs or tissues are embedded in paraffin by penetration at 55 to 65° C., preferably at 58 to 62° C. for 1 to 4 hours, preferably 1 to 3 hours. The paraffin blocks of organs or tissues prepared by the PFA-AMeX method are stored at low temperature before use.

At the time of use, the paraffin blocks thus prepared are sliced into thin sections using a microtome or the like. Then, the thin sections are deparaffinized and rehydrated. Deparaffinization and rehydration can be performed by known methods. For example, deparaffinization can be performed using xylene and toluene, while rehydration can be carried out using alcohol and acetone.

The resulting thin sections are stained, for example, by histochemistry, immunohistochemistry, or enzyme histochemistry for detection, identification, or quantitation.

When the prepared samples are stained by histochemistry (special staining), it is possible to use any staining method commonly available for paraffin-embedded sections (for example, PAS staining, giemsa staining, and toluidine blue staining). For staining by enzyme histochemistry, the sections may be stained by any staining method available for sections (for example, various staining such as with ALP, ACP, TRAP, or esterase). In addition, histopathological tissues can be stained by the following: hematoxylin-eosin staining for general staining; van Gieson staining, azan staining, and Masson Trichrome staining for collagen fiber staining; Weigert staining and Elastica van Gieson staining for elastic fiber staining; Watanabe's silver impregnation staining and PAM staining (periodic acid methenamine silver stain) for reticular fibers/basal membrane staining, etc.

Staining with immunohistochemistry and enzyme histochemistry can be performed by direct methods using primary antibodies labeled with an enzyme or labeling substance, or indirect methods using non-labeled primary antibodies and labeled secondary antibodies. However, such methods are not limited thereto. Antibodies can be labeled by conventional methods. Labeling substances include, for example, radioisotopes, enzymes, fluorescent substances, and biotin/avidin. The labeling substances may be those commercially available. Radioisotopes include, for example, $^{32}P$, $^{33}P$, $^{131}I$, $^{125}I$, $^{3}H$, $^{14}C$, and $^{35}S$. Enzymes include, for example, alkaline phosphatase, horse radish peroxidase, β-galactosidase, and β-glucosidase. Fluorescent substances include, for example, fluorescein isothiocyanate (FITC) and rhodamine. These may be commercially available. Labeling can be carried out by known methods.

Thin sections are stained, for example, by histochemistry, immunohistochemistry, or enzyme histochemistry for detection, identification, or quantitation.

Alternatively, detection, identification, or quantitation can be carried out by quantifying DNA or RNA in cells in organ/tissue samples. Assessment of the expression is not particularly limited, and conventional expression assessment methods can be used. RNAs include microRNAs, siRNAs, tRNAs, snRNAs, mRNAs, and non-coding RNAs. For example, Lgr5 mRNA is extracted according to conventional methods. Using the mRNA as a template, the transcriptional level of each gene can be determined by the Northern hybridization or RT-PCR method. DNA array techniques can also be used to determine the expression level of Lgr5.

Desired tissues, cells, or such can be collected from samples by the microdissection method, in particular, laser microdissection (LMD) method. The LMD method can collect a group of target cells from living tissues, and thus accurately determine which cells express a specific gene among various cells that constitute a tissue, and at what level the cells express the gene. Devices used for microdissection include, for example, the AS-LMD system (Leica Microsystems).

Moreover, the present invention provides kits and sets for use in the above-described various methods of the present invention. The kits and sets comprise antibodies against cell marker Lgr5. The kits and sets may comprise appropriate vessels (for example, bottles, vials, and test tubes) and labels. Such labels may include instructions.

Further, the kits and sets of the present invention may optionally comprise other materials, including filters, needles, syringes, and instruction manuals.

The above-described kits and sets may comprise, in addition to Lgr5 antibodies as an active ingredient, for example, sterile water, physiological saline, vegetable oils, detergents, lipids, solubilizing agents, buffers, protein stabilizers (BSA, gelatin, etc.), preservatives, blocking solutions, reaction solutions, reaction stop solutions, and reagents for treating samples, as needed.

The present invention also provides cancer stem cell inhibitors that comprise a modulator for a protein encoded by a gene comprising a nucleotide sequence of any one of the following:

(a) a polynucleotide comprising a nucleotide sequence of any one of SEQ ID NOs: 7 to 13;
(b) a polynucleotide that hybridizes under stringent conditions to a polynucleotide that comprises a nucleotide sequence complementary to a polynucleotide comprising the nucleotide sequence of any one of SEQ ID NOs: 7 to 13, wherein the polynucleotide comprises a nucleotide sequence encoding a protein functionally equivalent to a protein encoded by a gene comprising the nucleotide sequence of any one of SEQ ID NOs: 7 to 13; and
(c) a polynucleotide that comprises a nucleotide sequence encoding a protein functionally equivalent to the protein encoded by a gene comprising the nucleotide sequence of any one of SEQ ID NOs: 7 to 13, in which the protein has an addition, deletion, or substitution of at least one amino acid residue in the protein encoded by a gene comprising the nucleotide sequence of any one of SEQ ID NOs: 7 to 13.

The "modulator for a protein" refers to a compound that modulates the biological activity or expression level of a protein. "Modulation" means increasing and decreasing an activity, expression level, etc.

The modulators are not particularly limited, and include, for example, single compounds such as natural compounds, organic compounds, inorganic compounds, proteins, antibodies, peptides, and amino acids, as well as compound libraries, expression products of gene libraries, cell extracts, cell culture supernatants, products of fermenting microorganisms, extracts of marine organisms, plant extracts, prokaryotic cell extracts, unicellular eukaryote extracts, and animal cell extracts. These may be purified products or crude preparations such as extracts of plants, animals, and microorganisms. Methods for producing the modulators are also not particularly limited; the modulators may be isolated from natural materials, synthesized chemically or biochemically, or prepared by genetic engineering. The modulators preferably include antibodies, antisense oligonucleotides, ribozymes, aptamers, and siRNA.

The cancer stem cell inhibitor refers, for example, to an agent having the effects of suppressing cancer stem cell proliferation, suppressing cancer stem cell metastasis or recurrence, and killing cancer stem cells, and may have the effect of suppressing cancer cell proliferation, suppressing cancer cell metastasis or recurrence, killing cancer cells, or such. Herein, "metastasis" refers to a process where cancer spreads or travels from the primary site to another location in the body, resulting in development of similar cancer lesions at the new site. "Metastatic" or "metastasizing" cell refers to a cell that has left the primary site of the disease due to loss of adhesive contact to adjacent cells and has invaded into neighboring body structures via blood or lymphatic circulation. "Recurrence" means that, after partial resection of an organ to remove a malignant tumor from a cancer patient, or after postoperative chemotherapy, the same malignant tumor has reappeared in the remaining organ.

An above-described polynucleotide comprising the nucleotide sequence of any one of SEQ ID NOs: 7 to 13, the protein encoded by a gene comprising the nucleotide sequence, a protein comprising an amino acid sequence with an amino acid deletion, substitution, or addition in part of the protein, or a DNA encoding the protein can be appropriately prepared by methods known to those skilled in the art. Such deletions, substitutions, and additions can be readily introduced by appropriately combining methods known to those skilled in the art, for example, site-directed mutagenesis, homologous gene recombination, primer extension, and PCR.

"Functionally equivalent" means having an equivalent biological activity. An equivalent biological activity can be conserved with substitutions between amino acids of the same group (polar or non-polar amino acids; hydrophobic or hydrophilic amino acids; positively- or negatively-charged amino acids; aromatic amino acids, etc.) among amino acids constituting a protein of interest. Furthermore, to conserve an equivalent biological activity, it is preferable to maintain amino acids within functional domains of a protein of the present invention.

A polynucleotide that hybridizes under stringent conditions to a polynucleotide comprising a nucleotide sequence complementary to a polynucleotide comprising the nucleotide sequence of any one of SEQ ID NOs: 7 to 13 includes, for example, polynucleotides comprising a nucleotide sequence which has on overall average about 80% or more, preferably about 90% or more, more preferably about 95% or more, and yet more preferably 96%, 97%, 98%, and 99% sequence homology to the overall sequence of the polynucleotide.

Hybridization can be performed according to methods known in the art, such as those described in "Current protocols in molecular biology (edited by Frederick M. Ausubel et al., 1987)" and similar methods.

Herein, "stringent conditions" are, for example, "1×SSC, 0.1% SDS, 37° C." or similar conditions; more stringent conditions are "0.5×SSC, 0.1% SDS, 42° C." or similar conditions; and still more stringent conditions are "0.2×SSC, 0.1% SDS, 65° C." or similar conditions. With more stringent hybridization conditions as described above, polynucleotides with a higher homology to the probe sequence are expected to be isolated. However, the above-described combinations of SSC, SDS, and temperature conditions are examples, and those skilled in the art can achieve stringencies similar to the above by appropriately combining the above and other factors that determine hybridization stringency (for example, probe concentration, probe length, reaction time for hybridization, etc.).

<Proteins>

Proteins for use in the present invention can be easily prepared by any method known to those skilled in the art as follows. An expression vector containing a gene comprising a DNA encoding a protein is constructed. The protein is produced and accumulated by culturing transformants transformed with the expression vector. The transformants are harvested to prepare the protein.

Such an expression vector can be constructed according to methods known in the art, for example, by the following:
(1) excising a DNA fragment that comprises a gene comprising a DNA encoding a protein; and
(2) ligating the DNA fragment downstream of a promoter in an appropriate expression vector.

Such vectors used include *E. coli*-derived plasmids (for example, pBR322, pBR325, pUC18, and pUC118), *Bacillus subtilis*-derived plasmids (for example, pUB110, pTP5, and pC194), yeast-derived plasmids (for example, pSH19 and pSH15), bacteriophages such as λ, phage, and animal viruses such as retroviruses, vaccinia viruses, and Baculoviruses.

Promoters for use in the present invention may be any promoters as long as they are appropriate and compatible with a host to be used for gene expression. For example, when the host is *E. coli*, preferred promoters include the trp promoter, lac promoter, recA promoter, λPL promoter, and lpp promoter. When the host is *Bacillus subtilis*, preferred promoters include the SPO1 promoter, SPO2 promoter, and penP promoter. When the host is yeast, preferred promoters include the PHO5 promoter, PGK promoter, GAP promoter, and ADH promoter. When the host is an animal cell, promoters include the SRα promoter, SV40 promoter, LTR promoter, CMV promoter, and HSV-TK promoter.

In addition to those described above, if desired, enhancers, splicing signals, poly-A addition signals, selection markers, SV40 replication origins, or such known in the art can be added to expression vectors. As necessary, a protein for use in the present invention can be expressed as a fusion protein with another protein (for example, glutathione-S-transferase or Protein A). Such a fusion protein can be cleaved into individual proteins by using an appropriate protease.

Host cells include, for example, bacteria of the genus *Escherichia*, bacteria of the genus *Bacillus*, yeasts, insect cells, insects, and animal cells.

Specific examples of bacteria of the genus *Escherichia* include *Escherichia coli* K12 DH1 (Proc. Natl. Acad. Sci, USA, 60, 160 (1968)), JM103 (Nucleic Acids Research, 9, 309 (1981)), JA221 (Journal of Molecular Biology, 120, 517 (1978)), and HB101 (Journal of Molecular Biology, 41, 459 (1969)).

Bacteria of the genus *Bacillus* include, for example, *Bacillus subtilis* MI114 (Gene, 24, 255 (1983)) and 207-21 (Journal of Biochemistry, 95, 87 (1984)).

Yeasts include, for example, *Saccharomyces cerevisiae* AH22, AH22R-, NA87-11A, DKD-5D, and 20B-12; *Schizosaccaromyces pombe* NCYC1913 and NCYC2036; and *Pichia pastoris*.

Animal cells include, for example, monkey COS-7 cells, Vero cells, Chinese hamster CHO cells (hereinafter abbreviated as CHO cells), dhfr gene-deficient CHO cells, mouse L cells, mouse AtT-20 cells, mouse myeloma cells, rat GH3 cells, and human FL cells.

These host cells can be transformed according to methods known in the art. See, for example, the following references. Proc. Natl. Acad. Sci. USA, Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. USA), Vol. 75, 1929 (1978); and Virology, Vol. 52, 456 (1973).

Transformants thus prepared can be cultured according to methods known in the art.

For example, when hosts were bacteria of the genus *Escherichia*, in general, they are cultured at about 15 to 43° C. for about 3 to 24 hours. Aeration or stirring is performed as necessary. When hosts are bacteria of the genus *Bacillus*, in general, they are cultured at about 30 to 40° C. for about 6 to 24 hours. Aeration or stirring is performed as necessary.

When hosts are yeasts, in general, transformants are cultured at about 20° C. to 35° C. for about 24 to 72 hours in a medium adjusted to about pH 5 to 8. Aeration or stiffing is performed as necessary.

When hosts are animal cells, in general, transformants are cultured at about 30° C. to 40° C. for about 15 to 60 hours in a medium adjusted to about pH 6 to 8. Aeration or stirring is performed as necessary.

To isolate and purify a protein for use in the present invention from the above culture, for example, cells or bacteria are harvested after culture by a known method, and this is suspended in an appropriate buffer. After disrupting the cells or bacteria by sonication, lysozyme, and/or freeze-thawing, a crude protein extract is prepared by centrifugation or filtration. The buffer may contain protein denaturants such as urea and guanidine hydrochloride, and detergents such as Triton X-100™. When the protein is secreted to the culture medium, the supernatant is separated from the cells or bacteria after culture by a known method, and the supernatant is collected. A protein contained in the resulting culture supernatant or extract can be purified by appropriately combining known isolation/purification methods.

According to known or equivalent methods, a protein prepared as described above can be arbitrarily modified or a polypeptide can be partially removed from the protein by treating the protein produced by recombinants with an appropriate protein modification enzyme such as trypsin and chymotrypsin before or after purification.

The presence of a protein for use in the present invention can be assessed by various binding assays, enzyme immunoassays using specific antibodies, etc.

<Antibodies>

Antibodies for use in the present invention are not particularly limited as long as they bind to proteins for use in the present invention. The antibodies may be obtained as polyclonal or monoclonal antibodies using known methods. Particularly preferred antibodies for use in the present invention include monoclonal antibodies derived from mammals. Monoclonal antibodies derived from mammals include those produced by hybridomas and those produced by hosts transformed with expression vectors carrying antibody genes using gene engineering technologies. It is preferable that antibodies for use in the present invention specifically bind to proteins for use in the present invention.

Basically, hybridomas producing monoclonal antibodies can be prepared using known techniques by the following procedure. Specifically, immunization is carried out using as a sensitizing antigen a protein for use in the present invention according to conventional immunization methods. The resulting immune cells are fused with known parental cells by conventional cell fusion methods. Monoclonal antibody-producing cells are screened using conventional screening methods. More specifically, monoclonal antibodies can be prepared by the following procedure.

A gene sequence encoding the protein is inserted into a known expression vector system, and this is transformed into appropriate host cells. Then, the protein is purified from the host cells or culture supernatant by known methods.

Next, the protein is used as a sensitizing antigen. Alternatively, a partial peptide of the protein is used as a sensitizing antigen. In this case, the partial peptide can be prepared by chemical synthesis based on the amino acid sequence of the protein according to common methods known to those skilled in the art.

Such a partial polypeptide of the protein has, for example, at least 10 or more amino acids, preferably 50 or more amino acids, more preferably 70 or more amino acids, still more preferably 100 or more amino acids, and yet more preferably 200 or more amino acids of the amino acid sequence constituting the protein, and has, for example, a biological activity substantially equivalent to the function of the protein. The C terminus of the partial peptide is generally a carboxyl group (—COOH) or carboxylate (—COO—); however, the C terminus may also be amide (—CONH$_2$) or ester (—COOR). In addition, the partial peptides include those in which the amino group of the N-terminal methionine residue is protected with a protecting group, those in which a glutamyl residue resulting from in vivo N-terminal cleavage is pyroglutamine-oxidized, those in which a substituent group in the side chain of an amino acid in the molecule is protected with an appropriate protecting group, and conjugated peptides such as so-called glycopeptides linked with sugar chains.

Mammals that are immunized with a sensitizing antigen are not particularly limited, though it is preferable to take into consideration compatibility with the parent cell used for cell fusion. Thus, rodents such as mice, rats, or hamsters are generally selected.

Immunization of animals with a sensitizing antigen is performed according to known methods. For example, standard methods of delivering sensitizing antigen to mammals involve intraperitoneal or subcutaneous injection. More specifically, a sensitizing antigen is diluted to be an appropriate volume with PBS (phosphate-buffered saline), physiological saline, or the like. If desired, this may be mixed with an appropriate amount of a typical adjuvant, for example, Freund's complete adjuvant, made into an emulsion, and then administered to mammals several times every 4 to 21 days. An appropriate carrier may also be used for immunization with sensitizing antigens.

After the mammals are immunized as described above, an increase in the level of desired antibody in the serum is confirmed, immunocytes are collected from the mammals for cell fusion. Immunocytes that are preferably subjected to cell fusion are splenocytes in particular.

Regarding the other parent cell to be fused with the above-mentioned immunocytes, mammalian myeloma cells are used. For myeloma cells, it is preferable to use various known cell lines, for example, P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C. Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. E et al., J. Immunol. Methods (1980) 35, 1-21), S194 (Trowbridge, I. S. J. Exp. Med. (1978) 148, 313-323), and R210 (Galfre, G et al., Nature (1979) 277, 131-133).

In general, the above-described immunocytes and myeloma cells can be fused according to known methods, examples of which are described by Kohler and Milstein et al. (Kohler, G. and Milstein, C., Methods Enzymol. (1981) 73, 3-46).

More specifically, the above-described cell fusion is carried out, for example, in a typical nutrient culture medium in the presence of a cell fusion promoting agent. For example, polyethylene glycol (PEG), Sendai virus (HVJ), or such can be used as the fusion promoting agent. If desired, adjuvants such as dimethylsulfoxide can additionally be used to increase fusion efficiency.

It is possible to arbitrarily determine the proportion of immunocytes and myeloma cells used. The preferred ratio of myeloma cells to immunocytes is, for example, from 1:1 to 1:10. The culture medium used for the above-described cell fusion may be, for example, RPMI1640 medium, MEM medium, which are suitable for proliferation of the above-described myeloma cell lines, or other kinds of culture medium commonly used for culturing such cells. Furthermore, serum supplements such as fetal calf serum (FCS) may be used in combination.

The cell fusion is carried out by thoroughly mixing prescribed amounts of the above-described immunocytes and myeloma cells in the aforementioned culture medium, adding to the medium a PEG solution preheated to about 37° C. generally at a concentration of 30% to 60% (w/v), wherein the PEG has an average molecular weight of about 1,000 to 6,000, for example, and mixing them to form the desired fusion cells (hybridomas). An appropriate culture medium is then successively added. Cell fusing agents and such that are undesirable for the proliferation of hybridomas are removed by repeatedly removing the supernatant by centrifugation.

The hybridomas obtained in this manner are selected by culturing them in a common selection culture medium, for example, the HAT medium (a culture medium containing hypoxanthine, aminopterin, and thymidine). Culture in the HAT medium described above is continued for a sufficient time, usually from a few days to a few weeks, to allow death of all cells but the target hybridomas (the non-fused cells). The usual limiting dilution method is then performed to screen and clone hybridomas producing antibodies used the present invention.

In addition to methods obtaining the above-described hybridomas by immunizing non-human animals with an antigen, desired human antibodies having an activity of binding to the protein can also be obtained by in vitro sensitizing human lymphocytes with the protein and fusing the sensitized lymphocytes with human-derived myeloma cells having permanent cell division ability (see Japanese Patent Application Kokoku Publication No. (JP-B) H01-59878 (examined, approved Japanese patent application published for opposition)). Furthermore, human antibodies against a protein may be obtained from immortalized antibody-producing cells that are prepared by administering the protein as an antigen to a transgenic animal having a full repertoire of human antibody genes (see, International Patent Applications WO 94/25585, WO 93/12227, WO 92/03918, and WO 94/02602).

There are known techniques for obtaining human antibodies by panning using a human antibody library. For example, the V regions of human antibodies can be expressed as single-chain antibodies (scFvs) on the surface of phages using a phage display methods, from which phages presenting scFv that binds to an antigen can be selected. The DNA sequences encoding the V regions of human antibodies that bind to the antigen can be determined by analyzing the genes of selected phages. After identifying the DNA sequences of scFvs that bind to the antigen, the V region sequences are fused in frame with the C region sequences of a desired human antibody. Then, the resulting DNA is inserted into an appropriate expression vector to construct an expression vector. The expression vector is introduced into suitable cells for expression, such as those described above. The human antibody can be obtained by expressing the gene encoding the human antibody. These methods are already known (see WO 1992/001047, WO 1992/020791, WO 1993/006213, WO 1993/011236, WO 1993/019172, WO 1995/001438, and WO 1995/015388).

The hybridomas prepared in this manner that produce monoclonal antibodies can be passaged in a common culture medium and stored for a long time in liquid nitrogen.

Monoclonal antibodies may be obtained from the hybridomas using common techniques; for example, the hybridomas are cultured according to standard methods and the antibodies may be obtained from the culture supernatants. Alternatively, the hybridomas are administered to a compatible mammal for proliferation and then the antibodies may be obtained from the ascites fluid. The former method is suitable for obtaining highly pure antibodies, while the latter method is suitable for mass production of antibodies.

Monoclonal antibodies used in the present invention may be recombinant antibodies produced by genetic engineering techniques. They can be produced, for example, by cloning an antibody gene from a hybridoma, incorporating the antibody gene into an appropriate vector, and introducing the resulting vector into a host (see, for example, Vandamme, A. M. et al., Eur. J. Biochem. (1990), 192, p. 767-775, 1990).

Specifically, mRNAs encoding antibody variable (V) regions are isolated from hybridomas producing the antibodies. mRNAs can be isolated by preparing total RNAs using known methods, for example, guanidine-ultracentrifugation method (Chirgwin, J. M. et al., Biochemistry (1979) 18, 5294-5299), AGPC method (Chomczynski, P. et al., Anal. Biochem. (1987) 162, 156-159), or such. mRNAs of interest are prepared using the mRNA Purification Kit (Pharmacia) or such. The mRNAs can be prepared directly by using the QuickPrep mRNA Purification Kit (Pharmacia).

The obtained mRNAs are used to synthesize cDNAs of the antibody V regions using reverse transcriptase. cDNAs are synthesized using the AMV Reverse Transcriptase First-strand cDNA Synthesis Kit (Seikagaku Co.) or such. Alternatively, cDNA may be synthesized and amplified following the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using the 5'-Ampli FINDER RACE Kit (Clontech) and PCR, and such.

DNA fragments of interest are purified from the resulting PCR products, and ligated to vector DNAs. From this, a recombinant vector is produced. The recombinant vector is then introduced into E. coli or such, and the desired recombinant vector is prepared from a selected colony. The nucleotide sequences of DNAs of interest are then determined by known methods, for example, the dideoxynucleotide chain termination method.

A DNA encoding the antibody V region of interest is obtained, and then incorporated into an expression vector carrying a DNA that encodes a desired antibody constant region (C region).

To produce an antibody used in the present invention, the antibody gene is incorporated into an expression vector so that the gene will be expressed under the control of an expression regulatory region, for example, an enhancer and a promoter. Then, host cells are transformed with the resulting expression vector to express the antibody.

When expressing antibody genes, a DNA encoding an antibody heavy chain (H chain) or light chain (L chain) can be each separately incorporated into an expression vector to simultaneously transform the host cell, or alternatively DNAs encoding H and L chains can be incorporated into a single expression vector to transform the host cells (see, WO 94/11523).

Besides the above-described host cells, transgenic animals can also be used to produce recombinant antibodies. For example, an antibody gene is prepared as a fusion gene by inserting the antibody gene into a gene encoding a protein that is specifically produced in milk, such as goat casein. DNA fragments containing the fusion gene to which the antibody gene has been inserted is injected into goat embryos, which are then introduced into female goats. The desired antibody is then obtained from the milk produced by the transgenic goats, which are born from the goats that received the embryos, or from their offspring. Hormones may be suitably given to the transgenic goat to increase the production of milk containing the antibody of interests (Ebert, K. M. et al., Bio/Technology (1994) 12, 699-702).

In the present invention, in addition to the antibodies described above, artificially modified genetically-recombinant antibodies such as chimeric, humanized, and human antibodies can be used to reduce heterologous antigenicity against humans and such. Such modified antibodies can be produced using known methods. Monoclonal antibodies of the present invention include not only those derived from animals described above but also artificially modified genetically-recombinant antibodies such as chimeric antibodies, humanized antibodies, and bispecific antibodies.

A chimeric antibody can be obtained by linking a DNA encoding the antibody V region obtained as described above to a DNA encoding the human antibody C region, incorporating this into an expression vector, and then introducing it into a host for production. Useful chimeric antibodies can be obtained using this known method.

Humanized antibodies are also referred to as "reshaped human antibodies", which are antibodies obtained by grafting the complementarity determining regions (CDRs) of an antibody from a non-human mammal (e.g., mouse antibody) to the complementarity determining regions of a human antibody. General gene recombination procedures are also known (see, European Patent Application Publication No. EP 125023; International Patent Application Publication No. WO 96/02576).

Specifically, a DNA sequence designed to link a mouse antibody CDR to the framework region (FR) of a human antibody is synthesized by PCR, using as primers several oligonucleotides prepared to contain overlapping portions in both CDR and FR terminal regions (see methods described in WO 98/13388).

The human antibody framework region to be linked via CDR is selected such that complementarity determining region forms a favorable antigen-binding site. As necessary, amino acids of the framework region in the antibody variable region may be substituted so that the complementarity determining region of the reshaped human antibody forms a suitable antigen-binding site (Sato, K. et al., 1993, Cancer Res. 53, 851-856).

Human antibody C-regions are used as the C-regions of chimeric antibodies or humanized antibodies. For example, CH1, CH2, CH3, and CH4 can be used for the H chain, while Cκ and Cλ, can be used for the L chain. The human antibody C-region may be modified in order to improve stability of the antibody or its production.

A chimeric antibody is composed of the variable region of an antibody derived from a non-human mammal and the constant region derived from a human antibody. On the other hand, a humanized antibody is composed of the complementarity determining region of an antibody derived from a non-human mammal, and the framework region and C region derived from a human antibody. Since the antigenicity of humanized antibodies is low in the human body, and humanized antibodies are useful as an active ingredient in therapeutic agents of the present invention.

Antibodies used in the present invention are not limited to whole antibody molecules, and as long as they bind to proteins used in the present invention, antibody fragments and modification products thereof as well as divalent and monovalent antibodies are also included. Antibody fragments include, for example, Fab, F(ab')2, Fv, Fab/c having an Fab and the whole Fc, single chain Fv (scFv) in which Fv fragments from H and L chains are ligated via an appropriate linker, and Diabody. Specifically, antibody fragments are prepared by treating antibodies with an enzyme, for example, papain or pepsin. Alternatively, after genes encoding such antibody fragments are constructed and introduced into an expression vector, the antibody fragments are expressed in appropriate host cells using the vector (see, for example, Co, M. S. et al., J. Immunol. (1994) 152, 2968-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 652-663; Rousseaux, J. et al., Methods in Enzymology (1989) 121, 663-669; Bird, R. E. et al., TIBTECH (1991) 9, 132-137).

scFv is obtained by ligating antibody H-chain V region with an antibody L-chain V region. In this scFv, the H-chain and L-chain V regions are ligated via a linker, preferably via a peptide linker (Huston, J. S. et al., Proc. Natl. Acad. Sci. U.S.A. (1988) 85, 5879-5883). The H-chain V region and L-chain V region of an scFv may be derived from any of the antibodies described herein. For example, any single-chain peptides consisting of 12 to 19 amino acid residues may be used as a peptide linker for ligating the V regions.

A DNA encoding an scFv can be obtained by using, among DNAs encoding the antibody H chain or H chain V region and the antibody L chain or L chain V region mentioned above, all or DNA portion encoding amino acid sequence of interest as a template, amplifying by PCR using a primer pair that defines its two ends; and then carrying out a subsequent amplification using a combination of a DNA encoding the peptide linker portion, and primer pairs that define both ends of the linker DNA to be ligated to the H chain and L chain, respectively.

Once DNAs encoding scFvs are constructed, expression vectors carrying the DNAs and hosts transformed with the expression vectors can be obtained according to conventional methods. Furthermore, scFvs can be obtained using these hosts according to conventional methods.

Diabodies are dimers formed by linking two fragments (for example, scFv) in which a variable region is linked to another variable region via a linker or such, and typically have two VLs and two VHs (P. Holliger et al., Proc. Natl. Acad. Sci. USA, 90, 6444-6448 (1993); EP 404097; WO 93/11161; Johnson et al., Method in Enzymology, 203, 88-98, (1991); Holliger et al., Protein Engineering, 9, 299-305 (1996); Perisic et al., Structure, 2, 1217-1226 (1994); John et al., Protein Engineering, 12(7), 597-604 (1999); Holliger et al., Proc. Natl. Acad. Sci. USA., 90, 6444-6448 (1993); Atwell et al., Mol. Immunol. 33, 1301-1312 (1996); and such).

These antibody fragments can be produced, in a similar manner as described above, by obtaining their genes and expressing them in hosts. Herein, "antibody" comprises such antibody fragments.

The modified antibodies include antibodies of the present invention bound to various molecules such as polyethylene glycol (PEG). Antibodies can also be linked to cytotoxic substances such as radioisotopes, chemotherapeutic agents, bacterium-derived toxins, toxic peptides, and radioactive substances. Herein, "antibody" includes such modified antibodies. Such modified antibodies can be obtained by chemical modification of the prepared antibodies. Antibody modification methods have already been established in the art. In addition, a modified antibody in which a toxic peptide is linked can be obtained by expressing in appropriate host cells a fusion gene in which an antibody gene is linked in frame to a gene encoding the toxic peptide and then isolating it from the cell culture medium.

Chemotherapeutic agents to be conjugated with antibodies of the present invention to exert cytotoxic activity include, for example, the following chemotherapeutic agents: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, maytansinoid, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, and vincristine.

In the present invention, preferred chemotherapeutic agents are low molecular weight chemotherapeutic agents. Low molecular weight chemotherapeutic agents, even after conjugated with an antibody, have a less possibility to interfere with antibody function. In the present invention, low molecular weight chemotherapeutic agents typically have a molecular weight of 100 to 2000, preferably 200 to 1000. All chemotherapeutic agents described herein as an example are low molecular weight chemotherapeutic agents. In the present invention, such chemotherapeutic agents include prodrugs that are converted to active chemotherapeutic agents in vivo. Activation of prodrugs can be achieved via enzymatic or non-enzymatic conversion.

Furthermore, antibodies can be modified with toxic peptides (toxins). Preferred toxic peptides include, for example:
Diphtheria toxin A Chain (Langone J. J., et al., Methods in Enzymology (1983) 93, 307-308) *Pseudomonas* Exotoxin (Nature Medicine (1996) 2, 350-353)
Ricin A Chain (Fulton R. J. et al., J. Biol. Chem. (1986) 261, 5314-5319; Sivam G et al., Cancer Res. (1987) 47, 3169-3173; Cumber A. J. et al., J. Immunol. Methods (1990) 135, 15-24;
Wawrzynczak E. J. et al., Cancer Res. (1990) 50, 7519-7562; Gheeite V. et al., J. Immunol. Methods (1991) 142, 223-230)
Deglicosylated Ricin A Chain (Thorpe P. E. et al., Cancer Res. (1987) 47, 5924-5931)
Abrin A Chain (Wawrzynczak E. J. et al., Br. J. Cancer (1992) 66, 361-366; Wawrzynczak E. J., et al. Cancer Res. (1990) 50, 7519-7562; Sivam G, et al. Cancer Res. (1987) 47, 3169-3173;
Thorpe P. E. et al., Cancer Res. (1987) 47, 5924-5931)
Gelonin (Sivam G et al., Cancer Res. (1987) 47, 3169-3173; Cumber A. J. et al., J. Immunol. Methods (1990) 135, 15-24; Wawrzynczak E. J. et al. Cancer Res., (1990) 50, 7519-7562;
Bolognesi A. et al., Clin. exp. Immunol. (1992) 89, 341-346)
Pokeweed anti-viral protein fromseeds (PAP-s) (Bolognesi A. et al., Clin. exp. Immunol. (1992) 89, 341-346)
Briodin (Bolognesi A. et al., Clin. exp. Immunol. (1992) 89, 341-346)
Saporin (Bolognesi A., et al., Clin. exp. Immunol. (1992) 89, 341-346)
Momordin (Cumber A. J. et al., J. Immunol. Methods (1990) 135, 15-24)
Wawrzynczak E. J. et al., Cancer Res. (1990) 50, 7519-7562; Bolognesi A. et al., Clin. exp. Immunol. (1992) 89, 341-346)
Momorcochin (Bolognesi A. et al., Clin. exp. Immunol. (1992) 89, 341-346)
Dianthin 32 (Bolognesi A. et al., Clin. exp. Immunol. (1992) 89, 341-346)
Dianthin 30 (Stirpe F., Barbieri L., FEBS letter (1986) 195, 1-8)
Modeccin (Stirpe F., Barbieri L., FEBS letter (1986) 195, 1-8)

Viscumin (Stirpe F., Barbieri L., FEBS letter (1986) 195, 1-8)
Volkesin (Stirpe F., Barbieri L., FEBS letter (1986) 195, 1-8)
Dodecandrin (Stirpe F., Barbieri L., FEBS letter (1986) 195, 1-8)
Tritin (Stirpe F., Barbieri L., FEBS letter (1986) 195, 1-8)
Luffin (Stirpe F., Barbieri L., FEBS letter (1986) 195, 1-8)
Trichokirin (Casellas P., et al., Eur. J. Biochem. (1988) 176, 581-588; Bolognesi A., et al., Clin. exp. Immunol., (1992) 89, 341-346)

Herein, radioactive substance refers to a chemical substance comprising a radioisotope. Radioisotopes for use in the present invention are not particularly limited. It is possible to use any radioisotope; however, preferred radioisotopes are, for example, $^{32}P$, $^{14}C$, $^{125}I$, $^{3}H$, $^{131}I$, $^{186}Re$, and $^{188}Re$.

In another embodiment, antibodies can be modified by combining one, two or more low molecular weight chemotherapeutic agents and toxic peptides. Antibodies of the present invention can be conjugated with above-described low molecular weight chemotherapeutic agents via covalent or non-covalent bonds. Methods for preparing such antibodies conjugated with chemotherapeutic agents are publicly known.

Furthermore, antibodies used in the present invention may be bispecific antibodies. Bispecific antibodies of the present invention may be those having antigen-binding sites that each recognizes different epitopes in the protein used in the present invention or those which recognize the protein used in the present invention and a different protein. Alternatively, bispecific antibodies of the present invention may be those in which one antigen-binding domain recognizes the protein used in the present invention and the other recognizes a chemotherapeutic agent or a cytotoxic substance such as a cell-derived toxin. In this case, proliferation of cancer stem cells can be suppressed by allowing a cytotoxic substance to act directly on cancer stem cells expressing a protein used in the present invention and specifically damaging the cancer stem cells. The bispecific antibodies may be prepared by linking pairs of H and L chains from two types of antibodies, or by fusing hybridomas that produce different monoclonal antibodies to yield a fusion cell producing bispecific antibodies. Furthermore, the bispecific antibodies can be prepared using genetic engineering techniques.

Antibody genes constructed as described above can be expressed and obtained according to known methods. When mammalian cells are used, antibody genes can be expressed using a DNA in which a common useful promoter, an antibody gene to be expressed, and a poly A signal positioned downstream of the antibody gene on the 3' side are operably linked. Promoter/enhancer includes, for example, human cytomegalovirus immediate early promoter/enhancer.

Furthermore, other promoter/enhancers that can be used to express the antibody used in the present invention include viral promoter/enhancers of retroviruses, polyoma viruses, adenoviruses, simian virus 40 (SV40), and such; and mammalian cell-derived promoter/enhancers such as human elongation factor 1α (HEF1α).

When SV40 promoter/enhancer and HEF1α promoter/enhancer is used, gene expression can be easily carried out by the method of Mulligan et al. (Nature (1979) 277, 108) and the method by Mizushima et al. (Nucleic Acids Res. (1990) 18, 5322), respectively.

Replication origin derived from SV40, polyoma viruses, adenoviruses, bovine papilloma viruses (BPV), and such can be used. Furthermore, to increase the gene copy number in a host cell system, the expression vector may include, as a selection marker, the aminoglycoside transferase (APH) gene, thymidine kinase (TK) gene, E. coli xanthine-guanine phosphoribosyltransferase (Ecogpt) gene, dihydrofolate reductase (dhfr) gene, and such.

In the case of E. coli, the antibody gene can be expressed by an operably linked common useful promoter, a signal sequence for antibody secretion, and the antibody gene to be expressed. Such promoters include, for example, the lacz promoter and araB promoter. When the lacz promoter or araB promoter is used, the gene can be expressed by the method of Ward et al. (Nature (1098) 341, 544-546; FASEB J. (1992) 6, 2422-2427) or the method of Better et al. (Science (1988) 240, 1041-1043), respectively.

When an antibody is produced into the periplasm of E. coli, the pel B signal sequence (Lei, S. P. et al., J. Bacteriol. (1987) 169, 4379) may be used as a signal sequence for antibody secretion. After antibodies produced into the periplasm is separated, the antibody structure is appropriately refolded and then used.

Any expression system that uses, for example, eukaryotic cells or prokaryotic cells may be used to produce antibodies used in the present invention. Eukaryotic cells include, for example, animal cells such as established mammalian cell systems, insect cell systems, cells of filamentous fungi, and yeast cells. Prokaryotic cells include, for example, bacterial cells such as E. coli cells. Antibodies used in the present invention are preferably expressed in mammalian cells, for example, CHO, COS, myeloma, BHK, Vero, and HeLa cells.

Then, transformed host cells are cultured in vitro or in vivo to produce antibodies of interest. Host cells are cultured according to known methods. For example, DMEM, MEM, RPMI1640, or IMDM may be used as a culture medium, and this may also be used with serum supplements such as fetal calf serum (FCS).

Antibodies expressed and produced as described above can be isolated from cells or host animals and purified to be homogeneous. Antibodies used in the present invention can be isolated/purified by using affinity columns. For example, Protein A columns include Hyper D, POROS, and Sepharose EE (Pharmacia). It is also possible to use other common protein isolation/purification methods. Such methods are not particularly limited. For example, antibodies may be isolated/purified by appropriately selecting/combining chromatography columns other than the above-described affinity columns, filters, ultrafiltration, salting-out, dialysis, and such (Antibodies A Laboratory Manual. Ed Harlow, David Lane, Cold Spring Harbor Laboratory, 1988).

The antigen-binding activity (Antibodies A Laboratory Manual. Ed Harlow, David Lane, Cold Spring Harbor Laboratory, 1988) and ligand-receptor binding-inhibitory activity (Harada, A. et al., International Immunology (1993) 5, 681-690) of an antibody used in the present invention can be determined by using known methods.

Enzyme-linked immunosorbent assays (ELISAs), enzyme immunoassays (EIAs), radioimmunoassays (RIAs), and fluorescent antibody methods can be used to determine the antigen-binding activity of the antibody of the present invention. For example, when an enzyme immunoassay is used, samples containing an antibody of the present invention such as a culture supernatant of cells producing the antibody or the purified antibody are added to plates coated with a protein used in the present invention. A secondary antibody labeled with an enzyme such as alkaline phosphatase is added, and the plates are incubated. After washing, an enzyme substrate such as p-nitrophenyl phosphate is added and the absorbance is measured to evaluate the antigen-binding activity.

Antibodies used in the present invention may have a cytotoxic activity. Herein, the cytotoxic activity includes, for example, complement-dependent cytotoxicity (CDC) and antibody-dependent cell-mediated cytotoxicity (ADCC). Herein, CDC refers to a cytotoxic activity mediated by the complement system, while ADCC refers to an activity of damaging target cells, which is caused by binding of Fcγ receptor-carrying cells (immunocytes, etc.) via Fcγ receptor to the Fc portion of specific antibody upon binding of the antibody to cell-surface antigens on target cells.

Whether an antibody used in the present invention has ADCC or CDC can be measured by known methods (see, for example, Current protocols in Immunology, Chapter 7. Immunologic studies in humans, Editor, John E, Coligan et al., John Wiley & Sons, Inc., (1993)).

Specifically, cytotoxicity can be measured, for example, by the following method.

Preparation of Effector Cells

Spleen is removed from a CBA/N mouse or the like, and spleen cells are dispersed in RPMI1640 medium (GIBCO). After washing with the same medium containing 10% fetal bovine serum (FBS, HyClone), effector cells with a cell concentration adjusted to $5 \times 10^6$ cells/ml were prepared.

Preparation of Complement Solution

Baby Rabbit Complement (CEDARLANE) is diluted 10-fold with a medium (GIBCO) containing 10% FBS to prepare a complement solution.

Preparation of Target Cells

Cells expressing a protein used in the present invention (cancer stem cells, etc.) are radiolabeled by incubating them with 0.2 mCi of $^{51}$Cr-sodium chromate (Amersham Pharmacia Biotech) in DMEM medium containing 10% FBS for one hour at 37° C. After radiolabeled, the cells are washed three times with RPMI1640 medium containing 10% FBS, and the target cells with a cell concentration adjusted to $2 \times 10^5$ cells/ml were prepared.

ADCC Measurement

50 µl the target cells and 50 µl of the antibody used in the present invention are each added to a 96-well U-bottom plate (Becton Dickinson), and reacted for 15 minutes on ice. Thereafter, 100 µl of effector cells are added and incubated in a carbon dioxide incubator for four hours. The final antibody concentration is adjusted to 0 or 10 µg/ml. After incubation, 100 µl of the supernatant is collected and the radioactivity is measured with a gamma counter (COBRAI-IAUTO-GMMA, MODEL D5005, Packard Instrument Company). The cytotoxic activity (%) can be calculated according to:

(A−C)/(B−C)×100.

A represents the radioactivity (cpm) of each sample, B represents the radioactivity (cpm) of a sample where 1% NP-40 (nacalai tesque) has been added, and C represents the radioactivity (cpm) of a sample containing the target cells alone.

CDC Measurement

50 µl of the target cells and 50 µl of the antibody used in the present invention are each added to a 96-well flat-bottom plate (Becton Dickinson), and reacted for 15 minutes on ice. Thereafter, 100 µl of the complement solution is added, and incubated in a carbon dioxide incubator for four hours. The antibody final concentration is adjusted to 0 or 3 µg/ml. After incubation, 100 µl of the supernatant is collected to measure the radioactivity with a gamma counter. The cytotoxic activity can be calculated by the similar way as in the ADCC determination.

In case of measuring cytotoxic activity using an antibody conjugate, 50 µl each of target cells and an anti-ITM2A antibody conjugate are added to each well of a 96-well flat-bottomed plate (Becton Dickinson), and the plate is allowed to stand on ice for 15 minutes. Then, the plate is incubated in a carbon dioxide gas incubator for one to four hours. The antibody is prepared at a final concentration of 0 or 3 µg/ml. After incubation, 100 µl of a supernatant is collected from each well and the radioactivity is determined using a gamma counter. The cytotoxic activity of an antibody conjugate can be calculated according to the same formula as that used for ADCC activity measurements.

A non-limiting embodiment of antibodies of the present invention preferably includes HuARH460-16-2 antibody, which binds to the protein of SEQ ID NO: 15 (WO2007/098575; J. Clin. Oncol. 26: 2008 (abstr 14581)). Another non-limiting embodiment preferably includes 293AC1C3H9 and W6B3H10 antibodies, which bind to the protein of SEQ ID NO: 14 (WO2011089211). Even another non-limiting embodiment preferably includes antibody Catumaxomab (Removab®), which binds to the protein of SEQ ID NO: 16. The antibodies of the present invention also preferably include EJ212/007-CI2-5 antibody, which binds to the protein of SEQ ID NO: 17 (WO2008117049). Yet another non-limiting embodiment preferably includes SN3 antibody, which binds to the protein of SEQ ID NO: 18 (US2010-0166649). Still another non-limiting embodiment preferably includes YSCMA (YS110) antibody, which binds to the protein of SEQ ID NO: 19 (WO2007014169). Still yet another non-limiting embodiment preferably includes 22B5, 24C7, 1D9, and 2D2 antibodies, which bind to the protein of SEQ ID NO: 20 (WO2009100110).

Antisense oligonucleotides for use in the present invention include, for example, polynucleotides that are complementary or hybridize to a portion of or the whole polynucleotide comprising the nucleotide sequence of any one of SEQ ID NOs: 7 to 13. Furthermore, antisense oligonucleotides may be DNAs or RNAs, and may be modified as long as the modification does not adversely affect the function. Antisense oligonucleotides for use in the present invention include not only those having nucleotides which are perfectly complementary to corresponding nucleotides that constitute a specific region of DNA or mRNA but also those having mismatches as long as the DNA or mRNA can stably hybridize to the oligonucleotides.

Complementary nucleotides preferably include, for example, nucleotides having about 90% or more, more preferably about 95% or more, and most preferably 100% homology to a partial or the entire nucleotide sequence complementary to a DNA.

The number of nucleotides in an antisense oligonucleotide is preferably 5 to 50, more preferably 9 to 25. Such antisense DNAs can be produced by using known DNA synthesizer and others.

Ribozyme as used herein refers, for example, to a ribozyme that inhibits the translation into a protein by cleaving mRNA for the protein encoded by a gene comprising the nucleotide sequence of any one of SEQ ID NOs: 7 to 13.

Ribozymes can be designed based on the gene sequence encoding an above-described protein. For example, hammerhead ribozymes can be designed by the method described in FEBS Letter, Vol. 228, pp 228-230 (1988). Not only hammerhead ribozymes but also hairpin ribozymes, delta ribozymes, and all other ribozymes are included in the ribozymes defined herein, regardless of the type of ribozyme, as long as they inhibit the translation into an above-described protein by cleaving mRNA for the protein.

Aptamers for use in the present invention can be any nucleic acid molecules as long as they inhibit the biological activity of an above-described protein, for example, by specifically binding to the protein encoded by a gene comprising the nucleotide sequence of any one of SEQ ID NOs: 7 to 13. Such aptamers include RNA aptamers and DNA aptamers.

The aptamers may be double-stranded or single-stranded nucleic acid molecules; however, single-stranded nucleic acid molecules are preferred.

The number of nucleotides in an aptamer for use in the present invention is not particularly limited, as long as the nucleotide length allows specific binding to a protein of interest and inhibiting the biological activity of the protein. The length is, for example, 10 to 200 nucleotides, preferably 20 to 150 nucleotides, and more preferably 30 to 100 nucleotides.

In the present invention, aptamers can be prepared by known methods, for example, by the SELEX method (Ellington et al., (1990) Nature, 346, 818-822; Tuerk et al., (1990) Science, 249, 505-510).

Small interfering RNA (siRNA) is a double-stranded RNA, which was reported by Elbashir et al., consisting of 21 nucleotides complementary to a gene that suppresses the expression of a gene in cells (Elbashir S M, Harborth J, Lendeckel W, Yalcin A, Weber K, Tuschl T, (2001) Nature 411: 494-498).

siRNAs for use in the present invention can be any siRNAs, as long as they have the nucleotide sequence complementary to mRNA encoding the protein encoded by a gene comprising, for example, the nucleotide sequence of any one of SEQ ID NOs: 7 to 13 and can suppress the expression of the protein.

siRNA is, for example, double-stranded RNA having 3'-overhanging dinucleotide UU or TT, and hybridized sense RNA and antisense RNA of 19 nucleotides which are complementary to a gene of the present invention. siRNA can be prepared using kits available on the market. Alternatively, siRNA can be prepared by chemical synthesis. The length of siRNA is particularly preferably 21 nucleotides or more. However, the length may be 25 nucleotide or more, and siRNA of any length is acceptable as long as it can suppress the expression of an above-described mRNA. Furthermore, it has been reported that siRNAs labeled with Cy3, FAM, or the like have a comparable suppressive effect, and siRNAs modified with these are also acceptable.

In addition, expression vectors can be used to stably express siRNAs (Brummelkamp, T R et al., (2002) Science 296: 550-553; Paddison, P J et al., (2002) Genes & Dev. 16:948-958; Paul, C P et al., (2002) Nature Biotechnol. 20: 505-508; Sui, G et al., (2002) Proc. Natl. Acad. Sci. USA 99(6):5515-5520; Yu, J-Y et al., (2002) Proc. Natl. Acad. Sci. USA 99(9):6047-6052; Miyagishi, M. and Taira, K. (2002) Nature Biotechnol. 20: 497-500; Lee, N S et al., (2002) Nature Biotechnol. 20: 500-505). For example, an siRNA is expressed using a promoter recognized by RNA polymerase III, such as polymerase III H1 RNA or U6 promoter. The sequence of 20 or more nucleotides of the gene of interest is inserted between the promoter and transcription termination signal sequence and is expressed so that an inverted repeat is formed. The inserted sequence may be any sequence, as long as it has the nucleotide sequence complementary to the nucleotide sequence of an above-described mRNA and can suppress the expression of the mRNA.

The antisense oligonucleotides, ribozymes, siRNAs, and aptamers for use in the present invention may be chemically modified at the internucleoside linkages, bases, and/or sugars, and may have modified groups at the 5' end and/or 3' end to increase their in vivo stability. Examples include phosphorothioate, phosphorodithioate, phosphoramidothioate, phosphoramidate, phosphorodiamidate, methyl phosphonate, alkylphosphotriester, and formacetal. Base modifications include, for example, 5-fluorouracil, 5-bromouracil, 5-chrolouracil, 5-iodouracil, hypoxanthine, xanthine, 4-acetylcytosine, and 5-(carboxyhydroxyethyl)uracil. Sugar modifications include, for example, 2'-O-alkyl, 2'-O-alkyl-O-alkyl, and 2'-fluoro modifications. It is also possible to use the following sugars: arabinose, 2-fluoroarabinose, xylulose, and hexose.

Methods for administering antisense oligonucleotides, ribozymes, aptamers, and siRNAs to patients include not only direct in vivo administration to patients but also methods of introduction based on gene therapy using as a vehicle an appropriate vector such as retroviral vector, adenovirus vector, or adeno-associated virus vector. The methods also include administration in combination with an uptake-enhancing adjuvant using gene gun or catheters such as hydrogel catheters.

In the description and Tables herein, when nucleotides and amino acids are represented by abbreviations, these abbreviations are based on the abbreviations by IUPAC-IUB Commission on Biochemical Nomenclature, or the conventional abbreviations in the art. Regarding amino acids, when an optical isomer exists, it represents L form, unless otherwise specified.

<Cancer Stem Cell Inhibitors of the Present Invention>

The effective dosage of cancer stem cell inhibitors of the present invention is selected within the range of 0.001 to 1,000 mg/kg weight for each administration. Alternatively, the dosage may be selected within the range of 0.01 to 100,000 mg/body for each patient. However, the dosage of the inhibitors of the present invention is not limited to these doses. Meanwhile, with respect to the timing of administration, an inhibitor of the present invention may be administered before or after manifestation of clinical symptoms of diseases. The inhibitors of the present invention can be formulated according to conventional methods (Remington's Pharmaceutical Science, latest edition, Mark Publishing Company, Easton, US), and may contain both pharmaceutically acceptable carriers and additives. Such carriers and medical additives include, for example, water, pharmaceutically acceptable organic solvents, collagen, polyvinyl alcohol, polyvinylpyrrolidone, carboxyvinyl polymer, carboxymethylcellulose sodium, sodium polyacrylate, sodium alginate, water-soluble dextran, carboxymethyl starch sodium, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants that are acceptable as a medical additive. In practice, additives are selected alone or in appropriate combination from those listed above depending on the dosage form of an inhibitor of the present invention; but are not limited thereto. For example, when used as a preparation for injection, it can be used in a form in which the inhibitor is dissolved in a medium such as physiological saline, buffer, or glucose solution and an adsorption inhibitor such as Tween80, Tween20, gelatin, or human serum albumin is added; alternatively, the inhibitor of the preset invention may be in a lyophilized form for dissolution and reconstitution before use. As excipients for lyophilization, for example, sugar alcohols and saccharides such as mannitol and glucose can be used. The inhibitors of the present invention are generally administered by a parenteral route, for example, via injection (subcutaneous, intravenous, intramuscular, intraperitoneal, etc.), transdermal, transmucosal, intranasal, or pulmonary administration; however, the inhibitor can be administered orally.

Herein, "combined use" of a cancer stem cell inhibitor and an anti-cancer agent means that these agents may be administered at the same time or in succession; alternatively, one is administered at an interval after administration of the other.

Herein, cancer stem cell inhibitors can be used as various embodiments such as, for example, prevention of cancer recurrence, suppression of cancer recurrence, prevention of cancer metastasis or recurrence, suppression of cancer metastasis or recurrence, and adjuvant therapy for preventing postoperative recurrence for application.

Anti-cancer agents that are used in combination with a cancer stem cell inhibitor of the present invention include alkylating agents, metabolic antagonists, natural products, platinum complexes, and other pharmaceutical agents. Alkylating agents include nitrogen mustards, ethylenimines, methylmelamines, alkyl sulfonates, nitrosoureas, and triazens. Nitrogen mustards include, for example, mechlorethamine, cyclophosphamide, ifosfamide, melphalan, and chlorambucil. Ethylenimines and methylmelamines include, for example, hexamethylmelamine and thiotepa. Alkyl Sulfonates include busulfan. Nitrosoureas include, for example, carmustine (BCNU), lomustine (CCNU), semustine (methyl-CCNU), and streptozocin. Triazens include dacarbazine (DTIC). Metabolic antagonists include folic acid analogs, pyrimidine analogs, and purine analogs. Folic acid analogs include methotrexate. Pyrimidine analogs include, for example, fluorouracil (5-FU), doxifluridine (5'-DFUR; trade name: FURTULON), capecitabine (trade name: Xeloda), floxuridine (FudR), and cytarabine. Purine analogs include, for example, mercaptopurine (6-MP), thioguanine (TG), and pentostatin. Natural products include vinca alkaloids, epipodophyllotoxins, and antibiotics. Vinca alkaloids include, for example, vinblastine (VLB) and vincristine (VCR). Epipodophyllotoxins include, for example, etoposide and teniposide. Antibiotics include, for example, dactinomycin (actinomycin D), daunorubicin, doxorubicin, bleomycin, plicamycin, and mitomycin. Platinum complex refers to platinum coordination complex, and includes, for example, cisplatin (CDDP) carboplatin, and oxaliplatin. Other pharmaceutical agents include: topoisomerase inhibitors such as irinotecan and camptothecin; taxols, for example, paclitaxel, docetaxel; anthracenediones, for example, mitoxantrone; urea-substituted derivatives, for example, hydroxyurea; methyl hydrazines, for example, procarbazine hydrochloride (trade name: Natulan), vitamin A metabolites, for example, tretinoin (trade name: VESANOID), as well as include rituximab, alemtuzumab, trastuzumab, bevacizumab, cetuximab, panitumumab, trastuzumab, and gemutuzumab.

Regarding cancer stem cell vaccines of the present invention, for example, the protein encoded by a gene comprising the nucleotide sequence of any one of SEQ ID NOs: 7 to 13 can be used as an immunogen. In this case, aside from $CD8^+$ T cell antigens, antigens recognized by $CD4^+$ T cells are preferably used. Such antigens (helper epitopes) include highly immunogenic foreign antigens such as KLH and tetanus toxoid as well as helper epitopes of cancer antigens themselves.

When antigen proteins are administered in the form of granules as cholesterol-polysaccharide complexes or beads, they are incorporated into dendritic cells and such, the peptides are efficiently lead through the MHC class I antigen presentation pathway, and the $CD8^+$ T cells can be induced. Alternatively, fusions of an antigen protein with a bacteria-derived heat shock protein having strong adjuvant activity can be used for strong induction of $CD8^+$ T cells.

In addition to a protein (active ingredient), the vaccines may comprise pharmaceutically acceptable carriers, for example, adjuvants, for example, mineral gels such as aluminum hydroxide; detergents such as lysolecithin and pluronic polyol; polyanions; peptides; and oil emulsions. Alternatively, they may also be incorporated into liposomes or contain polysaccharides and/or other aggregates that are admixed in a vaccine.

Further, cancer stem cell vaccines of the present invention may comprise as an immunogen, for example, a polynucleotide comprising the nucleotide sequence of any one of SEQ ID NOs: 7 to 13. Such polynucleotides include, for example, DNAs; however, the polynucleotides are not limited to this example. A recombinant virus carrying an antigen DNA can induce potent anti-tumor immunity through overexpression of the antigen in cells. This allows simultaneous expression of numerous CTL and helper epitopes, allowing use in many patients regardless of the HLA type. When frequent immunization is required, it is preferable to prepare a number of different viral vectors. Since parasitic bacteria in the fat enable presentation of antigens by both MHC class I and class II, they are useful as vaccine vectors.

Direct DNA administration, as a DNA immunization method, has been demonstrated to have an effect as a method of immunization. Unmethylated CpG sequences of bacterium-derived DNAs such as plasmids have an adjuvant activity which leads to Th1 activation, which is essential for tumor rejection, through IL-12 production and such. Methods of immunization with plasmids carrying antigen genes using intramuscular injection or gene gun only produce a weak immunization effect; however, they can be used repeatedly and in combination with other immunization methods. To improve the immunization efficiency, leader sequences may be linked to epitopes. Alternatively, it is possible to use fusion genes where an epitope is linked directly to an HLA molecule.

Furthermore, cancer stem cell vaccines of the present invention may comprise, as an active ingredient, antigen-specific dendritic cells introduced with an above-described DNA or pulsed with the protein encoded by an above-described DNA.

Dendritic cells for use in producing the cancer stem cell vaccines of the present invention can be isolated directly from peripheral blood by the specific gravity centrifugal method, or can be induced from precursor cells using cytokines or the like. When dendritic cells are isolated directly by the specific gravity centrifugal method, peripheral blood after apheresis is fractionated and prepared by the specific gravity centrifugal method. When dendritic cells are prepared through induction by cytokines, it is possible to use, as precursor cells, peripheral blood mononuclear cell adherent cell fractions, $CD14^+$ cells which are peripheral blood monocytes, $CD34^+$ cells which are hematopoietic cells in the bone marrow or peripheral blood.

Herein, "pulsing" dendritic cells means that a protein of interest alone or in the presence of pharmaceutically acceptable carriers such as liposome is contacted with dendritic cells for a pre-determined time under a pre-determined condition. For example, the contact period ranges from several minutes to several days; the condition and contact method may be, for example, the same as those described in Chiriva-Internati, M. et al., Blood (2002) 100, p. 961-965 (protein) or Thuner, B. et al., J. Exp. Med. (1999) 190, p. 1669-1678 (peptide).

All prior-art documents cited herein are incorporated herein by reference.

EXAMPLES

Herein below, the present invention will be specifically described with reference to examples, however, it is not to be construed as being limited thereto.

Establishment of Human Colorectal Cancer Cell Lines with Immunodeficient NOG Mice Colon cancer specimens were obtained from patients with their consent under approval of the ethical committees of PharmaLogicals Research (Singapore) and Parkway Laboratory Services (Singapore). Tumor blocks were cut into small pieces with a razor blade, and grafted in the lateral region of NOG mice. Human colon cancer xenografts were maintained by passaging them in NOG mice provided by the Central Institute for Experimental Animals (Japan). Mice used in this experiment were treated in accordance with the animal experiment guidelines of PharmaLogicals Research. For histopathological examination, small blocks of xenograft tumors and surgical human tissue samples were fixed with 4% paraformaldehyde at 4° C. for 16 to 24 hours, and embedded in paraffin by the AMeX method (Sato Y, et al., (1986) Am J Pathol, 125: 431-435; Sato Y, et al., (1992) Am J Pathol, 140: 775-779; Suzuki M, et al. (2002) J Toxicol Sci, 27: 165-172). The thin sections were stained with eosin and hematoxylin and assessed by microscopic observation.

Isolation and In Vitro Culture of Colon CSCs

Tissues of xenograft were cut with a razor blade in order to prepare single cancer cell suspensions. After the suspensions were incubated at 37° C. for 3 hours in DPBS containing collagenase/dispase (Roche) and DNaseI (Roche), the suspensions were filtered through 40-μm Cell Strainers (BD Biosciences). The cells were suspended in the lysis buffer (BD Biosciences) to remove erythrocytes. The prepared xenograft-derived cells were cultured under 5% $CO_2$ atmosphere at 37° C. in DMEM/F12 (Invitrogen) containing N-2 Supplement (Invitrogen), 20 ng/ml human EGF (Invitrogen), 10 ng/ml human basic fibroblast growth factor (Sigma), 4 μg/ml heparin (Sigma), 4 mg/ml BSA (Invitrogen), 20 μg/ml human insulin zinc solution (Invitrogen), and 2.9 mg/ml glucose (Sigma) (Todaro M, et al. (2007) Cell Stem Cell 1: 389-402). Adherent and floating CSCs were cultured using conventional polystyrene-treated cell culture flasks (BD Biosciences) and Ultra-low attachment cell culture flasks (Corning), respectively.

In Vivo Tumor Formation Analysis

Cell suspensions were prepared by serial dilution. 100 μl of cancer cell suspensions in Hanks' balanced salt solution (Invitrogen) were subcutaneously inoculated into lateral region of mice using 50% matrigel (BD Bioscience). The tumor development was monitored over seven weeks. In order to inoculate single cell, cells were labeled using an FITC-labeled mouse anti-human CD326 (EpCAM) antibody (Miltenyi Biotec), and plated in a terasaki plate (Termo Fisher Scientific). Cell singularity was confirmed under a microscope. Single cells were inoculated into lateral region of mice using 50 μl of 50% matrigel. The tumor development was monitored over 10 weeks.

Establishment of Cells Expressing Full-length Human Lgr4, Lgr5, and Lgr6

Full-length human Lgr4, Lgr5, and Lgr6 cDNAs were cloned by PCR based on the sequences of NM_018490 (Lgr4), NM_001017403 (Lgr5), and NM_003667 (Lgr6). The cloned genes were expressed with or without adding HA tag to their N termini Cells of Chinese hamster ovary cell line CHO DG44 (Invitrogen) were transfected with expression plasmids using Gene Pulser (BioRad). Stable cell lines HA-Lgr4/DG, HA-Lgr5/DG, and HA-Lgr6/DG were selected using G418.

Preparation of Soluble Lgr5-Fc Protein

Soluble Lgr5 protein (amino acids 1 to 555) was expressed as a fusion protein with the Fc domain of mouse IgG2a in CHO DG44. Transfectants were screened by sandwich ELISA using a goat anti-mouse IgG2a (Bethyl laboratories) and HRP-rat anti-mouse IgG2a mAb (Serotec). A clone that produces sLgr5-Fc at the highest level was named 2D3. A culture supernatant of 2D3 was collected, and Lgr5-Fc protein was affinity-purified using a Protein A-Sepharose column (Pharmacia). Lgr5-Fc was used as an antigen in protein immunization and ELISA screening.

Generation of Anti-Lgr5 Monoclonal Antibody by Immunization with Lgr5-Fc Protein Balb/c mice (Charles River Japan) were immunized subcutaneously with 50 μg of Lgr5-Fc emulsified in Freund's complete adjuvant. After two weeks, the mice were injected with the same amount of Lgr5-Fc in Freund's incomplete adjuvant once a week over two weeks. Three days before cell fusion, 25 μg of Lgr5Fc was intravenously injected to the mice. Spleen lymphocytes derived from the immunized mice were fused with cells of mouse myeloma line P3-X63Ag8U1 (ATCC) using a conventional method (Kremer L and Marquez G (2004) Methods Mol. Biol., 239: 243-260). Hybridoma culture supernatants were screened for antibodies reactive to sLgr5-Fc by ELISA to establish Lgr5-specific mouse mAb 2L36, 2T15E-2 and 2U2E-2.

Flow Cytometry Analysis

Colon CSCs were incubated with labeled antibodies and analyzed using the EPICS ALTRA (Beckman Coulter) and FACSCalibur (Becton Dickinson)). Antibodies used were: PE-labeled mouse anti-human CD133 antibody (Miltenyi Biotec), PE-labeled mouse anti-human CD44 antibody (BD Pharmingen), FITC-labeled mouse anti-human CD326 (Ep-CAM) antibody (Miltenyi Biotec), PE-labeled mouse anti-human CD166 antibody (R&D Systems), PE-labeled mouse anti-human CD24 antibody (BD Pharmingen), PE-labeled mouse anti-human CD26 antibody (BD Pharmingen), and PE-labeled mouse anti-human CD29 antibody (BD Pharmingen).

Colon CSCs were incubated with mouse anti-human Lgr5 antibody (2T15E-2) and then with PR-labeled rat anti-mouse IgG antibody (Invitrogen) to stain Lgr5. The aldehyde dehydrogenase activity was measured using the AldeFluor Kit (Stemcell Technologies). Mouse cells were discriminated from human colon CSCs by staining with anti-mouse MHC class I antibody (Abcam), and PE- or APC-labeled goat anti-human IgG2a antibody (BioLegend). Dead cells were also removed using the 7-AAD Viability Dye (Beckman Coulter).

Western Blot Analysis

Protein was extracted using RIPA buffer (Sigma) supplemented with the Complete Mini Protease Inhibitor Cocktail (Roche). Proteins were fractionated by the NuPAGE Gel (Invitrogen) and transferred onto PVDF membrane. After blocking with PBS containing 1% skimmed milk, the membrane was probed with rabbit anti-human β-catenin antibody (Sigma), rabbit anti-human phospho-c-JUN antibody (Sigma), rabbit anti-human TCF1 antibody (Cell Signaling), rabbit anti-human TCF3 antibody (Cell Signaling), rabbit anti-human TCF4 antibody (Cell Signaling), rabbit anti-human Lgr5 antibody (Abcam), mouse anti-human E-cadherin antibody (Abcam), rabbit anti-human Snail antibody (Abcam), and mouse anti-human GAPDH antibody (Santa Cruz). Reactive bands were detected using BCIP/NBT substrate (KPL).

Quantitative Real-time Polymerase Chain Reaction

Total RNAs were isolated using the RNeasy Mini Kit including DNAase treatment (Qiagen). cDNAs were synthesized using the First-Strand cDNA Synthesis Kit (SABiosciences). Quantitative real-time PCR (QRT-PCR) analysis was performed with the SYBR Green/Rox qPCR (SABiosciences) using the Mx3005P Real-Time PCR System (Stratagene). The fold induction value was calculated according to the 2-ΔΔCt method. GAPDH and ACTB were used as a reference. All experiments were performed in triplicate.

Primers for Quantitative Real-time PCR Analysis

The following primers were used to amplify reactive transcripts.

```
Lgr5:
forward primer:
                                  (SEQ ID NO: 1)
5'-AGTTTATCCTTCTGGTGGTAGTCC-3';

reverse primer:
                                  (SEQ ID NO: 2)
5'-CAAGATGTAGAGAAGGGGATTGA-3';

GAPDH:
forward primer:
                                  (SEQ ID NO: 3)
5'-CTCTGCTCCTCCTGTTCGAC-3';

reverse primer:
                                  (SEQ ID NO: 4)
5'-ACGACCAAATCCGTTGACTC-3';

ACTB:
forward primer:
                                  (SEQ ID NO: 5)
5'-AAGTCCCTTGCCATCCTAAAA-3';

reverse primer:
                                  (SEQ ID NO: 6)
5'-ATGCTATCACCTCCCCTGTG-3'

Bmi1:
forward primer:
                                 (SEQ ID NO: 21)
5'-AACCATTGTTTGGATTTGGAAG-3';

reverse primer:
                                 (SEQ ID NO: 22)
5'-ACAAACTATGGCCCAATGCT-3';

Hopx:
forward primer:
                                 (SEQ ID NO: 23)
5'-CGTAACCTCGGCATACTTTCA-3';

reverse primer:
                                 (SEQ ID NO: 24)
5'-CGAGCAAGGACCTGAAAAAC-3'
```

Cell Proliferation Assay

Floating and adherent cells were plated at about 100 and $1\times10^4$ cells/well in 96-well plates, respectively. On days 0 and 3, viable cell counts were determined by the Cell Counting Kit-8 Assay (Doujindo) according to the manufacturer's protocol. Average absorbance on day 0 was taken as 100%. For chemosensitivity assay, floating and adherent cells were plated at about 100 and $1\times10^4$ cells/well in 96-well plates, respectively. After 24 hours of incubation, 10 μg/ml 5-FU (Hospira), 10 μg/ml irinotecan (Hospira), 50 mM TCF inhibitor FH535 (Merck), or 50 mM β-catenin inhibitor Cardamonin (Merck) were added to the plates. After three days of culture in the presence of the agents, the Cell Counting Kit-8 was added to the cells. The average absorbance of cells exposed to DMSO or medium alone was taken as 100%. All experiments were performed in triplicate.

Immunofluorescent Staining of Cultured Cells and Xenograft Tissues

For immunofluorescent cytochemistry, cells were fixed with 4% paraformaldehyde and methanol, and incubated with a mouse anti-human E-cadherin antibody (Abcam), rabbit anti-human Snail antibody (Abcam), or rabbit anti-human β-catenin antibody (Sigma)). Then, the cells were visualized using the AlexaFluor 488-labeled goat anti-mouse IgG antibody or goat anti-rabbit IgG antibody. For immunofluorescent cytochemistry, the fixed cells and thin sections derived from paraffin blocks of xenograft tumors were incubated with a mouse anti-human Lgr5 antibody (2U2E-2) or rabbit anti-human Snail antibody (Abcam), rabbit anti-human HLA-DMA antibody (Sigma), rabbit anti-TMEM173 antibody (Abcam), rabbit anti-human ZMAT3 antibody (Abcam), or rabbit anti-human GPR110 antibody (Abcam). After incubation with the primary antibody, Lgr5 protein was detected with a goat anti-mouse antibody conjugated with polymer-HRP (DAKO) and visualized with AlexaFluor 488-labeled tyramide (Invitrogen), while Snail, HLA-DMA, and TMEM173 proteins were detected with a biotinylated goat anti-rabbit antibody (VECTOR) and visualized with AlexaFluor 568-labeled streptavidin (Invitrogen). These cells and samples were also stained with DAPI (Invitrogen). ZMAT3 and GPR110 proteins were detected with a goat anti-rabbit antibody conjugated with polymer HRP (DAKO) and visualized with diaminobenzidine. The cells and samples were stained with Mayer's hematoxylin (Muto Pure Chemicals Co.).

Symmetric and Asymmetric Cell Division Assay

Lgr5-positive CSCs were stained with dye pKH67 (Sigma) according to the instruction manual. To differentiate Lgr5-positive CSCs, the cells were plated on 50% matrigel (BD Bioscience) layer in each well of 96-well plates, and were cultured in a stem cell medium supplemented with 5% heat-inactivated calf serum and 5% matrigel. Symmetric and asymmetric cell divisions were monitored using a fluorescent microscope.

Example 1

Establishment of Colon Cancer Xenografts

As described in a previous report (Fujii E. et al., (2008) Establishment and characterization of in vivo human tumor models in the NOD/SCID/gamma(c)(null) mouse. Pathol Int 58: 559-567), the present inventors established 11 types of human colon cancer xenografts using NOD/Shi-scid, IL-2Rγnull (NOG) mice (Table 1; the number of human colorectal cancer cell lines established with immunodeficient NOG mice).

TABLE 1

| | Adenocarcinoma | | | |
| Number of cases | G1 | G2 | G3 | Total |
| --- | --- | --- | --- | --- |
| | 4 | 46 | 3 | 53 |
| Established | 0 | 10 | 1 | 11 |
| Impracticable* | 0 | 6 | 0 | 6 |
| EBV lymphoma | 2 | 16 | 1 | 19 |
| Aggravated animal condition† | 1 | 12 | 1 | 14 |
| No viable cancer | 1 | 2 | 0 | 3 |

In the above Table 1, asterisk indicates cases established but unsuitable for experiment, and dagger indicates cases with infection and such.

As shown in Table 1, 17 types of colon cancer xenografts were established from samples of 53 human colorectal cancer patients. Except for the 17 types of xenografts, associated EBV-infected lymphoma cells occurred in 19 cases (which aggravated the condition of NOG mice); other infections were found in 14 cases; and no tumor growth was observed in three cases. Of the 17 types, 11 xenografts survived even after freeze-thawing, and had the capacity to reconstitute tumor, and showed similar histopathological features as those of the original tumors. Of the 11 types, 10 xenografts were derived from grade-2 moderately-differentiated adenocarcinomas, and the remaining one was derived from a grade-3 poorly-differentiated adenocarcinoma.

Of the 11 types, 10 xenografts were derived from moderately-differentiated colon cancer (MDCC), and the remaining one was derived from poorly-differentiated colon cancer (PDCC) (Table 2; histopathological classification of the original human colon cancers that were used to establish the 11 xenografts).

TABLE 2

Histopathological classification of original human tumor

| Line No. | Type | Grade | TNM | AJCC stage | Dukes' stage |
| --- | --- | --- | --- | --- | --- |
| PLR30 | Adenocarcinoma | G2 | pT3N0MX | II | B |
| PLR59 | Adenocarcinoma | G2 | pT3N2MX | III | C2 |
| PLR123 | Adenocarcinoma | G2 | pT4N1MX | III | C1 |
| PLR168 | Adenocarcinoma | G2 | pT3N0MX | II | B |
| PLR215 | Adenocarcinoma | G2 | pT3N0MX | II | B |
| PLR241 | Adenocarcinoma | G2 | pT4N3M1 | IV | D |
| PLR254 | Adenocarcinoma | G2 | pT4N2MX | III | C2 |
| PLR261 | Adenocarcinoma | G2 | pT3N0MX | II | B |
| PLR325 | Adenocarcinoma | G3 | pT4N1M1 | III | C1 |
| PLR379 | Adenocarcinoma | G2 | pT4N2MX | IIIC | C1 |
| PLR423 | Adenocarcinoma | G2 | pT3N0M1 | IV | D |

Figure 16:
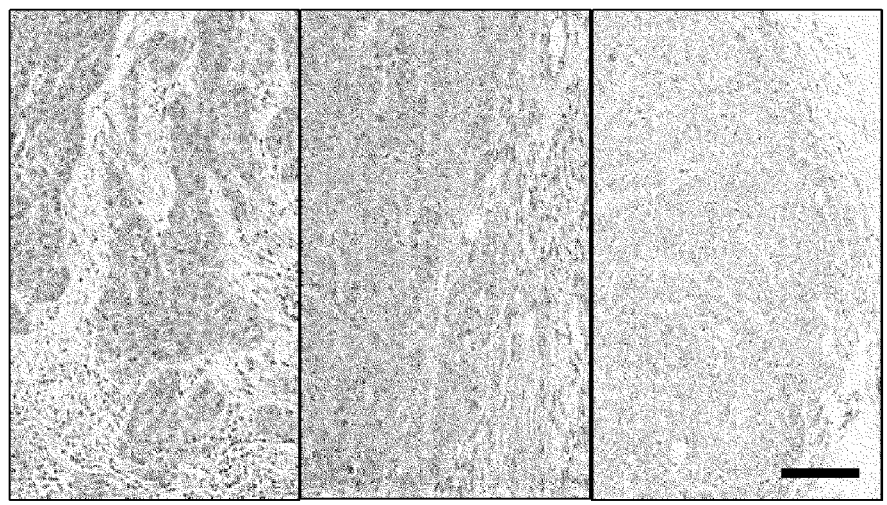
FIG. 16 shows photographs depicting histopathological features of xenograft tissues. Histopathological PDCC xenografts derived from a poorly-differentiated colon cancer (PDCC) xenograft reconstructed almost the same histopathological morphology as the original tumor. The PDCC xenografts did not have apparent epithelial duct structures (4 and 13 passages). Scale bar represents 100 μm.

Both MDCC and PDCC xenografts reconstituted histopathological morphologies almost equivalent to those of the original tumors. MDCC xenografts formed specific epithelial ducts which contained goblet cells, and small budding clusters (may undergo epithelial-mesenchymal transition (EMT)). In contrast, PDCC xenografts did not form such specific epithelial duct structures (FIGS. 1 and 16).

Example 2

Isolation of Colon CSCs

In order to isolate colon CSCs, the present inventors used two types of MDCC xenografts, i.e., PLR59 and PLR123. These xenografts were chosen by the present inventors because they grew rapidly even after 10 passages in NOG mice while maintaining the capacity to reconstitute tumors with epithelial ducts and small budding clusters (FIG. 1). Thus, the present inventors predicted that stable CSCs can be obtained from the xenografts.

Figure 2:
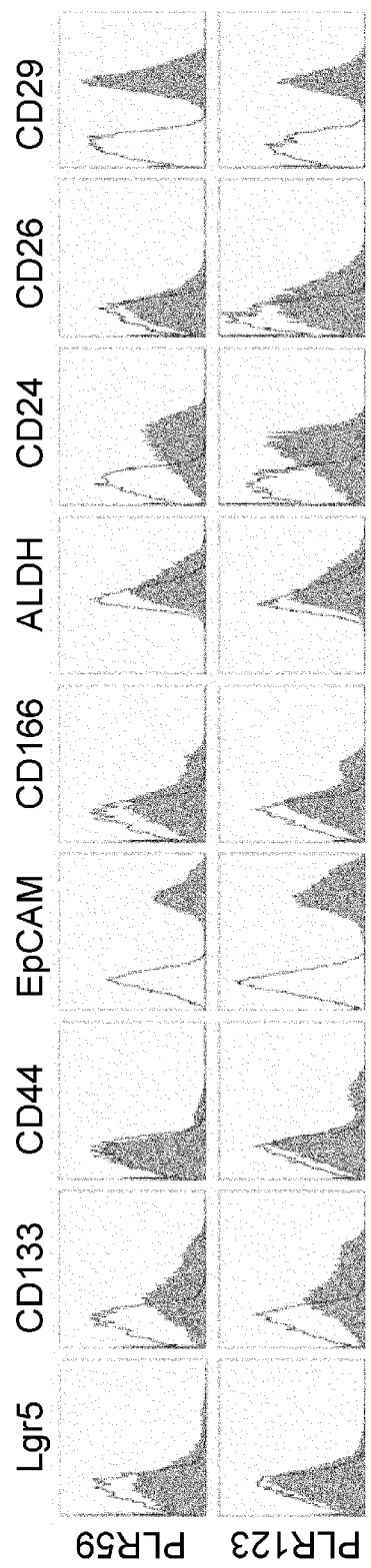
FIG. 2 is a diagram showing a result of flow cytometry analysis of cells from xenografts PLR59 and PLR123 for known CSC markers. The cells were stained with antibodies against the markers indicated and then analyzed with flow cytometry. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 3:
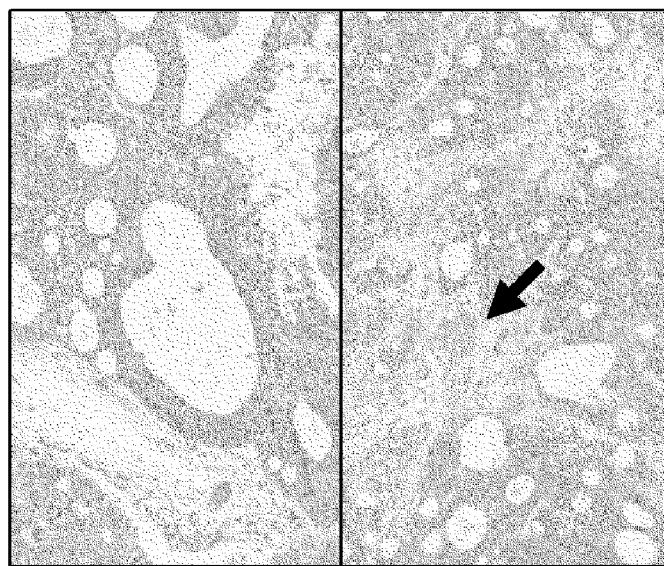
FIG. 3 shows photographs depicting histological images (HE stain) of tumors formed by injection of 100 cells each of PLR59 and PLR123 cells. The morphologies of the tumors derived from 100 cells each of PLR59 and PLR123 cells were highly similar to the original tumors. Arrows indicate budding clusters. Scale bar represents 100 μm.
Figure 3:
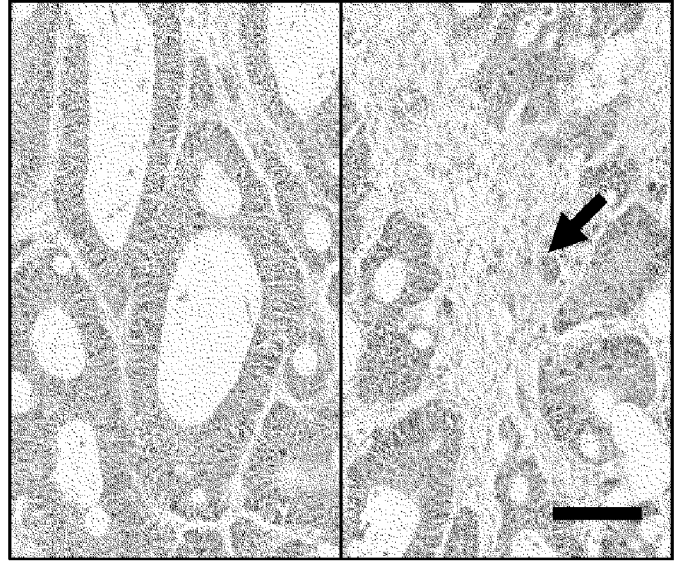
Figure 4:
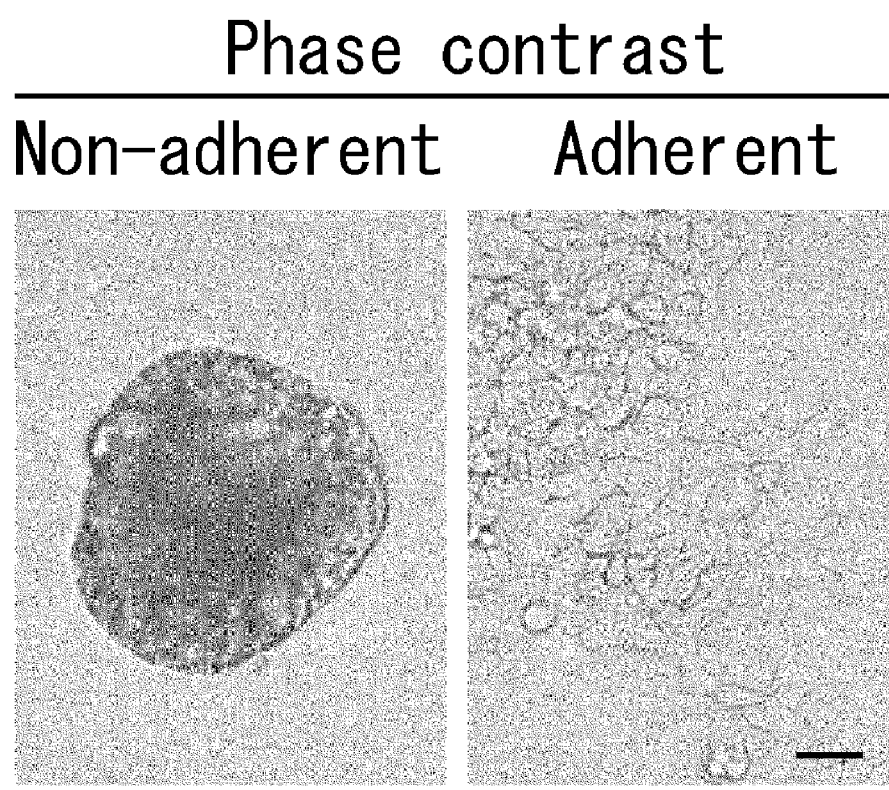
FIG. 4 shows photographs depicting a result of phase contrast microscopic observation of non-adherent and adherent cells. The cells were cultured in serum-free media supplemented with EGF and FGF. The non-adherent cells closely interacted together to form a spheroid-like structure, whereas the adherent cells proliferated without forming clusters. Scale bar represents 25 μm.
Figure 5:
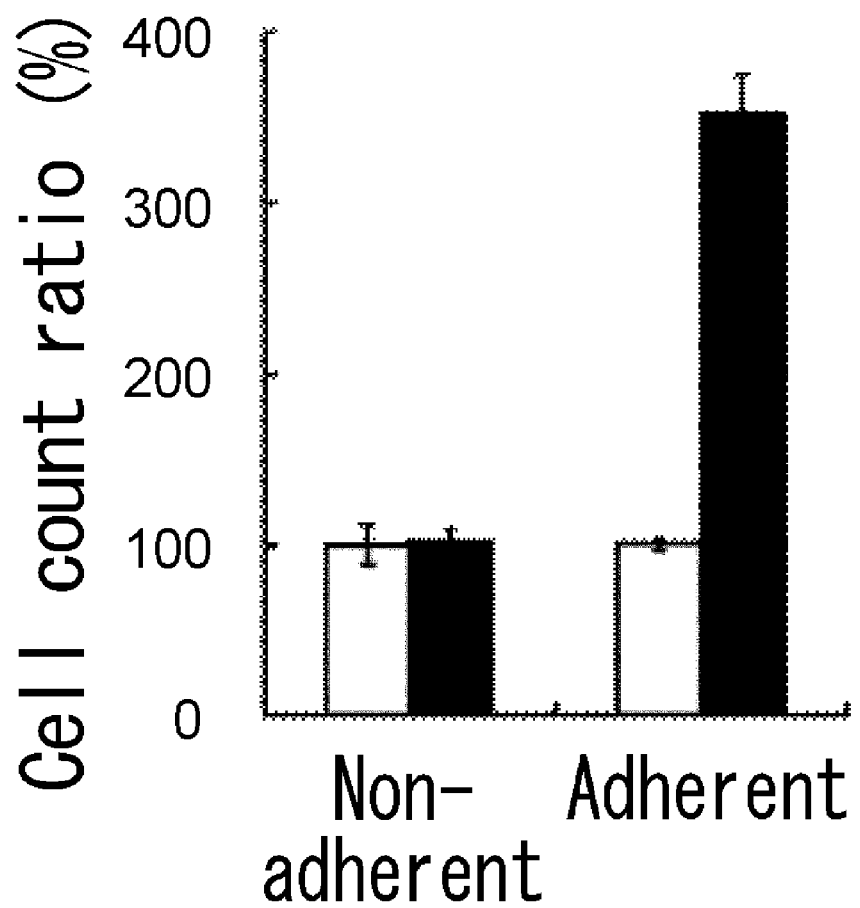
FIG. 5 is a diagram showing the proliferation of non-adherent and adherent CSCs. The viable cell count after three days of culture (black column) is shown in percentage to the count on day 0 (white column). The results were averaged from three experiments. The bar at the top of each column represents standard deviation.

Flow cytometry analysis of primary cells derived from PLR59 and PLR123 showed that CD44, ALDH, CD26, and Lgr5 were lower in the signal level than CD133, EpCAM, CD166, CD24, and CD29. This suggests the existence of a small population of CSCs (FIG. 2). When the cells were subcutaneously grafted to NOG mice, tumors were formed at about half of the injection sites by 100 cells derived from either xenograft (five out of 12 injection sites; Table 3), and the tumors highly resembled the original tumors in histopathological morphology (FIG. 3). At 10 cells/injection site, however, PLR59 and PLR123-derived cells injected subcutaneously did not form any tumors in NOG mice (Table 3). Table 3 shows the tumor formation ability of purified CSCs 49 hours after inoculation.

TABLE 3

| Cell line* | Specimen † | Number of cells/inoculation site | | |
| --- | --- | --- | --- | --- |
| | | 1,000 | 100 | 10 |
| PLR59 | Primary | 12$^+$/12$^‡$ | 5/12 | 0/12 |
| | | (100) | (42) | (0) |
| | Non-adherent (Lgr5−) | 6/6 | 6/6 | 1/6 |
| | | (100) | (100) | (17) |
| | Adherent (Lgr5+) | 6/6 | 6/6 | 6/6 |
| | | (100) | (100) | (100) |
| PLR123 | Primary | 12/12 | 5/12 | 0/12 |
| | | (100) | (42) | (0) |
| | Non-adherent (Lgr5−) | 6/6 | 5/6 | 2/6 |
| | | (100) | (83) | (33) |
| | Adherent (Lgr5+) | 6/6 | 6/6 | 6/6 |
| | | (100) | (100) | (100) |

In Table 3 shown above, the asterisk indicates tumor xenograft established in NOG mice, and dagger indicates cell preparation. Primary indicates a suspension of a single cell from a xenograft tumor tissue grown in a NOG mouse; non-adherent indicates cells prepared by in vitro culture under a non-adherent culture condition; and adherent indicates cells prepared by in vitro culture under an adherent condition. Plus symbol (single) indicates the number of animals exhibiting tumor, while plus symbol (double) indicates the total number of animals. Parenthesis indicates the percentage of tumor-bearing animals. Lgr5$^+$ represents Lgr5 positive, and Lgr5$^-$ represents Lgr5 negative.

Figure 6:
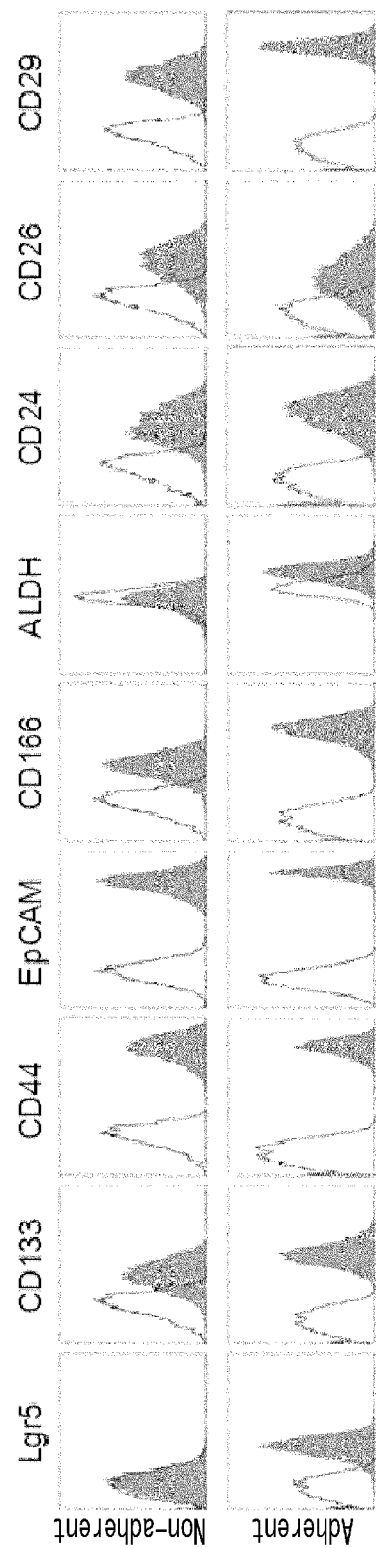
FIG. 6 is a diagram showing a result of flow cytometry analysis of non-adherent cells and adherent cells for known CSC markers. Both types of cells were positive for known CSC markers such as CD133, CD44, EpCAM, CD166, CD24, CD26, and CD29, while the adherent cells alone were positive for Lgr5 and ALDH activity. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 20:
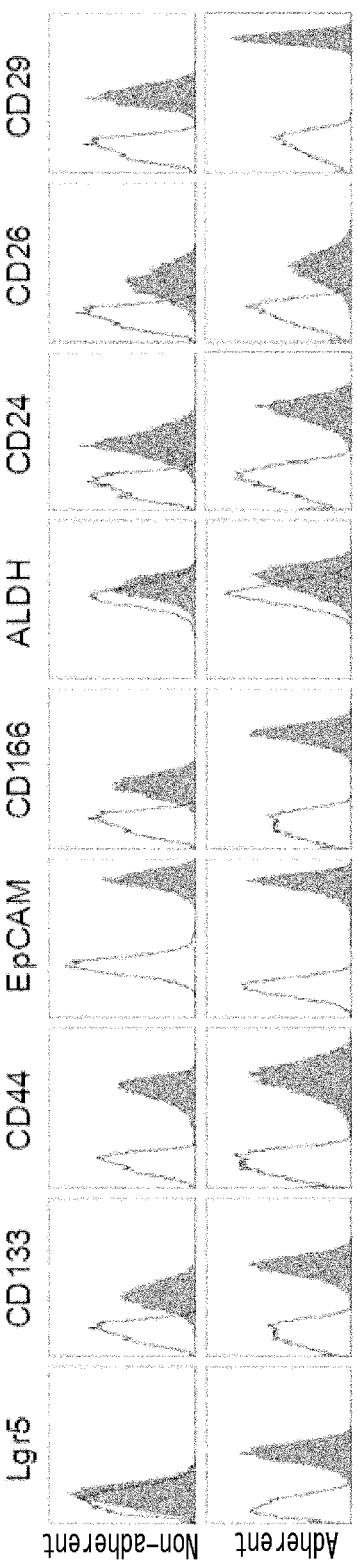
FIG. 20 is a diagram showing a result of flow cytometry analysis of non-adherent and adherent cells for known CSC markers. Adherent cells were positive for all markers reported, whereas non-adherent cells were negative for Lgr5 and ALDH. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.

Cells derived from PLR59 and PLR123 were cultured in serum-free media supplemented with EGF and FGF. This yielded adherent and non-adherent cells. The present inventors harvested the adherent and non-adherent cells and cultured them separately. The adherent cells were grown with a doubling time of about 2.5 days and exhibited mesenchymal cell-like morphology. The non-adherent cells, on the other hand, formed spheroid-like cell clusters but did not proliferate significantly (FIGS. 4, 5, 18, and 19). After one-week or longer culture, the cells were assessed for colon CSC markers. This demonstrated that both adherent and non-adherent cells were highly homogeneous. The adherent cells were of Lgr5$^+$, ALDH$^+$, CD133$^+$, CD44$^+$, EpCAM$^+$, CD166$^+$, CD24$^+$, CD26$^+$, and CD29$^+$. The non-adherent cells were of Lgr5$^-$ and ALDH$^-$, and thus were different from the adherent cells (FIGS. 6 and 20).

Figure 27:
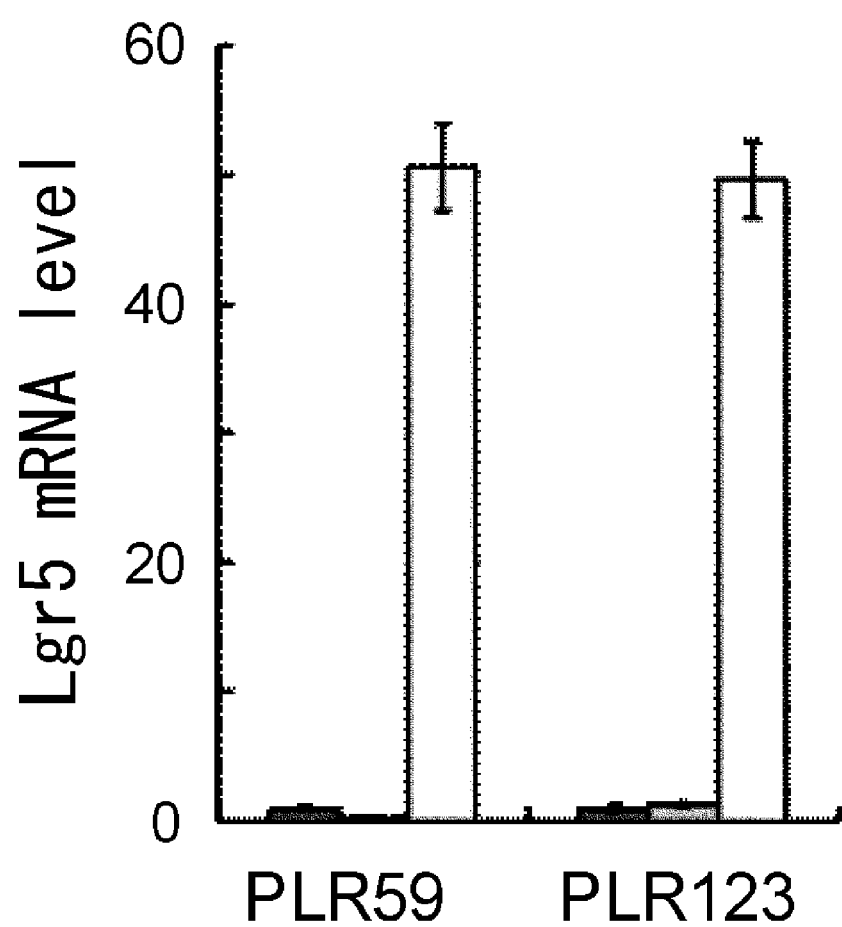
FIG. 27 is a diagram showing the levels of Lgr5 mRNA in pure CSCs. Levels of Lgr5 mRNA in adherent and non-adherent CSCs are shown as a ratio to the levels in primary cells from xenograft tumors PLR59 and PLR123. The level of Lgr5 mRNA in adherent CSCs (right, white column) was remarkably increased as compared to the level in the primary cells from xenografts (black column), while the level was not increased in non-adherent CSCs (gray column). Lgr5 mRNA levels were determined by quantitative PCR followed by normalization with the expression of GAPDH and ACTB. All experiments were performed in triplicate. Error bars represent standard deviation.

It has been reported that Wnt activity is also a characteristic of colon CSC spheroid culture and that Lgr5 is regulated via Wnt signaling (Vermeulen L, et al. (2010) Wnt activity defines colon cancer stem cells and is regulated by the microenvironment. Nat Cell Biol 12:468-476). Lgr5 mRNA was detected at a significant level in the adherent cells, while it was undetectable in non-adherent cells (FIG. 27).

Example 3

Analysis of Lgr5 Protein Expression

Figure 28:
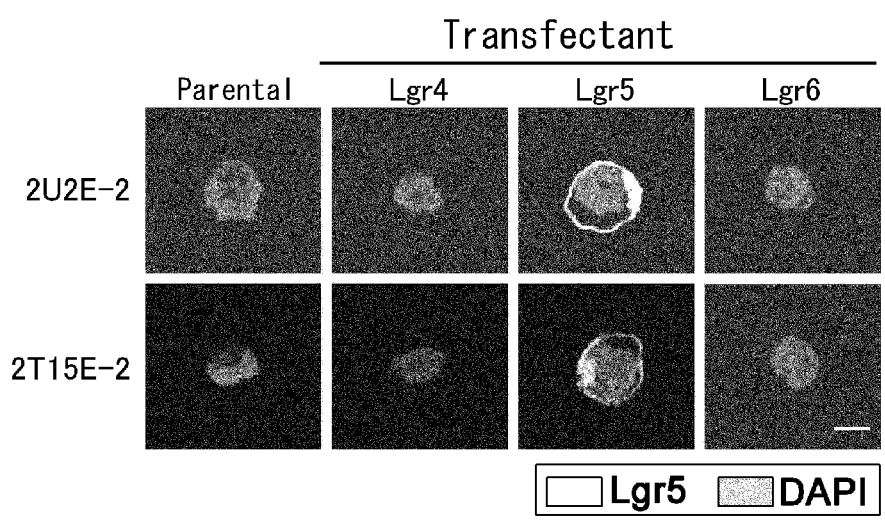
FIG. 28 shows photographs depicting a result of specificity assessment of anti-human Lgr5 monoclonal antibodies (mAbs) 2U2E-2 and 2L36 by immunofluorescence microscopy observation of DG44 cells transfected with Lgr4, Lgr5, or Lgr6 cDNA. The transfectants and non-transfected parental cells were fixed and treated with 5 µg/mL antibodies. Intense fluorescence (green signals at right) was observed in cells containing Lgr5 cDNA but not in parental cells and cells containing Lgr4 or Lgr6 cDNA. Scale bar represents 5 µm.
Figure 29:
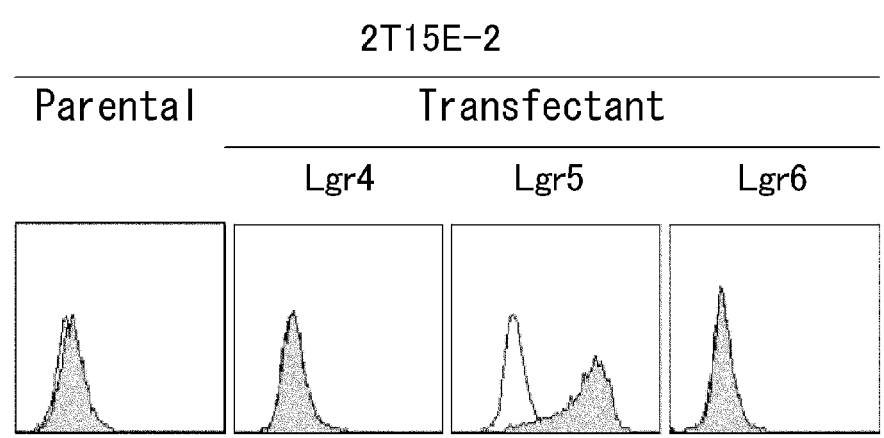
FIG. 29 is a diagram showing a result of specificity assessment of anti-human Lgr5 monoclonal antibody (mAb) 2T15E-2 by flow cytometry of DG44 cells transfected with Lgr4, Lgr5, or Lgr6 cDNA. The transfectants and non-transfected parental cells were incubated with monoclonal antibody 2T15E-2 and analyzed by FACS. Antibody 2T15E-2 reacted with cells containing Lgr5 cDNA but not with parental cell and cells containing Lgr4 or Lgr6 cDNA. The expression of Lgr4, Lgr5, and Lgr6 in the transfectants was assessed by Western blot analysis.

In order to assess the expression of Lgr5 protein, the present inventors prepared three types of Lgr5-specific monoclonal antibodies (2L36, 2T15E-2, and 2U2E-2) respectively for immunohistochemistry and flow cytometry analysis. The antibodies produced by the present inventors were highly specific to Lgr5 without any cross-reactivity to Lgr4 or Lgr6, both of which are highly homologous to Lgr5 (FIGS. 28 and 29). Using the antibodies, the present inventors demonstrated the expression of Lgr5 in the adherent CSCs. Some studies describe that ALDH serves as a colorectal cancer stem cell-specific marker in tumorigenesis. On the other hand, it was also reported that the involvement of ALDH activity as a marker was only assessed in terms of the coexistence of this marker in relation to CD44 positivity or CD133 positivity (Chu P, et al. (2009) Characterization of a subpopulation of colon cancer cells with stem cell-like properties. Int J Cancer 124:1312-1321; Huang E H, et al. (2009) Aldehyde dehydrogenase 1 is a marker for normal and malignant human colonic stem cells (SC) and tracks SC overpopulation during colon tumorigenesis. Cancer Res 69:3382-3389). In experiments by the present inventors, Lgr5-positive adherent cells were positive for ALDH whereas Lgr5-negative non-adherent cells were negative for ALDH.

Figure 37:
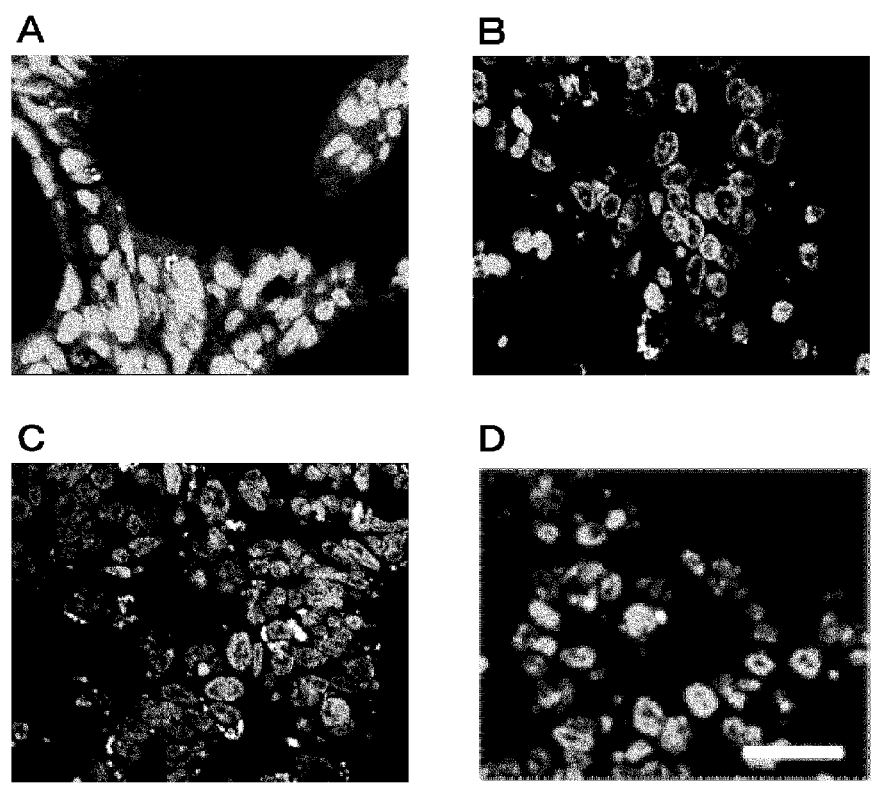
FIG. 37 shows photographs depicting immunostaining of tumor (PLR123) obtained by surgical resection, and a PLR123-derived xenograft model (5 passages (FIG. 37B), 10 passages (FIG. 37C), and 15 passages (FIG. 37D)) in terms of Lgr5. Tissue sections were stained with anti-Lgr5 antibody. "Original" indicates the tumor obtained from a patient by surgical resection (FIG. 37A). Scale bar represents 25 µm.

Lgr5-positive cells were detected in tumor tissues that were the origins of PLR59 and PLR123 as well as in xenograft cancer tissues therefrom through all passages (FIG. 37). The frequency of Lgr5-positive cells was low in the original tumor tissues (0.01% and 0.04% for PLR59 and PLR123, respectively). Regarding the xenograft cancer tissues, the frequency of Lgr5-positive cells was increased as passage number increased; however, there was no further change after tenth generation (FIG. 37). On the other hand, the tumor-reconstituting capacity of primary cells from PLR123 xenograft model was also potentiated as passage number increased. The ratio of CSCs in the primary cells, which was estimated based on the capacity to reconstitute tumor, was about 0.1% after 5 passages, and was increased to about 0.4% after 14 passages.

Example 4

Tumor-reconstituting Capacities of Lgr5-Positive and Lgr5-Negative Colon CSCs

If a group of colon cancer stem cells is characterized by Wnt signaling, Lgr5-positive adherent cells alone can form tumors in vivo. To confirm whether this prediction is true, the present inventors assessed the tumor-forming capacities of Lgr5-positive adherent cells and Lgr5-negative non-adherent cells.

Figure 17:
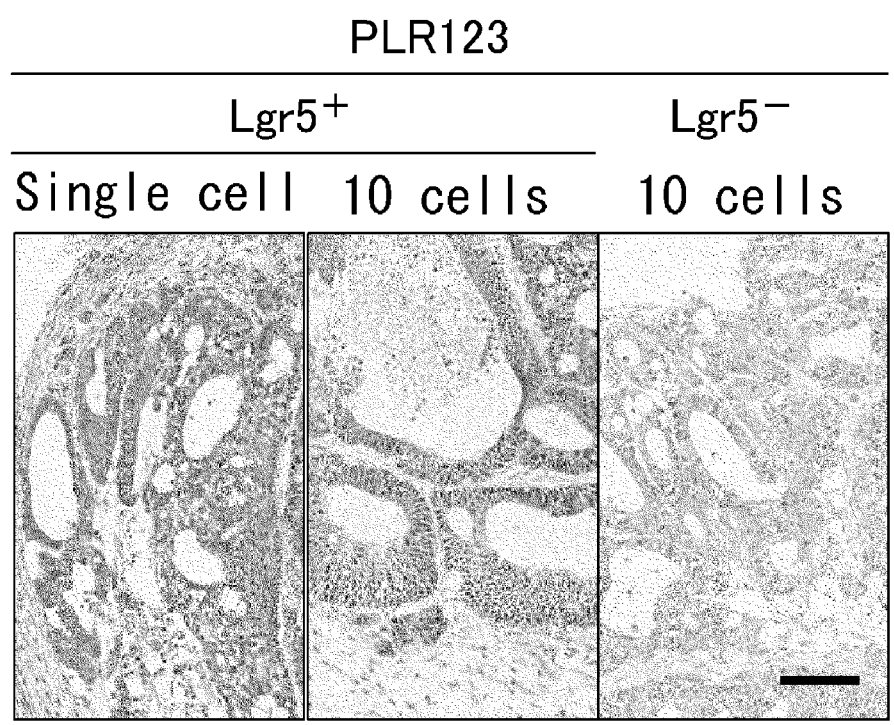
FIG. 17 shows photographs depicting a histopathological result on xenograft tumors that originated from a single or ten Lgr5-positive cells derived from PLR123, or ten Lgr5-negative cells derived from PLR123. The histopathological features of all tumors were highly similar to the original tumor. Scale bar represents 100 μm.
Figure 18:
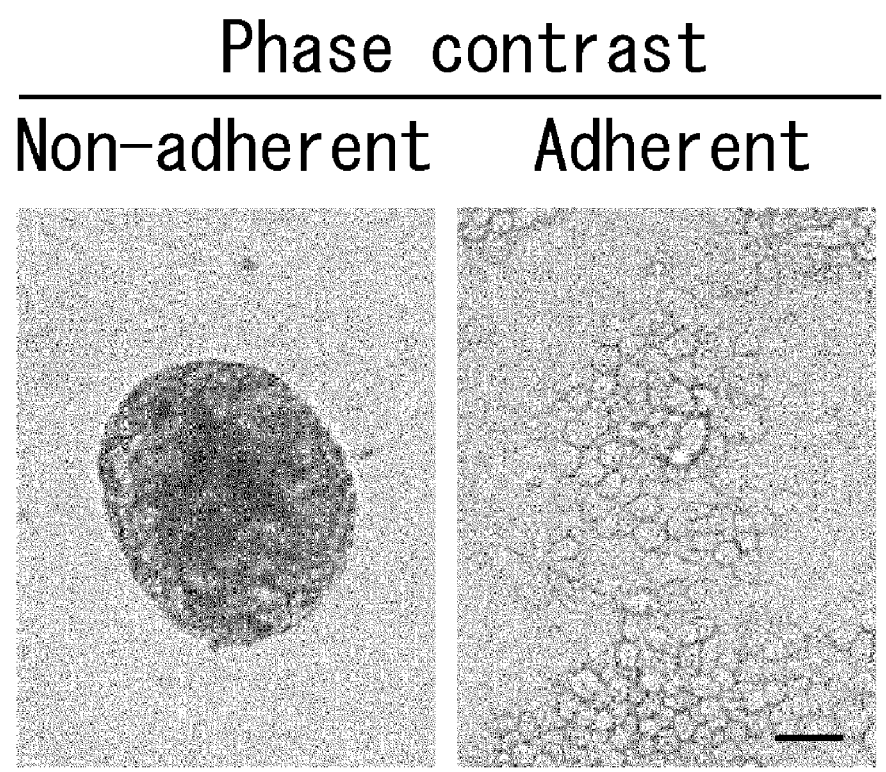
FIG. 18 shows photographs depicting a result of phase contrast microscopic observation of non-adherent and adherent colon CSCs. The cells were cultured in serum-free media supplemented with EGF and FGF. The non-adherent cells closely interacted together to form a spheroid-like structure, whereas the adherent cells proliferated without forming clusters. Scale bar represents 25 μm.
Figure 19:
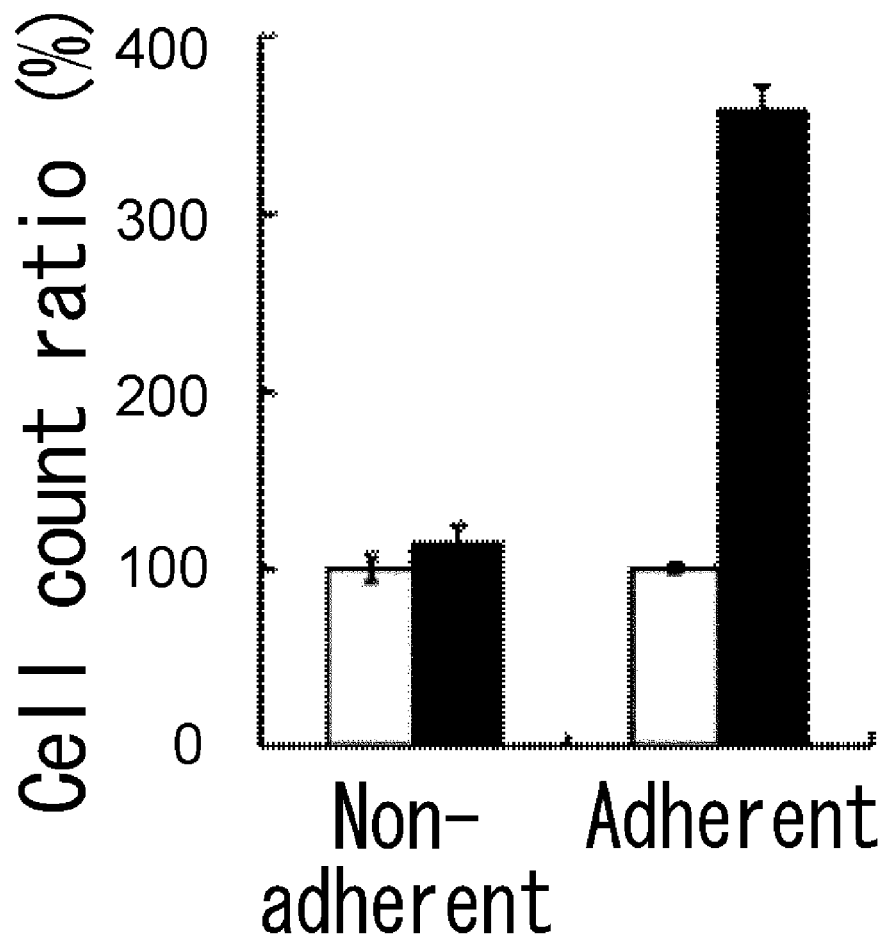
FIG. 19 is a diagram showing the proliferation of non-adherent and adherent CSCs. The viable cell count after three days of culture (black column) is shown in percentage to the count on day 0 (white column). The results were averaged from three experiments. The bar at the top of each column represents standard deviation.
Figure 30:
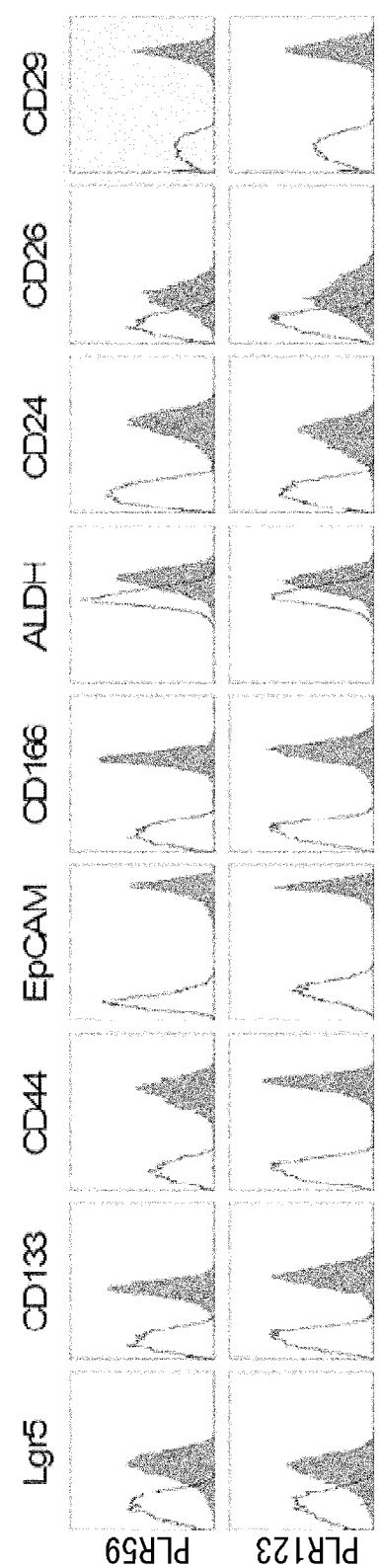
FIG. 30 is a diagram showing a result of flow cytometry analysis of adherent CSCs derived from xenografts PLR59 and PLR123. The cells were cultured for one month and analyzed for known cancer stem cell markers. Even after one month of in vitro culture, adherent CSCs derived from PLR59 and PLR123 were positive for all of known cancer stem cell markers. Gray area indicates the ALDH activity or fluorescence intensity of cells after staining with the indicated antibodies. White area indicates the treatment of cells by the ALDH activity in the presence of an ALDH inhibitor or the fluorescence intensity of cells after staining with isotype antibodies as a control.
Figure 38:
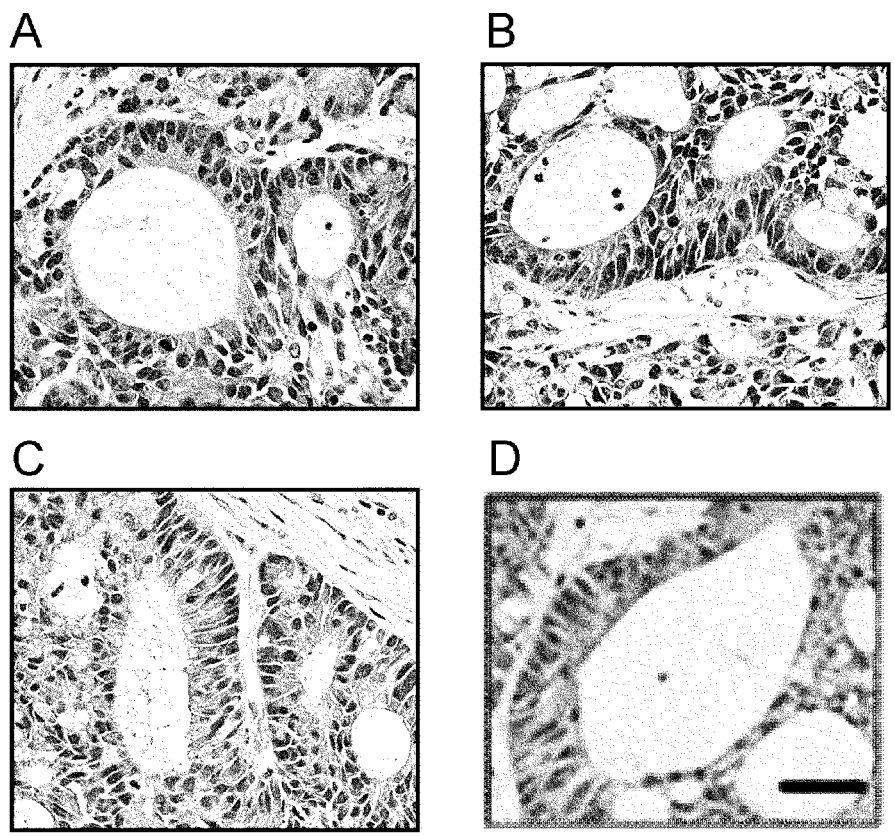
FIG. 38 shows photographs depicting a histopathological result (HE stain) on xenograft tumors derived from Lgr5-positive cells of PLR59 (FIGS. 38A and 38B) and PLR123 (FIGS. 38C and 38D). NOG mice were subcutaneously injected with ten (FIGS. 38A and 38C) or a single (FIGS. 38B and 38D) Lgr5-positive cell(s) obtained from PLR59 or PLR123 by adherent culture. All tumors showed histopathological features highly similar to the original tumors. Scale bar represents 50 µm.

The result showed that Lgr5-positive adherent cells were more potent than Lgr5-negative non-adherent cells in the activity to form tumors. However, both Lgr5-positive and Lgr5-negative cells had the capacity to form tumors in NOG mice. Subcutaneous injection of ten Lgr5-positive cells caused tumor formation at every injection site (six of six sites), while Lgr5-negative cells formed tumors at two of six injection sites (PLR123-derived cells) or at a single site (PLR59-derived cells) (Table 3). Lgr5-positive cells, even with injection of only one cell, reconstituted tumors at two of 12 injection sites (PLR123-derived cells) or at a single site (PLR59-derived cells). The histopathological morphologies of tumors derived from the Lgr5-positive and Lgr5-negative cells were almost the same as those of the original tumors (FIGS. 17 and 38). Furthermore, there was no change in the expression of cell surface markers and tumor-forming activity of the Lgr5-positive CSCs even after one month of culture (FIGS. 30 and 31).

Figure 39:
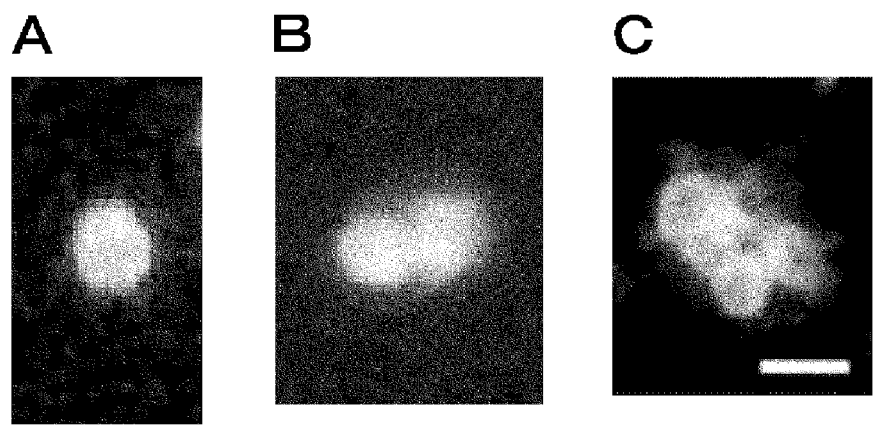
FIG. 39 shows photographs depicting symmetrical cell division of Lgr5-positive cells. Lgr5-positive cells stained with PKH67 dye were cultured for 72 hours, and then observed under a fluorescent microscope.
Figure 40:
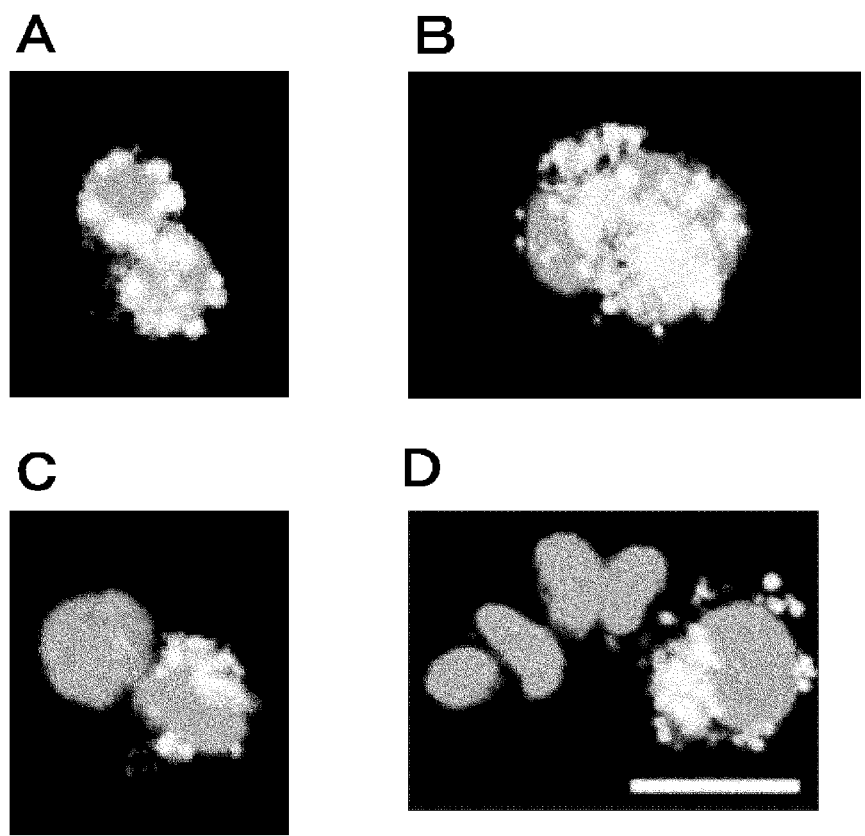
FIG. 40 shows photographs depicting symmetrical cell division of Lgr5-positive cells in the absence of matrigel and serum (FIGS. 40A and 40B), and asymmetrical cell division of Lgr5-positive cells in the presence of matrigel and serum (FIGS. 40C and 40D).

Under an adherent culture condition, the Lgr5-positive cells underwent symmetric cell division (FIG. 39). Meanwhile, in the presence of matrigel and serum, Lgr5 protein was distributed to one of two daughter cells under the same culture condition (FIGS. 40C and 40D), demonstrating that the Lgr5-positive cells undergo asymmetrical cell division. One of CSC's properties is symmetrical cell division for self-renewal, and another characteristic property is asymmetrical cell division. The Lgr5-positive adherent cells divided symmetrically under an adherent culture condition (FIG. 39), whereas, in the presence of matrigel and FBS, as seen from the fact that Lgr5 protein was distributed to one of daughter cells (FIG. 40), the Lgr5-positive cells underwent asymmetrical cell division, which resulted in two distinct progenies.

Figure 56:
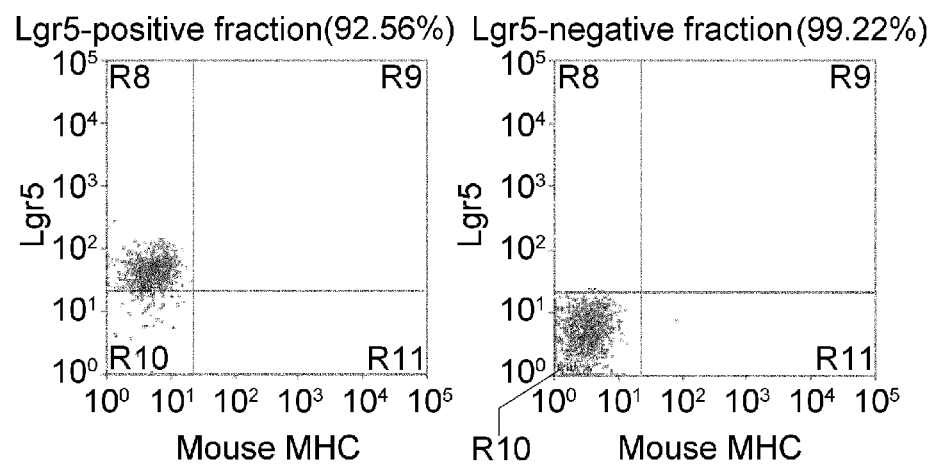
FIG. 56 shows the flow cytometry analysis of Lgr5-positive and -negative cell populations sorted from primary cells of a PLR123 xenograft formed from transplantation of Lgr5-positive cells. The percentage indicates the purity of sorted cell populations.
Figure 57:
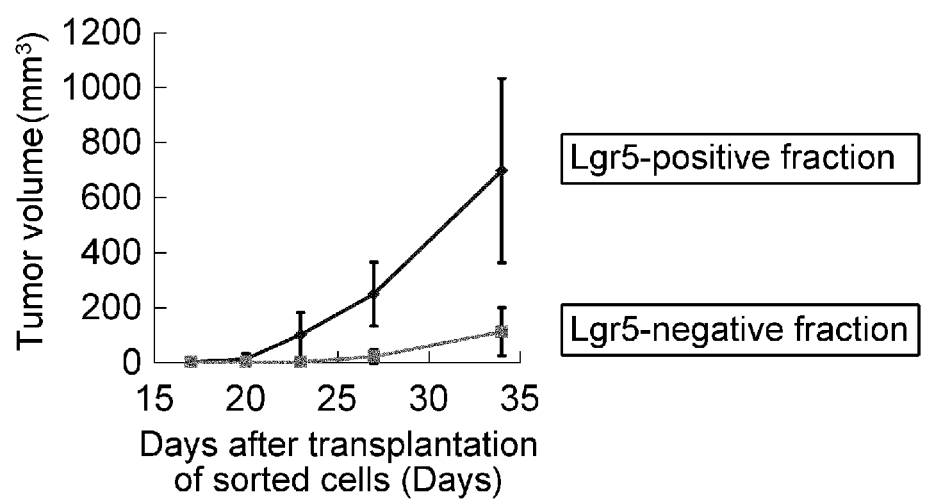
FIG. 57 shows tumor formation represented as a volume of the tumor formed in NOG mice which were subcutaneously grafted with 1000 Lgr5-positive or -negative cells suspended in matrigel after sorting. The mean and standard deviation are values obtained from six tumors.

Then, using antibody 2L36, an Lgr-positive cell population and an Lgr5-negative cell population were sorted from primary cells from xenografts prepared via transplantation of Lgr5-positive cells. About 93% of cells in the Lgr5-positive fraction were positive for Lgr5, while 99% or more of cells in the Lgr5-negative fraction were negative for Lgr5 (FIG. 56). The sorted Lgr5-positive cells formed colonies efficiently on matrigel in vitro, and formed tumors in NOG mice. In contrast, the Lgr5-negative cells did not form colonies in vitro and did not form tumors in NOG mice. When 1000 cells of the sorted Lgr5-positive cells were injected subcutaneously to NOG mice, they formed tumors large enough to be visible by day 34 after transplantation. When the sorted Lgr5-negative cells were injected in the same manner, they only formed very small colonies by day 34 after transplantation (FIG. 57).

Figure 58:
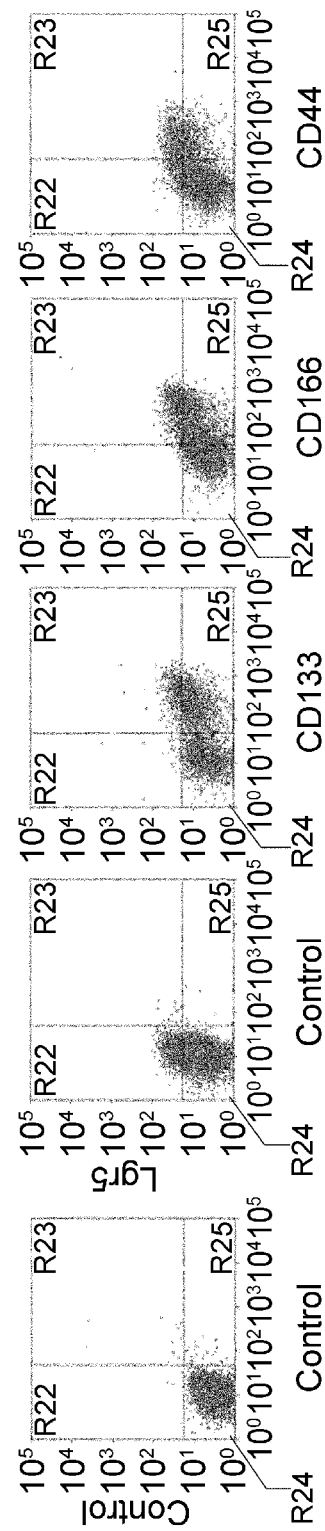
FIG. 58 shows the flow cytometry analysis of primary cells from a PLR123 xenograft using anti-Lgr5 antibody, anti-CD133 antibody, anti-CD166 antibody, or anti-CD44 antibody.

Then, the correlation of Lgr5 expression with other cancer stem cell markers was assessed by double staining for Lgr5, and CD133, CD166, or CD44. Most of the Lgr5-positive cells were positive for both CD133 and CD166. Meanwhile, most of the Lgr5-negative cells were CD133 or CD166 (FIG. 58). Thus, the cell population defined by marker Lgr5 was suggested to be a subpopulation of the cell population defined by CD133 positivity and CD166 cells.

Figure 59:
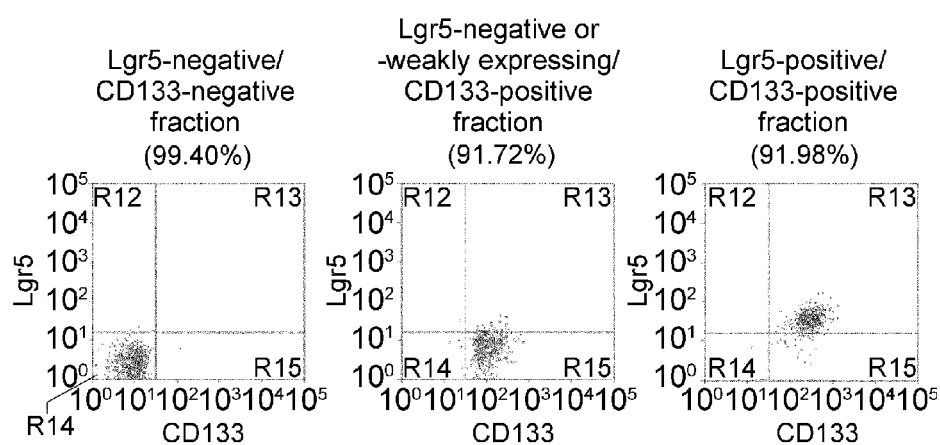
FIG. 59 shows the flow cytometry analysis of Lgr5-negative/CD133-negative, Lgr5-negative or Lgr5-weakly-expressing/CD133-positive, and Lgr5-positive/CD133-positive cell populations obtained from primary cells of a PLR123 xenograft. The percentage indicates the purity of sorted cell populations.
Figure 60:
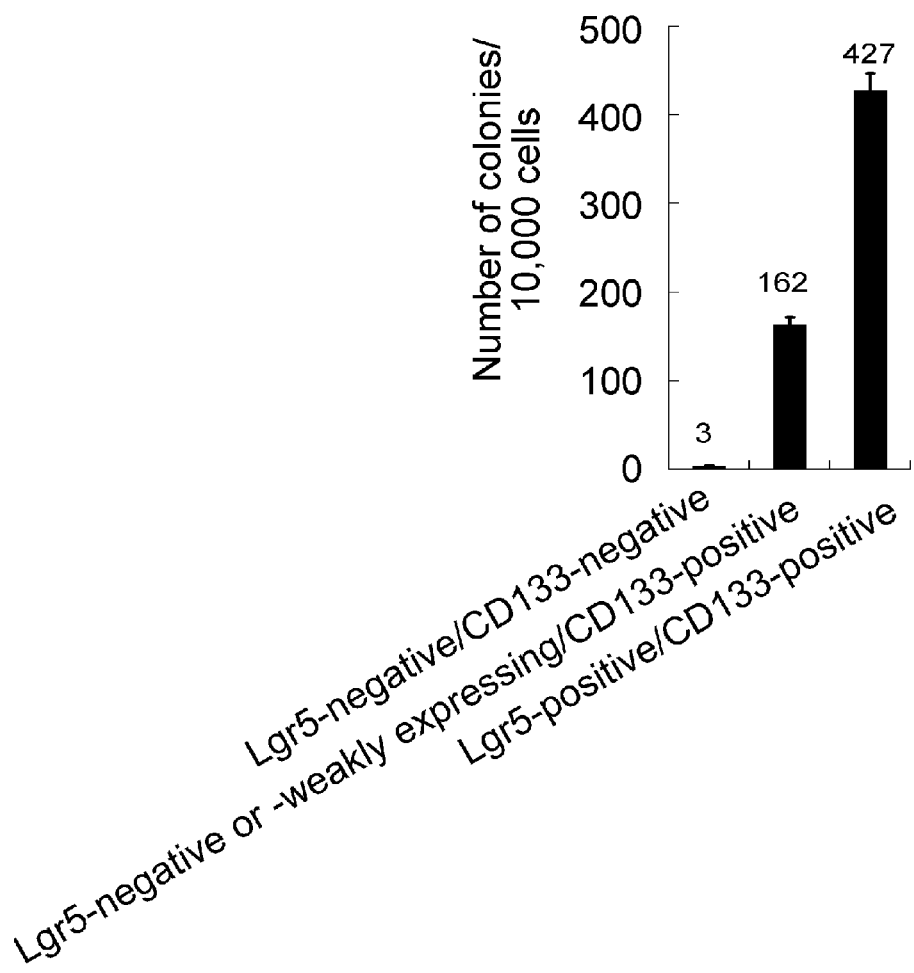
FIG. 60 shows a diagram depicting the colony-forming activities of Lgr5-negative/CD133-negative, Lgr5-negative or Lgr5-weakly-expressing/CD133-positive, and Lgr5-positive/CD133-positive cell populations, represented using the numbers of colonies formed after six days of culture following seeding on matrigel of the sorted Lgr5-negative/CD133-negative, Lgr5-negative or Lgr5-weakly-expressing/CD133-positive, and Lgr5-positive/CD133-positive cell populations. The mean and standard deviation are values obtained from three experiments.

Next, the Lgr5-negative cell population was sorted and assessed for its properties. Cells prepared from a xenograft were stained with an anti-Lgr5 antibody and an anti-CD133 antibody, and Lgr5-negative/CD133-negative, Lgr5-negative or Lgr5-weakly-expressing/CD133-positive, and Lgr5-positive/CD133-positive cell populations were sorted. The sorted fractions contained 90% or more of cells defined by the markers of interest (FIG. 59). The isolated Lgr5-negative or Lgr5-weakly-expressing/CD133-positive cells and Lgr5-positive/CD133-positive cells formed colonies on matrigel. Meanwhile, the Lgr5-negative/CD133-negative cells died after plating in a culture plate. The colony formation efficiency of the sorted Lgr5-negative/CD133-negative, Lgr5-negative or Lgr5-weakly-expressing/CD133-positive, and Lgr5-positive/CD133-positive cells were 0.03%, 1.6%, and 4.3%, respectively (FIG. 60).

The results described above demonstrate that Lgr5-positive and Lgr5-negative cells derived from PLR59 and PLR123 are highly pure colon CSCs, and that the Lgr5-positive and Lgr5-negative cells correspond to two independent CSC states in colon cancer.

Example 5

Effect of TCF and β-catenin

Figure 7:
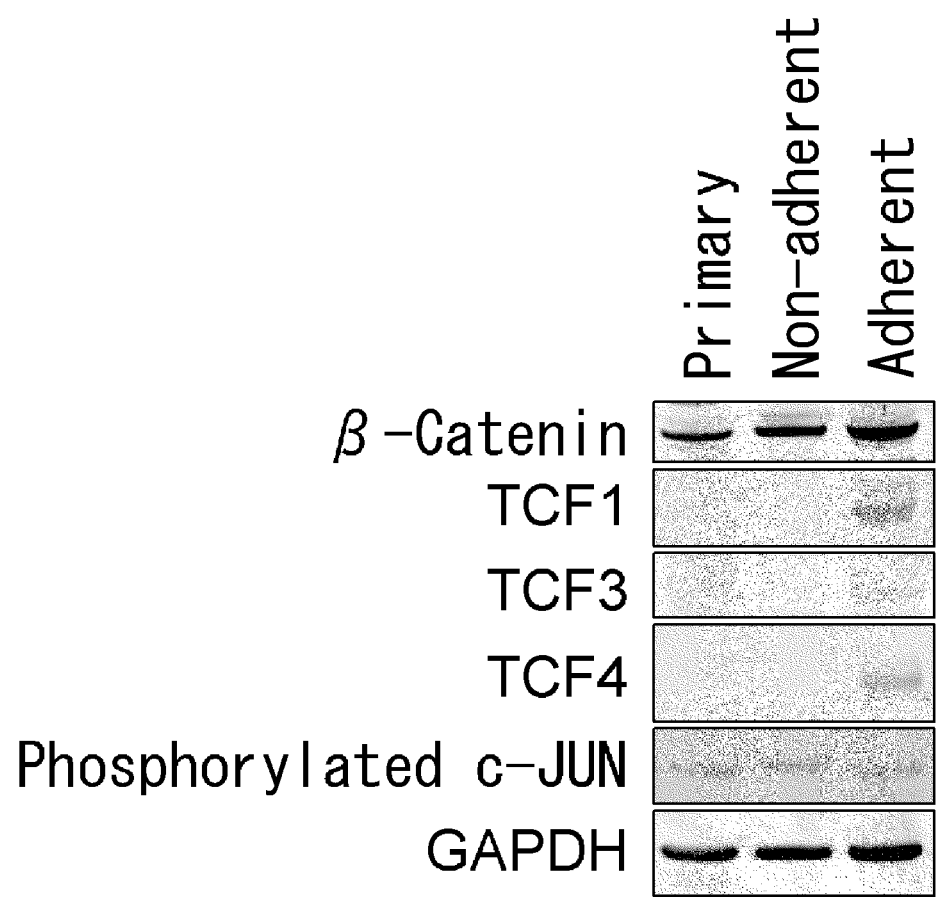
FIG. 7 is a photograph showing a result of Western blot analysis of primary cells, non-adherent CSCs, and adherent CSCs for β-catenin, TCF1, TCF3, TCF4, and phosphorylated c-JUN protein. Expression of all of the proteins was up-regulated in Lgr5-positive adherent CSCs as compared to the primary cells. GAPDH was also visualized as a loading control protein.
Figure 21:
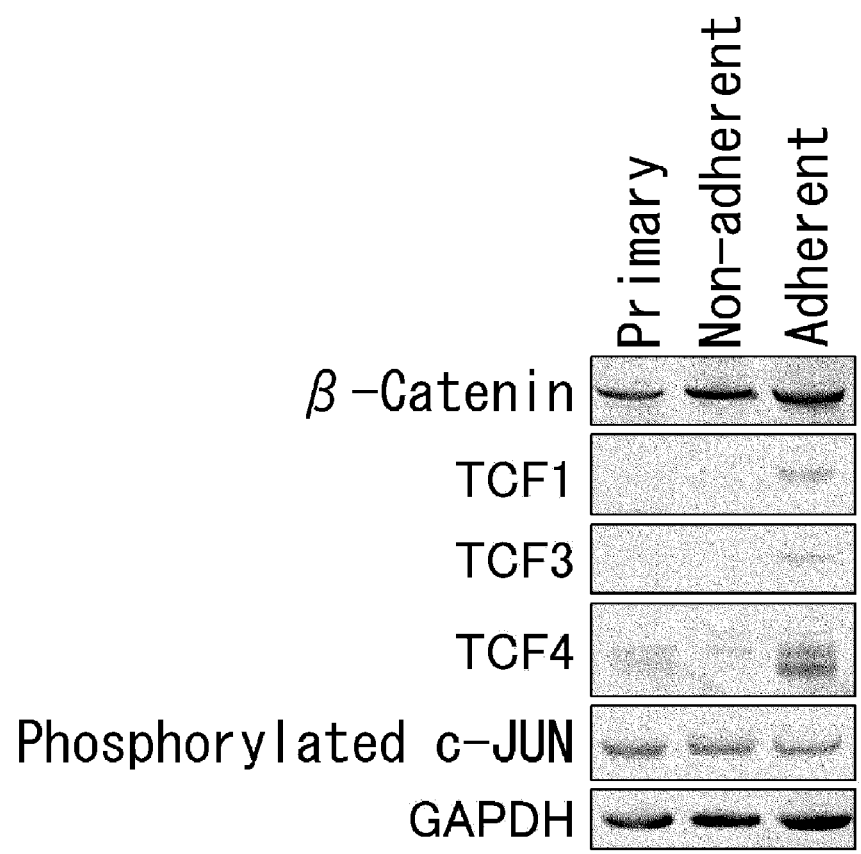
FIG. 21 shows photographs depicting a result of Western blot analysis of primary cells, non-adherent CSCs, and adherent CSCs for β-catenin, TCF1, TCF3, TCF4, and phosphorylated c-JUN protein. Expression of all of the proteins was up-regulated in Lgr5-positive adherent CSCs as compared to the primary cells. GAPDH was also visualized as a loading control protein.

In the Lgr5-positive cells, the levels of β-catenin, TCF1, TCF3, and TCF4 proteins were upregulated in accordance with the expression of Lgr5. This was not observed in the Lgr5-negative cells (FIGS. 7 and 21).

In recent years, Aguilera et al. have demonstrated that the Lgr5 gene has an AP1 box in its promoter and the phosphorylation of the N terminal region of c-Jun results in activation of Lgr5 transcription (Aguilera C, et al. (2011) c-Jun N-terminal phosphorylation antagonises recruitment of the Mbd3/NuRD repressor complex. Nature 469:231-235). In contrast, the present inventors revealed that the phosphorylation of the N terminal region of c-Jun was undetectable in Lgr5-positive CSCs as compared to Lgr5-negative CSCs (FIGS. 7 and 21).

To answer the question of whether Wnt signaling promotes the proliferation of colon CSCs, the present inventors assessed the effects of β-catenin/TCF inhibitor FH535 and Wnt/β-catenin inhibitor cardamonin (which induces β-catenin degradation) on the proliferation of colon CSCs.

Figure 8:
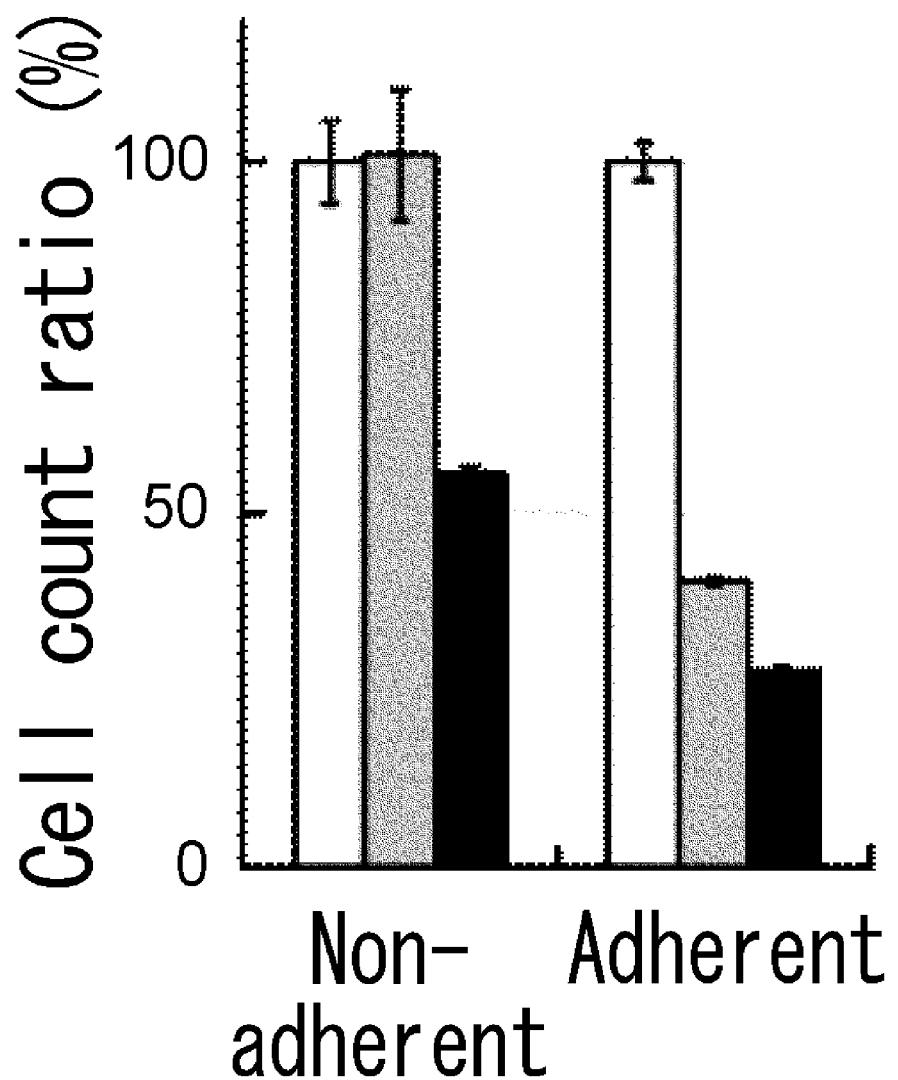
FIG. 8 is a diagram showing the inhibition of growth of Lgr5-positive adherent CSCs by FH535 (50 μM) and Cardamonin (50 μM). The viable cell count after three days of culture in the presence of FH535 (gray column) or Cardamonin (black column) is shown in percentage to the count in the presence of DMSO alone (white column). The results were averaged from three experiments. The bar at the top of each column represents standard deviation.
Figure 22:
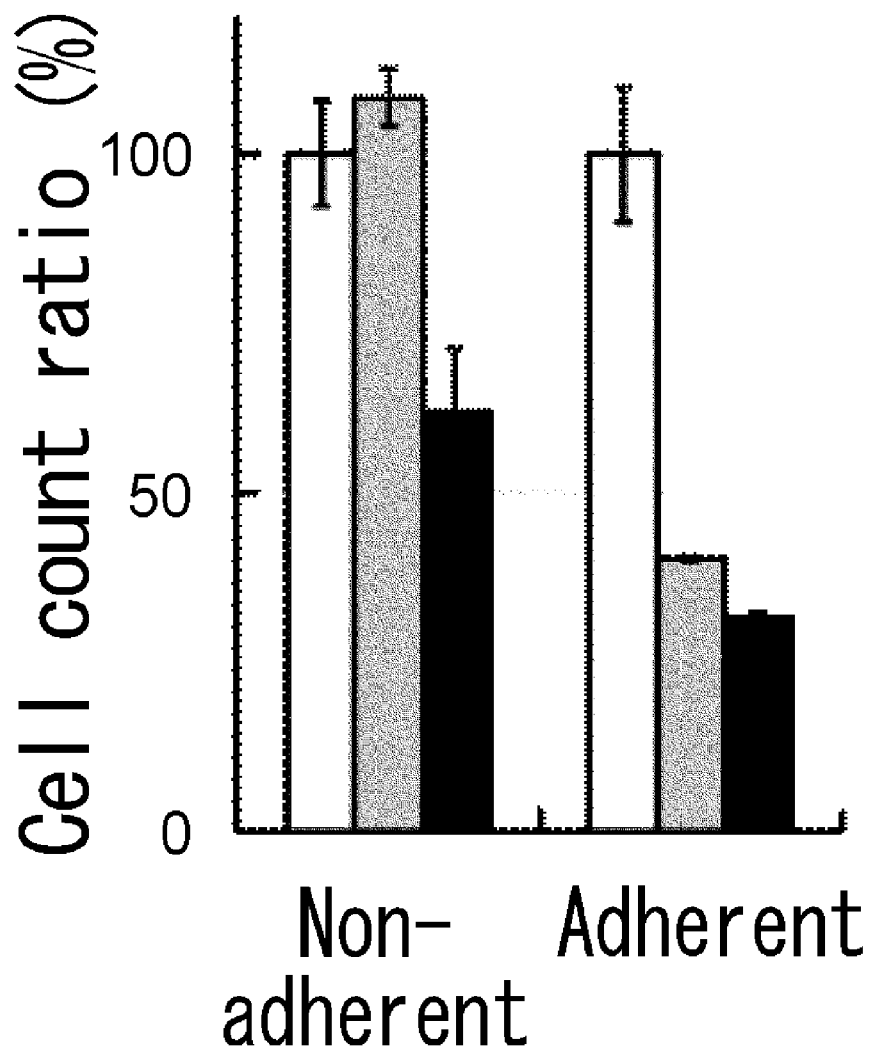
FIG. 22 is a diagram showing growth inhibition of Lgr5-positive adherent CSCs by FH535 (50 μm) and Cardamonin (50 μm). The viable cell count after three days of culture in the presence of FH535 (gray column) or Cardamonin (black column) is shown in percentage to the count on day 0 (white column).

The result showed that 50 μM FH535 significantly reduced the proliferation of Lgr5-positive colon CSCs but had no effect on the proliferation of Lgr5-negative colon CSCs (FIGS. 8 and 22). Meanwhile, 50 μM cardamonin reduced the viable cell count to 70% for the Lgr5-positive colon CSCs and to about 50% for the Lgr5-negative colon CSCs (FIGS. 8 and 22).

Figure 9:
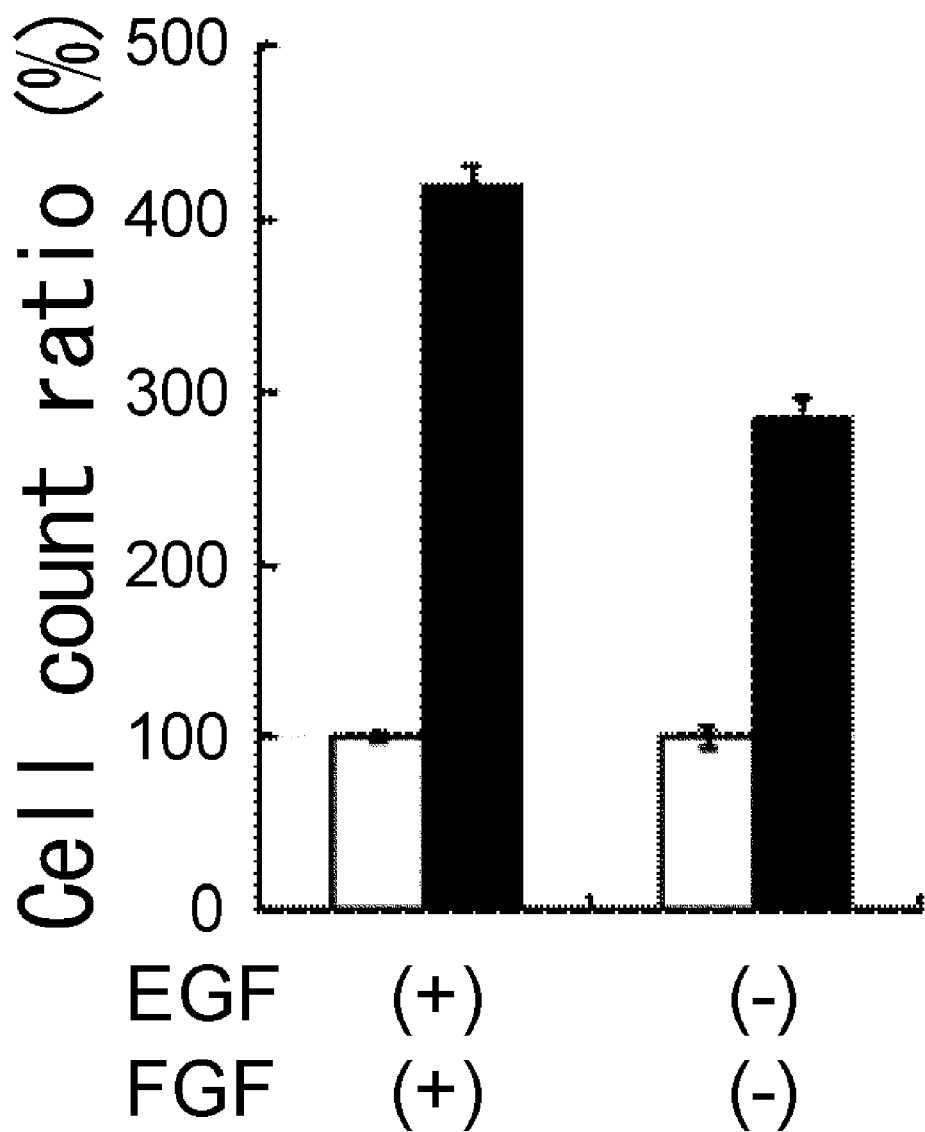
FIG. 9 is a diagram showing the proliferation of cells in the presence or absence of EGF and FGF. Adherent CSCs were cultured for three days in the presence or absence of EGF and FGF (black column). The viable cell count is shown in percentage to the count on day 0 (white column). The results were averaged from three experiments. The bar at the top of each column represents standard deviation.
Figure 23:
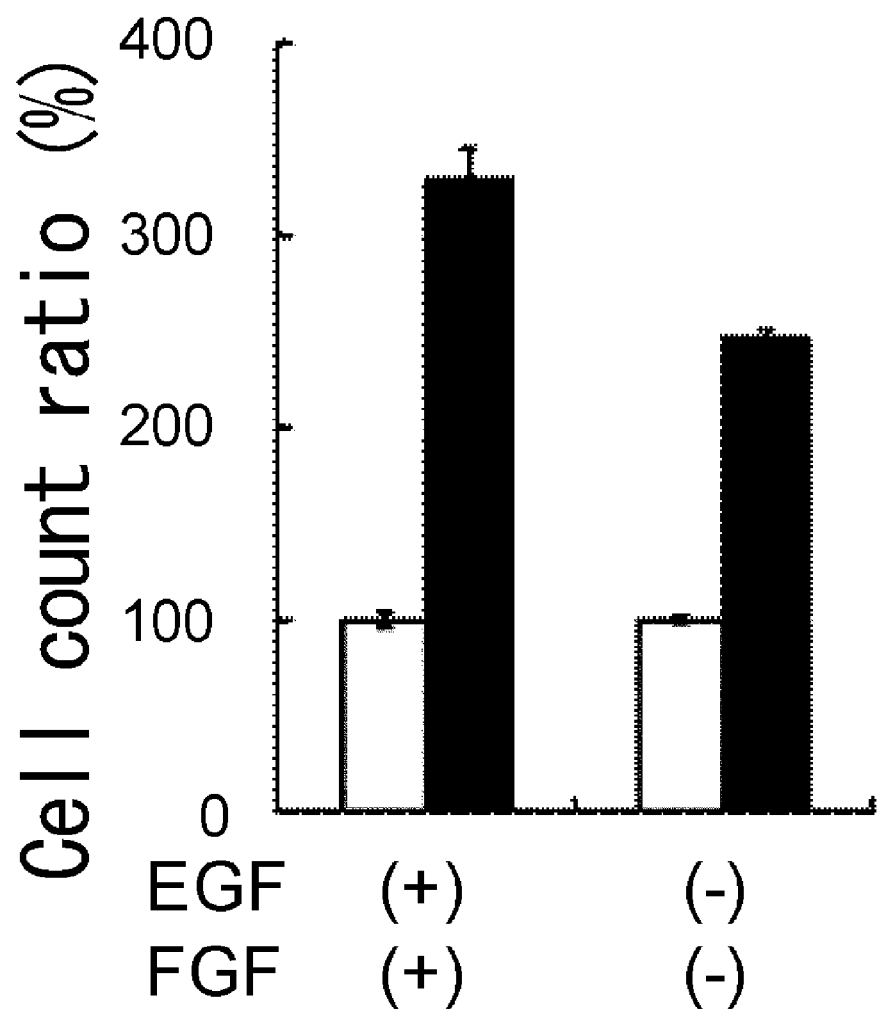
FIG. 23 is a diagram showing the proliferation of cells in the presence or absence of EGF and FGF. Adherent CSCs were cultured for three days in the presence or absence of EGF and FGF (black column). The viable cell count is shown in percentage to the count on day 0 (white column).

This result demonstrates that TCF mediates the proliferation of Lgr5-positive cells and that β-catenin is involved in the survival of colon CSCs. Interestingly, the Lgr5-positive cells proliferated even without supplement of EGF and FGF (FIGS. 9 and 23). This finding shows that colon CSCs have an intrinsic/autocrine mechanism for activating the Wnt signaling for their proliferation.

Example 6

Ability of Colon CSCs to Convert from Lgr5-positive to Lgr5-negative State

Figure 10:
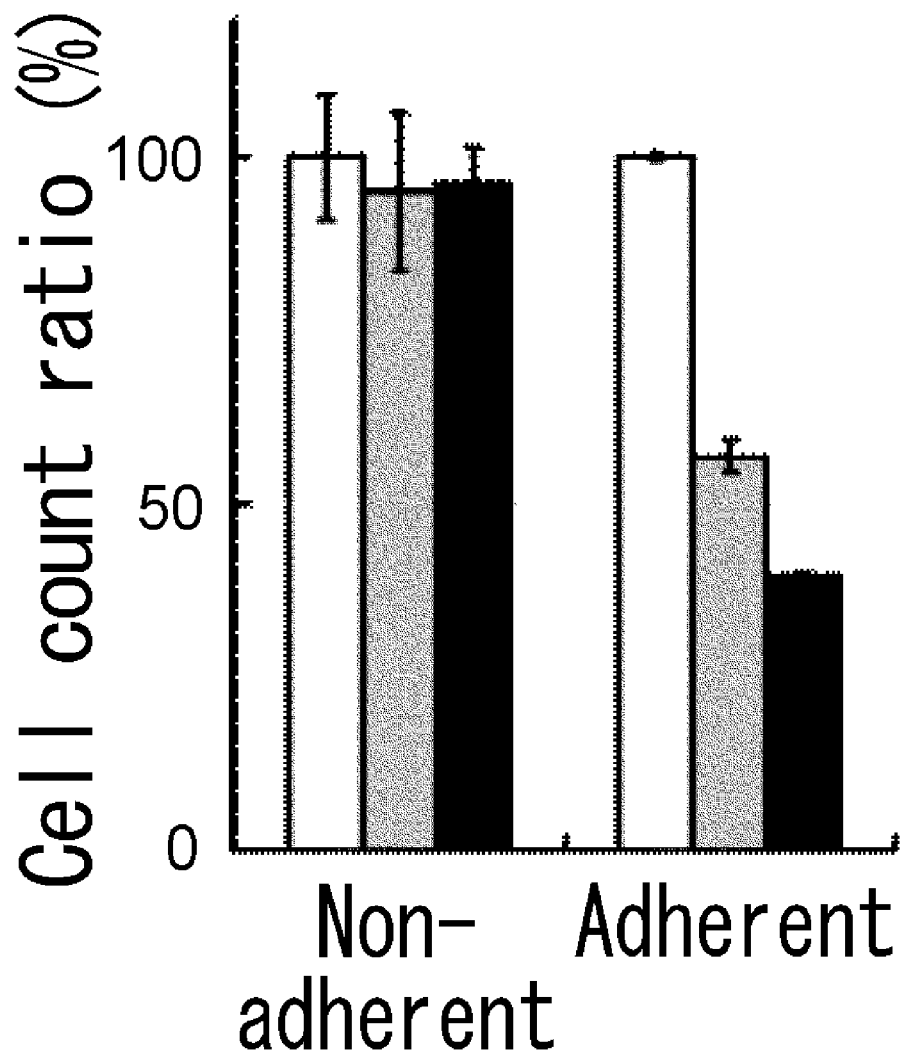
FIG. 10 is a diagram showing the effect of chemotherapeutic agents on the proliferation of Lgr5-positive adherent CSCs and Lgr5-negative non-adherent CSCs. The viable cell count after treatment with 5-FU (10 μg/ml; gray column) or irinotecan (10 μg/ml; black column) is shown in percentage to the viable cell count after culturing without the chemotherapeutic agents (white column). The results were averaged from three experiments. The bar at the top of each column represents standard deviation.
Figure 11:
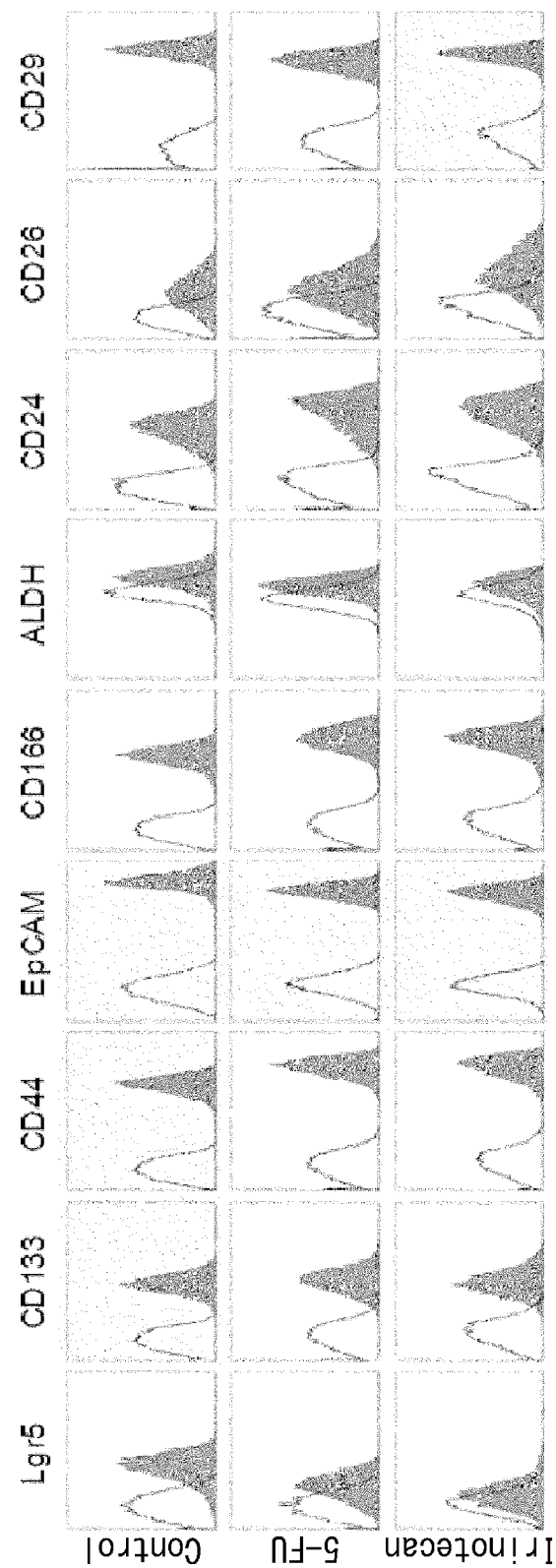
FIG. 11 is a diagram showing a change in Lgr5 expression after treatment of adherent CSCs with a chemotherapeutic agent. This figure shows a result of flow cytometry. The upper panels show the result in the absence of chemotherapeutic agent (control); the middle panels show cells treated with 5-FU; and the bottom panels show cells treated with irinotecan. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 24:
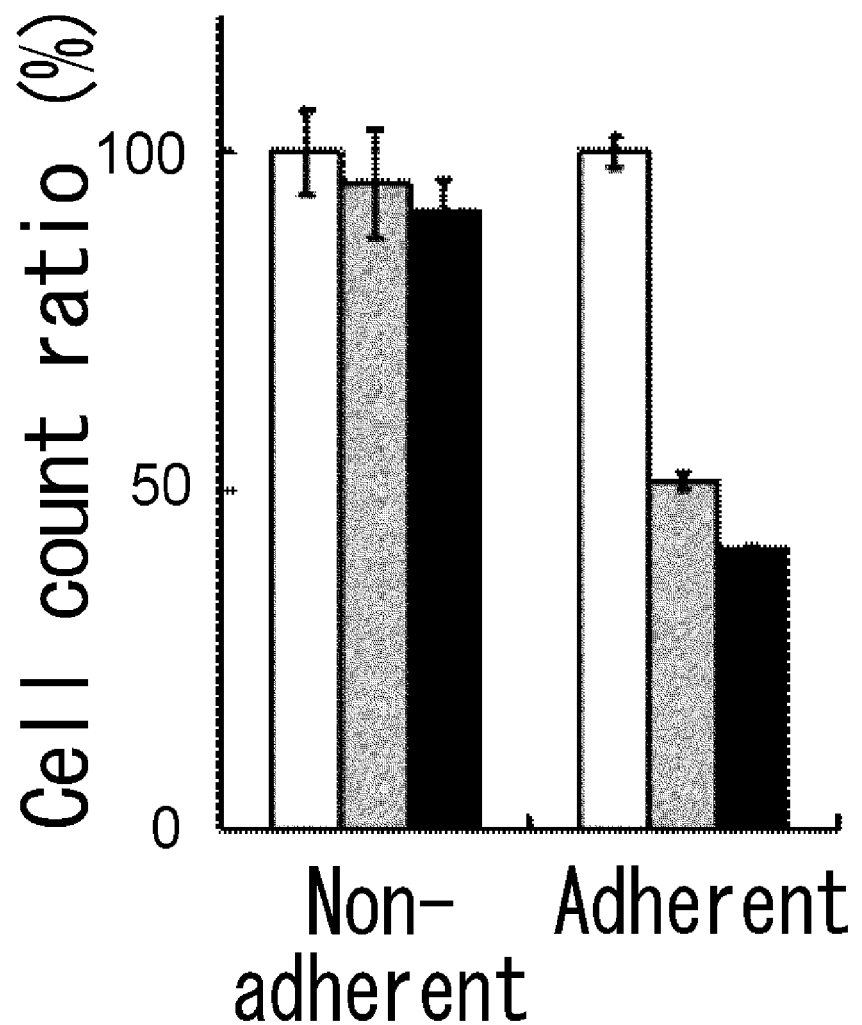
FIG. 24 is a diagram showing the effect of 5-FU (10 μg/ml) and irinotecan (10 μg/ml) on the growth of Lgr5-positive adherent CSCs and Lgr5-negative non-adherent CSCs. The viable cell count after treatment with 5-FU (gray column) or irinotecan (black column) is shown in percentage to that after culturing without the agents (white column).
Figure 25:
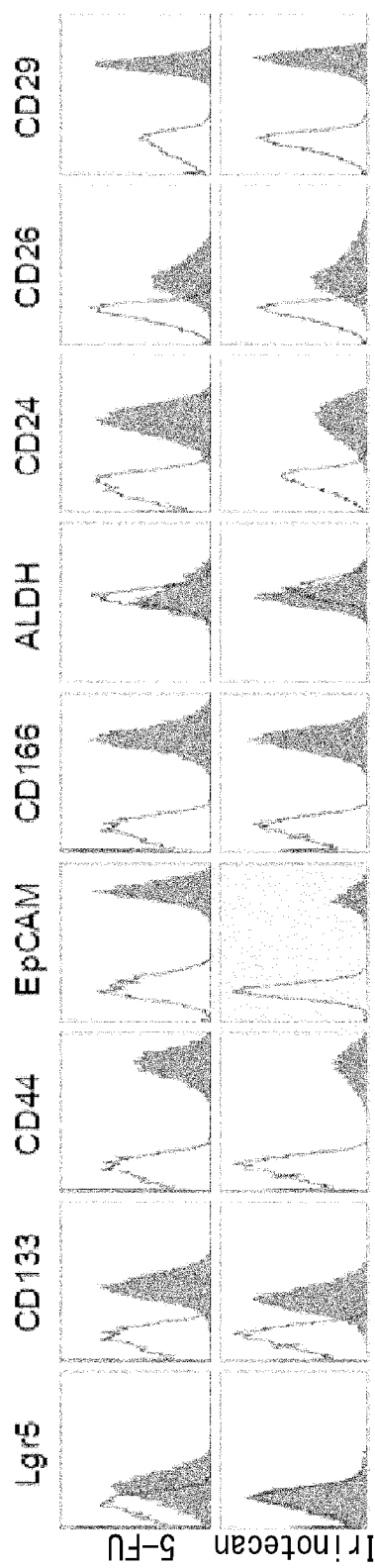
FIG. 25 is a diagram showing a result of flow cytometry analysis of cells for CSC markers after treatment with 5-FU or irinotecan. The upper panels show cells treated with 5-FU, and the bottom panels show cells treated with irinotecan. Gray area indicates the ALDH activity or fluorescence intensity of cells after staining with the indicated antibodies. White area indicates the ALDH activity in the presence of an ALDH inhibitor or the fluorescence intensity of cells after staining with isotype antibodies as a control.
Figure 32:
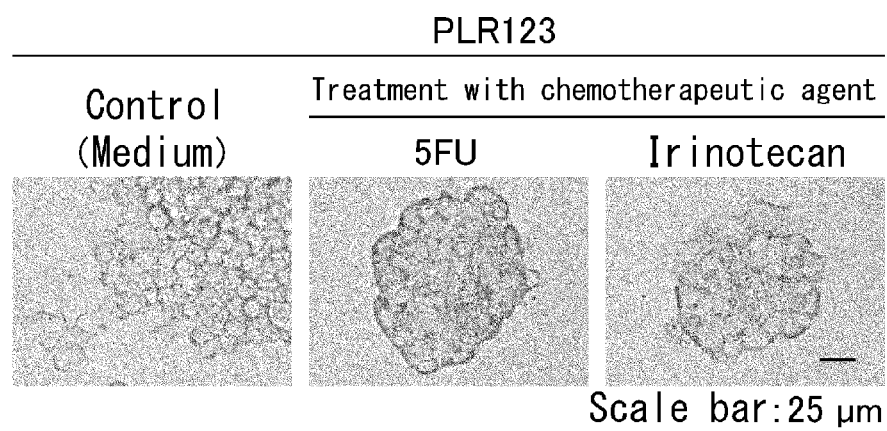
FIG. 32 shows photographs depicting the phenotypic interconversion of colon CSCs depending on the culture condition or chemotherapeutic treatment. Lgr5-positive CSCs were tested for the sensitivity to 5-FU and irinotecan. Both 5-FU and irinotecan significantly inhibited the proliferation of Lgr5-positive colon CSCs. After three days of exposure to the 5-FU or irinotecan, cells resistant to the chemotherapeutic drugs arose. The drug-resistant cells exhibited a dense, compressed morphology. Scale bar represents 25 µm.

One of CSC's properties is resistance to chemotherapeutic agents. Thus, the present inventors tested colon CSCs for the sensitivity to 5-FU and irinotecan. As described above, the Lgr5-positive cells proliferated with a doubling time of about 2.5 days. Meanwhile, the Lgr5-negative CSCs were in a quiescent state in terms of growth. Both 5-FU and irinotecan significantly inhibited the proliferation of Lgr5-positive colon CSCs, while they did not affect the proliferation and survival of Lgr5-negative colon CSCs (FIGS. 10 and 24). Three-day exposure of the Lgr5-positive colon CSCs to 5-FU or irinotecan caused the appearance of cells resistant to the chemotherapeutic agents. Surprisingly, the drug-resistant cells were negative for Lgr5 and had changed in morphology (FIGS. 11, 32, and 25). This finding demonstrates the transition from the Lgr5-positive to Lgr5-negative state.

Figures 1, 41:
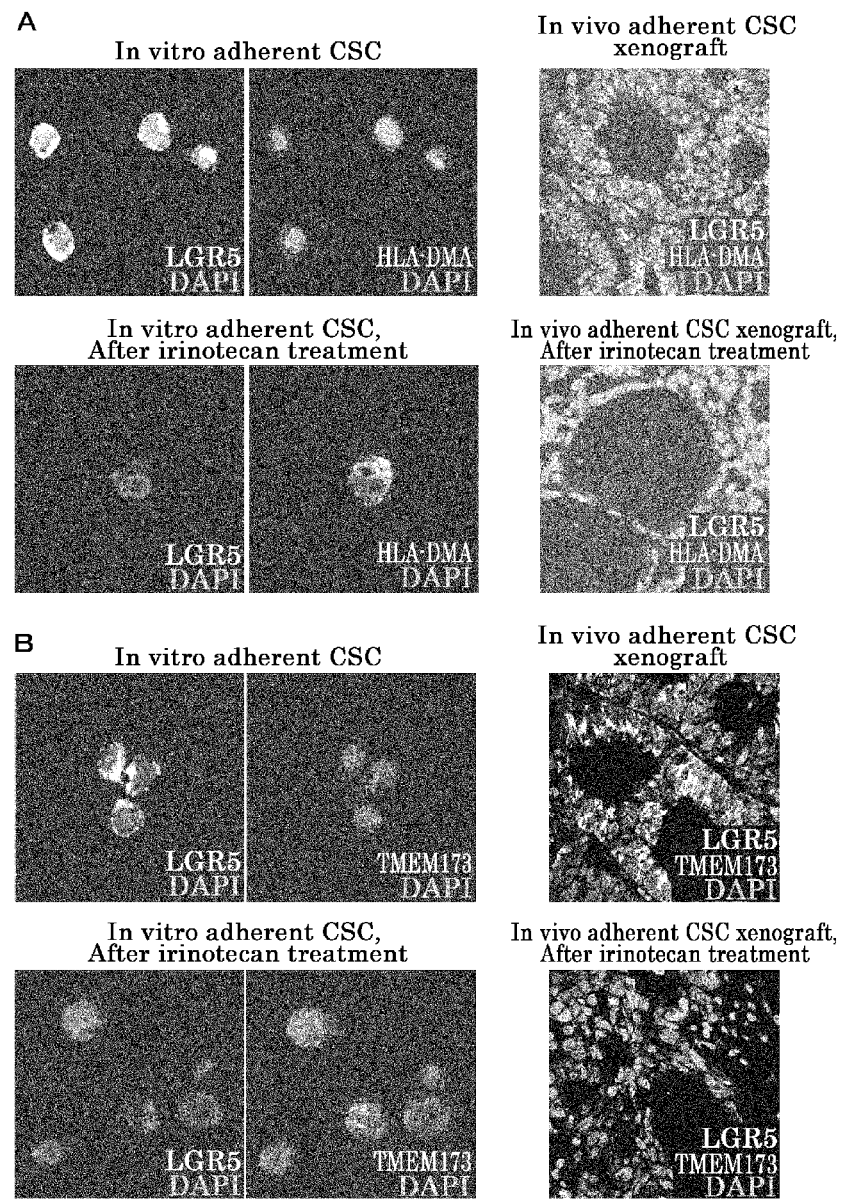
Figures 2, 41:
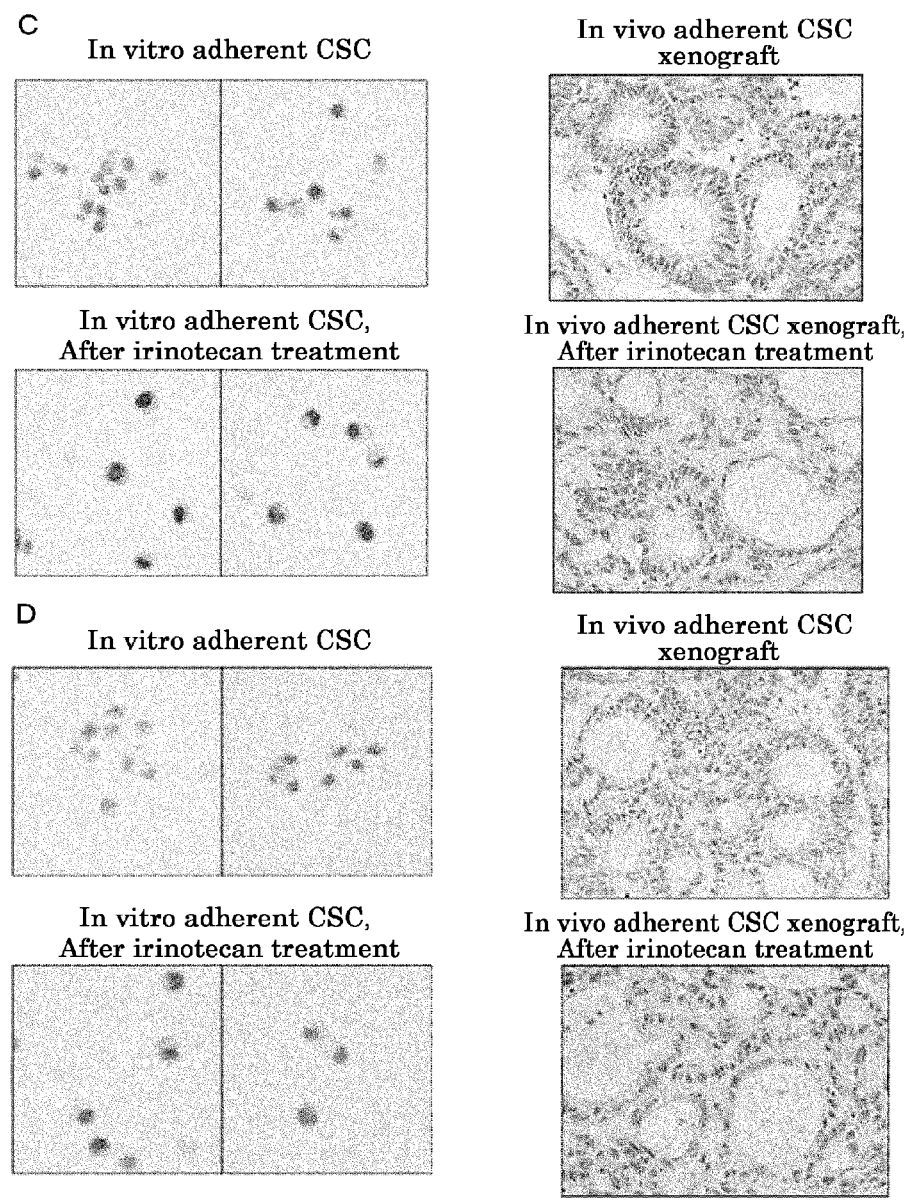

HLA-DMA, TMEM173, ZMAT3, and GPR110 were chosen as markers for use in specific detection of such CSCs stably negative for Lgr5. Immunostaining performed using specific antibodies against the above molecules yielded a specific staining pattern with colon CSCs that converted to negative for Lgr5 after three days of irinotecan exposure (FIG. 41). Furthermore, this immunostaining method was demonstrated to be applicable to tissue sections prepared from paraffin blocks, which are used commonly (FIG. 41). These findings suggest that HLA-DMA, TMEM173, ZMAT3, GPR110 can serve as specific markers for CSCs that converted to negative for Lgr5.

Figure 42:
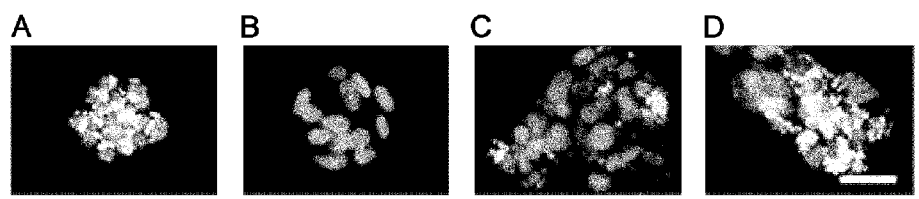
FIG. 42 shows photographs depicting immunostained images of irinotecan-treated Lgr5-positive CSCs (PLR123). The cells were immunostained for Lgr5. The immunostained images include those before irinotecan treatment (FIG. 42A) and after irinotecan treatment (FIG. 42B). From Lgr5-negative cells inoculated again and cultured in the absence of irinotecan, Lgr5-positive cells appeared at the latest by four days after reinoculation (FIG. 42C), and expanded by eight days after reinoculation (FIG. 42D). Scale bar represents 50 µm.
Figure 43:
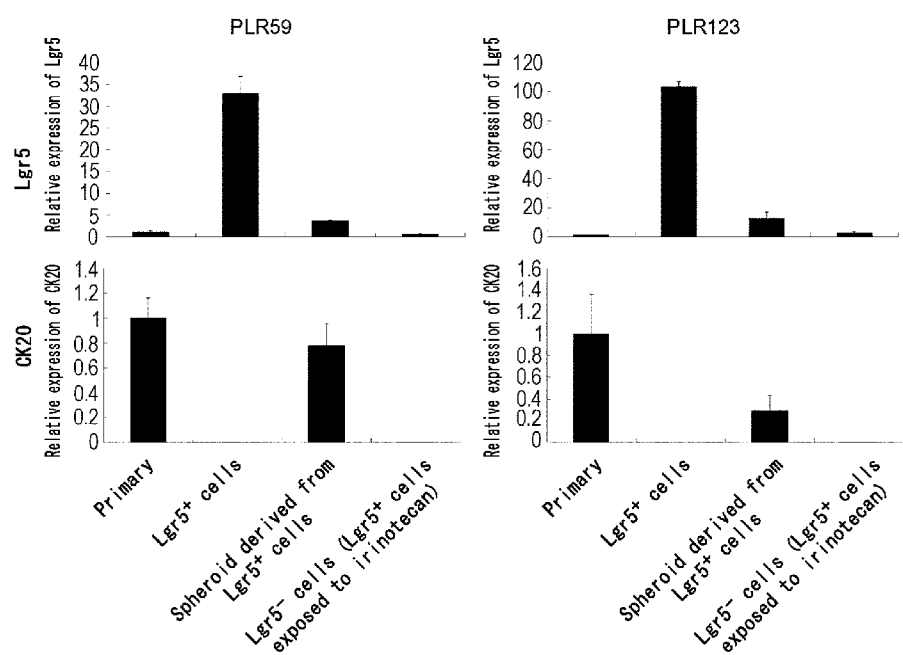
FIG. 43 shows graphs depicting transcript levels for the Lgr5 gene determined by quantitative real-time PCR. The level of Lgr5 mRNA was high in Lgr5-positive cells prepared by adherent culture. The level was decreased under the spheroid culture condition and was almost undetectable in Lgr-negative cells after irinotecan treatment. Meanwhile, in Lgr5-positive and -negative cells, the mRNA level for the CK20 gene was below the detection limit. The level was increased in Lgr5-positive cells of the spheroid culture condition.
Figure 44:
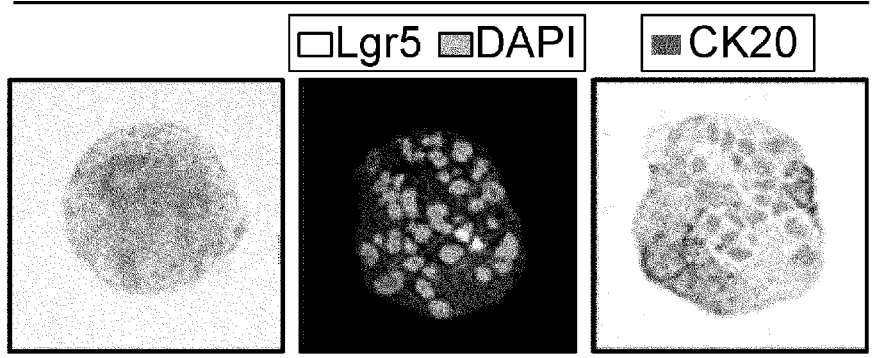
FIG. 44 shows photographs depicting the expression of Lgr5 and CK20 proteins assessed by immunohistochemical staining Spheroid cultures of Lgr5-positive CSCs (PLR59 (FIG. 44A) and PLR123 (FIG. 44B)) were fixed and sliced into thin sections and then reacted with Lgr5 antibody (2L36) and CK20 antibody (DAKO). The spheroids contained a small number of Lgr5-positive cells as well as a large number of CK20-positive cells that were negative for Lgr5.
Figure 44:
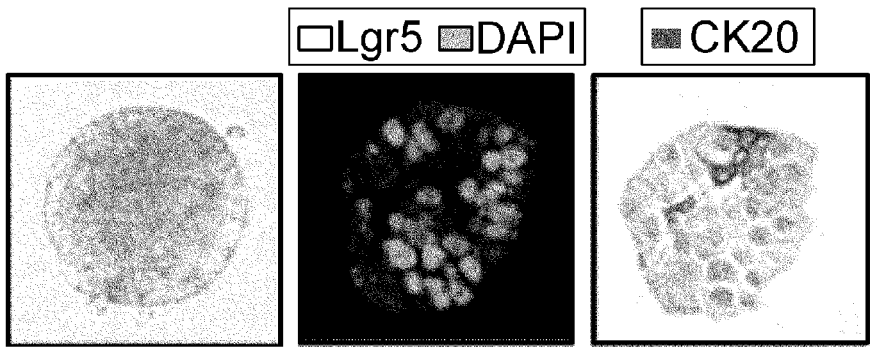
Figure 45:
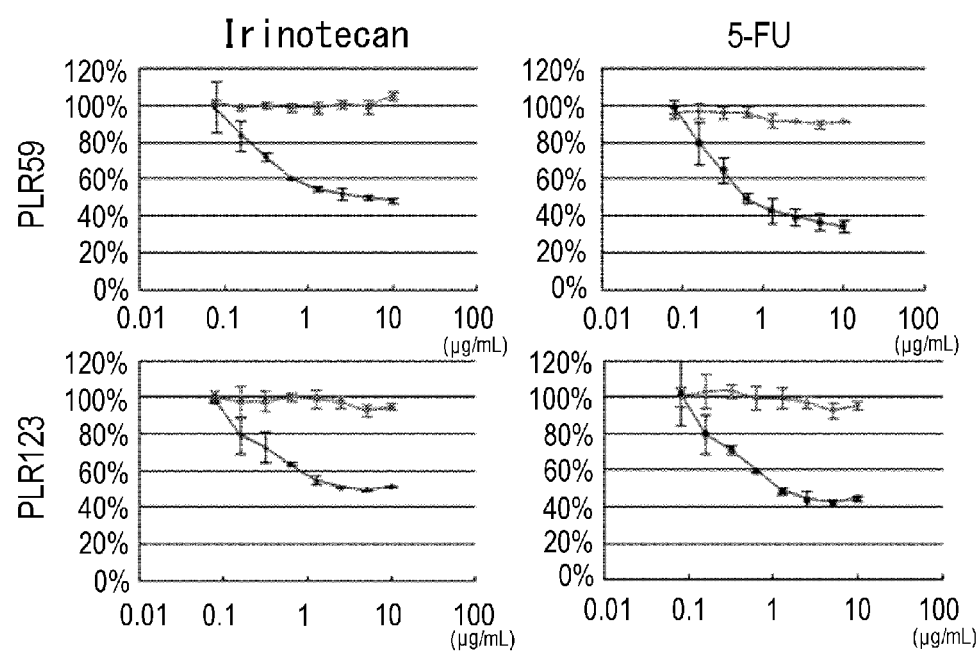
FIG. 45 shows graphs depicting the percentage of viable cells, relative to non-treated control cells, of Lgr5-positive (dark line) and -negative (gray line) CSCs (PLR59 and PLR123) cultured for three days in the absence or presence of irinotecan or 5-FU at each concentration indicated on the horizontal axis. Lgr5-negative cells were fully resistant to both growth inhibitors.
Figure 46:
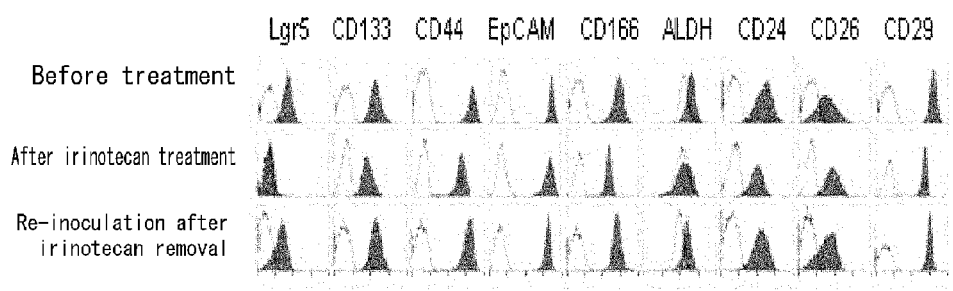
FIG. 46 is a diagram showing the expression of CSC markers. "Before treatment" indicates the expression of CSC markers in Lgr5-positive cells prepared by an adherent culture, which are derived from a PLR123 xenograft model. "After irinotecan treatment" indicates the expression of CSC markers in Lgr5-negative cells prepared via irinotecan treatment. "Secondary inoculation after irinotecan removal" indicates the expression of CSC markers in Lgr5-negative cells re-inoculated to an irinotecan-free medium. Gray area indicates the ALDH activity or fluorescence intensity of cells after staining with the indicated antibodies. White area indicates the ALDH activity in the presence of an ALDH inhibitor.
Figure 61:
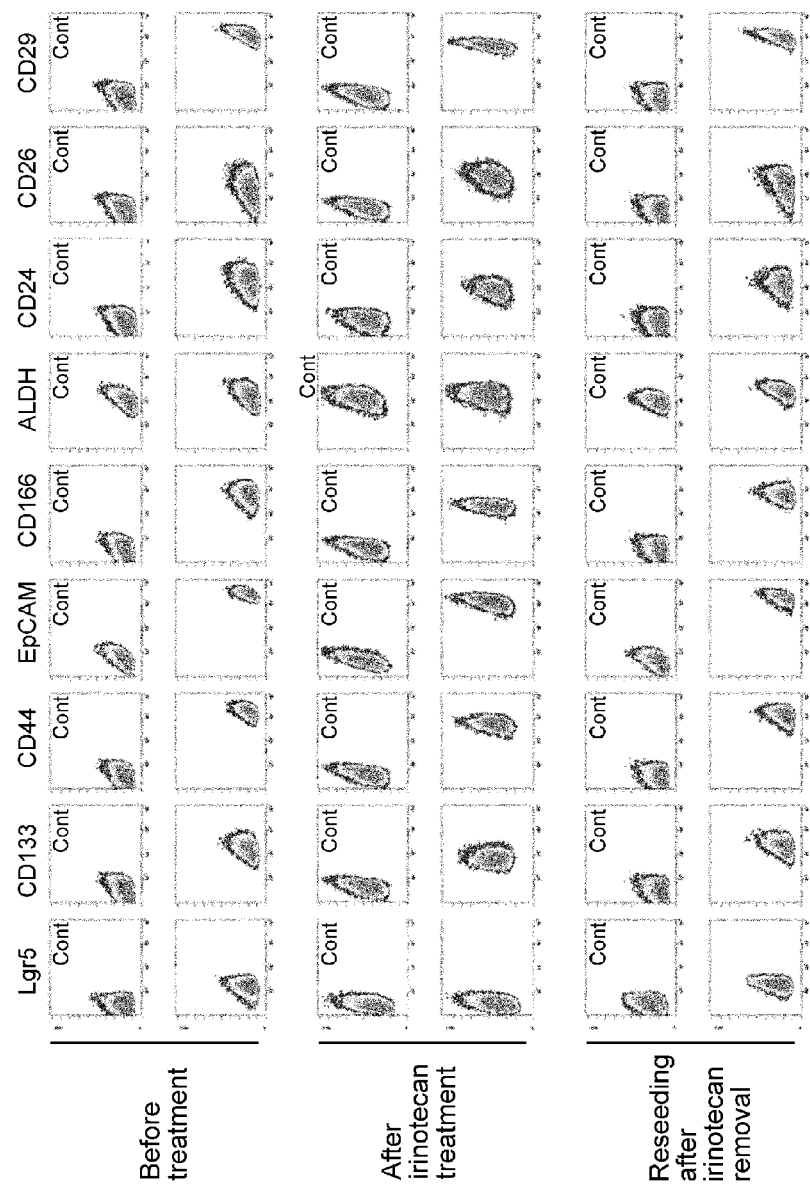
FIG. 61 shows a diagram depicting the expression levels of stem cell markers. The expression levels of stem cell markers of Lgr5-positive cells obtained from a xenograft of PLR123 cells and isolated by adherent culture, before irinotecan treatment, after irinotecan treatment, and of cells reseeded after irinotecan treatment, are analyzed using a flow cytometer. X axis indicates fluorescence intensity, and Y axis indicates side scatter.
Figure 62:
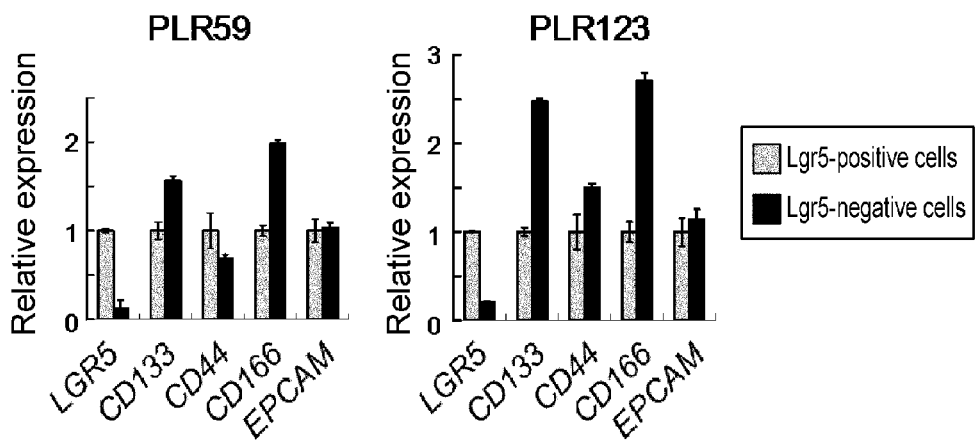
FIG. 62 shows a diagram depicting the expression levels of Lgr5, CD133, CD44, CD166, and EPCAM examined by RT-qPCR.

The fluorescence representing Lgr5 positivity (FIG. 42A), which had been observed before irinotecan treatment, disappeared after the treatment (FIG. 42B). From Lgr5-negative cells again inoculated and cultured in the absence of irinotecan, Lgr5-positive cells appeared four days after the inoculation (FIG. 42C), and expanded by eight days after the inoculation (FIG. 42D). All the Lgr5-negative drug-resistant cells are negative for Lgr5 (FIGS. 42 and 43) and remained negative for CK20 (FIG. 44). This suggests that the transition of colon CSCs from the actively proliferating state to a quiescent state is correlated with the disappearance of Lgr5 molecule. The correlation was also verified by in vitro growth inhibitor-resistance assay (FIG. 45). In addition, the ALDH activity was reduced, while there was no alteration in other CSC markers (FIGS. 46, 61, and 62).

The Lgr5-negative cells prepared via irinotecan treatment were assessed for the tumor-forming activity. Subcutaneous injection of ten cells derived from PLR59 and PLR123 resulted in formation of tumors in two and one NOG mice (Table 4), respectively. Table 4 shows the tumor-forming activity of Lgr5-negative CSCs 49 hours after inoculation. In Table 4 shown below, asterisk indicates tumor xenografts established in NOG mice; plus symbol (single) indicates the number of animals bearing tumors, and plus symbol (double) indicates the total number of animals.

TABLE 4

| Cell | Number of cells/ inoculation site | | |
|---|---|---|---|
| line* | 1,000 | 100 | 10 |
| PLR59 | 6⁺/6‡ | 6/6 | 2/6 |
| PLR123 | 6/6 | 6/6 | 1/6 |

Figure 12:
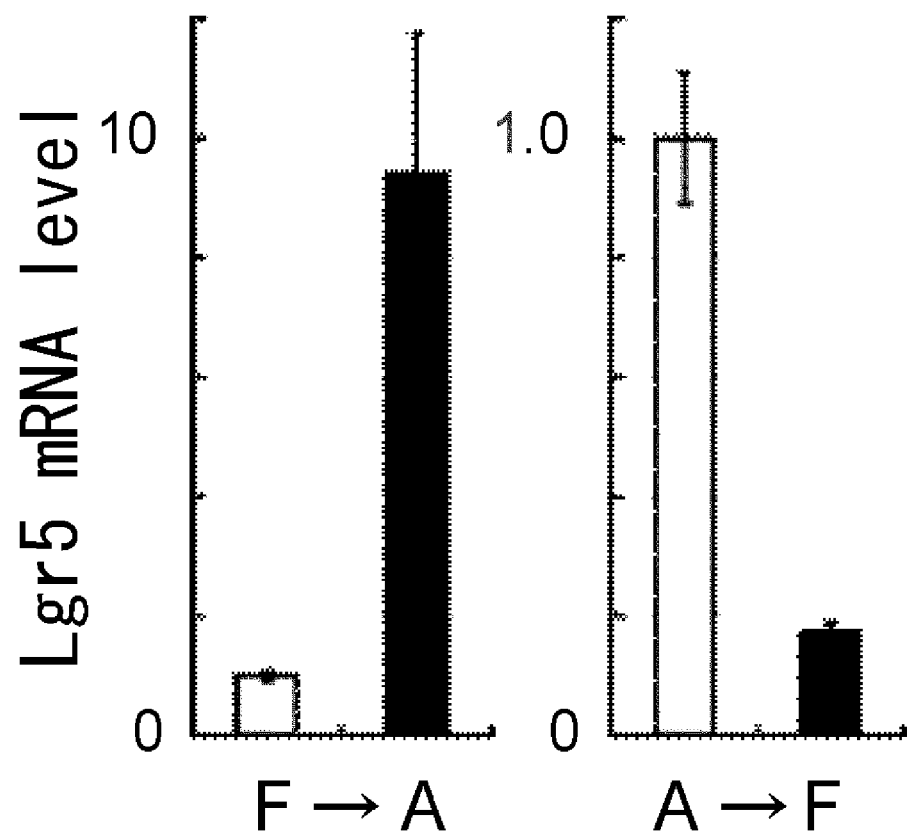
FIG. 12 is a diagram showing Lgr5 mRNA levels in cells before and after switching to adherent culture or suspension culture (normalized to 1). F→A represents the switching from suspension culture to adherent culture, while A→F represents the switching from adherent culture to suspension culture. The results were averaged from three experiments. The bar at the top of each column represents standard deviation.
Figure 33:
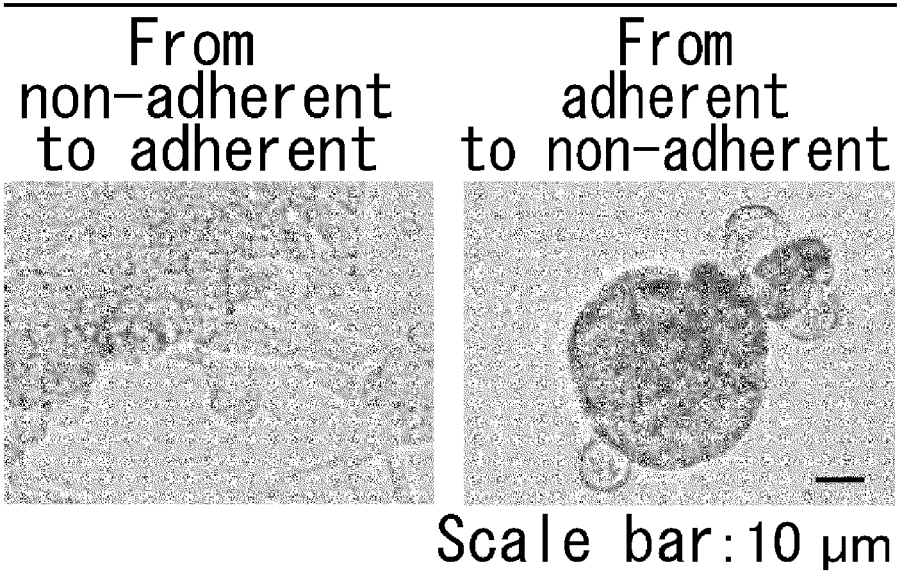
FIG. 33 shows photographs depicting the morphological interconversion of CSCs. When Lgr5-negative colon CSCs were dispersed and then cultured in a flat-bottomed plate, some of the cells adhered to the plate bottom, became positive for Lgr5, and showed a mesenchymal cell-like morphology (at left). On the other hand, when Lgr5-positive adherent colon CSCs were cultured in an ultra-low adherent plate, some of the cells halted their growth and formed a spheroid-like structure. Scale bar represents 10 µm.

In addition, the present inventors carried out examinations to assess whether Lgr5-negative colon CSCs undergo a transition into an Lgr5-positive state. When Lgr5-negative colon CSCs were separated and cultured with normal cell culture plates, the following was observed: some of the cells adhered to the bottom of the plates became positive for Lgr5, exhibited mesenchymal cell-like morphology (FIGS. 12 and 33), and started to proliferate. On the other hand, when Lgr5-positive adherent colon CSCs were cultured in an ultra low adherent plate, the present inventors observed that some of the cells halted their growth and formed a spheroid-like structure and that the Lgr5 mRNA level was very low (FIGS.

Figure 47:
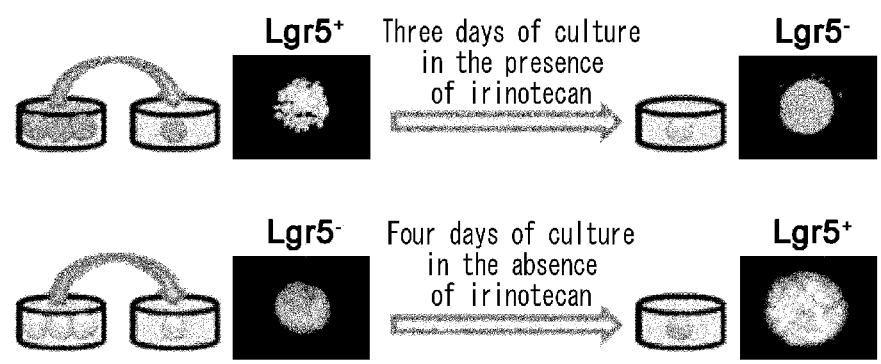
FIG. 47 is a diagram showing interconversion between Lgr5-positive and -negative cells. Lgr5-positive cells were collected by FACS. After limiting dilution, the cells were inoculated and cultured for three days in the presence of irinotecan under adherent culture conditions. On the other hand, irinotecan-treated Lgr5-negative cells were diluted by limiting dilution, and then inoculated and cultured for four days in the absence of irinotecan under adherent culture conditions. Lgr5 expression was visualized with PE-labeled anti-mouse IgG antibody (indicated in red) or AlexaFluo 488-labeled anti-mouse IgG antibody (indicated in green).

12 and 33). The transition from the Lgr5-positive to Lgr5-negative state (and the reverse) was also confirmed by observations using a single cell in culture. When single Lgr5-positive cells were individually cultured in a multi-well plate, the cells underwent a transition into the Lgr5-negative state within three days after irinotecan treatment. When single Lgr5-negative cells prepared via irinotecan treatment were individually cultured in a multi-well plate in the absence of irinotecan, 19 to 43% of the cells underwent a transition into the Lgr5-positive state within four days (FIG. 47 and Table 5).

TABLE 5

| Transition of state | Cell line | Number of cells | | |
|---|---|---|---|---|
| | | Lgr5 positive | Lgr5 negative | Total |
| Lgr5 positive to negative | PLR59 | 0 (0%) | 132 (100%) | 132 |
| | PLR123 | 1 (1%) | 173 (99%) | 174 |
| Lgr5 negative to positive | PLR59 | 18 (19%) | 78 (81%) | 96 |
| | PLR123 | 29 (43%) | 39 (57%) | 68 |

Table 5 shows cell count ratios of Lgr5-positive and -negative cells stained by immunocytochemistry using an anti-Lgr5 antibody (antibody 2L36). Number in parenthesis represents the ratio of Lgr5-positive or -negative cell count.

Figure 63:
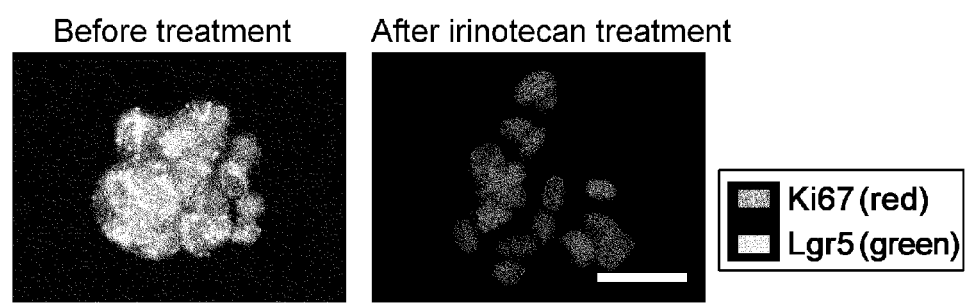
FIG. 63 shows double-staining using anti-Lgr5 antibody and anti-Ki67 antibody of in vitro cultured cells of Lgr5-positive and -negative cells obtained by treating adherent Lgr5-positive cells with irinotecan. Scale bar represents 50 µm.

Furthermore, to assess the proliferation of Lgr5-positive and -negative cells, in vitro cultured Lgr5-positive and -negative cells were double-stained using an anti-Lgr5 antibody and an anti-Ki67 antibody. The result showed that the expression of Lgr5 was correlated with Ki67 staining. Specifically, Lgr5-positive cells were positive for Ki67, while Lgr5-negative cells were negative for Ki67 (FIG. 63).

Figure 64:
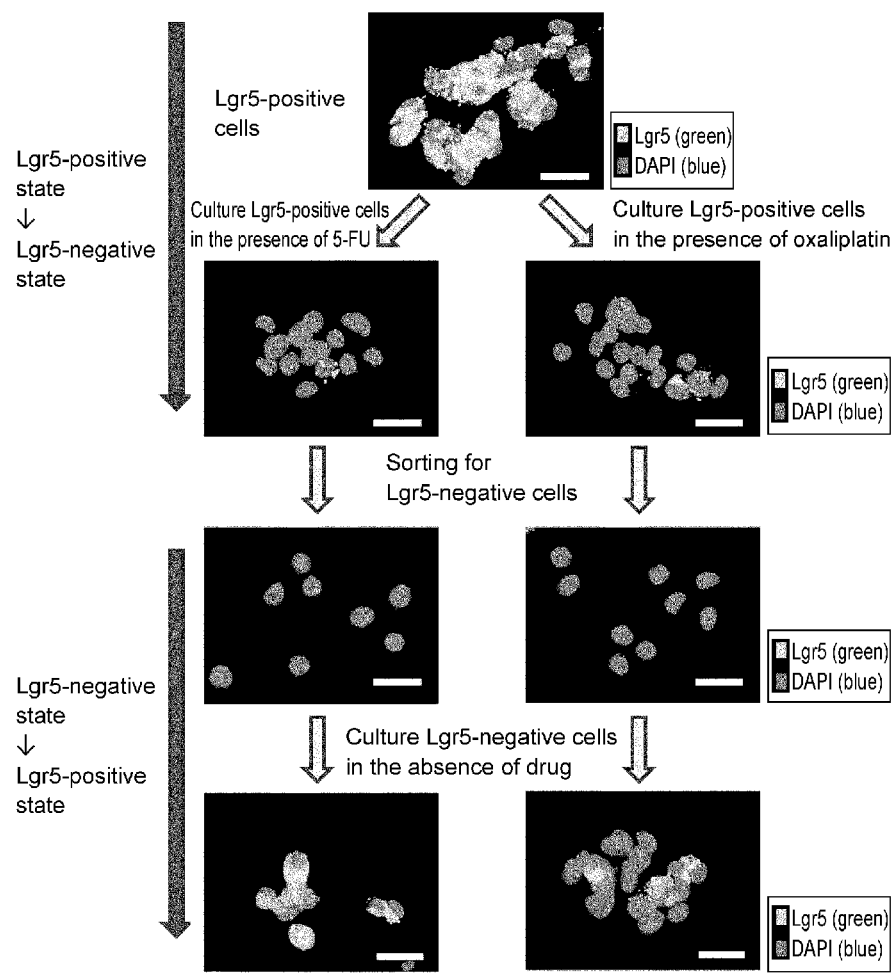
FIG. 64 shows a photograph depicting transition into an Lgr5-negative state by 5-FU or oxaliplatin. Scale bar represents 50 µm.

Then, it was tested whether drugs other than irinotecan also caused transition from the Lgr5-positive state to Lgr5-negative state (and the opposite). Lgr5-positive cells were incubated under an adherent condition in the presence of 5-FU or oxaliplatin for 24 hours, and then cultured in the absence of the drug for 48 hours. The cells were analyzed for the expression of Lgr5 by IHC using an anti-Lgr5 antibody (antibody 2L36). After treatment with 5-FU or oxaliplatin, most of the Lgr5-positive cells underwent transition into the Lgr5-negative state. Next, Lgr5-negative cells sorted using MoFlo XDP cell sorter and treated with 5-FU or oxaliplatin were cultured for four days in the absence of the drug. The cells were analyzed for Lgr5 expression. The result showed that a small number of Lgr5-positive cells appeared in the sorted Lgr5-negative cell population within four days (FIG. 64).

Thus, the present inventors concluded that colon CSCs underwent interconversion between the Lgr5-positive and -negative states and the transition does not require any exogenous factor and/or niche environment.

Example 7

In Vitro and In Vivo EMT of Lgr5-positive Colon CSCs

Figure 13:
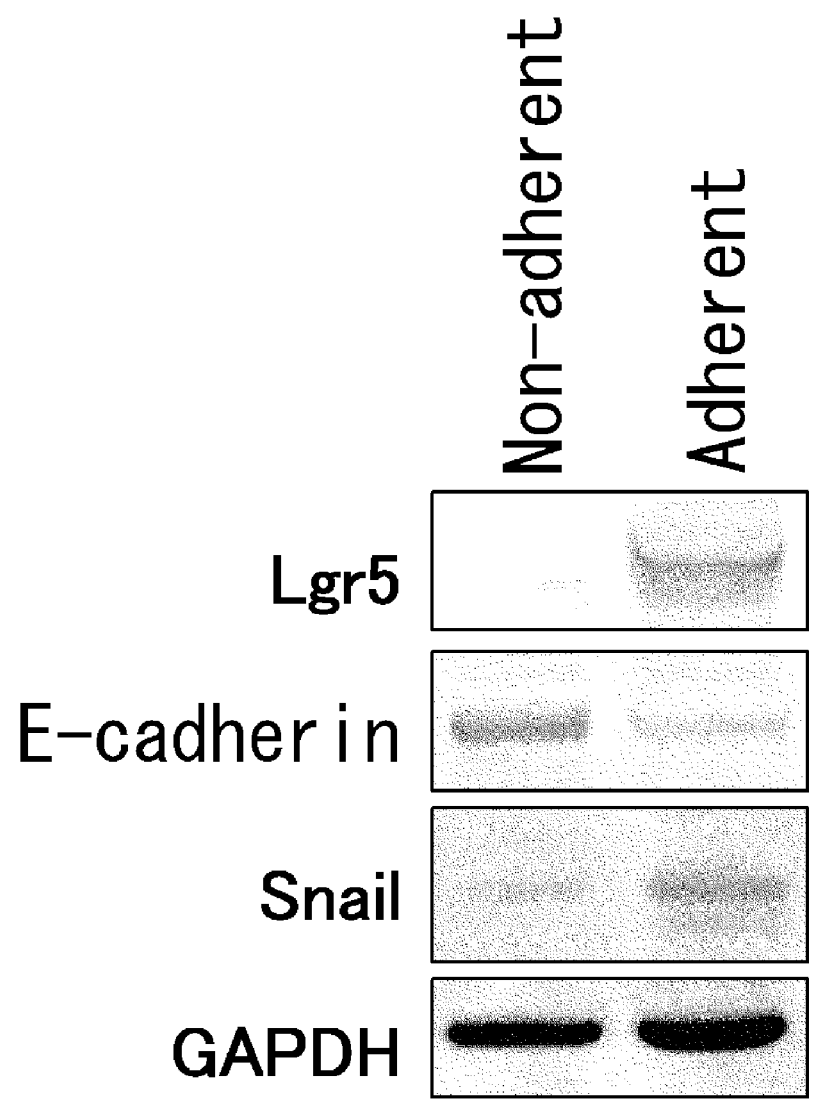
FIG. 13 shows photographs depicting a result of Western blot analysis of Lgr5-negative non-adherent CSCs and Lgr5-positive adherent CSCs for E-cadherin and Snail. Non-adherent CSCs expressed E-cadherin at a high level, while adherent CSCs expressed Snail at a high level. GADPH was used as a loading control.
Figure 14:
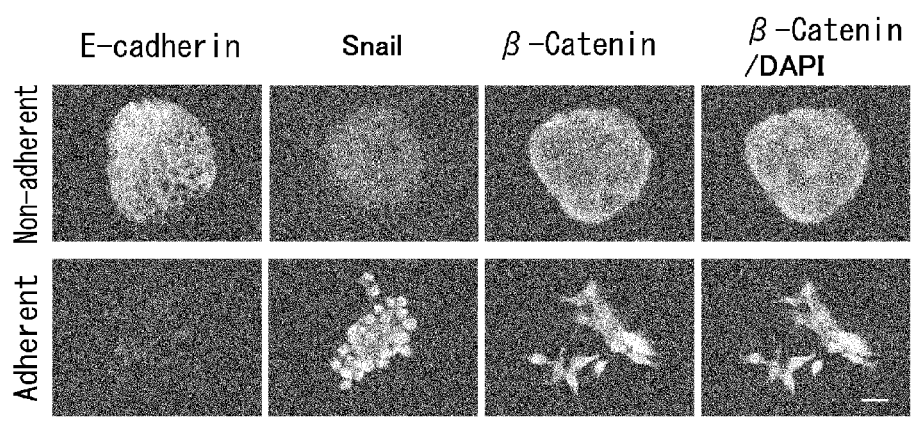
FIG. 14 shows photographs depicting a result of immunocytochemistry of Lgr5-negative non-adherent CSCs and Lgr5-positive adherent CSCs using E-cadherin antibody, Snail antibody, and β-catenin antibody. Non-adherent CSCs were epithelium-like cells expressing cell-surface E-cadherin and β-catenin at high levels, while adherent CSCs were mesenchyme-like cells with nuclear localization of Snail and β-catenin. Scale bar represents 25 μm.
Figure 15:
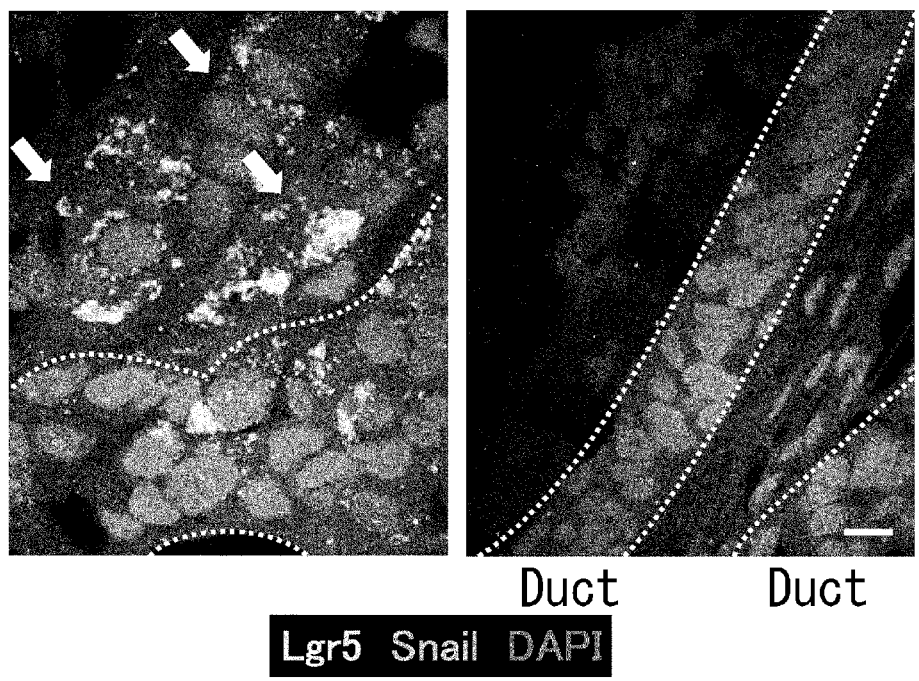
FIG. 15 shows photographs depicting a result of immunohistochemistry of xenograft tissues using anti-Lgr5 antibody and anti-Snail antibody. The concomitant expression of nuclear Snail and cytoplasmic Lgr5 was detected in EMT-like cells of budding areas (left panel), while such expression was not observed in the ducts (right panel). Arrows indicate Lgr5-positive budding cells. Scale bar represents 10 μm.
Figure 26:
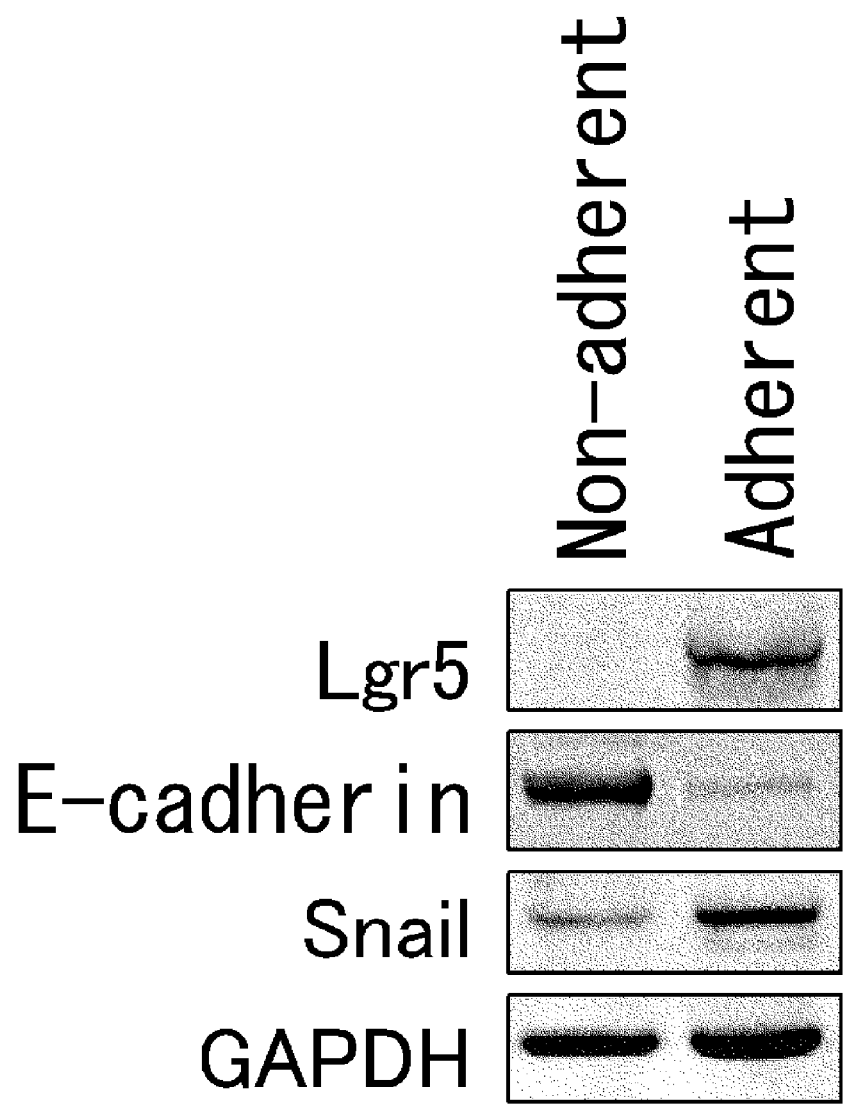
FIG. 26 shows photographs depicting a result of Western blot analysis of Lgr5-negative non-adherent CSCs and Lgr5-positive adherent CSCs for E-cadherin and Snail. Non-adherent CSCs expressed E-cadherin at a high level and adherent CSCs expressed Snail at a high level. GADPH was used as a loading control.

Mesenchymal-like cells expressing nuclear β-catenin are considered migratory CSCs and metastatic CSCs that undergo EMT (Brabletz T, Jung A, Spaderna S, Hlubek F, Kirchner T (2005) Opinion: migrating cancer stem cells—an integrated concept of malignant tumor progression. Nat Rev Cancer 5:744-749). Since the morphology of Lgr5-positive colon CSCs was similar to that of mesenchymal cells, the present inventors tested whether Lgr5-positive colon CSCs correspond to migratory CSCs. Western blot analysis revealed low level expression of cell-surface E-cadherin, high level expression of Snail, and nuclear β-catenin (which is characteristic of EMT) in the Lgr5-positive colon CSCs (FIGS. 13, and 14, and 26). In contrast, the Lgr5-negative colon CSCs did not show any evidence of EMT. Specifically, cell-surface E-cadherin was expressed at a high level; Snail was expressed at a low level, and there was no nuclear localization of β-catenin. Furthermore, concomitant expression of Snail and Lgr5 was observed in cells that underwent EMT in budding areas of xenograft tumor tissues (FIG. 15). This finding supports the view that the Lgr5-positive colon CSCs correspond to migratory stem cells. In recent years, Pang et al. have reported that a subpopulation of CD26[+] CSCs has great metastatic capacity (Pang R, et al. (2010) A subpopulation of CD26+ cancer stem cells with metastatic capacity in human colorectal cancer. Cell Stem Cell 6:603-615). Results by the present inventors revealed that both Lgr5-positive and Lgr5-negative CSCs expressed CD26 on the cell surface, suggesting the need to further study the importance of CD26 in metastasis.

Figure 35:
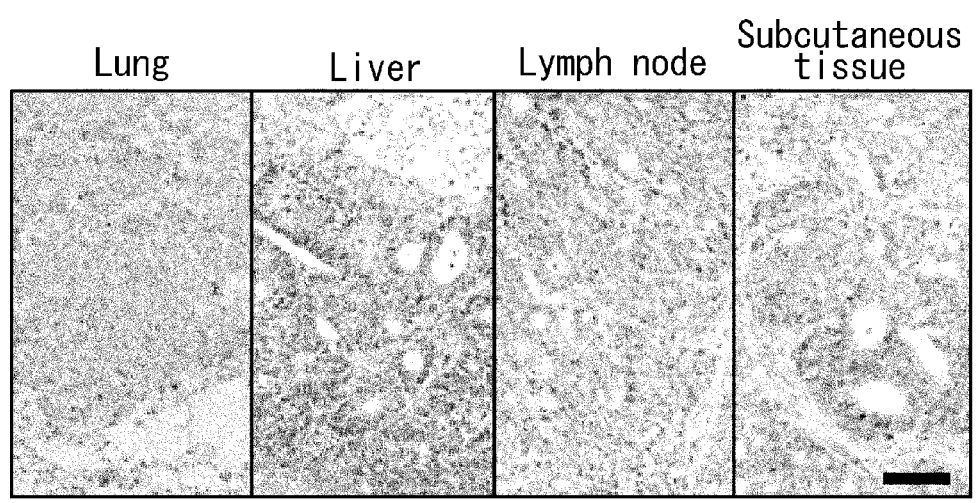
FIG. 35 shows photographs depicting a result of histopathological experiments on tumors in the lungs, liver, lymph nodes, and subcutaneous tissues. In the lungs, tumor cells formed undifferentiated tumor foci. Meanwhile, in the liver and other organs, tumor cells formed a ductal structure involving multiple differentiation stages. Scale bar represents 100 µm.
Figure 36:
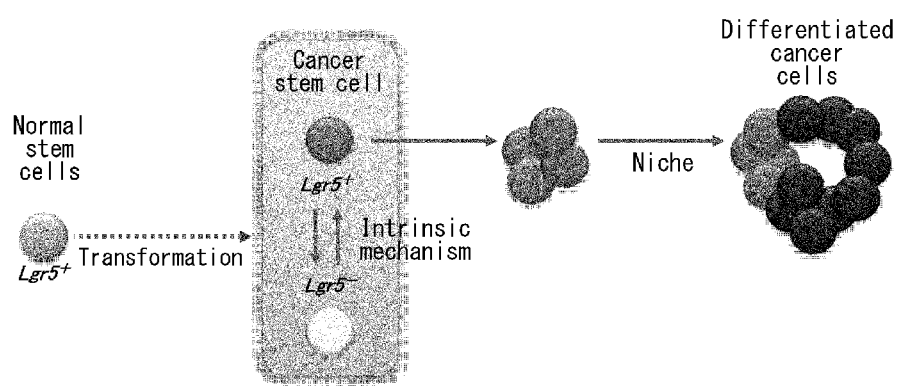
FIG. 36 is a schematic diagram for the proposed colon CSC model. CSCs undergo an intrinsic interconversion between two types of independent states in response to environmental changes such as the presence of anti-cancer drugs. According to previous findings, normal colon stem cells expressing Lgr5 transform into CSCs via mutation in multiple genes. Established CSC lines in the growth phase express Lgr5, and undergo EMT. Under a specific stressful environment, the cells can change into the Lgr5-negative quiescent state. Niche/environment is involved in stimulating the transition of CSCs to the differentiation stage.

Previous experiments by the present inventors demonstrated that the Lgr5-positive colon CSCs formed tumors in multiple tissues including lung, liver, lymph node, and subcutaneous tissues. Interestingly, in the liver, lymph node, and subcutaneous tissues, tumors with epithelial ductal structures were reconstituted by at least 40 days after intravenous injection of tumor cells, whereas such structures were not reconstituted in the lung (FIGS. 34 and 35).

Figure 48:
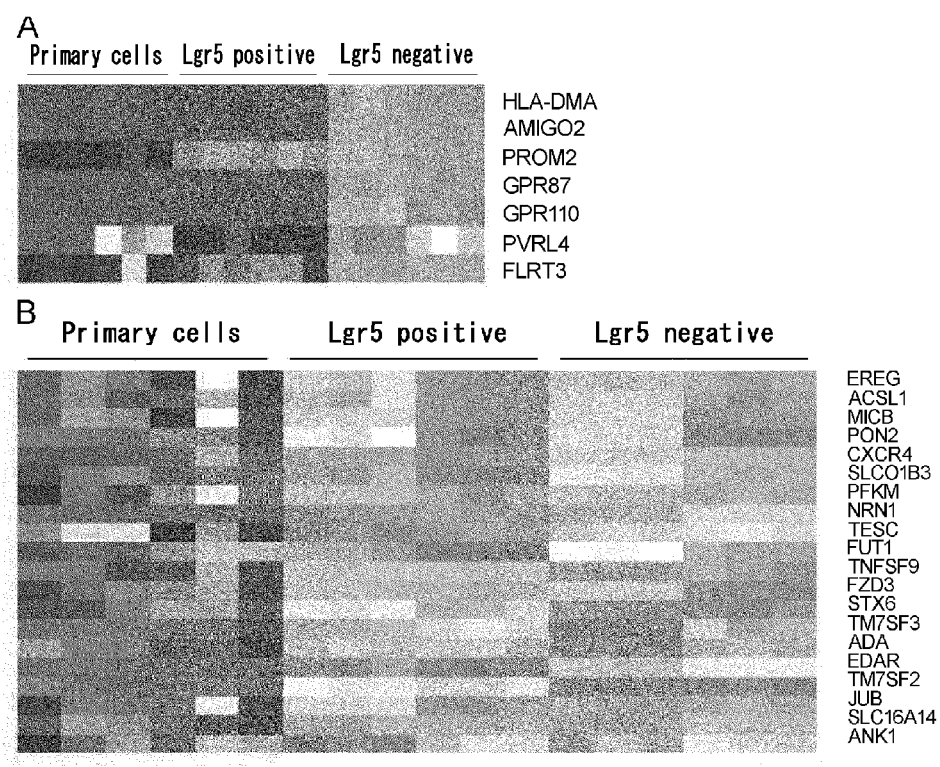
FIG. 48 shows diagrams depicting heat maps for (A) seven genes the expression of which was significantly up-regulated in Lgr5-negative cells as compared to Lgr5-positive cells and for (B) 20 genes the expression levels of which were elevated in Lgr5-positive and Lgr5-negative cells as compared to primary cells derived from xenograft animals. RNAs were prepared from Lgr5-positive and -negative CSCs derived from PLR59 and PLR123, and primary cells isolated from xenograft animals. RNAs were analyzed using Affymetrix U133.
Figure 49:
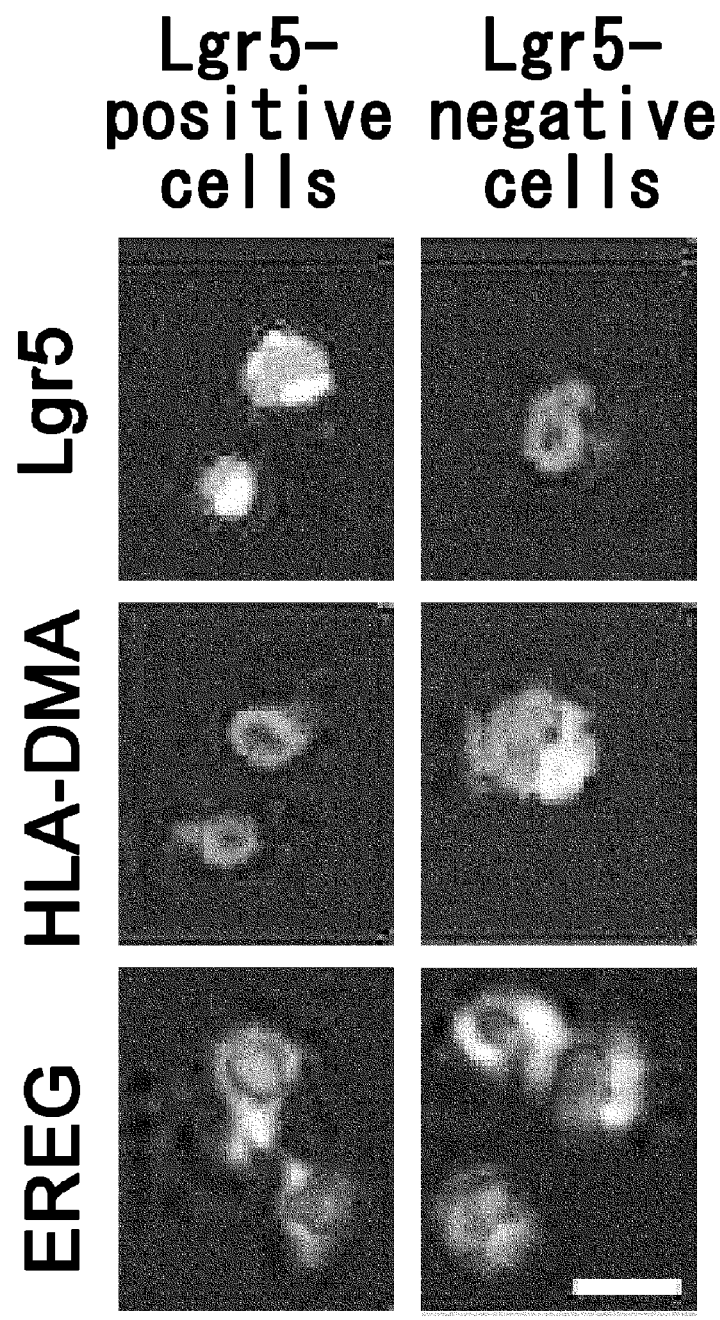
FIG. 49 shows photographs depicting the binding of anti-HLA-DMA antibody and anti-EREG antibody to Lgr5-positive and Lgr5-negative CSCs with immunohistochemical staining. CSCs (PLR123) were fixed and treated with anti-HLA-DMA antibody (Dako) and anti-EREG antibody (EP27). Intense fluorescence signals (red for both HLA-DMA and EREG) were observed on Lgr5-negative cells treated with anti-HLA-DMA antibody, whereas weak fluorescence (green) or no fluorescence was detected on Lgr5-positive cells. Fluorescence signals were detected on both Lgr5-negative and -positive cells treated with anti-EREG antibody.
Figure 50:
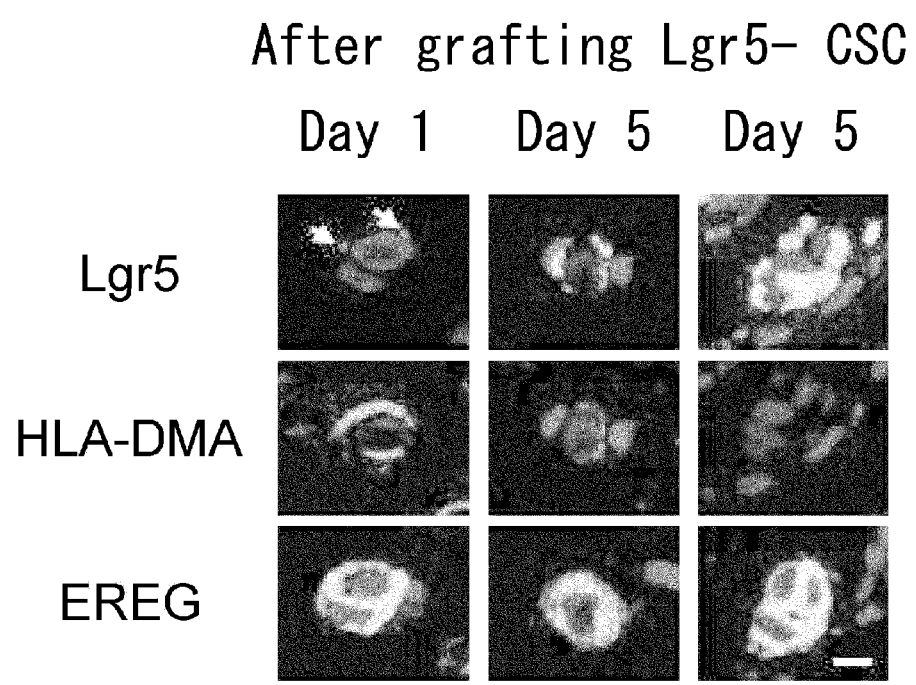
FIG. 50 shows photographs depicting the transition from Lgr5-negative CSCs to Lgr5-positive CSCs at an early stage of tumor formation. In NOG mice injected with PLR123 xenograft animal-derived LGR5-negative CSCs, tumors derived from Lgr5-negative CSCs were stained with antibodies against Lgr5 (green), HLA-DMA (red), and EREG (green). Lgr5-weakly-expressing, HLA-DMA-positive, EREG-positive cells, and Lgr5-positive, HLA-DMA-negative, EREG-positive cells were observed to be present on day 5. Scale bar represents 10 µm.
Figure 51:
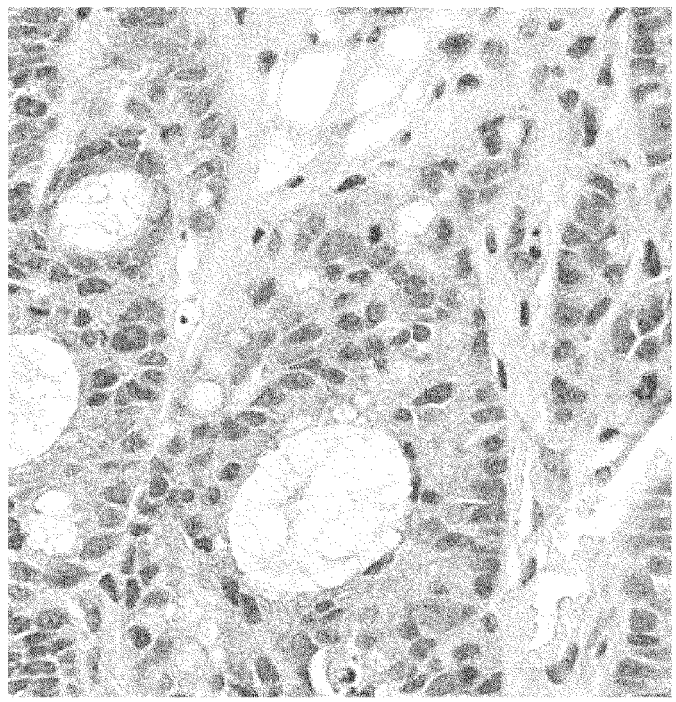
FIG. 51 shows the reconstitution of tumor hierarchy from LGR5-negative CSCs. Photographs depicting the tissue structure (FIG. 51A) and an image obtained by immunofluorescence microscopic observation using anti-Lgr5 antibody and anti-E-cadherin antibody (FIG. 51B) are shown. Green and red indicate the presence of Lgr5 and E-cadherin, respectively. Scale bar represents 50 µm.
Figure 51:
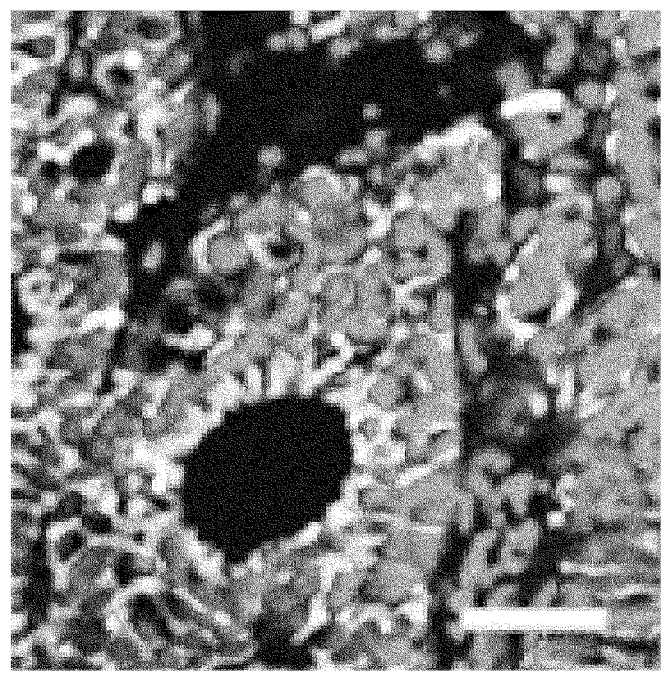

Next, the present inventors examined whether Lgr5-negative CSCs directly form the hierarchical organization of cancer or first undergo transition to Lgr5-positive cells in vivo. To find markers for detecting Lgr5-negative CSCs, gene expression profiling was carried out using Lgr5-positive cells, Lgr5-negative cells, and primary cells from xenograft tumors. As a result, HLA-DMA was selected from molecules whose expression can be detected at high level in the Lgr5-negative CSCs as compared to the Lgr5-positive CSC and primary cells (FIG. 48). By immunohistochemistry using anti-Lgr5 antibody, anti-HLA-DMA antibody, and anti-EREG antibody, HLA-DMA was demonstrated to be specifically expressed in the Lgr5-negative CSCs (FIG. 49). HLA-DMA is also expressed in macrophages. Then, to rule out the possibility that cells stained by immunohistochemistry using the anti-HLA-DMA antibody are macrophages, the present inventors tested not only HLA-DMA but also other markers expressed in CSCs. Immunohistochemistry using an antibody against EREG expressed in both Lgr5-positive and -negative CSCs (FIG. 48) confirmed that EREG was expressed in both of Lgr5-positive and Lgr5-negative CSCs (FIG. 49). It was demonstrated that Lgr5-negative CSCs could be identified as cells that are positive for both HLA-DMA and EREG by detection using both markers in combination. After injection of a homogeneous population of Lgr-negative CSCs to NOG mice, cells expressing Lgr5 only weakly for one day after the injection, which however remained positive for HLA-DMA and EREG, were appeared. Then, cells that are negative for HLA-DMA but remain positive for Lgr5 and EREG appeared by five days after the injection (FIG. 50). Tumors derived from Lgr5-negative CSCs had specific ductal structures and included Lgr5-positive cells (FIG. 51).

Figure 52:
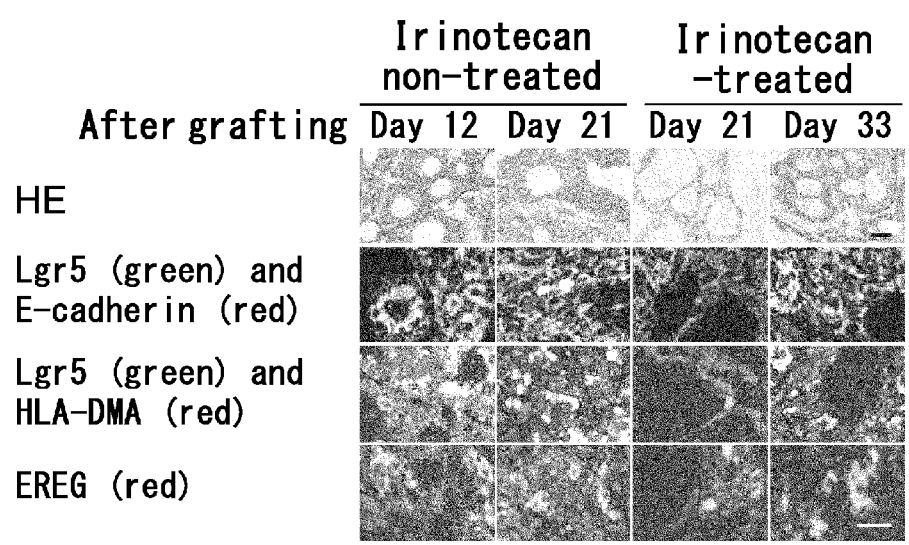
FIG. 52 shows photographs depicting histopathology (HE) (first row), immunostaining using Lgr5 antibody (green) and E-cadherin antibody (red) (second row), immunostaining using Lgr5 antibody (green) and HLA-DMA antibody (red) (third row), and immunostaining using EREG antibody (red) (fourth row), of tumors after irinotecan treatment. Mice bearing tumors derived from LGR5-positive CSCs (PLR123) were treated with irinotecan, and their tumors were observed. Irinotecan or vehicle was administered to mice at days 12, 15, and 18 after tumor grafting. Scale bar represents 25 µm.
Figure 53:
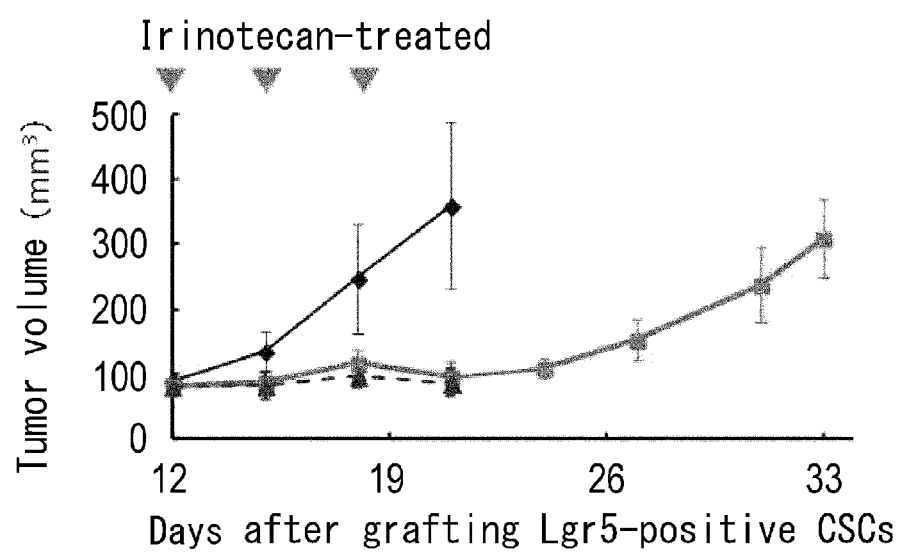
FIG. 53 Irinotecan was administered at a dose of 120 mg/kg/day to NOG mice at days 12, 15, and 18 after grafting tumors derived from LGR5-positive CSCs (PLR123). This figure is a graph showing tumor volumes in control mice administered with vehicle (closed diamond) and mice administered with irinotecan (closed square or triangle). Each value represents mean±standard deviation.
Figure 54:
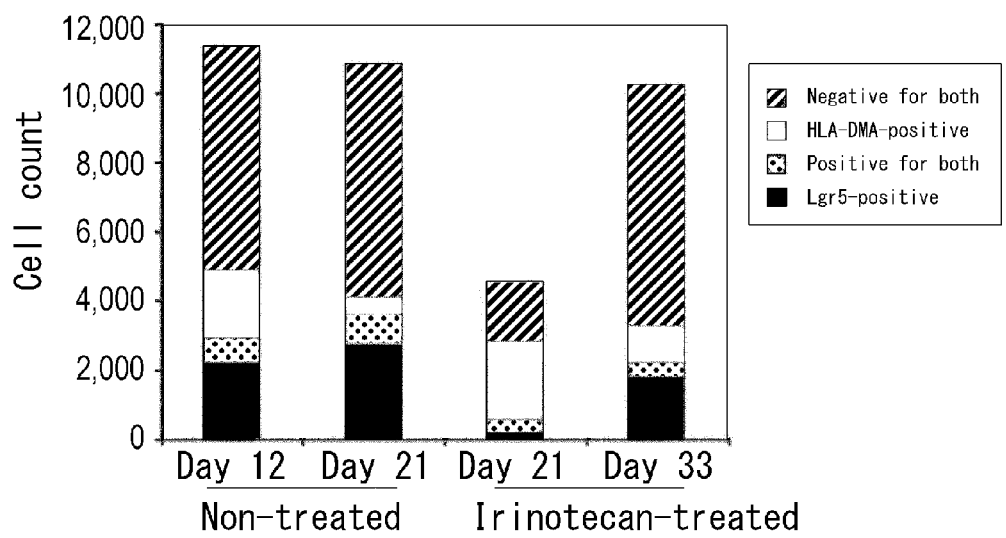
FIG. 54 is a graph showing the numbers of Lgr5-positive and HLA-DMA-positive cells in xenograft tumor tissues. Thin sections of tissues were treated with Lgr5 antibody and HLA-DMA antibody, and then the numbers of Lgr5-positive and HLA-DMA-positive cells were counted. Values represent the total numbers of cells counted for respective groups (n=3).
Figure 66:
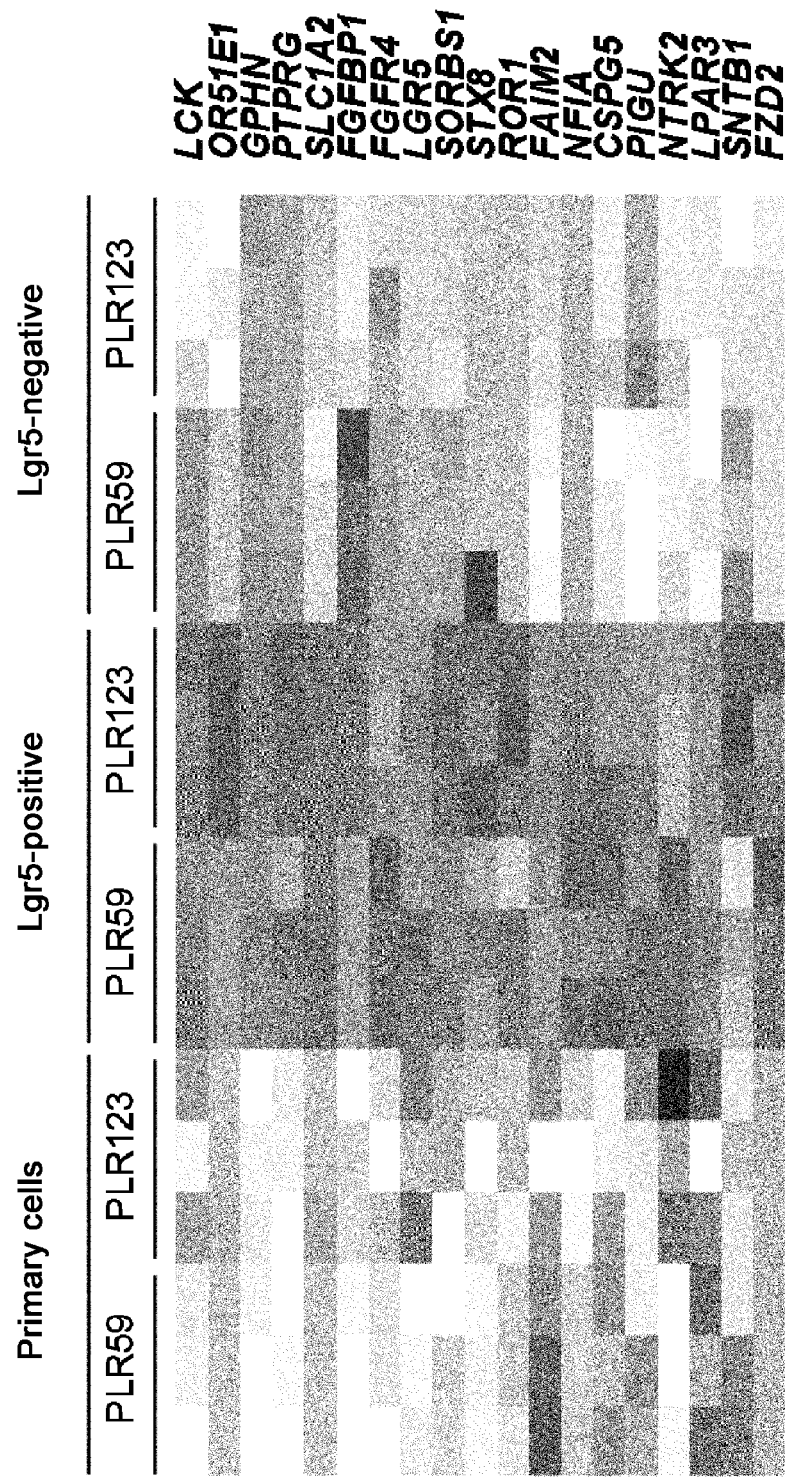
FIG. 66 shows a heat map of genes expressed at high levels in Lgr5-positive cells.

To probe the possibility of in vivo transition to a growth inhibitor-resistant state, irinotecan was administered at the maximum tolerated dose (MTD) (120 mg/kg) into the peritoneal cavities of NOG mice bearing tumors derived from Lgr5-positive CSCs. Tumor growth was inhibited almost completely (FIG. 53), and the ductal structures were collapsed extensively (FIG. 52). This condition resulted in a dramatic decrease of Lgr5-positive cells (FIGS. 52 and 54). The number of Lgr5-negative and HLA-DMA-positive cells increased significantly after irinotecan treatment. By contrast, in vehicle-treated control mice, about one third of cancer cells were positive for Lgr5 in both ductal and budding areas (FIG. 52). Both Lgr5-positive cells and HLA-DMA-positive and Lgr5-negative cells were positive for EREG, and were identified to be CSCs (FIG. 52). After irinotecan treatment, Lgr5-positive cells appeared again from xenografts and Lgr5-negative cells prepared by treating Lgr5-positive cells with irinotecan for three days (FIG. 66).

Example 8

Presence of Lgr5-negative and -positive CSCs in Clinical Tumor Specimens

Figure 55:
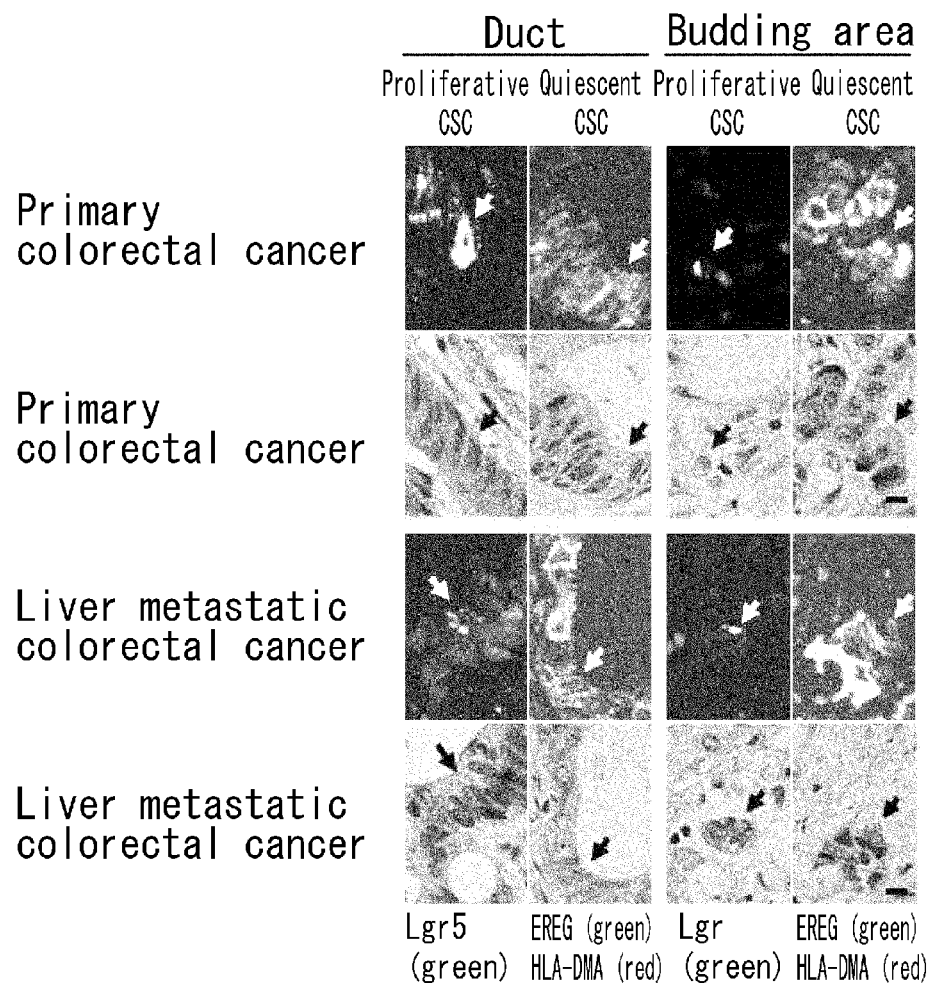
FIG. 55 shows photographs depicting the same tissue sections from primary and liver metastatic large intestine cancers isolated from patients, which were stained with HE (second and fourth rows), and antibodies against Lgr5 (green), HLA-DMA (red), and EREG (green) (first and third rows). Positivity for Lgr5 indicates proliferating CSCs, while positivity for EREG and HLA-DMA implies Lgr5-negative quiescent CSCs. Both Lgr5-negative and -positive CSCs were detected in ductal structures and budding areas of primary and liver metastatic tumors. Lgr5-positive CSCs were also found as single cells in stromal regions. The same staining patterns were also observed in multiple tumor tissues isolated from different patients. Arrows indicate CSCs. Scale bar represents 10 µm.

Proliferating and quiescent CSCs were identified by immunohistochemistry using anti-Lgr5 antibody (2U2E-2), anti-HLA-DMA antibody, and anti-EREG antibody (FIG. 55 and Table 6). Proliferative CSC represents Lgr5-positive cell, while quiescent ones represents HLA-DMA-positive and EREG-positive cell (Table 6). Lgr5-positive cells which are positive for both HLA-DMA and EREG, and Lgr5-negative cells which are positive for both HLA-DMA and EREG were present in a very small number in primary and metastatic large intestine cancer specimens isolated from large intestine cancer patients (FIG. 55). Both Lgr5-positive and -negative cells were detected in eight of 12 specimens of human large intestinal cancer tissues. Meanwhile, either Lgr5-positive or Lgr5-negative cells were observed in the remaining four specimens. Throughout all specimens, Lgr5-positive cells accounted for 0.003 to 1.864%, and Lgr5-negative cells accounted for 0.001 to 10.243% (Table 6).

TABLE 6

| Property of CSC | | Case number | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Duct | Proliferative | P[†] | P | P | P | P | P | P | P | P | N | P | N |
| | Quiescent | N | P | N | P | P | P | P | P | P | P | N | P |
| Budding area | Proliferative | P | N | N | P | P | N | N | P | P | P | N | N |
| | Quiescent | N | P | N | P | N | P | N | P | N | N | N | P |
| Frequency | Proliferative | 1.864 | 0.786 | 0.136 | 0.121 | 0.119 | 0.095 | 0.063 | 0.054 | 0.018 | 0.010 | 0.003 | 0.000 |
| | Quiescent | 0.000 | 0.243 | 0.000 | 0.187 | 0.001 | 0.228 | 0.045 | 0.065 | 0.003 | 0.003 | 0.000 | 0.073 |

(P[†] indicates that proliferating or quiescent CSCs were detected; N indicates that proliferating or quiescent CSCs were undetectable)
(Frequency indicates cell percentage)

Figure 65:
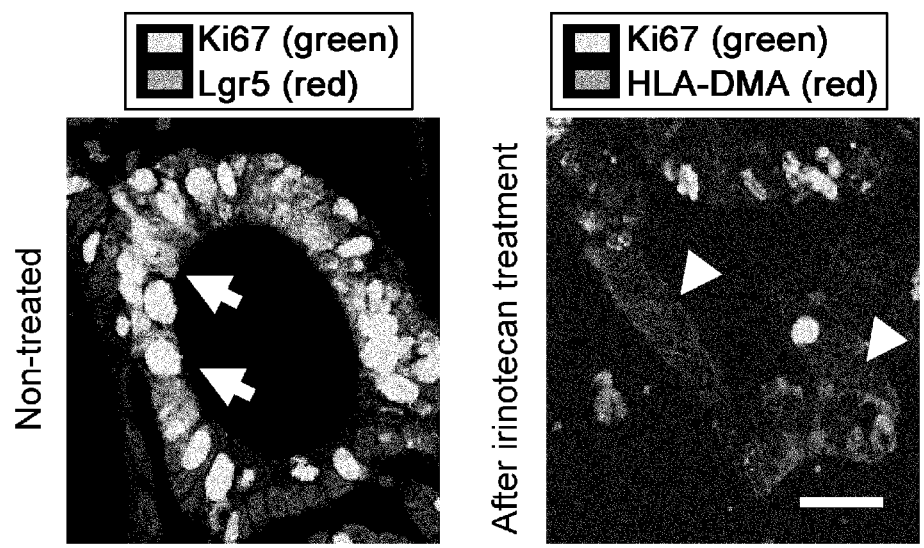
FIG. 65 is a photograph showing Ki67 staining of Lgr5-positive cells and HLA-DMA-positive cells in a xenograft at 21 days after transplantation of Lgr5-positive cells. Arrows indicate Lgr5-positive cells, and arrowheads indicate HLA-DMA positivity. Scale bar represents 25 µm.

(FIG. 52). Furthermore, xenografts were excised from mice on day 21 after transplantation of irinotecan-treated or non-treated Lgr5-positive cells. Sections from the xenografts were double-stained with an anti-Ki67 antibody and an anti-Lgr5 antibody or an anti-HLA-DMA antibody. The result of double staining for Ki67 and Lgr5 or HLA-DMA, which is a marker for Lgr5-negative cells, also confirmed a correlation between Lgr5 expression and Ki67 staining in xenografts, similarly to the observation using in vitro cultured cells. Specifically, the Lgr5-positive cells were positive for Ki67, while the Lgr5-negative/HLA-DMA-positive cells were negative for Ki67 (FIG. 65). The results described above, when considered together, suggest that Lgr5-negative CSCs are the origin of large intestine cancer after growth inhibitor treatment and reconstitute cancer hierarchy via Lgr5-positive cells.

Figure 67:
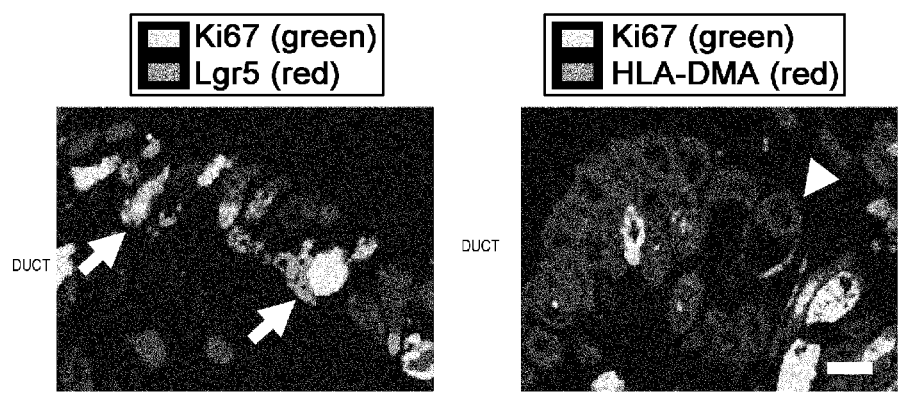
FIG. 67 shows photographs depicting Ki67 staining of Lgr5-positive cells and HLA-DMA-positive cells in colon cancer tissues isolated from patients. Arrows indicate Lgr5-positive cells, and arrowhead indicates HLA-DMA positivity. Scale bar represents 10 µm.

Further, RNA extracted from primary cells isolated from xenografts, adherent Lgr5-positive cells, and Lgr5-negative cells prepared by treating Lgr5-positive cells with irinotecan for three days were analyzed by DNA microarray and RT-qPCR to search for markers that are expressed differentially in those cells. The result showed that adherent Lgr5-positive cells expressed LCK, FGFBP1, ROR1, PIGU, and such at high levels as compared to primary cells isolated Both Lgr5-positive and -negative CSCs were detected in the ductal and budding areas (FIG. 55). Furthermore, in ducts, Lgr5-positive and -negative CSCs were not limited to particular areas but distributed at random over the entire ducts. Then, Ki67 staining was performed to analyze Lgr5-positive cells and HLA-DMA-positive cells in large intestine cancer tissues derived from patients. The result showed that Lgr5-positive cells were also positive for Ki67 in clinical tumor specimens whereas Lgr5-negative/HLA-DMA-positive cells were negative for Ki67 (FIG. 67).

INDUSTRIAL APPLICABILITY

The present invention provides cancer stem cells isolated using cell markers, substantially homogeneous cancer stem cell populations containing the cancer stem cells, and methods for producing the cancer stem cell populations. The present invention enables preparation of a large quantity of homogeneous cancer stem cells and cancer stem cell populations. Use of these cancer stem cells and cancer stem cell populations in high-throughput screening analyses for candidate pharmaceutical substances will dramatically increase the chances of discovering agents and diagnostic markers that are effective for cancer recurrence and metastasis in cancer patients. The present invention also provides new cancer stem cell markers and new cancer stem cell inhibitors.

The invention claimed is:

1. An isolated cancer stem cell, wherein the cancer stem cell is
   a) of human origin;
   b) positive for Lgr5, ALDH activity cell marker, LCK, FGFBP1, ROR1 and PIGU;
   c) adherent in serum free culture;
   d) generated by grafting a cancer into a non-human animal and passaging; and
   e) regenerates the hierarchical order of human cancer.

2. The cancer stem cell of claim 1, which is a mesenchymal cell.

3. The cancer stem cell of claim 1, which is derived from a gastrointestinal cancer.

4. The cancer stem cell of claim 3, wherein the gastrointestinal cancer is a large intestine cancer.

5. The cancer stem cell of claim 1, which is positive for one or more of cell markers CD133, CD44, EpCAM, CD166, CD24, CD26, CD29, and EREG.

6. The cancer stem cell of claim 5, which is positive for cell markers CD133, CD44, EpCAM, CD166, CD24, CD26, CD29, and EREG.

7. The cancer stem cell of claim 1, which has the ability of epithelial-mesenchymal transition.

8. A homogeneous cancer stem cell population comprising the cancer stem cell of claim 1.

* * * * *

SEQUENCE LISTING

<160> NUMBER OF SEQ ID NOS: 24

<210> SEQ ID NO 1
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 1
agtttatcct tctggtggta gtcc                                            24

<210> SEQ ID NO 2
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 2
caagatgtag agaagggat tga                                              23

<210> SEQ ID NO 3
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 3
ctctgctcct cctgttcgac                                                 20

<210> SEQ ID NO 4
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 4
acgaccaaat ccgttgactc                                                 20

<210> SEQ ID NO 5
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 5
aagtcccttg ccatcctaaa a                                               21

<210> SEQ ID NO 6
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 6
atgctatcac ctcccctgtg                                                 20

<210> SEQ ID NO 7
<211> LENGTH: 2598
<212> TYPE: DNA
<213> ORGANISM: Homo sapiens

<400> SEQUENCE: 7

| | |
|---|---|
| atggccctcg tactcggctc cctgttgctg ctggggctgt gcgggaactc cttttcagga | 60 |
| gggcagcctt catccacaga tgctcctaag gcttggaatt atgaattgcc tgcaacaaat | 120 |
| tatgagaccc aagactccca taaagctgga cccattggca ttctctttga actagtgcat | 180 |
| atctttctct atgtggtaca gccgcgtgat ttcccagaag atactttgag aaaattctta | 240 |
| cagaaggcat atgaatccaa aattgattat gacaagccag aaactgtaat cttaggtcta | 300 |
| aagattgtct actatgaagc agggattatt ctatgctgtg tcctggggct gctgtttatt | 360 |
| attctgatgc ctctggtggg gtatttcttt tgtatgtgtc gttgctgtaa caatgtggt | 420 |
| ggagaaatgc accagcgaca aaggaaaat gggcccttcc tgaggaaatg ctttgcaatc | 480 |
| tccctgttgg tgatttgtat aataataagc attggcatct tctatggttt tgtggcaaat | 540 |
| caccaggtaa gaacccggat caaaggagt cggaaactgg cagatagcaa tttcaaggac | 600 |
| ttgcgaactc tcttgaatga actccagag caaatcaaat atatattggc ccagtacaac | 660 |
| actaccaagg acaaggcgtt cacagatctg aacagtatca attcagtgct aggaggcgga | 720 |
| attcttgacc gactgagacc caacatcatc cctgttcttg atgagattaa gtccatggca | 780 |
| acagcgatca aggagaccaa agaggcgttg agaaacatga cagcaccctt gaagagcttg | 840 |
| caccaacaaa gtacacagct agcagcagt ctgaccagcg tgaaaactag cctgcggtca | 900 |
| tctctcaatg accctctgtg cttggtgcat ccatcaagtg aaacctgcaa cagcatcaga | 960 |
| ttgtctctaa gccagctgaa tagcaaccct gaactgaggc agcttccacc cgtggatgca | 1020 |
| gaacttgaca acgttaataa cgttcttagg acagatttgg atggcctggt ccaacagggc | 1080 |
| tatcaatccc ttaatgatat acctgacaga gtacaacgcc aaaccacgac tgtcgtagca | 1140 |
| ggtatcaaaa gggtcttgaa ttccattggt tcagatatcg acaatgtaac tcagcgtctt | 1200 |
| cctattcagg atatactctc agcattctct gtttatgtta ataacactga agttacatc | 1260 |
| cacagaaatt tacctacatt ggaagagtat gattcatact ggtggctggg tggcctggtc | 1320 |
| atctgctctc tgctgaccct catcgtgatt ttttactacc tgggcttact gtgtggcgtg | 1380 |
| tgcggctatg acaggcatgc caccccgacc acccgaggct gtgtctccaa caccggaggc | 1440 |
| gtcttcctca tggttggagt tggattaagt ttcctctttt gctggatatt gatgatcatt | 1500 |
| gtggttctta cctttgtctt tggtgcaaat gtggaaaaac tgatctgtga accttacacg | 1560 |
| agcaaggaat tattccgggt tttggataca ccctacttac taaatgaaga ctgggaatac | 1620 |
| tatctctctg gaagctatt taataaatca aaaatgaagc tcacttttga acaagtttac | 1680 |
| agtgactgca aaaaaaatag aggcacttac ggcactcttc acctgcagaa cagcttcaat | 1740 |
| atcagtgaac atctccaacat taatgagcat actggaagca taagcagtga attggaaagt | 1800 |
| ctgaaggtaa atcttaatat ctttctgttg ggtgcagcag gaagaaaaaa ccttcaggat | 1860 |
| tttgctgctt gtggaataga cagaatgaat tatgacagct acttggctca gactggtaaa | 1920 |
| tcccccgcag gagtgaatct tttatcattt gcatatgatc tagaagcaaa agcaaacagt | 1980 |
| ttgcccccag gaaatttgag gaactccctg aaaagagatg cacaaactat taaaacaatt | 2040 |
| caccagcaac gagtccttcc tatagaacaa tcactgagca ctctatacca aagcgtcaag | 2100 |
| atacttcaac gcacagggaa tggattgttg gagagagtaa ctaggattct agcttctctg | 2160 |
| gattttgctc agaacttcat cacaaacaat acttcctctg ttattattga ggaaactaag | 2220 |
| aagtatggga gaacaataat aggatatttt gaacattatc tgcagtggat cgagttctct | 2280 |

| | |
|---|---|
| atcagtgaga aagtggcatc gtgcaaacct gtggccaccg ctctagatac tgctgttgat | 2340 |
| gtctttctgt gtagctacat tatcgacccc ttgaatttgt tttggtttgg cataggaaaa | 2400 |
| gctactgtat ttttacttcc ggctctaatt tttgcggtaa aactggctaa gtactatcgt | 2460 |
| cgaatggatt cggaggacgt gtacgatgat gttgaaacta tacccatgaa aaatatggaa | 2520 |
| aatggtaata atggttatca taaagatcat gtatatggta ttcacaatcc tgttatgaca | 2580 |
| agcccatcac aacattga | 2598 |

<210> SEQ ID NO 8
<211> LENGTH: 2229
<212> TYPE: DNA
<213> ORGANISM: Homo sapiens

<400> SEQUENCE: 8

| | |
|---|---|
| atggacaagt tttggtggca cgcagcctgg ggactctgcc tcgtgccgct gagcctggcg | 60 |
| cagatcgatt tgaatataac ctgccgcttt gcaggtgtat tccacgtgga gaaaaatggt | 120 |
| cgctacagca tctctcggac ggaggccgct gacctctgca aggctttcaa tagcaccttg | 180 |
| cccacaatgg cccagatgga gaaagctctg agcatcggat ttgagacctg caggtatggg | 240 |
| ttcatagaag ggcacgtggt gattccccgg atccacccca actccatctg tgcagcaaac | 300 |
| aacacagggg tgtacatcct cacatccaac acctcccagt atgacacata ttgcttcaat | 360 |
| gcttcagctc cacctgaaga agattgtaca tcagtcacag acctgcccaa tgcctttgat | 420 |
| ggaccaatta ccataactat tgttaaccgt gatggcaccc gctatgtcca gaaaggagaa | 480 |
| tacagaacga atcctgaaga catctacccc agcaacccta ctgatgatga cgtgagcagc | 540 |
| ggctcctcca gtgaaaggag cagcacttca ggaggttaca tcttttacac cttttctact | 600 |
| gtacacccca tcccagacga agacagtccc tggatcaccg acagcacaga cagaatccct | 660 |
| gctaccactt tgatgagcac tagtgctaca gcaactgaga cagcaaccaa gaggcaagaa | 720 |
| acctgggatt ggtttcatg gttgtttcta ccatcagagt caaagaatca tcttcacaca | 780 |
| acaacacaaa tggctggtac gtcttcaaat accatctcag caggctggga gccaaatgaa | 840 |
| gaaaatgaag atgaaagaga cagacacctc agttttttctg gatcaggcat tgatgatgat | 900 |
| gaagatttta tctccagcac catttcaacc acaccacggg cttttgacca cacaaaacag | 960 |
| aaccaggact ggacccagtg gaacccaagc cattcaaatc cggaagtgct acttcagaca | 1020 |
| accacaagga tgactgatgt agacagaaat ggcaccactg cttatgaagg aaactggaac | 1080 |
| ccagaagcac accctcccct cattcaccat gagcatcatg aggaagaaga cccccacat | 1140 |
| tctacaagca caatccaggc aactcctagt agtacaacgg aagaaacagc tacccagaag | 1200 |
| gaacagtggt ttggcaacag atggcatgag ggatatcgcc aaacacccaa gaagactcc | 1260 |
| cattcgacaa cagggacagc tgcagcctca gctcatacca gccatccaat gcaaggaagg | 1320 |
| acaacaccaa gcccgaggga cagttcctgg actgatttct caacccaat ctcacacccc | 1380 |
| atgggacgag tcatcaagc aggaagaagg atggatatgg actccagtca agtataacg | 1440 |
| cttcagccta ctgcaaatcc aaacacaggt ttggtggaag atttggacag gacaggacct | 1500 |
| cttttcaatga caacgcagca gagtaattct cagagcttct ctacatcaca tgaaggcttg | 1560 |
| gaagaagata aagaccatcc aacaacttct actctgacat caagcaatag gaatgatgtc | 1620 |
| acaggtggaa gaagagaccc aaatcattct gaaggctcaa ctactttact ggaaggttat | 1680 |
| acctctcatt acccacacac gaaggaaagc aggacccttca tcccagtgac ctcagctaag | 1740 |
| actgggtcct ttgagttac tgcagttact gttggagatt ccaactctaa tgtcaatcgt | 1800 |

| | |
|---|---:|
| tccttatcag gagaccaaga cacattccac cccagtgggg ggtcccatac cactcatgga | 1860 |
| tctgaatcag atggacactc acatgggagt caagaaggtg gagcaaacac aacctctggt | 1920 |
| cctataagga cacccaaat tccagaatgg ctgatcatct tggcatccct cttggccttg | 1980 |
| gctttgattc ttgcagtttg cattgcagtc aacagtcgaa gaaggtgtgg gcagaagaaa | 2040 |
| aagctagtga tcaacagtgg caatggagct gtggaggaca gaaagccaag tggactcaac | 2100 |
| ggagaggcca gcaagtctca ggaaatggtg catttggtga acaaggagtc gtcagaaact | 2160 |
| ccagaccagt ttatgacagc tgatgagaca aggaacctgc agaatgtgga catgaagatt | 2220 |
| ggggtgtaa | 2229 |

<210> SEQ ID NO 9
<211> LENGTH: 945
<212> TYPE: DNA
<213> ORGANISM: Homo sapiens

<400> SEQUENCE: 9

| | |
|---|---:|
| atggcgcccc cgcaggtcct cgcgttcggg cttctgcttg ccgcggcgac ggcgactttt | 60 |
| gccgcagctc aggaagaatg tgtctgtgaa aactacaagc tggccgtaaa ctgctttgtg | 120 |
| aataataatc gtcaatgcca gtgtacttca gttggtgcac aaaatactgt catttgctca | 180 |
| aagctggctg ccaaatgttt ggtgatgaag gcagaaatga atggctcaaa acttgggaga | 240 |
| agagcaaaac ctgaaggggc cctccagaac aatgatgggc tttatgatcc tgactgcgat | 300 |
| gagagcgggt ctctttaagg caagcagtgc aacggcacct ccatgtgctg gtgtgtgaac | 360 |
| actgctgggg tcagaagaac agacaaggac actgaaataa cctgctctga gcgagtgaga | 420 |
| acctactgga tcatcattga actaaaacac aaagcaagag aaaaacctta tgatagtaaa | 480 |
| agtttgcgga ctgcacttca gaaggagatc acaacgcgtt atcaactgga tccaaaattt | 540 |
| atcacgagta ttttgtatga gaataatgtt atcactattg atctggttca aaattcttct | 600 |
| caaaaaactc agaatgatgt ggacatagct gatgtggctt attattttga aaagatgtt | 660 |
| aaaggtgaat ccttgtttca ttctaagaaa atggacctga cagtaaatgg ggaacaactg | 720 |
| gatctggatc ctggtcaaac tttaatttat tatgttgatg aaaaagcacc tgaattctca | 780 |
| atgcagggtc taaaagctgg tgttattgct gttattgtgg ttgtggtgat agcagttgtt | 840 |
| gctggaattg ttgtgctggt tatttccaga agaagagaa tggcaaagta tgagaaggct | 900 |
| gagataaagg agatgggtga gatgcatagg gaactcaatg cataa | 945 |

<210> SEQ ID NO 10
<211> LENGTH: 1752
<212> TYPE: DNA
<213> ORGANISM: Homo sapiens

<400> SEQUENCE: 10

| | |
|---|---:|
| atggaatcca gggggccag ttcctgccgt ctgctcttct gcctcttgat ctccgccacc | 60 |
| gtcttcaggc caggccttgg atggtatact gtaaattcag catatggaga taccattatc | 120 |
| atacccttgcc gacttgacgt acctcagaat ctcatgtttg gcaaatggaa atatgaaaag | 180 |
| cccgatggct cccagtatt tattgccttc agatcctcta caagaaaag tgtgcagtac | 240 |
| gacgatgtac cagaatacaa agacagattg aacctctcag aaaactacac tttgtctatc | 300 |
| agtaatgcaa ggatcagtga tgaaagagag tttgtgtgca tgctagtaac tgaggacaac | 360 |
| gtgtttgagg cacctacaat agtcaaggtg ttcaagcaac catctaaacc tgaaattgta | 420 |

| | |
|---|---|
| agcaaagcac tgtttctcga acagagcag ctaaaaaagt tgggtgactg catttcagaa | 480 |
| gacagttatc cagatggcaa tatcacatgg tacaggaatg gaaaagtgct acatcccctt | 540 |
| gaaggagcgg tggtcataat ttttaaaaag gaaatggacc cagtgactca gctctatacc | 600 |
| atgacttcca ccctggagta caagacaacc aaggctgaca tacaaatgcc attcacctgc | 660 |
| tcggtgacat attatggacc atctggccag aaaacaattc attctgaaca ggcagtattt | 720 |
| gatatttact atcctacaga gcaggtgaca atacaagtgc tgccaccaaa aaatgccatc | 780 |
| aaagaagggg ataacatcac tcttaaatgc ttagggaatg caaccctcc cccagaggaa | 840 |
| ttttttgtttt acttaccagg acagcccgaa ggaataagaa gctcaaatac ttacacactg | 900 |
| acggatgtga ggcgcaatgc aacaggagac tacaagtgtt ccctgataga caaaaaaagc | 960 |
| atgattgctt caacagccat cacagttcac tatttggatt tgtccttaaa cccaagtgga | 1020 |
| gaagtgacta gacagattgg tgatgcccta cccgtgtcat gcacaatatc tgctagcagg | 1080 |
| aatgcaactg tggtatggat gaaagataac atcaggcttc gatctagccc gtcatttcct | 1140 |
| agtcttcatt atcaggatgc tggaaactat gtctgcgaaa ctgctctgca ggaggttgaa | 1200 |
| ggactaaaga aaagagagtc attgactctc attgtagaag gcaaacctca ataaaaatg | 1260 |
| acaaagaaaa ctgatcccag tggactatct aaaacaataa tctgccatgt ggaaggtttt | 1320 |
| ccaaagccag ccattcaatg gacaattact ggcagtggaa gcgtcataaa ccaaacagag | 1380 |
| gaatctcctt atattaatgg caggtattat agtaaaatta tcatttcccc tgaagagaat | 1440 |
| gttacattaa cttgcacagc agaaaaccaa ctggagagaa cagtaaactc cttgaatgtc | 1500 |
| tctgctataa gtattccaga acacgatgag gcagacgaga taagtgatga aaacagaaa | 1560 |
| aaggtgaatg accaggcaaa actaattgtg ggaatcgttg ttggtctcct ccttgctgcc | 1620 |
| cttgttgctg gtgtcgtcta ctggctgtac atgaagaagt caaagactgc atcaaaacat | 1680 |
| gtaaacaagg acctcggtaa tatggaagaa aacaaaaagt tagaagaaaa caatcacaaa | 1740 |
| actgaagcct aa | 1752 |

<210> SEQ ID NO 11
<211> LENGTH: 243
<212> TYPE: DNA
<213> ORGANISM: Homo sapiens

<400> SEQUENCE: 11

| | |
|---|---|
| atgggcagag caatggtggc caggctcggg ctggggctgc tgctgctggc actgctccta | 60 |
| cccacgcaga tttattccag tgaaacaaca actggaactt caagtaactc ctcccagagt | 120 |
| acttccaact ctgggttggc cccaaatcca actaatgcca ccaccaaggc ggctggtggt | 180 |
| gccctgcagt caacagccag tctcttcgtg gtctcactct ctcttctgca tctctactct | 240 |
| taa | 243 |

<210> SEQ ID NO 12
<211> LENGTH: 2301
<212> TYPE: DNA
<213> ORGANISM: Homo sapiens

<400> SEQUENCE: 12

| | |
|---|---|
| atgaagacac cgtggaaggt tcttctggga ctgctgggtg ctgctgcgct tgtcaccatc | 60 |
| atcaccgtgc ccgtggttct gctgaacaaa ggcacagatg atgctacagc tgacagtcgc | 120 |
| aaaacttaca ctctaactga ttacttaaaa aatacttata gactgaagtt atactcctta | 180 |
| agatggattt cagatcatga atatctctac aaacaagaaa ataatatctt ggtattcaat | 240 |

```
gctgaatatg gaaacagctc agttttcttg gagaacagta catttgatga gtttggacat    300
tctatcaatg attattcaat atctcctgat gggcagttta ttctcttaga atacaactac    360
gtgaagcaat ggaggcattc ctacacagct tcatatgaca tttatgattt aaataaaagg    420
cagctgatta cagaagagag gattccaaac aacacacagt gggtcacatg gtcaccagtg    480
ggtcataaat tggcatatgt ttggaacaat gacatttatg ttaaaattga accaaattta    540
ccaagttaca gaatcacatg gacggggaaa gaagatataa tatataatgg aataactgac    600
tgggtttatg aagaggaagt cttcagtgcc tactctgctc tgtggtggtc tccaaacggc    660
actttttag catatgccca atttaacgac acagaagtcc cacttattga atactccttc    720
tactctgatg agtcactgca gtacccaaag actgtacggg ttccatatcc aaaggcagga    780
gctgtgaatc caactgtaaa gttctttgtt gtaaatacag actctctcag ctcagtcacc    840
aatgcaactt ccatacaaat cactgctcct gcttctatgt tgataggga tcactacttg    900
tgtgatgtga catgggcaac acaagaaaga atttctttgc agtggctcag gaggattcag    960
aactattcgg tcatggatat ttgtgactat gatgaatcca gtggaagatg gaactgctta   1020
gtggcacggc aacacattga aatgagtact actggctggg ttggaagatt taggccttca   1080
gaacctcatt ttacccttga tggtaatagc ttctacaaga tcatcagcaa tgaagaaggt   1140
tacagacaca tttgctattt ccaaatagat aaaaaagact gcacatttat tacaaaaggc   1200
acctgggaag tcatcgggat agaagctcta accagtgatt atctatacta cattagtaat   1260
gaatataaag gaatgccagg aggaaggaat ctttataaaa tccaacttag tgactataca   1320
aaagtgacat gcctcagttg tgagctgaat ccggaaaggt gtcagtacta ttctgtgtca   1380
ttcagtaaag aggcgaagta ttatcagctg agatgttccg gtcctggtct gcccctctat   1440
actctacaca gcagcgtgaa tgataaaggg ctgagagtcc tggaagacaa ttcagctttg   1500
gataaaatgc tgcagaatgt ccagatgccc tccaaaaaac tggacttcat tattttgaat   1560
gaaacaaaat tttggtatca gatgatcttg cctcctcatt ttgataaatc caagaaatat   1620
cctctactat tagatgtgta tgcaggccca tgtagtcaaa aagcagacac tgtcttcaga   1680
ctgaactggg ccacttacct tgcaagcaca gaaaacatta tagtagctag ctttgatggc   1740
agaggaagtg gttaccaagg agataagatc atgcatgcaa tcaacagaag actgggaaca   1800
tttgaagttg aagatcaaat tgaagcagcc agacaatttt caaaaatggg atttgtggac   1860
aacaaacgaa ttgcaatttg gggctggtca tatggagggt acgtaacctc aatggtcctg   1920
ggatcgggaa gtgcgtgtt caagtgtgga atagccgtgg cgcctgtatc ccggtgggag   1980
tactatgact cagtgtacac agaacgttac atgggtctcc caactccaga agacaacctt   2040
gaccattaca gaaattcaac agtcatgagc agagctgaaa attttaaaca agttgagtac   2100
ctccttattc atggaacagc agatgataac gttcactttc agcagtcagc tcagatctcc   2160
aaagccctgg tcgatgttgg agtggatttc caggcaatgt ggtatactga tgaagaccat   2220
ggaatagcta gcagcacagc acaccaacat atatataccc acatgagcca cttcataaaa   2280
caatgtttct ctttacctta g                                             2301
```

<210> SEQ ID NO 13
<211> LENGTH: 2406
<212> TYPE: DNA
<213> ORGANISM: Homo sapiens

<400> SEQUENCE: 13

```
atgaatttac aaccaattttt ctggattgga ctgatcagtt cagtttgctg tgtgtttgct      60
caaacagatg aaaatagatg tttaaaagca aatgccaaat catgtggaga atgtatacaa     120
gcagggccaa attgtgggtg gtgcacaaat tcaacatttt tacaggaagg aatgcctact     180
tctgcacgat gtgatgattt agaagcctta aaaagaagg gttgccctcc agatgacata      240
gaaaatccca gaggctccaa agatataaag aaaaataaaa atgtaaccaa ccgtagcaaa     300
ggaacagcag agaagctcaa gccagaggat attactcaga tccaaccaca gcagttggtt     360
ttgcgattaa gatcagggga gccacagaca tttacattaa aattcaagag agctgaagac     420
tatcccattg acctctacta cccttatgga ctgtcttact caatgaaaga cgatttggag     480
aatgtaaaaa gtcttggaac agatctgatg aatgaaatga ggaggattac ttcggacttc     540
agaattggat ttggctcatt tgtggaaaag actgtgatgc cttacattag cacaacacca     600
gctaagctca ggaacccttg cacaagtgaa cagaactgca ccagcccatt tagctacaaa     660
aatgtgctca gtcttactaa taaggagaaa gtatttaatg aacttgttgg aaaacagcgc     720
atatctggaa atttggattc tccagaaggt ggtttcgatg ccatcatgca agttgcagtt     780
tgtggatcac tgattggctg gaggaatgtt acacggctgc tggtgttttc cacagatgcc     840
gggtttcact ttgctggaga tgggaaactt ggtggcattg ttttaccaaa tgatggacaa     900
tgtcacctgg aaaataatat gtacacaatg agccattatt atgattatcc ttctattgct     960
caccttgtcc agaaactgag tgaaaataat attcagacaa ttttttgcagt tactgaagaa    1020 tttcagcctg tttacaagga gctgaaaaac ttgatcccta agtcagcagt aggaacatta    1080
tctgcaaatt ctagcaatgt aattcagttg atcattgatg catacaattc cctttcctca    1140
gaagtcattt tggaaaacgg caaattgtca gaaggcgtaa caataagtta caaatcttac    1200
tgcaagaacg gggtgaatgg aacaggggaa aatggaagaa atgttccaa tatttccatt     1260 ggagatgagg ttcaatttga aattagcata acttcaaata gtgtccaaa aaaggattct     1320 gacagcttta aaattaggcc tctgggcttt acggaggaag tagaggttat tcttcagtac    1380
atctgtgaat gtgaatgcca aagcgaaggc atccctgaaa gtcccaagtg tcatgaagga    1440
aatgggacat ttgagtgtgg cgcgtgcagg tgcaatgaag ggcgtgttgg tagacattgt    1500
gaatgcagca cagatgaagt taacagtgaa gacatggatg cttactgcag gaaagaaaac    1560
agttcagaaa tctgcagtaa caatggagag tgcgtctgcg gacagtgtgt ttgtaggaag    1620
agggataata caaatgaaat ttattctggc aaattctgcg agtgtgataa tttcaactgt    1680
gatagatcca atggcttaat ttgtggagga atggtgtttt gcaagtgtcg tgtgtgtgag    1740
tgcaacccca actacactgg cagtgcatgt gactgttctt tggatactag tacttgtgaa    1800
gccagcaacg gacagatctg caatggccgg gcatctgcg agtgtggtgt ctgtaagtgt    1860
acagatccga gtttcaagg gcaaacgtgt gagatgtgtc agacctgcct tggtgtctgt    1920
gctgagcata agaatgtgt tcagtgcaga gccttcaata aggagaaaa gaaagacaca     1980 tgcacacagg aatgttccta ttttaacatt accaaggtag aaagtcggga caaattaccc    2040
cagccggtcc aacctgatcc tgtgtcccat gtaaggaga aggatgttga cgactgttgg    2100 ttctattta cgtattcagt gaatgggaac aacgaggtca tggttcatgt tgtggagaat    2160
ccagagtgtc ccactggtcc agacatcatt ccaattgtag ctggtgtggt tgctggaatt    2220
gttcttattg gccttgcatt actgctgata tggaagcttt taatgataat tcatgacaga    2280
agggagtttg ctaaatttga aaaggagaaa atgaatgcca aatgggacac gcaagaaat     2340 ccgatttaca agagtcctat taataatttc aagaatccaa actacggacg taaagctggt    2400
``` ctctaa 2406

<210> SEQ ID NO 14
<211> LENGTH: 865
<212> TYPE: PRT
<213> ORGANISM: Homo sapiens

<400> SEQUENCE: 14

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365
```

-continued

```
Asp Arg Val Gln Arg Gln Thr Thr Thr Val Val Ala Gly Ile Lys Arg
370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
            405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
            485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
            565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
            610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
            645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
            675                 680                 685

Glu Gln Ser Leu Ser Thr Leu Tyr Gln Ser Val Lys Ile Leu Gln Arg
            690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
            725                 730                 735

Glu Glu Thr Lys Lys Tyr Gly Arg Thr Ile Gly Tyr Phe Glu His
            740                 745                 750

Tyr Leu Gln Trp Ile Glu Phe Ser Ile Ser Glu Lys Val Ala Ser Cys
            755                 760                 765

Lys Pro Val Ala Thr Ala Leu Asp Thr Ala Val Asp Val Phe Leu Cys
770                 775                 780
```

```
Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
            805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
            835                 840                 845

Asp His Val Tyr Gly Ile His Asn Pro Val Met Thr Ser Pro Ser Gln
            850                 855                 860

His
865

<210> SEQ ID NO 15
<211> LENGTH: 742
<212> TYPE: PRT
<213> ORGANISM: Homo sapiens

<400> SEQUENCE: 15

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65              70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
            115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
            195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
            275                 280                 285
```

```
His Leu Ser Phe Ser Gly Ser Gly Ile Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro
                405                 410                 415

Lys Glu Asp Ser His Ser Thr Thr Gly Thr Ala Ala Ala Ser Ala His
                420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700
```

```
Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
                740

<210> SEQ ID NO 16
<211> LENGTH: 314
<212> TYPE: PRT
<213> ORGANISM: Homo sapiens

<400> SEQUENCE: 16

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
                35                  40                  45

Thr Ser Val Gly Ala Gln Asn Thr Val Ile Cys Ser Lys Leu Ala Ala
            50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
                100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
                180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
            210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
                260                 265                 270

Val Val Val Val Ile Ala Val Val Ala Gly Ile Val Val Leu Val Ile
            275                 280                 285

Ser Arg Lys Lys Arg Met Ala Lys Tyr Glu Lys Ala Glu Ile Lys Glu
            290                 295                 300

Met Gly Glu Met His Arg Glu Leu Asn Ala
305                 310

<210> SEQ ID NO 17
```

<211> LENGTH: 583
<212> TYPE: PRT
<213> ORGANISM: Homo sapiens

<400> SEQUENCE: 17

```
Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Pro Cys Arg Leu Asp Val Pro
        35                  40                  45

Gln Asn Leu Met Phe Gly Lys Trp Lys Tyr Glu Lys Pro Asp Gly Ser
50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125

Lys Val Phe Lys Gln Pro Ser Lys Pro Glu Ile Val Ser Lys Ala Leu
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Phe Lys Lys Glu Met
            180                 185                 190

Asp Pro Val Thr Gln Leu Tyr Thr Met Thr Ser Thr Leu Glu Tyr Lys
        195                 200                 205

Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270

Asn Gly Asn Pro Pro Glu Glu Phe Leu Phe Tyr Leu Pro Gly Gln
        275                 280                 285

Pro Glu Gly Ile Arg Ser Ser Asn Thr Tyr Thr Leu Thr Asp Val Arg
    290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
        355                 360                 365

Asp Asn Ile Arg Leu Arg Ser Ser Pro Ser Phe Ser Ser Leu His Tyr
    370                 375                 380

Gln Asp Ala Gly Asn Tyr Val Cys Glu Thr Ala Leu Gln Glu Val Glu
```

```
                385                 390                 395                 400
        Gly Leu Lys Lys Arg Glu Ser Leu Thr Leu Ile Val Glu Gly Lys Pro
                        405                 410                 415

Gln Ile Lys Met Thr Lys Lys Thr Asp Pro Ser Gly Leu Ser Lys Thr
                        420                 425                 430

Ile Ile Cys His Val Glu Gly Phe Pro Lys Pro Ala Ile Gln Trp Thr
                        435                 440                 445

Ile Thr Gly Ser Gly Ser Val Ile Asn Gln Thr Glu Glu Ser Pro Tyr
                        450                 455                 460

Ile Asn Gly Arg Tyr Tyr Ser Lys Ile Ile Ile Ser Pro Glu Glu Asn
        465                 470                 475                 480

Val Thr Leu Thr Cys Thr Ala Glu Asn Gln Leu Glu Arg Thr Val Asn
                        485                 490                 495

Ser Leu Asn Val Ser Ala Ile Ser Ile Pro Glu His Asp Glu Ala Asp
                        500                 505                 510

Glu Ile Ser Asp Glu Asn Arg Glu Lys Val Asn Asp Gln Ala Lys Leu
                        515                 520                 525

Ile Val Gly Ile Val Val Gly Leu Leu Leu Ala Ala Leu Val Ala Gly
                        530                 535                 540

Val Val Tyr Trp Leu Tyr Met Lys Lys Ser Lys Thr Ala Ser Lys His
        545                 550                 555                 560

Val Asn Lys Asp Leu Gly Asn Met Glu Glu Asn Lys Lys Leu Glu Glu
                        565                 570                 575

Asn Asn His Lys Thr Glu Ala
                        580

<210> SEQ ID NO 18
<211> LENGTH: 80
<212> TYPE: PRT
<213> ORGANISM: Homo sapiens

<400> SEQUENCE: 18

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Ala Ala Gly Gly Ala Leu Gln Ser
        50                  55                  60

Thr Ala Ser Leu Phe Val Val Ser Leu Ser Leu His Leu Tyr Ser
65                  70                  75                  80

<210> SEQ ID NO 19
<211> LENGTH: 766
<212> TYPE: PRT
<213> ORGANISM: Homo sapiens

<400> SEQUENCE: 19

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
                35                  40                  45

Leu Lys Asn Thr Tyr Arg Leu Lys Leu Tyr Ser Leu Arg Trp Ile Ser
```

-continued

```
                50                  55                  60
Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
                100                 105                 110

Phe Ile Leu Leu Glu Tyr Asn Tyr Val Lys Gln Trp Arg His Ser Tyr
                115                 120                 125

Thr Ala Ser Tyr Asp Ile Tyr Asp Leu Asn Lys Arg Gln Leu Ile Thr
                130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
                195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Gly Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
                275                 280                 285

Ala Pro Ala Ser Met Leu Ile Gly Asp His Tyr Leu Cys Asp Val Thr
                290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
                340                 345                 350

Trp Val Gly Arg Phe Arg Pro Ser Glu Pro His Phe Thr Leu Asp Gly
                355                 360                 365

Asn Ser Phe Tyr Lys Ile Ile Ser Asn Glu Glu Gly Tyr Arg His Ile
                370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
                435                 440                 445

Leu Asn Pro Glu Arg Cys Gln Tyr Tyr Ser Val Ser Phe Ser Lys Glu
                450                 455                 460

Ala Lys Tyr Tyr Gln Leu Arg Cys Ser Gly Pro Gly Leu Pro Leu Tyr
465                 470                 475                 480
```

-continued

Thr Leu His Ser Ser Val Asn Asp Lys Gly Leu Arg Val Leu Glu Asp
            485                 490                 495

Asn Ser Ala Leu Asp Lys Met Leu Gln Asn Val Gln Met Pro Ser Lys
        500                 505                 510

Lys Leu Asp Phe Ile Ile Leu Asn Glu Thr Lys Phe Trp Tyr Gln Met
            515                 520                 525

Ile Leu Pro Pro His Phe Asp Lys Ser Lys Tyr Pro Leu Leu Leu
        530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
            565                 570                 575

Ser Phe Asp Gly Arg Gly Ser Gly Tyr Gln Gly Asp Lys Ile Met His
        580                 585                 590

Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
        610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                    645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                    725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765

<210> SEQ ID NO 20
<211> LENGTH: 801
<212> TYPE: PRT
<213> ORGANISM: Homo sapiens

<400> SEQUENCE: 20

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr

```
                85                  90                  95
Asn Arg Ser Lys Gly Thr Ala Glu Lys Leu Lys Pro Glu Asp Ile Thr
            100                 105                 110
Gln Ile Gln Pro Gln Gln Leu Val Leu Arg Leu Arg Ser Gly Glu Pro
        115                 120                 125
Gln Thr Phe Thr Leu Lys Phe Lys Arg Ala Glu Asp Tyr Pro Ile Asp
    130                 135                 140
Leu Tyr Tyr Leu Met Asp Leu Ser Tyr Ser Met Lys Asp Asp Leu Glu
145                 150                 155                 160
Asn Val Lys Ser Leu Gly Thr Asp Leu Met Asn Glu Met Arg Arg Ile
            165                 170                 175
Thr Ser Asp Phe Arg Ile Gly Phe Gly Ser Phe Val Glu Lys Thr Val
        180                 185                 190
Met Pro Tyr Ile Ser Thr Thr Pro Ala Lys Leu Arg Asn Pro Cys Thr
    195                 200                 205
Ser Glu Gln Asn Cys Thr Ser Pro Phe Ser Tyr Lys Asn Val Leu Ser
210                 215                 220
Leu Thr Asn Lys Gly Glu Val Phe Asn Glu Leu Val Gly Lys Gln Arg
225                 230                 235                 240
Ile Ser Gly Asn Leu Asp Ser Pro Glu Gly Gly Phe Asp Ala Ile Met
            245                 250                 255
Gln Val Ala Val Cys Gly Ser Leu Ile Gly Trp Arg Asn Val Thr Arg
        260                 265                 270
Leu Leu Val Phe Ser Thr Asp Ala Gly Phe His Phe Ala Gly Asp Gly
    275                 280                 285
Lys Leu Gly Gly Ile Val Leu Pro Asn Asp Gly Gln Cys His Leu Glu
290                 295                 300
Asn Asn Met Tyr Thr Met Ser His Tyr Tyr Asp Tyr Pro Ser Ile Ala
305                 310                 315                 320
His Leu Val Gln Lys Leu Ser Glu Asn Asn Ile Gln Thr Ile Phe Ala
            325                 330                 335
Val Thr Glu Glu Phe Gln Pro Val Tyr Lys Glu Leu Lys Asn Leu Ile
        340                 345                 350
Pro Lys Ser Ala Val Gly Thr Leu Ser Ala Asn Ser Ser Asn Val Ile
    355                 360                 365
Gln Leu Ile Ile Asp Ala Tyr Asn Ser Leu Ser Ser Glu Val Ile Leu
370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
            405                 410                 415
Asn Ile Ser Ile Gly Asp Glu Val Gln Phe Glu Ile Ser Ile Thr Ser
        420                 425                 430
Asn Lys Cys Pro Lys Lys Asp Ser Asp Ser Phe Lys Ile Arg Pro Leu
    435                 440                 445
Gly Phe Thr Glu Glu Val Glu Val Ile Leu Gln Tyr Ile Cys Glu Cys
450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
            485                 490                 495
Gly Arg His Cys Glu Cys Ser Thr Asp Glu Val Asn Ser Glu Asp Met
        500                 505                 510
```

-continued

```
Asp Ala Tyr Cys Arg Lys Glu Asn Ser Ser Glu Ile Cys Ser Asn Asn
            515                 520                 525

Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
    595                 600                 605

Gly Arg Gly Ile Cys Glu Cys Gly Val Cys Lys Cys Thr Asp Pro Lys
610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Cys Ser Tyr Phe Asn Ile Thr Lys
            660                 665                 670

Val Glu Ser Arg Asp Lys Leu Pro Gln Pro Val Gln Pro Asp Pro Val
    675                 680                 685

Ser His Cys Lys Glu Lys Asp Val Asp Asp Cys Trp Phe Tyr Phe Thr
690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
    755                 760                 765

Glu Lys Met Asn Ala Lys Trp Asp Thr Gln Glu Asn Pro Ile Tyr Lys
770                 775                 780

Ser Pro Ile Asn Asn Phe Lys Asn Pro Asn Tyr Gly Arg Lys Ala Gly
785                 790                 795                 800

Leu
```

<210> SEQ ID NO 21
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 21
aaccattgtt tggatttgga ag                                          22

<210> SEQ ID NO 22
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 22

```
-continued acaaactatg gcccaatgct                                          20

<210> SEQ ID NO 23
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 23
cgtaacctcg gcatactttc a                                        21

<210> SEQ ID NO 24
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 24
cgagcaagga cctgaaaaac                                          20
```